United States Patent [19]
Miyake et al.

[11] Patent Number: 4,788,185
[45] Date of Patent: Nov. 29, 1988

[54] CEPHALOSPORIN COMPOUNDS

[75] Inventors: Akio Miyake, Hirakata; Masahiro Kondo, Osaka; Masahiko Fujino, Takarazuka, all of Japan

[73] Assignee: Takeda Chemical Industries, Ltd., Osaka, Japan

[21] Appl. No.: 726,438

[22] Filed: Apr. 23, 1985

[30] Foreign Application Priority Data

Apr. 23, 1984 [WO] PCT Int'l Appl. .... PCT/JP84/00212
May 25, 1984 [WO] PCT Int'l Appl.... PCT/JP84/00270
Mar. 1, 1985 [WO] PCT Int'l Appl. ... PCT/JP85/00102
Apr. 17, 1985 [NO] Norway ................................. 851538

[51] Int. Cl.$^4$ .................. C07D 501/46; A61K 31/545
[52] U.S. Cl. .................... 514/205; 514/201; 540/221; 540/222; 540/225; 540/227
[58] Field of Search ............................. 544/25, 26, 27; 540/222, 225, 221, 224, 227; 514/205, 206, 201

[56] References Cited

U.S. PATENT DOCUMENTS

| | | | |
|---|---|---|---|
| 4,024,133 | 5/1977 | Cook et al. | 424/246 |
| 4,098,888 | 7/1978 | Ochiai et al. | 424/246 |
| 4,138,555 | 2/1979 | Cook et al. | 424/246 |
| 4,165,430 | 8/1979 | Bradshaw et al. | 424/246 |
| 4,200,572 | 4/1980 | Gleason et al. | 260/239 A |
| 4,207,234 | 6/1980 | Kamiya et al. | 260/239 A |
| 4,258,041 | 3/1981 | O'Callaghan et al. | 424/246 |
| 4,278,671 | 7/1981 | Ochiai et al. | 424/246 |
| 4,278,793 | 7/1981 | Durckheimer et al. | 544/27 |
| 4,355,160 | 10/1982 | Ochiai et al. | 544/27 |
| 4,380,541 | 4/1983 | Ochiai et al. | 424/246 |
| 4,388,316 | 6/1983 | Lunn et al. | 424/246 |
| 4,427,675 | 1/1984 | Ayrs et al. | 540/222 |
| 4,486,586 | 12/1984 | Namta et al. | 544/27 |
| 4,510,138 | 4/1985 | Ochiai et al. | 424/246 |
| 4,665,065 | 5/1987 | Myake et al. | 540/222 |

FOREIGN PATENT DOCUMENTS 3316798 11/1984 Fed. Rep. of Germany .
0137441 4/1985 Fed. Rep. of Germany .
0062321 10/1982 United Kingdom .

Primary Examiner—Nicholas S. Rizzo
Attorney, Agent, or Firm—Wegner & Bretschneider

[57] ABSTRACT

A compound of the formula;

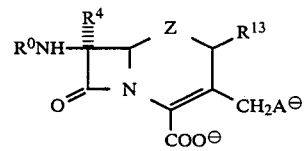

wherein $R^0$ stands for hydrogen atom, nitrogen-containing heterocyclic group, acyl group or esterified carboxyl group, Z stands for S, S→O, O or $CH_2$, $R^4$ stands for hydrogen atom, methoxy group or formamido group, $R^{13}$ stands for hydrogen atom, methyl group, hydroxyl group or halogen atom and A stands for an optionally substituted imidazol-1-yl group forming a condensed ring at the 2,3- or 3,4-position or a physiologically or pharmaceutically acceptable salt or ester thereof.

This compound is novel and has excellent antibacterial activity.

34 Claims, No Drawings

CEPHALOSPORIN COMPOUNDS

This invention relates to novel antibacterial compounds having excellent antibacterial action, a method of preparing same and a pharmaceutical composition.

The present invention relates to a compound of the formula;

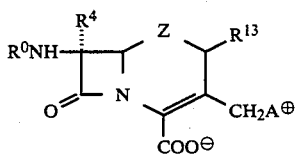

wherein $R^0$ stands for hydrogen atom, nitrogen-containing heterocyclic group, acyl group or esterified carboxyl group, Z stands for S, S→O, O or $CH_2$, $R^4$ stands for hydrogen atom, methoxy group or formamido group, $R^{13}$ stands for hydrogen atom, methyl group, hydroxyl group or halogen atom, and A stands for an optionally substituted imidazol-1-yl group forming a condensed ring at the 2,3-position or the 3,4-position or a physiologically or pharmaceutically acceptable salt or ester thereof, methods of preparing them and to pharmaceutical compositions. More specifically, the antibacterial compounds of the present invention are cephem compounds representable by the general formula [I] (Z=S, S→O) as well as oxa-(Z=O) or carba-(Z=$CH_2$) derivatives thereof.

The cephem compounds in the present specification are a group of compounds named on the basis of "cepham" disclosed in "The Journal of the American Chemical Society" Vol. 84, p. 3400 (1962), and include, among the cepham compounds, those having a double bond at the the 3,4-position.

The compounds of this invention have a characteristic feature in having at the 3-position an imidazolyl-1-yl group which forms a condensed ring at the 2,3-position or the 3,4-position. The present inventors succeeded in synthesizing the compounds representable by the general formula [I] and having such a structural feature, and examined the antibacterial activities and antibacterial spectrum, resulting in the findings that the compounds [I] have strong antibacterial action against various bacteria, especially against cephalosporin-resistant bacteria set forth above, and that they show specific antibacterial action against bacteria belonging to the genus Pseudomonas, and completed the present invention.

Reference is made as follows to the group names and symbols used in the present specification. Unless otherwise specifically defined, those groups and symbols are of the following meanings respectively.

"Alkyl group" is preferably a straight-chain or branched lower alkyl group having 1-6 carbon atoms (hereinafter sometimes mentioned briefly as "$C_{1-6}$ alkyl group"), which is exemplified by methyl, ethyl, n-propyl, isopropyl, n-butyl, isobutyl, sec-butyl, tert-butyl, n-pentyl or n-hexyl.

"Alkenyl group" is preferably a straight-chain or branched lower alkenyl group having 2-6 carbon atoms (hereinafter sometimes mentioned briefly as "$C_{2-6}$ alkenyl group"), which is exemplified by vinyl, allyl, 1-propenyl, isopropenyl, 1-butenyl, 2-butenyl, 3-butenyl, methallyl, or 1,1-dimethylallyl.

"Alkynyl group" is preferably a straight-chain or branched lower alkynyl group having 2-6 carbon atoms (hereinafter sometimes mentioned briefly as "$C_{2-6}$ alkynyl group"), which is exemplified by ethynyl, 1-propynyl or propargyl.

"Cycloalkyl group" is preferably a 3-7 membered alicyclic hydrocarbon group having 3-10 carbon atoms (hereinafter sometimes mentioned briefly as "$C_{3-10}$ cycloalkyl group"), which is exemplified by cyclopropyl, cyclobutyl, cyclopentyl, cyclohexyl, cycloheptyl, norbornyl or adamantyl.

"Cycloalkenyl group" is preferably a 5-6 membered alicyclic hydrocarbon group having double bond (hereinafter sometimes mentioned briefly as "$C_{5-6}$ cycloalkenyl group"), which is exemplified by cyclopentenyl, cyclopentadienyl, cyclohexenyl or cyclohexadienyl.

"Aryl group" is preferably an aromatic hydrocarbon group having 6-10 carbon atoms (hereinafter sometims mentioned briefly as "$C_{6-10}$ aryl group"), which is exemplified by phenyl, α-naphthyl, β-naphthyl or biphenylyl.

"Aralkyl group" is preferably an aryl-substituted alkyl group having 7-12 carbon atoms (hereinafter sometimes mentioned briefly as "$C_{7-12}$ aralkyl group"), which is exemplified by benzyl, 1-phenylethyl, 2-phenylethyl, phenylpropyl or naphthylmethyl. Incidentally, the $C_{7-12}$ aralkyl group, in combination with the di-$C_{6-10}$ aryl-methyl group and tri-$C_{6-10}$ aryl-methyl group, is sometimes stated as "$C_{7-19}$ aralkyl group".

"Diarylmethyl group" means methyl group substituted with two $C_{6-10}$ aryl groups mentioned above (hereinafter sometimes mentioned briefly as "di-$C_{6-10}$ aryl-methyl group"), which is exemplified by benzhydryl.

"Triarylmethyl group" means methyl group substituted with three $C_{6-10}$ aryl groups mentioned above (hereinafter sometimes mentioned briefly as "tri-$C_{6-10}$ arylmethyl group"), which is exemplified by trityl.

The aryl group of "arylmethylene group" is preferably a $C_{6-10}$ aryl group mentioned above, hence "arylmethylene group" being hereinafter sometimes called "$C_{6-10}$ arylmethylene group", which is exemplified by benzylidene ($C_6H_5CH=$).

The alkyl grop of "alkoxy group" is preferably a $C_{1-6}$ alkyl group mentioned above, hence "alkoxy group" being hereinafter sometimes called "$C_{1-6}$ alkoxy group", which is exemplified by methoxy, ethoxy, n-propoxy, isopropoxy, n-butoxy, tert-butoxy, amyloxy or hexyloxy.

The cycloalkyl group of "cycloalkyloxy group" is preferably a $C_{3-10}$ cycloalkyl group mentioned above, hence "cycloalkyloxy group" being hereinafter sometimes called "$C_{3-10}$ cycloalkyloxy group", which is exemplified by cyclopropyloxy, cyclopentyloxy, cyclohexyloxy or norbornyloxy.

The aryl group of "aryloxy group" is preferably a $C_{6-10}$ aryl group mentioned above, hence "aryloxy group" being hereinafter sometimes called "$C_{6-10}$ aryloxy group", which is exemplified by phenoxy or naphthyloxy.

The aralkyl group of "aralkyloxy group" is preferably a $C_{7-19}$ aralkyl group mentioned above, hence "aralkyloxy group" being hereinafter sometimes called "$C_{7-19}$ aralkyloxy group", which is exemplified by benzyloxy, 1-phenylethyloxy, 2-phenylethyloxy, naphthylmethyloxy, benzhydryloxy or trityloxy.

The alkyl group of "alkylthio group" is preferably a $C_{1-6}$ alkyl group mentioned above, hence "alkylthio group" being hereinafter sometimes called "$C_{1-6}$ alkylthio group", which is exemplified by methylthio, ethylthio, n-propylthio or n-butylthio.

The alkylthio group of "aminoalkylthio group" is preferably a $C_{1-6}$alkylthio group mentioned above, hence "aminoalkylthio group" being hereinafter called "amino $C_{1-6}$ alkylthio group", which is exemplified by aminomethylthio, 2-aminoethylthio or 3-aminopropylthio.

The alkenyl group of "alkenylthio group" is preferably a $C_{2-6}$alkenyl group mentioned above, hence "alkenylthio group" being hereinafter sometimes called "$C_{2-6}$ alkenylthio group", which is exemplified by vinylthio, allylthio, 1-propenylthio or isopropenylthio.

The cycloalkyl group of "cycloalkylthio group" is preferably a $C_{3-10}$ cycloalkyl group mentioned above, hence "cycloalkylthio group" being hereinafter sometimes called "$C_{3-10}$ cycloalkylthio group", which is exemplified by cyclopropylthio or cyclohexylthio.

The aryl group of "arylthio group" is preferably a $C_{6-10}$ aryl group mentioned above, hence "arylthio group" being hereinafter sometimes called "$C_{6-10}$ arylthio group", which is exemplified by phenylthio or naphthylthio.

The aralkyl group of "aralkylthio group" is preferably a $C_{7-19}$aralkyl group mentioned above, hence "aralkylthio group" being hereinafter sometimes called "$C_{7-19}$ aralkylthio group", which is exemplified by benzylthio, phenylethylthio, benzhydrylthio or tritylthio.

The alkyl group of "monoalkylamino group" is preferably a $C_{1-6}$alkyl group mentioned above, hence "monoalkylamino group" being hereinafter sometimes called "mono-$C_{1-6}$ alkylamino group", which is exemplified by methylamino, ethylamino, n-propylamino, n-butylamino, tert-butylamino, n-pentylamino or n-hexylamino.

The alkyl group of "dialkylamino group" is peferably a $C_{1-6}$ alkyl group mentioned above, hence "dialkylamino group" being hereinafter sometimes called "di-$C_{1-6}$ alkylamino group", which is exemplified by dimethylamino, diethylamino, methylethylamino, di-(n-propyl)amino or di-(n-butyl)amino.

The alkyl group of "trialkylammonium group" is preferably a $C_{1-6}$alkyl group mentioned above, hence "trialkylammonium group" being hereinafter sometimes called "tri-$C_{1-6}$ alkylammonium group", which is exemplified by trimethylammonium [$(CH_3)_3N^{\oplus}$—] or triethylammonium. The trialkylammonium group is necessarily accompanied by a corresponding anion exemplified by halogenide ion (chloride ion, bromide ion, iodide ion, etc.), sulfate ion, nitrate ion, carbonate ion, organic carboxylate ion (e.g oxalate ion or trifluoroacetate ion), organic sulfonate ion (e.g. methanesulfonate ion or p-toluenesulfonate ion). The organic carboxylate ion and the organic sulfonate ion may sometimes be present in the same molecule.

The cycloalkyl group of "cycloalkylamino group" is preferably a $C_{3-10}$cycloalkyl group mentioned above, hence "cycloalkylamino group" being hereinafter sometimes called "$C_{3-10}$ cycloalkylamino", which is exemplified by cyclopropylamino, cyclopentylamino or cyclohexylamino.

The aryl group of "arylamino group" is preferably a $C_{6-10}$ aryl group mentioned above, hence "arylamino group" being hereinafter sometimes called "$C_{6-10}$ arylamino group", which is exemplified by anilino or N-methylanilino.

The aralkyl group of "aralkylamino group" is preferably a $C_{7-19}$aralkyl group mentioned above, hence "aralkylamino group" being hereinafter sometimes called "$C_{7-19}$ aralkylamino group", which is exemplified by benzylamino, 1-phenylethylamino, 2-phenylethylamino, benzhydrylamino or tritylamino.

"Cyclic amino group" means a group formed by removing one of the hydrogen atoms bonding to the ring-forming nitrogen atom of such a nitrogen-containing heterocyclic ring or that saturated at its double bond as described hereafter, which is exemplified by 1H-tetrazol-1-yl, 1H-pyrrol-1-yl, pyrrolino, pyrrolidino, 1H-imidazol-1-yl, imidazolino, imidazolidino, 1H-pyrazol-1-yl, pyrazolino, pyrazolidino, piperidino, piperazino or morpholino.

The alkyl group of "hydroxyalkyl group" is preferably a $C_{1-6}$ alkyl group mentioned above, hence "hydroxyalkyl group" being hereinafter sometimes called "hydroxy $C_{1-6}$ alkyl group", which is exemplified by hydroxymethyl, 1-hydroxyethyl, 2-hydroxyethyl or 3-hydroxypropyl.

The alkyl group of "mercaptoalkyl group" is preferably a $C_{1-6}$alkyl group mentioned above, hence "mercaptoalkyl group" being hereinafter sometimes called "mercapto $C_{1-6}$ alkyl group", which is exemplified by mercaptomethyl, 1-mercaptoethyl or 2-mercaptoethyl.

The alkoxy group of "alkoxyalkyl group" is preferably a $C_{1-6}$alkoxy group mentioned above and the alkyl group of "alkoxyalkyl group" is preferably $C_{1-6}$ alkyl group mentioned above, hence "alkoxyalkyl group" being hereinafter sometimes called "$C_{1-6}$ alkoxy $C_{1-6}$ alkyl group", which is exemplified by methoxymethyl, ethoxymethyl or 2-methoxyethyl.

The alkylthio group of "alkylthioalkyl group" is preferably a $C_{1-6}$alkylthio group mentioned above and the alkyl group of "alkylthioalkyl group" is preferably a $C_{1-6}$ alkyl group mentioned above, hence "alkylthioalkyl group" being hereinafter sometimes called "$C_{1-6}$ alkylthio $C_{1-6}$ alkyl group", which is exemplified by methylthiomethyl or 2-methylthioethyl.

The alkyl group of "aminoalkyl group" is preferably a $C_{1-6}$ alkyl group mentioned above, hence "aminoalkyl group" being hereinafter sometimes called "amino $C_{1-6}$ alkyl group", which is exemplified by aminomethyl, 2-aminoethyl or 3-aminopropyl.

"Monoalkylaminoalkyl group" is preferably a "mono-$C_{1-6}$ alkyl amino $C_{1-6}$ alkyl group", which is exemplified by methylaminomethyl, ethylaminomethyl, 2-(N-methylamino)ethyl or 3-(N-methylamino)propyl.

Dialkylaminoalkyl group is preferably a "di-$C_{1-6}$ alkylamino $C_{1-6}$ alkyl group", which is exemplified by N,N-dimethylaminomethyl, N,N-diethylaminomethyl, 2-(N,N-dimethylamino)ethyl, 2-(N,N-diethylamino)ethyl or 3-(N,N-diethylamino)propyl.

The cyclic amino group of "cyclic-amino alkyl group" is preferably the one mentioned above and the alkyl group of "cyclic-aminoalkyl group" is preferably a $C_{1-6}$ amino group mentioned above, hence hereinafter "cyclic-amino alkyl group" being sometimes called "cyclic-amino $C_{1-6}$ alkyl group", which is exemplified by pyrrolidinomethyl, piperidinomethyl, piperazinomethyl, morpholinomethyl or 2-(morpholino)ethyl.

The cyclic aminoalkyl group of "cyclic aminoalkylamino group" is preferably a cyclic-amino $C_{1-6}$ alkyl group mentioned above, hence hereinafter "cyclic aminoalkylamino group" being sometimes called "cyclic-amino $C_{1-6}$ alkylamino group", which is exemplified by pyrrolidinomethylamino, piperizinomethylamino, piperazinomethylamino or morpholinomethylamino.

The alkyl group of "halogenoalkyl group" is preferably a $C_{1-6}$ alkyl group mentioned above, hence hereinafter "halogenoalkyl group" being sometimes called "halogeno $C_{1-6}$ alkyl group", which is exemplified by fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl.

The alkyl group of "cyanoalkyl group" is preferably a $C_{1-6}$ alkyl group mentioned above, hence hereinafter "cyanoalkyl group" being sometimes called "cyano $C_{1-6}$ alkyl group", which is exemplified by cyanomethyl or 2-cyanoethyl.

The alkyl group of "carboxyalkyl group" is preferably a $C_{1-6}$ alkyl group mentioned above, hence hereinafter "carboxyalkyl group" being called sometimes "carboxy $C_{1-6}$ alkyl group", which is exemplified by carboxymethyl, 1-carboxyethyl or 2-carboxyethyl.

The alkyl group of "sulfoalkyl group" is preferably a $C_{1-6}$ alkyl group mentioned above, hence hereinafter "sulfoalkyl group" being called sometimes "sulfo $C_{1-6}$ alkyl group", which is exemplified by sulfomethyl or 2-sulfoethyl.

The alkanoyl group of "alkanoylalkyl group" is preferably a $C_{2-6}$ alkanoyl group mentioned hereafter and the alkyl group of "alkanoylalkyl group" is preferably a $C_{1-6}$ alkyl group mentioned above, hence hereinafter "alkanoylalkyl group" being sometimes called "$C_{2-6}$ alkanoyl $C_{1-6}$ alkyl group", which is exemplified by acetylmethyl, 1-acetylethyl or 2-acetylethyl.

The alkanoyloxy group of "alkanoyloxyalkyl group" is preferably a $C_{2-6}$ alkanoyloxy group to be described hereafter and the alkyl group of "alkanoyloxyalkyl group" is preferably a $C_{1-6}$ alkyl group mentioned above, hence hereinafter "alkanoyloxyalkyl group" being sometimes called "$C_{2-6}$ alkanoyloxy $C_{1-6}$ alkyl group", which is exemplified by acetoxymethyl, 1-acetoxyethyl or 2-acetoxyethyl.

The alkoxycarbonyl group of "alkoxycarbonylalkyl group" is preferably a $C_{1-10}$ alkoxy-carbonyl group to be described hereafter and the alkyl group of "alkoxycarbonylalkyl group" is preferably a $C_{1-6}$ alkyl group mentioned above, hence hereinafter "alkoxycarbonylalkyl group" being sometimes called "$C_{1-10}$ alkoxy-carbonyl $C_{1-6}$ alkyl group", which is exemplified by methoxycarbonylmethyl, ethoxycarbonylmethyl or tert-butoxycarbonylmethyl.

The alkyl group of "carbamoylalkyl group" is preferably a $C_{1-6}$ alkyl group, hence hereinafter "carbamoylalkyl group" being sometimes called "carbamoyl $C_{1-6}$ alkyl group", which is exemplified by carbamoylmethyl.

The alkyl group of "carbamoyloxyalkyl group" is preferably a $C_{1-6}$ alkyl group, hence hereinafter "carbamoylalkyl group" being called sometimes "carbamoyloxy $C_{1-6}$ alkyl group", which is exemplified by carbamoyloxymethyl.

"Halogen atom" is exemplified by fluorine, chlorine, bromine or iodine.

"Alkanoyl group" is preferably a aliphatic acyl group having 1–6 carbon atoms, hereinafter sometimes called simply "$C_{1-6}$ alkanoyl group", which is exemplified by formyl, acetyl, propionyl, butyryl, isobutyryl, valeryl, isovaleryl or pivaloyl. These alkanoyl groups, except formyl, are sometimes called "$C_{2-6}$ alkanoyl group".

"Alkenoyl group" is preferably the one having 3–5 carbon atoms (hereinafter sometimes simply called "$C_{3-5}$ alkenoyl group"), which is exemplified by acryloyl, crotonoyl or maleoyl.

The cycloalkyl group of "cycloalkylcarbonyl group" is preferably a $C_{3-10}$ cycloalkyl group mentioned above, hence hereinafter "cycloalkyl carbonyl group" being sometimes called "$C_{3-10}$ cycloalkyl-carbonyl group", which is exemplified by cyclopropylcarbonyl, cyclobutylcarbonyl, cyclopentylcarbonyl, cyclohexylcarbonyl, cycloheptylcarbonyl or adamantylcarbonyl.

The cycloalkenyl group of "cycloalkenylcarbonyl group" is preferably a $C_{5-6}$ cycloalkenyl group, hence hereinafter "cycloalkenylcarbonyl group" being called sometimes "$C_{5-6}$ cycloalkenyl-carbonyl group", which is exemplified by cyclopentenylcarbonyl, cyclopentadienylcarbonyl, cyclohexenylcarbonyl or cyclohexadienylcarbonyl.

The aryl group of "arylcarbonyl group" is preferably a $C_{6-10}$ aryl group mentioned above, hence hereinafter "arylcarbonyl group" being called sometimes "$C_{6-10}$ arylcarbonyl group", which is exemplified by benzoyl or naphthoyl.

The aralkyl group of "aralkylcarbony group" is preferably a $C_{7-19}$ aralkyl group, hence hereinafter "aralkylcarbonyl group" being sometimes called "$C_{7-19}$ aralkylcarbonyl group", which is exemplified by phenylacetyl, phenylpropionyl, α,α-diphenylacetyl or α,α,α-triphenylacetyl.

The alkyl group of "alkoxycarbonyl group" includes, in this specification, $C_{3-10}$ cycloalkyl group mentioned above, besides lower alkyl groups having 1–8 carbon atoms, hence hereinafter "alkoxycarbonyl group" being sometimes called "$C_{1-10}$ alkoxy-carbonyl group", which is exemplified by methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl or norbornyloxycarbonyl.

The aryloxy group of "aryloxycarbonyl" is preferably a $C_{6-10}$ aryloxy group mentioned above, hence hereinafter "aryloxycarbonyl group" being sometimes called "$C_{6-10}$ aryloxy-carbonyl group", which is exemplified by phenoxycarbonyl or naphthyloxycarbonyl.

The aralkyloxy group of "aralkyloxycarbonyl group" is preferably a $C_{7-19}$ aralkyloxy group mentioned above, which is exemplified by benzyloxycarbonyl, benzhydryloxycarbonyl or trityloxycarbonyl.

"Substituted oxycarbonyl group" means the above-mentioned $C_{1-10}$ alkoxy-carbonyl group, $C_{6-10}$ aryloxycarbonyl group or $C_{7-19}$ aralkyloxy-carbonyl group.

The alkylthio group of "alkylthiocarbonyl group" is preferably a $C_{1-6}$ alkylthio group mentioned above, hence "alkylthiocarbonyl group" being hereinafter called sometimes "$C_{1-6}$ alkylthio-carbonyl group", which is exemplified by methylthiocarbonyl, ethylthiocarbonyl, n-propylthiocarbonyl or n-butylthiocarbonyl.

The alkanoyl group of "alkanoyloxy group" is preferably a $C_{1-6}$ alkanoyl group mentioned above, hence "alkanoyloxy group" being hereinafter called "$C_{1-6}$ alkanoyloxy group, which is exemplified by formyloxy, acetoxy, propionyloxy, butyryloxy, valeryloxy or pivaloyloxy. These alkanoyloxy groups, except formyloxy, are sometimes called "$C_{2-6}$ alkanoyloxy group".

The alkenoyl group of "alkenoyloxy group" is preferably a $C_{3-5}$ alkenoyl group mentioned above, hence "alkenoyloxy group" being hereinafter called sometimes "$C_{3-5}$ alkenoyloxy group", which is exemplified by acryloyloxy or crotonoyloxy.

The alkyl group of "monoalkylcarbamoyl group" is preferably a $C_{1-6}$alkyl group mentioned above, hence "monoalkylcarbamoyl group" being hereinafter sometimes called "mono-$C_{1-6}$ alkylcarbamoyl group", which is exemplified by N-methylcarbamoyl or N-ethylcarbamoyl.

The alkyl group of "dialkylcarbamoyl group" is preferably a $C_{1-6}$alkyl group, hence "dialkylcarbamoyl group" being hereinafter sometimes called "di-$C_{1-6}$ alkylcarbamoyl group", which is exemplified by N,N-dimethylcarbamoyl or N,N-diethylcarbamoyl.

The monoalkylcarbamoyl group of "monoalkylcarbamoyloxy group" is preferably a mono-$C_{1-6}$ alkylcarbamoyl group mentioned above, hence "monoalkylcarbamoyloxy group" being hereinafter sometimes called "mono-$C_{1-6}$ alkylcarbamoyloxy group", which is exemplified by N-methylcarbamoyloxy or N-ethylcarbamoyloxy.

The dialkylcarbamoyl group of "dialkylcarbamoyloxy group" is preferably a di-$C_{1-6}$ alkylcarbamoyl group mentioned above, hence "dialkylcarbamoyloxy group" being hereinafter sometimes called "di-$C_{1-6}$ alkylcarbamoyloxy group", which is exemplified by N,N-dimethylcarbamoyloxy or N,N-diethylcarbamoyloxy.

The alkyl group of "alkylsulfonyl group" is preferably a $C_{1-6}$alkyl group mentioned above, hence "alkylsulfonyl group" being hereinafter sometimes called "$C_{1-6}$ alkylsulfonyl group", which is exemplified by methanesulfonyl or ethanesulfonyl.

The aryl group of "arylsulfonyl group" is preferably a $C_{6-10}$ aryl group mentioned above, hence "arylsulfonyl group" being hereinafter sometimes called "$C_{6-10}$ arylsulfonyl group", which is exemplified by, among others, benzenesulfonyl.

The aralkyl group of "aralkylsulfonyl group" is preferably a $C_{7-19}$ aralkyl group mentioned above, hence "aralkylsulfonyl group" being hereinafter sometimes called "$C_{7-19}$ aralkylsulfonyl group", which is exemplified by phenylmethanesulfonyl or diphenylmethanesulfonyl.

The alkylsulfonyl group of "alkylsulfonyloxy group" is preferably a $C_{1-6}$ alkylsulfonyl group mentioned above, hence "alkylsulfonyloxy group" being hereinafter sometimes called "$C_{1-6}$ alkylsulfonyloxy group", which is exemplified by methanesulfonyloxy or ethanesulfonyloxy.

The arylsulfonyl group of "arylsulfonyloxy group" is preferably a $C_{6-10}$ arylsulfonyl group, hence "arylsulfonyloxy group" being hereinafter sometimes called "$C_{6-10}$ arylsulfonyloxy group", which is exemplified by, among others, benzenesulfonyloxy.

The aralkylsulfonyl group of "aralkylsulfonyloxy group" is preferably a $C_{7-19}$ aralkylsulfonyl group mentioned above, hence "aralkylsulfonyloxy group" being hereinafter sometimes called "$C_{7-19}$ arylsulfonyloxy group", which is exemplified by phenylmethanesulfonyloxy or diphenylmethanesulfonyloxy.

"Amino acid residue" means acyl groups formed by removing hydroxyl group of the carboxyl group of conventional amino acids, which is exemplified by glycyl, alanyl, valyl, leucyl, isoleucyl, seryl, threonyl, cysteinyl, cystinyl, methionyl, aspartyl, glutamyl, lysyl, arginyl, phenylglycyl, phenylalanyl, tyrosyl, histidyl, triptophanyl or prolyl.

"Nitrogen-containing heterocyclic ring" means 5–8 membered ring containing one to several, preferably 1–4, nitrogen atoms (optionally oxidized) or condensed ring thereof, which may contain, besides nitrogen atoms, one to several, prefrably 1–2, hetero atoms such as oxygen atom or sulfur atom.

"Nitrogen-containing heterocyclic group" means a group formed by removing one hydrogen atom bonding to ring-forming carbon atom of the above nitrogen-containing heterocyclic ring.

"Heterocyclic group" means a group formed by removing one hydrogen atom bonding to carbon atom of a heterocyclic ring, which means 5–8 membered ring containing one to several, preferably 1–4, hetero atoms such as nitrogen atom (optionally oxidized), oxygen atom or sulfur atom, or condensed ring thereof, which is exemplified by 2- or 3-pyrrolyl, 3-, 4- or 5-pyrazolyl, 2-, 4- or 5-imidazolyl, 1,2,3- or 1,2,4-triazolyl, 1H- or 2H-tetrazolyl, 2- or 3-furyl, 2- or 3-thienyl, 2-, 4- or 5-oxazolyl, 3-, 4- or 5-isoxazolyl, 1,2,3-oxadiazol-4- or 5-yl, 1,2,4-oxadiazol-3- or 5-yl, 1,2,5- or 1,3,4-oxadiazolyl, 2-, 4- or 5-thiazolyl, 3-, 4- or 5-isothiazolyl, 1,2,3-thiadiazol-4- or 5-yl, 1,2,4-thiadiazol-3- or 5-yl, 1,2,5- or 1,3,4-thiadiazolyl, 2- or 3-pyrrolidinyl, 2-, 3- or 4-pyridyl, 2-, 3- or 4-pyridyl-N-oxide, 3- or 4-pyridazinyl, 3- or 4-pyridazinyl-N-oxide, 2-, 4- or 5-pyrimidinyl, 2-, 4- or 5-pyrimidinyl-N-oxide, pyrazinyl, 2-, 3- or 4-piperidinyl, piperazinyl, 3H-indol-2- or 3-yl, 2-, 3- or 4-pyranyl, 2-, 3- or 4-thiopyranyl, benzopyranyl, quinolyl, pyrido[2,3-d]pyrimidyl, 1,5-, 1,6-, 1,7-, 1,8-, 2,6- or 2,7-naphthylidyl, thieno[2,3-d]pyridyl, pyrimidopyrimidyl, pyrazinoquinolyl, or benzopyranyl.

Heterocyclic groups of "heterocycle-oxy group", "heterocycle-thio group", "heterocycle-amino group", "heterocycle-carbonyl group", "heterocycleacetyl group" and "heterocycle-carboxamido group" are all preferably "heterocyclic group" mentioned above.

"Quaternary ammonium group" means a group in which the bonding hand is the unpaired electron located on one of the tertiary nitrogen atoms of the above-mentioned nitrogen-containing heterocyclic ring, and per se quaternarized, necessarily being accompanied to corresponding anion. The quaternary ammonium group is exemplified by oxazolium, thiazolium, isoxazolium, isothiazolium, pyridinium or quinolinium. The anion is exemplified by hydroxide ion, halogenide ion (e.g. chloride ion, bromide ion or iodide ion), sulfate ion, nitrate ion, carbonate ion, organic carboxylate ion (e.g. oxalate ion or trifluoroacetate ion) or organic sulfonate ion (e.g. p-toluenesulfonate ion), the latter two being sometimes intramolecular ones.

The groups bearing asterisk * at the right shoulder are "optionally substituted groups". For example, alkyl* group means "optionally substituted alkyl group". The number of substituents is not restricted to one, but depending on the substituents, two to several, preferably 2–3, which may be the same or different.

"$C_{6-10}$ aryl* group", "$C_{7-12}$ aralkyl* group", "$C_{6-10}$ aryl*oxy group" and "$C_{7-19}$ aralkyl*oxy group" are preferably "phenyl* group", "benzyl* group", "phenoxy* group" and "benzyl*oxy group", respectively.

In the compound [I] of the present invention, the substituent $R^0$ stands for hydrogen atom, nitrogen-containing heterocyclic group, acyl group or esterified carboxyl group. Among them, those compounds [I] in which $R^0$ is nitrogen-containing heterocyclic group or acyl group have a strong antibacterial action against various bacteria, especially against cephalosporin-resistant bacteria, and they show specific antibacterial action against bacteria belonging to the genus Pseudomonas. On the other hand, compounds [I], wherein $R^0$ is hydrogen atom or esterified carboxyl group, are useful intermediates for producing compounds [I] wherein $R^0$ is nitrogen-containing heterocyclic group or acyl group.

The nitrogen-containing heterocyclic group (hereinafter sometimes denoted as the symbol $R^a$) as the substituent $R^0$ is a "nitrogen-containing heterocyclic group" as mentioned above, which is exemplified by 2-pyrrolyl, 3-pyrrolyl, 3-pyrazolyl, 4-pyrazolyl, 5-pyrazolyl, 2-imidazolyl, 4-imidazolyl, 5-imidazolyl, 1,2,3-triazolyl, 1,2,4-triazolyl, 1H-tetrazolyl, 2H-tetrazolyl, 2-oxazolyl, 4-oxazolyl, 5-oxazolyl, 3-isoxazolyl, 4-isoxazolyl, 5-isoxazolyl, 1,2,3-oxadiazol-4-yl, 1,2,3-oxadiazol-5-yl, 1,2,4-oxadiazol-3-yl, 1,2,4-oxadiazol-5-yl, 1,2,5-oxadiazolyl, 1,3,4-oxadiazolyl, 2-thiazolyl, 4-thiazolyl, 5-thiazolyl, 4-isothiazolyl, 4-isothiazolyl, 5-isothiazolyl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazolyl, 1,3,4-thiadiazolyl, 2-pyrrolidinyl, 3-pyrrolidinyl, 2-pyridyl, 3-pyridyl, 4-pyridyl, 2-pyridyl-N-oxide, 3-pyridyl-N-oxide, 4-pyridyl-N-oxide, 3-pyridazinyl, 4-pyridazinyl, 3-pyridazinyl-N-oxide, 4-pyridazinyl-N-oxide, 2-pyrimidinyl, 4-pyrimidinyl, 5-pyrimidinyl, 2-pyrimidinyl-N-oxide, 4-pyrimidinyl-N-oxide, 5-pyrimidinyl-N-oxide, pyrazinyl, 2-piperidinyl, 3-piperidinyl, 4-piperidinyl, piperazinyl, 3H-indol-2-yl, or 3H-indol-3-yl, especially preferably 2-pyridyl, 3-pyridyl, 4-pyridyl, 2-imidazolyl, 4-imidazolyl or 5-imidazolyl.

The above-mentioned nitrogen-containing heterocyclic groups may have one or more substituents on the ring, in the number of two to several, preferably 2–3, which may be the same or different depending on the kinds of the substituents. These substituents on the nitrogen-containing heterocyclic ring are exemplified by an alkyl group, cycloalkyl group, aryl group, aralkyl group, hydroxyl group, alkoxy group, mercapto group, alkylthio group, amino group, monoalkylamino group, dialkylamino group, halogen atom, nitro group, azido group, cyano group, carboxyl group, alkoxycarbonyl group, alkanoyl grup, alkanoyloxy group, carbamoyl group, monoalkylcarbamoyl group, dialkylcarbamoyl group, carbamoyloxy group, monoalkylcarbamoyloxy group or dialkylcarbamoyloxy group.

As the nitrogen-containing heterocyclic group having one or more substituents, especially preferable are 2-imidazolyl group having as substituents the above-mentioned alkyl group, aryl group or halogen atom, or N-substituted pyridinium-4-yl groups having as substituents the above-mentioned alkyl group or aralkyl group on the nitrogen atom of the 4-pyridyl group to thereby quaternarize the nitrogen atom. The substituted 2-imidazolyl group is exemplified by 1-methyl-2-imidazolyl or 4-chloro-2-imidazolyl, and the N-substituted pyridinium-4-yl group is exemplified by N-methylpyridinium-4-yl, N-ethylpyridinium-4-yl, N-benzylpyridinium-4-yl or N-(p-fluorobenzyl)pyridinium-4-yl, respectively.

The acyl group (hereinafter sometimes denoted as the symbol $R^b$) as the substituent $R^0$ means the acyl group substituted on the amino group at the 6-position of conventional penicillin derivatives or the acyl group substituted on the amino group at the 7-position of conventional cephalosporin derivatives. Such an acyl group is exemplified by alkanoyl group, alkenoyl group, cycloalkyl-carbonyl group, cycloalkenyl-carbonyl group, aryl-carbonyl group or heterocycle-carbonyl group which may be substituted, and more specifically $C_{1-6}$ alkanoyl* group, $C_{3-5}$ alkenoyl* group, $C_{3-10}$ cycloalkyl-carbonyl group, $C_{5-6}$ cycloalkenyl-carbonyl group, $C_{6-10}$ aryl* carbonyl group and heterocycle*carbonyl group, respectively.

The $C_{1-6}$ alkanoyl group is exemplified by formyl, acetyl, propionyl, butyryl, isobutyryl, valeryl, isovaleryl and pivaloyl.

The substituents of "optionally substituted $C_{1-6}$ alkanoyl group" represented by the $C_{1-6}$ alkanoyl* group are exemplified by (1) heterocycle*carbonyl group in case of $C_1$ alkanoyl (i.e. formyl) and (2) "substituent $S^1$" described below in case of $C_{2-6}$ alkanoyl group (i.e. acetyl, propionyl, butyryl, isobutyryl valeryl, isovaleryl, pivaloyl, etc.). The "substituent $S^1$" is exemplified by $C_{3-10}$ cycloalkyl* group $C_{5-6}$ cycloalkenyl* group, $C_{6-10}$ aryl* group, hydroxyl group, $C_{1-6}$ alkoxy group, $C_{3-10}$ cycloalkyloxy group, $C_{6-10}$ aryl*oxy group, $C_{7-19}$ aralkyl*oxy group, mercapto group, $C_{1-6}$ alkyl*thio group, amino $C_{1-6}$ alkylthio group, $C_{2-6}$ alkenyl*thio group, $C_{3-10}$ cycloalkylthio group, $C_{6-10}$ aryl*thio group, $C_{7-19}$ aralkyl*thio group, amino group, mono-$C_{1-6}$ alkylamino group, di-$C_{1-6}$ alkylamino group, $C_{3-10}$ cycloalkylamino group, $C_{6-10}$ aryl*amino group, $C_{7-19}$ aralkyl*amino group, cyclic amino* group, halogen atom, nitro group, azido group, cyano group, carboxyl group, acyl+ group, substituted oxycarbonyl group, $C_{1-6}$ alkylthio-carbonyl group, acyl+oxy group, acyl-+amino group, acyl+aminoalkylthio group, carbamoyl group, mono-$C_{1-6}$ alkylcarbamoyl group, di-$C_{1-6}$ alkylcarbamoyl group, carbamoyloxy group, mono-$C_{1-6}$ alkylcarbamoyloxy group, di-$C_{1-6}$ alkylcarbamoyloxy group, sulfo group, hydroxysulfonyloxy group, $C_{1-6}$ alkylsulfonyl group, $C_{6-10}$ aryl*sulfonyl group, $C_{7-19}$ aralkyl*sulfonyl group, $C_{1-6}$ alkylsulfonyloxy group, $C_{6-10}$ aryl*sulfonyloxy group, $C_{7-19}$ aralkyl*sulfonyloxy group, ureido* group, sulfamoyl* group, heterocyclic* group, heterocycle*oxy group, heterocycle*thio group, heterocycle*aminogroup, heterocycle*carbonyl group, heterocycle* carboxamido group or quaternary ammonium* group. The number of these substituents is not restricted to one, and in case there are two or more substituents, these substituents may be the same or different. To state further, two of these substituents may be combined to form C=C double bond or C=N double bond as described below.

The substituents (hereinafter referred to as "substituent $S^2$") of "optionally substituted $C_{3-5}$ alkenoyl group" are exemplified by $C_{3-10}$ cycloalkyl group, $C_{6-10}$ aryl* group, $C_{1-6}$ alkoxy group, $C_{6-10}$ aryl*oxy group, $C_{7-19}$ aralkyl*oxy group, halogen atom, cyano group, carboxyl group, acyl+ group, substituted oxycarbonyl group, acyl+oxy group, heterocyclic* group or quaternary ammonium* group.

The substituents of "optionally substituted $C_{6-10}$ aryl-carbonyl group" represented by $C_{6-10}$ aryl* carbonyl group as well as "optionally substituted heterocyclic group" represented by heterocycle* carbonyl group (hereinafter collectively referred to as "substituent $S^3$" are exemplified by $C_{1-6}$ alkyl group, $C_{2-6}$ alkenyl group, $C_{6-10}$ aryl group, $C_{7-12}$ aralkyl group, di-$C_{6-10}$ arylmethyl group, tri-$C_{6-10}$ aryl-methyl group, hydroxyl group, $C_{1-6}$ alkoxy group, $C_{6-10}$ aryloxy group, $C_{7-19}$ aralkyloxy group, mercapto group, $C_{1-6}$ alkylthio group, $C_{6-10}$ arylthio group, $C_{7-19}$ aralkylthio group, amino group, mono-$C_{1-6}$ alkylamino group, di-$C_{1-6}$ alkylamino group, hydroxy $C_{1-6}$ alkyl group, mercapto $C_{1-6}$ alkyl group, halogeno-$C_{1-6}$ alkyl group, carboxy $C_{1-6}$ alkyl group, halogen atom, nitro group, azido group, cyano group, carboxyl group, substituted oxycarbonyl group, acyl+ group, acyl+oxy group, acyl+amino group, carbamoyl group, thiocarbamoyl group, $C_{1-6}$ alkylsulfonyl group, $C_{6-10}$ arylsulfonyl group or $C_{7-19}$ aralkylsulfonyl group.

Among the above-mentioned substituents ($S^1$, $S^2$ and $S^3$) of $C_{1-6}$ alkanoyl group, $C_{3-5}$ alkenoyl group, $C_{6-10}$ aryl-carbonyl group and heterocycle*carbonyl group, those which are not described below are of the same meaning as afore-mentioned.

The substituents of the $C_{6-10}$ aryl group of $C_{6-10}$ aryl* group, phenyl* group, $C_{6-10}$ aryl*oxy group, phenoxy* group, $C_{6-10}$ aryl*thio group, $C_{6-10}$ aryl*amino group, $C_{6-10}$ aryl*sulfonyl group and $C_{6-10}$ aryl*sulfonyloxy group are also of the class of the above-mentioned substituents $S^3$.

The substituents of the aromatic ring of the $C_{7-12}$ or $C_{7-19}$ aralkyl groups of $C_{7-12}$ aralkyl* group, benzyl* group, $C_{7-19}$ aralkyl*oxy group, benzyl*oxy group, $C_{7-19}$ aralkyl*thio group, $C_{7-19}$ aralkyl*amino group, $C_{7-19}$ aralkyl*sulfonyl group and $C_{7-19}$ aralkyl*sulfonyloxy group are also of the class of the above-mentioned substituents $S^3$.

The substituents of the heterocyclic ring of heterocyclic* group, heterocycle*oxy group, heterocycle*thio group, heterocycle*amino group, heterocycle*acetyl group and heterocycle*carboxaido group are also of the class of the above-mentioned substituents $S^3$.

The substituents on the nitrogen-containing heterocyclic ring of quaternary ammonium* group are also of the class of the above-mentioned substituents $S^3$.

The substituents of the $C_{1-6}$ alkyl group of "optionally substituted $C_{1-6}$ alkyl group" representable by $C_{1-6}$ alkyl* group are also of the class of the above-mentioned substituents $S^1$.

The substituents of the "optionally substituted $C_{3-10}$ cycloalkyl group" and "optionally substituted $C_{5-6}$ cycloalkenyl group" representable by $C_{3-10}$ cycloalkyl group and $C_{5-6}$cycloalkenyl* group are also of the class of by the above-mentioned substituents $S^3$.

The substituents of the $C_{1-6}$ alkylthio groups of "optionally substituted $C_{1-6}$ alkylthio group" representable by $C_{1-6}$ alkyl*thio group (these substituents are hereinafter referred to as "substituent $S^4$") are exemplified by hydroxyl group, $C_{1-6}$ alkoxy group, $C_{3-10}$ cycloalkyloxy group, $C_{6-10}$ aryl*oxy group, $C_{7-19}$ aralkyl*oxy group, mercapto group, $C_{1-6}$ alkylthio group, $C_{3-10}$ cycloalkylthio group, $C_{6-10}$ aryl*thio group, $C_{7-19}$ aralkyl*thio group, amino group, mono-$C_{1-6}$ alkylamino group, di-$C_{1-6}$ alkylamino group, cyclic amino* group, halogen atom, cyano group, carboxyl group, carbamoyl group, acyl+oxy group, sulfo group, or quaternary ammonium*group.

The substituents of the $C_{2-6}$ alkenylthio group of "optionally substituted $C_{2-6}$ alkenylthio group" representable by a $C_{2-6}$ alkenyl*thio group (these substituents are hereinafter referred to as "substituent $S^5$") are exemplified by halogen atom, cyano group, carboxyl group, carbamoyl group, mono-$C_{1-6}$ alkylcarbamoyl group, di-$C_{1-6}$ alkylcarbamoyl group or thiocarbamoyl group.

"Acyl+ group" means the above-mentioned $C_{1-6}$ alkanoyl group, $C_{6-10}$ aryl*carbonyl group, $C_{7-19}$ aralkyl*carbonyl group, heterocycle*carbonyl group or heterocycle*acetyl group. Representative acyl+ groups are exemplified by formyl, acetyl, propionyl, n-butyryl, isobutyryl, valeryl, pivaloyl, n-hexanoyl, chloroacetyl, dichloroacetyl, trichloroacetyl, 3-oxobutyryl, 4-chloro-3-oxobutyryl, 3-carboxypropionyl, 4-carboxybutyryl, 3-ethoxycarbamoylpropionyl, benzoyl, naphthoyl, p-methylbenzoyl, p-hydroxybenzoyl, p-methoxybenzoyl, p-chlorobenzoyl, p-nitrobenzoyl, o-carboxybenzoyl, o-(ethoxycarbonylcarbamoyl)benzoyl, o-(ethoxycarbonylsulfamoyl)benzoyl, phenylacetyl, p-methylphenylacetyl, p-hydroxyphenylacetyl, p-methoxyphenylacetyl, 2,2-diphenylacetyl, 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl or 5-amino-3-thiadiazolylacetyl.

The acyl+ group of "acyl+oxy group and "acyl+amino group" means the above-mentioned acyl+ group. Therefore, "acyl+oxy group" is exemplified by formyloxy, acetoxy, propionyloxy, butyryloxy, varleryloxy, pivaloyloxy, chloroacetoxy, dichloroacetoxy, trichloroacetoxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoyl)benzoyloxy, o-(ethoxycarbonylsulfamoyl)benzoyloxy, phenylacetyloxy, p-methylphenylacetyloxy, p-methoxyphenylacetyloxy, p-chlorophenylacetyloxy, 2,2-diphenylacetyloxy, thienylcarbonyloxy, furylcarbonyloxy, thiazolylacetyloxy, thienylacetyloxy or furylacetyloxy, and "acyl+amino group" is exemplified by acetamido ($CH_3CONH-$), benzamido ($C_6H_5CONH-$), phenylacetamido ($C_6H_5CH_2CONH-$) or 2-thienylacetamido

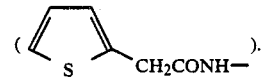

The acyl+amino group and alkylthio group of "acyl+aminoalkylthio group" mean respectively the above-mentioned acyl+amino group and $C_{1-6}$ alkylthio group, hence such "acyl+amino $C_{1-6}$ alkylthio group" are exemplified by acetamidomethylthio or 2-acetamidoethylthio.

"Arylacyl+ group" is preferably "$C_{6-10}$ aryl-acyl+ group", which is exemplified by benzoyl, phthaloyl, naphthoyl or phenylacetyl.

"Arylacyl+oxy group" is preferably "$C_{6-10}$ arylacyl+oxy group", as exemplified by benzoyloxy, naphthoyloxy or phenylacetyloxy.

The substituents of the ureido group of "optionally substituted ureido group" represented by "ureido* group" are exemplified by $C_{1-6}$ alkyl group, $C_{6-10}$ aryl* group, $C_{7-19}$ aralkyl* group, acyl+ group, carbamoyl group, sulfo group (which may form a salt with e.g. sodium or potassium), sulfamoyl group or amidino group.

The substituents of the sulfamoyl group of "optionally substituted sulfamoyl group" represented by "sulfamoyl* group" are exemplified by $C_{1-6}$ alkyl group or amidino group.

The substituents of "optionally substituted carbamoyl group" representable by "carbamoyl* group" and "carbamoyl*oxy group" are exemplified by $C_{1-6}$ alkyl group, $C_{6-10}$ aryl* group, $C_{7-12}$ aralkyl* group or acyl+ group, including the case where the nitrogen atom of carbamoyl group is the ring-forming nitrogen atom of the nitrogen-containing heterocyclic ring.

The substituents of "optionally substituted thiocarbamoyl group" represented by "thiocarbamoyl* group" are exemplified by $C_{1-6}$ alkyl group, $C_{6-10}$ aryl* group, $C_{7-12}$ aralkyl* group or acyl+ group, including the case where the nitrogen atom of thiocarbamoyl group is the ring-forming nitrogen atom of the nitrogen-containing heterocyclic ring.

The substituents of the cyclic amino group of "optionally substituted cyclic amino group" represented by cyclic amino* group" (these substituents are hereinafter referred to as "substituent $S^6$") are exemplified by $C_{1-6}$ alkyl group, $C_{2-6}$ alkenyl group, $C_{3-10}$ cycloalkyl group, $C_{6-10}$ aryl* group, $C_{7-12}$ aralkyl* group, di-$C_{6-10}$ aryl-methyl group, tri-$C_{6-10}$ aryl-methyl group, hydroxyl group, $C_{1-6}$ alkoxy group, $C_{6-10}$ aryl*oxy group, $C_{7-19}$ aralkyl*oxy group, mercapto group, $C_{1-6}$ alkylthio group, $C_{6-10}$ aryl*thio group, $C_{7-19}$ aralkyl*thio groups, amino group, mono-$C_{1-6}$ alkylamino group, di-$C_{1-6}$ alkylamino group, $C_{6-10}$ aryl*amino group, $C_{7-19}$ aralkyl*amino group, halogen atom, nitro group, azido group, oxo group, thioxo group, cyano group, carboxyl group, acyl+ group, substituted oxycarbonyl group, acyl+oxy group, acyl+amino group, carbamoyl group, carbamoyloxy group, thiocarbamoyl group or sulfo group.

The formyl group substituted with the heterocycle*-carbonyl group mentioned above as one of the $C_{1-6}$ alkanoyl* groups is acyl group having a formula of heterocycle*—CO—CO—, and the heterocyclic* group is also mentioned here those exemplified above, but preferably, optionally substituted oxazolyl group, thiazolyl group, oxadiazolyl group or thiadiazolyl group, for example. These heterocycle*—CO—CO— groups are exemplified by 2-(2-, 4- or 5-oxazolyl)-2-oxoacetyl, 2-(2-, 4- or 5-thiazolyl)-2-oxoacetyl, 2-(2-amino-4-thiazolyl)-2-oxoacetyl, 2-(1,2,4-oxadiazol-3- or 5-yl)-2-oxoacetyl, 2-(1,2,4-thiadiazol-3- or 5-yl)-2-oxoacetyl or 2-(5-amino-1,2,4-thiadiazol-3-yl)-2-oxoacetyl.

The $C_{2-6}$ alkanoyl* group is most preferably a substituted acetyl group. The number of substituents of the substituted acetyl group is 1–3, and, as these substituents, "substituent $S^1$" mentioned above as substituents of $C_{1-6}$ alkanoyl groups are also mentioned here. When the number of substituents is 2–3, these substituents may be the same or different, and two of them may be combined to form a double bond. Mono- and di-substituted acetyl groups can be shown by $R^{15}CH_2CO-$ and

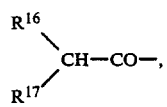

respectively. On the other hand, preferable tri-substituted acetyl groups are those in which two of the substituents are combined to form C=C double bond or C=N double bond, which can be shown by

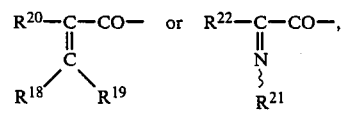

respectively, wherein $R^{15}$—$R^{17}$, $R^{20}$ and $R^{22}$ mean the above-mentioned substituent ($S^1$), and $R^{18}$, $R^{19}$ and $R^{21}$ will be described hereafter. The detailed description about acetyl groups having these substituents ($R^{15}$—$R^{22}$) is given as follows.

(i) $R^{15}CH_2CO-$

The symbol $R^{15}$ means the above-mentioned substituents ($S^1$) of a $C_{1-6}$ alkyl group, and use is often made of particularly a $C_{5-6}$ cycloalkenyl group, $C_{6-10}$ aryl* group, $C_{6-10}$ aryl*oxy group, $C_{1-6}$ alkyl*thio group, $C_{2-6}$ alkenyl*thio group, $C_{6-10}$ aryl*thio group, amino group, cyclic amino group, cyano group, acyl+ group, acyl+oxy group, heterocyclic* group, heterocycle*thio group or quaternary ammonium* group, for example. Acyl groups of $R^{15}CH_2CO-$ are exemplified by 1,4-cyclohexadienylacetyl, phenylacetyl, p-tolylacetyl, p-hydroxyphenylacetyl, p-methoxyphenylacetyl, p-chlorophenylacetyl, o-aminomethylphenylacetyl, phenoxyacetyl, p-hydroxyphenoxyacetyl, p-chlorophenoxyacetyl, cyanomethylthioacetyl, difluoromethylthioacetyl, trifluoromethylthioacetyl, (2-carboxyethyl)thioacetyl, (2-amino-2-carboxyethyl)thioacetyl, (2-chlorovinyl)thioacetyl, (2-carboxyvinyl)thioacetyl, (2-fluoro-2-carbamoylvinyl)thioacetyl, (1,2-dichlorovinyl)thioacetyl, (2-chloro-2-carboxyvinyl)thioacetyl, phenylthioacetyl, p-hydroxyphenylthioacetyl, glycyl, 1H-tetrazolyl-1-ylacetyl, 3,5-dichloro-4-oxo-1,4-dihydropyridin-1-ylacetyl, cyanoacetyl, acetoacetyl, benzoylacetyl, furylcarbonylacetyl, thienylcarbonylacetyl, (1H-tetrazolyl)acetyl, 1-methyl-1H-tetrazolylacetyl, (2-furyl)acetyl, (2-thienyl)acetyl, (3-thienyl)acetyl, (4-oxozolyl)acetyl, (4-thiazolyl)acetyl, (2-amino-4-thiazolyl)acetyl, (1,2,4-thiadiazol-3-yl)acetyl, (5-amino-1,2,4-thiadiazol-3-yl)acetyl, (2-pyridyl)acetyl, (4-pyridyl)acetyl, (2-imidazolyl)thioacetyl, (2-pyridyl)thioacetyl, (4-pyridyl)thioacetyl, (2-thienyl)thioacetyl, hydroxypyridylthioacetyl, (5-isothiazolyl)thioacetyl, (3-methylthio-5-isothiazolyl)thioacetyl, (4-cyano-5-isothiazolyl)thioacetyl, (4-cyano-2-methyl-3-oxo-2,3-dihydroisothiazol-5-yl)thioacetyl, pyridiniumacetyl or quinoliniumacetyl.

(ii) 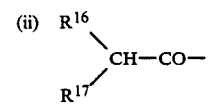

The symbol $R^{16}$ means the above-mentioned substituents ($S^1$), and use is often made of particularly a $C_{5-6}$ cycloalkenyl group, $C_{6-10}$ aryl* group, $C_{6-10}$ aryl*oxy group, $C_{1-6}$ alkyl*thio group, $C_{2-6}$ alkenyl*thio group, $C_{6-10}$ aryl*thio group, cyclic amino group, cyano group, heterocyclic* group, heterocycle*thio group, heterocycle*carboxamido group or quaternary ammonium* group for example. The symbol $R^{17}$ means the above-mentioned substituents, especially preferable being hydroxyl group, mercapto group, amino group, amino group substituted with amino acid residue, hydrazino group, azido group, ureido* group, acyl+oxy group, acyl+amino group, carboxyl group, substituted oxycarbonyl group, sulfo group, sulfamoyl group, carbamoyl group or heterocycle*carboxamido group, for example. Among them, those wherein the substituent $R^{17}$ is amino (i.e. $R^{16}CH-CO-$ with $NH_2$)

are sometimes especially classified as "amino acid residue". The acyl group

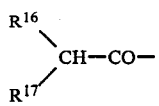

is exemplified by 2-amino-2-(1,4-cyclohexadienyl)acetyl, mandelyl, α-azidophenylacetyl, α-carboxyphenylacetyl, α-(phenoxycarbonyl)phenylacetyl, α-(o-hydroxyphenyl)oxycarbonylphenylacetyl, α-(p-tolyloxycarbonyl)phenylacetyl, α-sulfophenylacetyl, α-sulfo-p-hydroxyphenylacetyl, α-ureidophenylacetyl, α-(Nγ-sulfoureido)phenylacetyl, α-carboxy-p-hydroxyphenylacetyl, α-(formyloxy)phenylacetyl, α-(2-amino-3-carboxypropionamido)phenylacetyl, α-(3-amino-3-carboxypropionamido)phenylacetyl, α-(3,4-dihydroxybenzamido)phenylacetyl, α-(5-carboxy-4-imidazolylcarboxamido)phenylacetyl, α-(1,3-dimethyl-4-pyrazolylcarboxamido)phenylacetyl, 5-phenyl-3-isoxazolylcarboxamido)phenylacetyl, α-[1-(p-methoxyphenyl)-4-chloro-1,2,3-triazol-5-ylcarboxamido]-phenylacetyl, α-(4-oxo-1,4-dihydropyridin-3-ylcarboxamido)phenylacetyl, α-[2-oxo-5-(3,4-dihydroxyphenyl)-1,2-dihydropyridin-3-ylcarboxamido]phenylacetyl, α-(4-oxo-4H-1-thiopyran-3-ylcarboxamido)phenylacetyl, α-(4-hydroxy-1,5-naphthylidin-3-ylcarboxamido)-phenylacetyl, α-(4-ethyl-2,3-dioxopiperazinocarboxamido)phenylacetyl, α-(4-ethyl-2,3-dioxopiperazinocarboxamido)-p-hydroxyphenylacetyl, α-(4-ethyl-2,3-dioxopiperazinocarboxamido)-p-benzyloxyphenylacetyl, α-(4-ethyl-2,3-dioxopiperazinocarboxamido)-p-sulfophenylacetyl, α-(4-ethyl-2,3-dioxopiperazinocarboxamido)-p-methoxyphenylacetyl, α-(2-oxoimidazolidinocarboxamido)phenylacetyl, α-(2-oxo-3-methanesulfonylimidazolidinocarboxamido)phenylacetyl, α-(6,7-dihydroxy-4-oxo-4H-benzopyran-3-ylcarboxamido)phenylcetyl, α-(6,7-dihydroxy-2-oxo-2H-benzopyran-3-ylcarboxamido)phenylacetyl, α-hydroxy-2-thienylacetyl, α-hydroxy-3-thienylacetyl, α-carboxy-3-thienylacetyl, α-amino-α-(2-aminothiazol-4-yl)acetyl, α-formamido-60-(2-aminothiazol-4-yl)acetyl, α-acetamido-α-(2-aminothiazol-4-yl)acetyl, α-formamido-α-(2-amino-5-chlorothiazol-4-yl)acetyl, α-acetamido-α-(2-amino-5-chlorothiazol-4-yl)acetyl, α-formamido-α-(5-amino-1,2,4-thiadiazol-3-yl)acetyl, α-acetamido-α-(5-amino-1,2,4-thiadiazol-3-yl)acetyl, α-hydrazino-α-(2-aminothiazol-4-yl)acetyl, α-hydroxy-α-(2-aminothiazol-4-yl)acetyl, α-ureido-α-(2-aminothiazol-4-yl)acetyl, α-[Nγ-(m-hydroxyphenyl)ureido]-phenylacetyl, α-[Nγ-(2-methyl-6-hydroxypyrimidin-5-yl)ureido]phenylacetyl, α-[Nγ-(3,4-diacetoxybenzoyl)ureido]phenylacetyl, α-[Nγ-(3,4-dihydroxycinnamoyl)ureido]phenylacetyl, α-[Nγ-(3,4-diacetoxybenzamidoacetyl)ureido]phenylacetyl, α-[Nγ-(2-furylcarbonyl)ureido]phenylacetyl, α-[Nγ-(6,7-dihydro-4-oxo-4H-benzopyran-3-ylcarbonyl)ureido]phenylacetyl, α-(2-chlorovinylthio)phenylacetyl, α-carbamoyl-α-(2-chlorovinylthio)acetyl, α-(4-ethyl-2,3-dioxopiperazinocarboxamido)-α-(2-chlorovinylthio)acetyl, α,α-bis(4-ethyl-2,3-dioxo-1-piperazinocarboxamido)acetyl, α-(2-amino-4-thiazolyl)-α-(4-ethyl-2,3-dioxo-1-piperazinocarboxamido)acetyl, α-(4-hydroxy-6-methylnicotinamide)-α-phenylacetyl, α-(4-hydroxy-6-methylnicotinamide)-α-(4-hydroxyphenyl)acetyl, α-[5,8-dihydro-2-(4-formyl-1-piperazinyl)-5-oxopyrido[2,3-d]pyrimidine-6-carboxamido]-α-phenylacetyl, α-(3,5-dioxo-1,2,4-triazine-6-carboxamido)-α-(4-hydroxyphenyl)acetyl, α-(3-furfurylideneamino-2-oxoimidazolidine-1-carboxamido)-α-phenylacetyl, α-(coumarine-3-carboxamido)-α-phenylacetyl, α-(4-hydroxy-7-methyl-1,8-naphthylidine-3-carboxamido)-α-phenylacetyl, α-(4-hydroxy-7-trifluoromethylquinoline-3-carboxamido)-α-phenylacetyl, N-[2-(2-amino-4-thiazolyl)acetyl]-D-phenylglycyl, α-(6-bromo-1-ethyl-1,4-dihydro-4-oxothieno[2,3-b]pyridine-3-carboxamido)-α-phenylacetyl, α-(4-ethyl-2,3-dioxo-1-piperazinocarboxamido)-α-thienylacetyl, α-(4-n-pentyl-2,3-dioxo-1-piperazinocarboxamido-α-thienylacetyl, α-(4-n-octyl-2,3-dioxo-1-piperazinocarboxamido)-α-thienylacetyl, α-(4-cyclohexyl-2,3-dioxo-1-piperazinocarboxamido)-α-thienylacetyl, α-[4-(2-phenylethyl)-2,3-dioxo-1-piperazinocarboxamido]-α-thienylacetyl or α-(3-fufurylideneamino-2-oxoimidazolidine-1-carboxamido)-α-(4-hydroxyphenyl)acetyl. And the amino acid residue

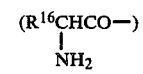

is also here exemplified by alanyl, valyl, leucyl, isoleucyl, seryl, threonyl, cysteinyl, cystinyl, methionyl, aspartyl, glutamyl, lysyl, arginyl, phenylglycyl, phenylalanyl, tyrosyl, histidyl, tryptophanyl or prolyl. The amino group of these amino acid residues may be protected with an amino-protecting group as mentioned below. The amino-protecting amino acid residue is exemplified by N-benzyloxycarbonylalanyl or N-benzyloxycarboxamidophenylglycyl. The amino group of the amino acid residue may be further substituted with another amino acid residue. Such acyl group is the residue of dipeptide, as exemplified by phenylglycylalanyl, benzyl Nα-benzyloxycarbonyl-γ-glutamylalanyl, alanyl-phenylglycyl, γ-aspartyl-phenylglycyl or γ-glytamyl-alanyl. The amino group of the amino acid residue may be substituted with cyclic carbamoyl group. Such acyl group is exemplified by N-(4-ethyl-2,3-dioxo-1-piperazinocarbonyl)alanyl, N-(4-ethyl-2,3-dithioxo-1-piperazinocarbonyl)phenylglycyl or N-(4-ethyl-2,3-dioxo-1-piperazinocarbonyl)threonyl. As one of the acyl group

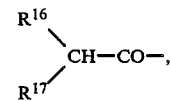

an acyl group representable by

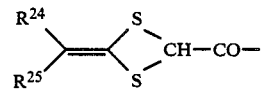

[wherein $R^{24}$ and $R^{25}$ are the same or different and stand for hydrogen atom, halogen atom (fluorine, chlorine, bromine and iodine), hydroxymethyl group, difluoromethyl group, trifluoromethyl group, formyl group, cyano group, azido group, carboxyl group, carbamoyl group, $C_{1-6}$ alkylthio group or $C_{6-10}$ aryl*thio group] is used as well, which is exemplified by

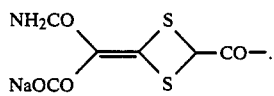

(iii) 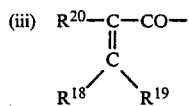

The symbol $R^{20}$ means above-mentioned substituents ($S^1$), and use is often made of particularly $C_{6-10}$ aryl* group, $C_{6-10}$ aryl*oxy group, $C_{6-10}$ aryl*thio group, heterocyclic* group or heterocycle*thio group, for example. The symbol $R^{18}$ stands for hydrogen atom or halogen atom (fluorine, chlorine, bromine and iodine), preferably chlorine. The symbol $R^{19}$ stands for $C_{1-6}$ alkyl group, $C_{6-10}$ aryl* group, $C_{1-6}$ alkylthio group, halogen atom, cyano group, amino group, $C_{1-6}$ alkylsulfonyl group, $C_{6-10}$ aryl*sulfonyl group, carbamoyl group, $C_{1-6}$ alkoxyimidoyl group or heterocyclic* group. The $C_{1-6}$ alkoxy group of the $C_{1-6}$ alkoxyimidoyl group is preferably the above-mentioned $C_{1-6}$ alkoxy group, hence the $C_{1-6}$ alkoxyimidoyl group being exemplified by methoxyimidoyl

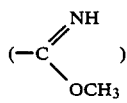

or ethoxyimidoyl. Other groups than the above are named also here by those mentioned in the foregoing as they are. Hence, the acyl group

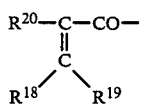

is exemplified by 2-(2-amino-4-thiazolyl)-3-chloroacryloyl, 2-(2-amino-4-thiazolyl)crotonoyl, 2-(2-amino-4-thiazolyl)cinnamoyl, 2-(2-amino-4-thiazolyl)-3-methanesulfonylacryloyl, 2-(2-amino-4-thiazolyl)-3-benzenesulfonylacryloyl, 2-(5-amino-1,2,4-thiadiazol-3-yl)-2-pentenoyl, 2-(5-amino-1,2,4-thiadiazol-3-yl)-3-chloroacryloyl, 2-(5-amino-1,2,4-thiadiazol-3-yl)crotonoyl, 2-(2-amino-5-chloro-4-thiazolyl)-3-chloroacryloyl or 2-(2-amino-5-chloro-4-thiazolyl)crotonoyl.

(iv) 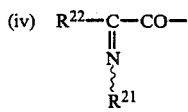

The symbol $R^{22}$ means the afore-mentioned substituents ($S^1$), and use is often made of especially $C_{3-10}$ cycloalkyl* group, $C_{5-6}$ cycloalkenyl* group, $C_{6-10}$ aryl* group, $C_{1-6}$ alkoxy group, $C_{6-10}$ aryl*oxy group, $C_{1-6}$ alkyl*thio group, amino $C_{1-6}$ alkylthio group, $C_{6-10}$ aryl*thio group, $C_{7-19}$ aralkyl*thio group, cyano group, acyl+ group, carbamoyl group or heterocyclic* group. Among them, especially preferable are $C_{6-10}$ aryl* group and heterocyclic* group. Substitutents of these $C_{6-10}$ aryl group and heterocyclic groups are preferably $C_{1-6}$ alkyl group, hydroxyl group, amino group and halogen atom (fluorine, chlorine, bromine and iodine). Hence, the groups preferably included in the substituent $R^{22}$ are exemplified by phenyl, p-hydroxyphenyl, 2-furyl, 2-thienyl, 4-oxazolyl, 2-amino-4-oxazolyl, 2-amino-5-chloro-4-oxazolyl, 4-thiazolyl, 2-amino-4-thiazolyl, 2-amino-5-chloro-4-thiazolyl, 2-amino-5-bromo-4-thiazolyl, 2-amino-5-fluoro-4-thiazolyl, 2-amino-4-thiazolyl-3-oxide, 2-imino-3-hydroxythiazolin-4-yl, 3-isoxazolyl, 5-amino-3-isoxazolyl, 3-isothiazolyl, 5-amino-3-isothiazolyl, 1,2,4-oxadiazol-3-yl, 5-amino-1,2,4-oxadiazol-3-yl, 1,2,4-thiadiazol-3-yl, 1,2,4-thiadiazol-3-yl, 5-amino-1,2,4-thiadiazol-3-yl, 1,3,4-oxadiazolyl, 2-amino-1,3,4-oxadiazol-5-yl, 1,3,4-thiadiazolyl, 2-amino-1,3,4-thiadiazol-5-yl, 1-($C_{1-6}$ alkyl-5-amino-1,2,4-triazol-3-yl, 4-($C_{1-6}$ alkyl)-5-amino-1,2,4-triazol-3-yl, 1-($C_{1-6}$ alkyl)-2-amino-4-imidazolyl, 2-amino-6-pyridyl, 4-amino-2-pyrimidyl, 2-amino-5-pyrimidyl, 3-pyrazolyl or 4-pyrazolyl. The symbol $R^{21}$ stands for $OR^{23}$ group (wherein $R^{23}$ stands for hydrogen atom or optionally substituted hydrocarbon residue). Here, groups representable by

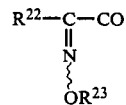

are syn-isomers representable by

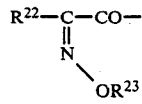

or anti-isomers representable by

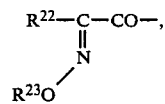

or a mixture thereof. Among them are preferable those wherein the substituent $R^{22}$ is heterocyclic* group, which are syn-isomers. These acyl groups are shown by the formula;

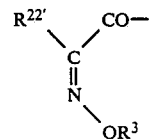

[wherein $R^{22'}$ stands for heterocyclic* group and $R^3$ stands for hydrogen atom or optionally substituted hydrocarbon residue]. Among them, most preferable ones are those in which the heterocyclic* group $R^{22'}$ is a substituted thiazolyl group or thiadiazolyl group, namely those representable by the formula;

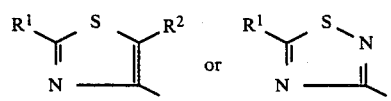

[wherein R¹ stands for optionally protected amino group and R² stands for hydrogen atom, halogen atom or nitro group]. Hence, most preferable R$^b$ group is representable by the formula;

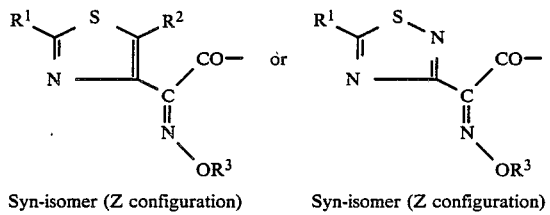

Syn-isomer (Z configuration)     Syn-isomer (Z configuration)

Accordingly, preferable ones of compound [I] having the acyl group R$^b$ as the substituent R$_o$ are those of the following structure;

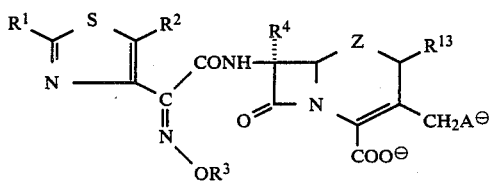 [VII]

or

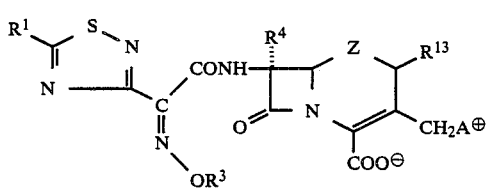 [VIII]

[each symbol is as defined above].

Detailed description about the substituents R¹, R² and R³ is as follows.

R¹ stands for an optionally protected amino group. In the field of synthesis of β-lactam and peptide, protecting groups of amino group have been extensively studied, and the method of protection has already been established. In the present invention as well, any of those known amino-protecting groups may suitably be employed. As such amino-protecting groups, there may be mentioned for example $C_{1-6}$ alkanoyl* group, $C_{3-5}$ alkenoyl* group, $C_{6-10}$ aryl*carbonyl group, phthaloyl group, heterocycle*carbonyl group, $C_{1-6}$ alkyl*sulfonyl group, camphorsulfonyl group, $C_{6-10}$ aryl*sulfonyl group, substituted oxycarbonyl group, carbamoyl* group, thiocarbamoyl* group, $C_{6-10}$ aryl*methyl group, di-$C_{6-10}$ aryl*methyl group, tri-$C_{6-10}$ aryl*methyl group, $C_{6-10}$ aryl*methylene group, $C_{6-10}$ aryl*thio group, substituted silyl group or 2-$C_{1-10}$ alkoxy-carbonyl-1-methyl-1-ethenyl group.

As "$C_{1-6}$ alkanoyl* group", there may concretely be mentioned here formyl, acetyl, propionyl, butyryl, valeryl, pivaloyl, succinyl, glutaryl, monochloroacetyl, dichloroacetyl, trichloroacetyl, monobromoacetyl, monofluoroacetyl, difluoroacetyl, trifluoroacetyl, monoiodoacetyl, 3-oxobutyryl, 4-chloro-3-oxobutyryl, phenylacetyl, p-chlorophenylacetyl, phenoxyacetyl or p-chlorophenoxyacetyl. As "$C_{3-5}$ alkenoyl* group", there may concretely be mentioned here acryloyl, crotonoyl, maleoyl, cinnamoyl, p-chlorocinnamoyl or β-phenylcinnamoyl.

As "$C_{6-10}$ aryl*carbonyl group", there may be mentioned, for example, benzoyl, naphthoyl, p-toluoyl, p-tert-butylbenzoyl, p-hydroxybenzoyl, p-methoxybenzoyl, p-tert-butoxybenzoyl, p-chlorobenzoyl or p-nitrobenzoyl.

As the heterocycle*carbonyl group, there may be mentioned those as described hereinafter.

As "$C_{1-6}$ alkyl*sulfonyl group", there may be mentioned, for example, methanesulfonyl or ethanesulfonyl.

As "$C_{6-10}$ aryl*sulfonyl group", there may be mentioned here benzenesulfonyl, naphthalenesulfonyl, p-toluenesulfonyl, p-tert-butylbenzenesulfonyl, p-methoxybenzenesulfonyl, p-chlorobenzenesulfonyl or p-nitrobenzenesulfonyl, for example.

"Substituted oxycarbonyl group" means not only the the above-mentioned one, i.e. $C_{1-10}$ alkoxy-carbonyl group, $C_{6-10}$ aryloxy-carbonyl group or $C_{7-19}$ aralkyloxycarbonyl group, but contains here one having substituent, and therefore there may be mentioned here methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl or cyclohexyloxycarbonyl, for example.

"Carbamoyl* group" is exemplified here by carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl or N-(p-methoxyphenyl)carbamoyl.

"Carbamoyl*oxy group" is exemplified here by carbamoyloxy, N-methylcarbamoyloxy, N,N-dimethylcarbamoyloxy, N-ethylcarbamoyloxy or N-phenylcarbamoyloxy.

Thiocarbamoyl* group" is exemplified here by thiocarbamoyl, N-methylthiocarbamoyl or N-phenylthiocarbamoyl, for example. "$C_{6-10}$ aryl*methyl group" is exemplified by benzyl, naphthylmethyl, p-methylbenzyl, p-methoxybenzyl, p-chlorobenzyl or p-nitrobenzyl.

"Di-$C_{6-10}$ aryl*methyl group" is exemplified by benzhydryl or di-(p-tolyl)methyl.

"Tri-$C_{6-10}$ aryl*methyl group" is exemplified by trityl or tri-(p-tolyl)methyl.

"$C_{6-10}$ aryl*methylene group" is exemplified by benzylidene, p-methylbenzylidene or p-chlorobenzylidene.

"$C_{6-10}$ aryl*thio group" is exemplified by o-nitrophenylthio.

"Substituted silyl group" means a silyl group, together with the amino group to be protected, representable by the general formula; $R^6R^7R^8SiNH$, $(R^6R^7R^8Si)_2N$ or

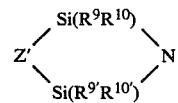

[wherein $R^6$, $R^7$, $R^8$, $R^9$, $R^{10}$, $R^{9'}$ and $R^{10'}$ are the same or different and stand for $C_{1-6}$ alkyl group or $C_{6-10}$ aryl* group, and Z' stands for $C_{1-3}$ alkylene group e.g. methylene, ethylene or propylene], which is exemplified by trimethylsilyl, tert-butyldimethylsilyl or —Si(CH$_3$)$_2$CH$_2$CH$_2$Si(CH$_3$)$_2$—.

The C$_{1-10}$ alkoxy-carbonyl group of "2-C$_{1-10}$ alkoxycarbonyl-1-methyl-1-ethenyl group" is preferably one of those as mentioned in the foregoing. Hence, 2-C$_{1-10}$ alkoxycarbonyl-1-methyl-1-ethenyl group is exemplified by 2-methoxycarbonyl-1-methyl-1-ethenyl, 2-ethoxycarbonyl-1-methyl-1-ethenyl, 2-tert-butoxycarbonyl-1-methyl-1-ethenyl, 2-cyclohexyloxycarbonyl-1-methyl-1-ethenyl or 2-norbornyloxycarbonyl-1-methyl-1-ethenyl.

The symbol R$^2$ stands for hydrogen atom, halogen atom or nitro group. As the halogen atom are mentioned here fluorine, chlorine, bromine, etc., preferably chlorine.

The symbol R$^3$ stands for hydrogen atom or a substituted hydrocarbon residue. The hydrocarbon residue may be exemplified by C$_{1-16}$ alkyl group, C$_{2-6}$ alkenyl group, C$_{2-6}$ alkynyl group, C$_{3-10}$ cycloalkyl group or C$_{5-6}$ cycloalkenyl group, especially preferably, C$_{1-3}$ alkyl group or a substituted C$_{1-3}$ alkyl group. The C$_{1-6}$ alkyl group is, also here, preferably one of those described in the foregoing and may be exemplified by methyl, ethyl, n-propyl, isopropyl, n-butyl, isobutyl, sec-butyl, tert-butyl, n-pentyl or n-hexyl, especially preferably, methyl, ethyl and n-propyl. The C$_{2-6}$ alkenyl group is also here, preferably one of those described in the foregoing and may be exemplified by vinyl, allyl, isopropenyl, methallyl, 1,1-dimethylallyl, 2-butenyl or 3-butenyl. The C$_{2-6}$ alkynyl group may be exemplified by ethylnyl, 1-propynyl, 2-propynyl or propargyl. The C$_{3-10}$ cycloalkyl group is, also here, preferably the above-mentioned C$_{3-8}$ cycloalkyl group and may be exemplified by cyclopropyl, cyclobutyl, cyclopentyl, cyclohexyl, cycloheptyl or adamantyl. The C$_{5-6}$ cycloalkenyl group may be exemplifed by 2-cyclopentenyl, 3-cyclopentenyl, 2-cyclohexenyl, 3-cyclohexenyl, cyclopentadienyl or cyclohexadienyl. Substituents of these hydrocarbon residues may be exemplified by hydroxyl group, C$_{1-6}$ alkyl group, C$_{2-6}$ alkenyl group, C$_{2-6}$ alkynyl group, C$_{3-10}$ cycloalkyl group, C$_{5-6}$ cycloalkenyl group, C$_{6-10}$ aryl group, C$_{7-19}$ aralkyl group, heterocyclic group, C$_{1-6}$ alkoxy group, C$_{3-10}$ cycloalkyloxy group, C$_{6-10}$ aryloxy group, C$_{7-19}$ aralkyloxy group, heterocycle-oxy group, mercapto group, C$_{1-6}$ alkylthio group, C$_{3-10}$ cycloalkylthio group, C$_{6-10}$ arylthio group, C$_{7-19}$ aralkylthio group, heterocyclethio group, amino group, mono-C$_{1-6}$ alkylamino group, di-C$_{1-6}$ alkylamino group, tri-C$_{1-6}$ alkylammonium group, C$_{3-10}$ cycloalkylamino group, C$_{6-10}$ arylamino group, C$_{7-19}$ aralkylamino group, heterocycle-amino group, cyclic amino group, azido group, nitro group, halogen atom, cyano group, carboxyl group, C$_{1-10}$ alkoxycarbonyl group, C$_{6-10}$ aryloxy-carbonyl group, C$_{7-19}$ aralkyloxy-carbonyl group, C$_{6-10}$ aryl-acyl$^+$ group, C$_{1-6}$ alkanoyl group, C$_{3-5}$ alkenoyl group, C$_{6-10}$ aryl-acyl$^+$oxy group, C$_{2-6}$ alkanoyloxy group, C$_{3-5}$ alkenoyloxy group, carbamoyl* group, thiocarbamoyl* group, carbamoyl*oxy group, phthalimido group, C$_{1-6}$ alkanoylamino group, C$_{6-10}$ aryl-acyl$^+$amino group, carboxyamino group, C$_{1-10}$ alkoxy-carboxamido group, C$_{6-10}$ aryloxy-carboxamido group or C$_{7-19}$ aralkyloxy-carboxamido group, and two or more of them, same or different, may be present. As substituents of the hydrocarbon residues, more specifically stating, the C$_{1-6}$ alkyl group stands for the above-mentioned groups, i.e. methyl, ethyl, n-propyl, isopropyl, n-butyl, isobutyl, sec-butyl, tert-butyl, n-pentyl or n-hexyl, the C$_{2-6}$ alkenyl group stands for the above-mentioned groups, i.e. vinyl, allyl, isopropenyl, methallyl, 1,1-dimethylallyl, 2-butenyl or 3-butenyl, the C$_{2-6}$ alkynyl group stands for the above-mentioned groups, i.e. ethynyl, 1-propynyl, 2-propynyl or propargyl, the C$_{3-10}$ cycloalkyl group stands for the above-mentioned groups, i.e. cyclopropyl, cyclobutyl, cyclopentyl, cyclohexyl, cycloheptyl or adamantyl, the C$_{5-6}$ cycloalkenyl group stands for the above-mentioned groups, i.e. cyclopropenyl, 2-cyclopentenyl, 3-cyclopentenyl, 2-cyclohexenyl, 3-cyclohexenyl, cyclopentadienyl or cyclohexadienyl, the C$_{6-10}$ aryl group stands for the above-mentioned groups, i.e. phenyl, naphthyl or biphenylyl, the C$_{7-19}$ aralkyl group stands for the above-mentioned groups, i.e. benzyl, 1-phenylethyl, 2-phenylethyl, phenylpropyl, naphthylmethyl or benzhydryl, the C$_{1-6}$ alkoxy group stands for the above-mentioned groups, i.e. methoxy, ethoxy, n-propoxy, isopropoxy, n-butoxy, tert-butoxy, n-pentyloxy or n-hexyloxy, the C$_{3-10}$ cycloalkyloxy group stands for the above-mentioned groups, i.e. cyclopropyloxy or cyclohexyloxy, the C$_{6-10}$ aryloxy group stands for the above-mentioned groups, i.e. phenoxy or naphthyloxy, the C$_{7-19}$ aralkyloxy group stands for the above-mentioned groups, i.e. benzyloxy, 1-phenylethyloxy, 2-phenylethyloxy or benzhydryloxy, the C$_{1-6}$ alkylthio group stands for the above-mentioned groups, i.e. methylthio, ethylthio, n-propylthio or n-butylthio, the C$_{3-10}$ cycloalkylthio group stands for the above-mentioned groups, i.e. cyclopropylthio or cyclohexylthio, the C$_{6-10}$ arylthio group stands for the above-mentioned groups, i.e. phenylthio or naphthylthio, the C$_{7-19}$ aralkylthio group stands for the above-mentioned groups, i.e. benzylthio, phenylethylthio or benzhydrylthio, the mono-C$_{1-6}$ alkylamino group stands for the above-mentioned groups, i.e. methylamino, ethylamino, n-propylamino, or n-butylamino, the di-C$_{1-6}$ alkylamino group stands for the above-mentioned groups, i.e. dimethylamino, diethylamino, methylethylamino, di-(n-propyl)amino or di-(n-butyl)amino, the tri-C$_{1-6}$ alkylammonium group stands for the above-mentioned groups, i.e. trimethylammonium or triethylammonium, the C$_{3-10}$ cycloalkylamino group stands for the above-mentioned groups, i.e. cyclopropylamino, cyclopentylamino or cyclohexylamino, the C$_{6-10}$ arylamino group stands for the above-mentioned groups, i.e. anilino or N-methylanilino, the C$_{7-19}$ aralkylamino group stands for the above-mentioned groups, i.e. benzylamino, 1-phenylethylamino, 2-phenylethylamino or benzhydrylamino, the cyclic amino group stands for the above-mentioned groups, i.e. pyrrolidino, piperidino, piperazino, morpholino or 1-pyrrolyl, the halogen atom stand for here fluorine, chlorine, bromine or iodine, the C$_{1-10}$ alkoxy-carbonyl group stands for the above-mentioned groups, i.e. methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl or norbornyloxycarbonyl, the C$_{6-10}$ aryloxy-carbonyl group stands for the above-mentioned groups, i.e. phenoxycarbonyl or naphthyloxycarbonyl, the C$_{7-19}$ aralkyloxycarbonyl group stands for the above-mentioned groups, i.e. benzyloxycarbonyl or benzhydryloxycarbonyl, the C$_{6-10}$ aryl-acyl$^+$ group stands for the above-mentioned groups, i.e. benzoyl, naphthoyl, phthaloyl or phenylacetyl, the C$_{1-6}$ alkanoyl group stands for the above-mentioned groups, i.e formyl acetyl, propionyl, butyryl, valeryl, pivaloyl, succinyl or glutaryl, the C$_{3-5}$ alkenoyl group stands for the above-mentioned groups, i.e.

acrylolyl, crotonoyl or maleoyl, the $C_{6-10}$ aryl-acyl-+oxy group stands for the above-mentioned groups, i.e. benzoyloxy, naphthoyloxy or phenylacetoxy, the $C_{2-6}$ alkanoyloxy group stands for the above-mentioned groups, i.e. acetoxy, propionyloxy, butyryloxy, valeryloxy or pivaloyloxy, the $C_{3-5}$ alkenoyloxy group stands for the above-mentioned groups, i.e. acryloyloxy or crotonoyloxy, the carbamoyl* group stands for the above-mentioned groups, i.e. carbamoyl, N-methylcarbamoyl, N,N-dimethylcarbamoyl, N-ethylcarbamoyl N,N-diethylcarbamoyl, N-phenylcarbamoyl, N-acetylcarbamoyl, N-benzoylcarbamoyl, N-(p-methoxyphenyl)carbamoyl and, in addition, pyrrolidinocarbonyl, piperidinocarbonyl, piperazinocarbonyl or morpholinocarbonyl, the thiocarbamoyl* group stands for the above-mentioned groups, i.e. thiocarbamoyl, N-methylthiocarbamoyl or N-phenylthiocarbonyl, the carbamoyl*oxy group stands for the above-mentioned group, i.e. carbamoyloxy, N-methylcarbamoyloxy, N,N-dimethylcarbamoyloxy, N-ethylcarbamoyloxy or N-phenylcarbamoyloxy, "$C_{1-6}$ alkanoylamino group" stands for e.g acetamido, propionamido, butyramido, valeramido or pivalamido, "$C_{6-10}$ aryl-acyl+amino group" stands for e.g. benzamido, naphthoylamido or phthalimido, "$C_{1-10}$ alkoxy-carboxamido group" stands for e.g. methoxycarboxamido ($CH_3OCONH-$), ethoxycarboxamido or tert-butoxycarboxamido, "$C_{6-10}$ aryloxy-carboxamido group" stands for e.g. phenoxycarboxamido ($C_6H_5OCONH-$), and "$C_{7-19}$ aralkyloxy-carboxamido group" stands for e.g. benzyloxycarboxamido ($C_6H_5CH_2OCONH-$) or benzhydryloxycarboxamido. The heterocyclic group, heterocyclic groups of heterocycle-oxy group, heterocycle-thio group and heterocycle-amino group are also here such groups as formed by removing one hydrogen atom bonding to the carbon atom of the heterocyclic ring. Such a heterocyclic ring as above may be exemplified by a 5- or 8-membered ring containing one to several, preferably 1–4, hetero atoms such as oxygen atom or sulfur atom. Such heterocyclic groups may be exemplified also here by those concretely mentioned above, including 2-pyrrolyl, as they are. Hence, "heterocycle-oxy group" is exemplified by thiazolyloxy, and "heterocycle-thio group" is exemplified by thiazolylthio, and "heterocycle-amino group" is exemplified by thiazolylamino or thiadiazolylamino. Preferable substituted hydrocarbon residues are $C_{1-3}$ alkyl groups ($C_{1-3}$ alkyl group means methyl, ethyl, n-propyl, isopropyl, etc.) substituted with e.g. hydroxyl group, cycloalkyl group, alkoxy group, alkylthio group, amino group, trialkylammonium group, halogen atom, carboxyl group, alkoxycarbonyl group, carbamoyl group, cyano group, azido group or heterocyclic group, which may concretely be mentioned, among many others, cyclopropylmethyl, methoxymethyl, ethoxymethyl, 1-methoxyethyl, 2-methoxyethyl, 1-ethoxyethyl, 2-hydroxyethyl, methylthiomethyl, 2-aminoethyl, 2-(trimethylammonium)ethyl, 2-(triethylammonium)ethyl, fluoromethyl, difluoromethyl, trifluoromethyl, 2-fluoroethyl, 2,2-difluoroethyl, chloromethyl, 2-chloroethyl, 2,2-dichloroethyl, 2,2,2-trichloroethyl, 2-bromoethyl, 2-iodoethyl, 2,2,2-trifluoroethyl, carboxymethyl, 1-carboxyethyl, 2-carboxyethyl, 2-carboxypropyl, 3-carboxypropyl, 1-carboxybutyl, cyanomethyl, 1-carboxy-1-methylethyl, methoxycarbonylmethyl, ethoxycarbonylmethyl, tert-butoxycarbonylmethyl, 1-methoxycarbonyl-1-methylethyl, 1-ethoxycarbonyl-1-methylethyl, 1-tert-butoxycarbonyl-1-methylethyl, 1-benzyloxycarbonyl-1-methylethyl, 1-pivaloyloxycarbonyl-1-methylethyl, carbamoylmethyl, 2-azidoethyl, 2-(pyrazolyl)ethyl, 2-(imidazolyl)ethyl, 2-(2-oxopyrrolidin-3-yl)ethyl or 2-amino-4-thiazolylmethyl. Most preferable ones among the above-exemplified hydrocarbon residues are straight-chain $C_{1-3}$ alkyl groups, e.g. methyl, ethyl and n-propyl; straight-chain or branched $C_{1-3}$ alkyl groups substituted with halogen atom, hydroxyl group, alkoxy group, carboxyl group, alkoxycarbonyl group or cyano group, e.g. 2-fluoroethyl, 2-chloroethyl, 2-hydroxyethyl, 2-methoxyethyl, cyanomethyl, carboxymethyl, tert-butoxycarbonylmethyl, 1-carboxy-1-methylethyl or 1-tert-butoxycarbonyl-1-methylethyl; allyl group and propargyl group. If the symbol $R^{3'}$ represents a preferable hydrocarbon residue exemplified above or hydrogen atom, the compounds [I] of this invention having as $R^0$ an acyl group of

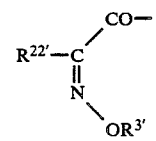

(wherein $R^{22'}$ stands for a heterocyclic* group) possess strong antibacterial activity, and, especially against resistant-bacteria, show excellent bactericidal action. As mentioned in the foregoing, compounds whose heterocyclic* group $R^{22'}$ is shown by the formula

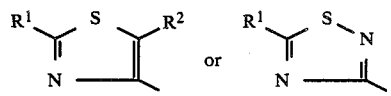

(wherein $R^1$ stands for an optimally protected amino group and $R^2$ stands for hydrogen atom, halogen atom or nitro group) are most preferable. Hence, especially preferable compounds [I] are those having the following structural formula.

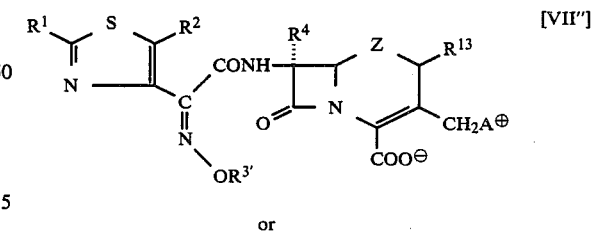 [VII'']

or

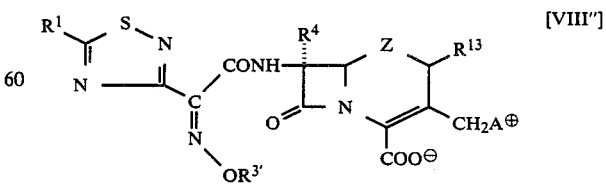 [VIII'']

[wherein symbols are of the same meaning as defined above].

Preferable examples of the acyl group shown by

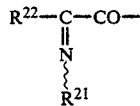

are 2-(2-aminothiazol-4-yl)-2(Z)-(hydroxyimino)acetyl, 2-(2-aminothiazol-4-yl)-2(Z)-(methoxyimino)acetyl, 2-(2-chloroacetamidothiazol-4-yl)-2(Z)-(methoxyimino)acetyl, 2-(2-aminothiazol-4-yl)-2(Z)-(ethoxyimino)acetyl, 2-(2-aminothiazol-4-yl)-2(Z)-(n-propoxyimino)acetyl, 2-(2-aminothiazol-4-yl)-2(Z)-(isopropoxyimino)acetyl, 2-(2-aminothiazol-4-yl)-2(Z)-(n-butoxyimino)acetyl, 2-(2-aminothiazol-4-yl)-2(Z)-(n-hexyloxyimino)acetyl, 2-(2-aminothiazol-4-yl)-2(Z)-(cyclopropylmethyloxyimino)acetyl, 2-(2-aminothiazol-4-yl)-2(Z)-(benzyloxyimino)acetyl, 2-(2-aminothiazol-4-yl)-2(Z)-(allyloxyimino)acetyl, 2-(2-aminothiazol-4-yl)-2(Z)-(propargyloxyimino)acetyl, 2-(2-aminothiazol-4-yl)-2(Z)-(methoxymethyloxyimino)acetyl, 2-(2-aminothiazol-4-yl)-2(Z)-(ethoxymethyloxyimino)acetyl, 2-(2-aminothiazol-4-yl)-2(Z)-[(1-methoxyethyl)oxyimino]acetyl, 2-(2-aminothiazol-4-yl)-2(Z)-[(2-methoxyethyl)oxyimino]acetyl, 2-(2-aminothiazol-4-yl)-2(Z)-[(2-ethoxyethyl)oxyimino]acetyl, 2-(2-aminothiazol-4-yl)-2(Z)-[(1-ethoxyethyl)oxyimino]acetyl, 2-(2-aminothiazol-4-yl)-2(Z)-[(2-hydroxyethyl)oxyimino]acetyl, 2-(2-aminothiazol-4-yl)-2(Z)-(methylthiomethyloxyimino)acetyl, 2-(2-aminothiazol-4-yl)-2(Z)-[(2-aminoethyl)oxyimino]acetyl, 2-(2-aminothiazol-4-yl)-2(Z)-(fluoromethyloxyimino)acetyl, 2-(2-aminothiazol-4-yl)-2(Z)-(difluoromethyloxyimino)acetyl, 2-(2-aminothiazol-4-yl)-2(Z)-(trifluoromethyloxyimino)acetyl, 2-(2-aminothiazol-4-yl)-2(Z)-[(2-fluoroethyl)oxyimino]acetyl, 2-(2-aminothiazol-4-yl)-2(Z)-[(2,2-difluoroethyl)oxyimino]acetyl, 2-(2-aminothiazol-4-yl)-2(Z)-(chloromethyloxyimino)acetyl, 2-(2-aminothiazol-4-yl)-2(Z)-[(2-chloroethyl)oxyimino]acetyl, 2-(2-aminothiazol-4-yl)-2(Z)-[(2,2-dichloroethyl)oxyimino]acetyl, 2-(2-aminothiazol-4-yl)-2(Z)-[(2,2,2-trichloroethyl)oxyimino]acetyl, 2-(2-aminothiazol-4-yl)-2(Z)-[(2-bromoethyl)oxyimino]acetyl, 2-(2-aminothiazol-4-yl)-2(Z)-[(2-iodoethyl)oxyimino]acetyl, 2-(2-aminothiazol-4-yl)-2(Z)-[(2,2,2-trifluoroethyl)oxyimino]acetyl, 2-(2-aminothiazol-4-yl)-2(Z)-(carboxymethyloxyimino)acetyl, 2-(2-aminothiazol-4-yl)-2(Z)-(1-carboxyethyloxyimino)acetyl, 2-(2-aminothiazol-4-yl)-2(Z)-[(2-carboxyethyl)oxyimino]acetyl, 2-(2-aminothiazol-4-yl)-2(Z)-(1-carboxypropyloxyimino)acetyl, 2-(2-aminothiazol-4-yl)-2(Z)-[(3-carboxypropyl)oxyimino]acetyl, 2-(2-aminothiazol-4-yl)-2(Z)-[(1-carboxybutyl)oxyimino]acetyl, 2-(2-aminothiazol-4-yl)-2(Z)-(cyanomethyloxyimino)acetyl, 2-(2-aminothiazol-4-yl)-2(Z)-[(1-carboxy-1-methylethyl)oxyimino]acetyl, 2-(2-aminothiazol-4-yl)-2(Z)-(methoxycarbonylmethyloxyimino)acetyl, 2-(2-aminothiazol-4-yl)-2(Z)-(ethoxycarbonylmethyloxyimino)acetyl, 2-(2-aminothiazol-4-yl)-2(Z)-[(tert-butoxycarbonylmethyl)oxyimino]acetyl, 2-(2-aminothiazol-4-yl)-2(Z)-[1-(tert-butoxycarbonyl)ethoxyimino]acetyl, 2-(2-aminothiazol-4-yl)-2(Z)-[(1-methoxycarbonyl-1-methylethyl)oxyimino]acetyl, 2-(2-aminothiazol-4-yl)-2(Z)-[(1-ethoxycarbonyl-1-methylethyl)oxyimino]acetyl, 2-(2-aminothiazol-4-yl)-2(Z)-[(1-tert-butoxycarbonyl-1-methylethyl)oxyimino]acetyl, 2-(2-aminothiazol-4-yl)-2(Z)-[1-(tert-butoxycarbonyl)propoxyimino]acetyl, 2-(2-aminothiazol-4-yl)-2(Z)-[(1-benzyloxycarbonyl-1-methylethyl)oxyimino]acetyl, 2-(2-aminothiazol-4-yl)-2(Z)-[(1-pivaloyloxycarbonyl-1-methylethyl)oxyimino]acetyl, 2-(2-aminothiazol-4-yl)-2(Z)-(carbamoylmethyloxyimino)acetyl, 2-(2-aminothiazol-4-yl)-2(Z)-[1-(1-carbamoyl-1-methyl)ethyloxyimino]acetyl, 2-(2-aminothiazol-4-yl)-2(Z)-[(2-azidoethyloxyimino]acetyl, 2-(2-aminothiazol-4-yl)-2(Z)-(phenoxycarbonyloxyimino)acetyl, 2-(2-amino-5-chlorothiazol-4-yl)-2(Z)-(hydroxyimino)acetyl, 2-(2-amino-5-chlorothiazol-4-yl)-2(Z)-(methoxyimino)acetyl, 2-(2-amino-5-chlorothiazol-4-yl)-2(Z)-(ethoxyimino)acetyl, 2-(2-amino-5-chlorothiazol-4-yl)-2(Z)-(n-propoxyimino)acetyl, 2-(2-amino-5-chlorothiazol-4-yl)-2(Z)-[(2-fluoroethyl)oxyimino]acetyl, 2-(2-amino-5-chlorothiazol-4-yl)-2(Z)-[(2-chloroethyl)oxyimino]acetyl, 2-(2-amino-5-chlorothiazol-4-yl)-2(Z)-(carboxymethyloxyimino)acetyl, 2-(2-amino-5-chlorothiazol-4-yl)-2(Z)-[(tert-butoxycarbonylmethyl)oxyimino]acetyl, 2-(2-amino-5-chlorothiazol-4-yl)-2(Z)-[(1-carboxy-1-methylethyl)oxyimino]acetyl, 2-(2-amino-5-chlorothiazol-4-yl)-2(Z)-[(1-tert-butoxycarbonyl-1-methylethyl)oxyimino]acetyl, 2-(2-amino-5-bromothiazol-4-yl)-2(Z)-(ethoxyimino)acetyl, 2-(5-amino-1,2,4-thiadiazol-3-yl)-2(Z)-(hydroxyimino)acetyl, 2-(5-amino-1,2,4-thiadiazol-3-yl)-2(Z)-(methoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)-[(2-fluoroethyl)oxyimino]acetyl, 2-(5-amino-1,2,4-thiadiazol-3-yl)-2(Z)-[(2-chloroethyl)oxyimino]acetyl, 2-(5-amino-1,2,4-thiadiazol-3-yl)-2(Z)-(carboxymethyloxyimino)acetyl, 2-(5-amino-1,2,4-thiadiazol-3-yl)-2(Z)-[(1-carboxy-1-methylethyl)oxyimino]acetyl, 2-(5-amino-1,2,4-thiadiazol-3-yl)-2(Z)-[(1-tert-butoxycarbonyl-1-methylethyl)oxyimino]acetyl, 2-(5-aminoisoxazol-3-yl)-2(Z)-(ethoxyimino)acetyl, 2-(5-amino-1,2,4-oxadiazol-3-yl)-2(Z)-(ethoxyimino)acetyl, 2-(2-imino-3-hydroxythiazolin-4-yl)-2(Z)-(ethoxyimino)acetyl, 2-(2-amino-3-oxidothiazol-4-yl)-2(Z)-(ethoxyimino)acetyl, 2-thienyl-2(Z)-(methoxyimino)acetyl, 2-thienyl-2(Z)-(ethoxyimino)acetyl, 2-furyl-2(Z)-(methoxyimino)acetyl, 2-furyl-2(Z)-(ethoxyimino)acetyl, 2-(1,3,4-thiadiazolyl)-2(Z)-(ethoxyimino)acetyl, 2-(p-hydroxyphenyl)-2(Z)-(ethoxyimino)acetyl, 2-phenyl-2(Z)-(ethoxyimino)acetyl, 2-phenyl-2(Z)-(hydroxyimino)acetyl, 2-[p-(γ-D-glutamyloxy)phenyl]-2(Z)-(hydroxyimino)acetyl or 2-[p-(3-amino-3-carboxypropoxy)phenyl]-2(Z)-(hydroxyimino)acetyl.

The $C_{1-6}$ alkanoyl* group described as one of the acyl groups ($R^b$) includes, besides the above-mentioned $C_{1-6}$ alkanoyl group, heterocycle*—CO—CO—, $R^{15}CH_2CO—$,

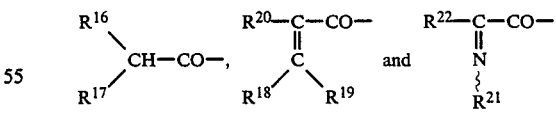

trifluoroacetyl, 4-carboxybutyl, 5-amino-5-carboxyvaleryl, 5-oxo-5-carboxyvaleryl, N-[2-(2-amino-4-thiazolyl)-2(Z)-(methoxyimino)acetyl]-D-alanyl, N-[2-(2-amino-4-thiazolyl-2(Z)-(methoxyimino)acetyl]-D-phenylglycyl or 2-(2-amino-4-thiazolyl)-2-[2-(2-amino-4-thiazolyl)-2(Z)-(methoxyimino)acetamido]acetyl.

The $C_{3-5}$ alkenoyl* groups as acyl groups ($R^b$) other than $C_{1-6}$ alkanoyl* groups, may be mentioned also here the afore-mentioned acryloyl, crotonoyl, maleoyl, cinnamoyl, p-chlorocinnamoyl or β-phenylcinnamoyl; the $C_{3-10}$ cycloalkyl-carbonyl groups may be mentioned also here the afore-mentioned cyclopropylcarbonyl, cyclobutylcarbonyl, cyclopentylcarbonyl, cyclohexylcarbonyl, cycloheptylcarbonyl or adamantylcarbonyl; $C_{5-6}$ cycloalkenyl-carbonyl groups may be mentioned also here the afore-mentioned cyclopentenylcarbonyl, cyclopentadienylcarbonyl, cyclohexenylcarbonyl or cyclohexadienylcarbonyl; $C_{6-10}$ aryl*carbonyl group may be mentioned also here benzoyl, naphthoyl, p-toluoyl, p-tert-butylbenzoyl, p-hydroxybenzoyl, p-methoxybenzoyl, p-tert-butoxybenzoyl, p-chlorobenzoyl or p-nitrobenzoyl; and "heterocycle*carbonyl group" is exemplified by 2- or 3-pyrrolylcarbonyl, 3-, 4- or 5-pyrazolylcarbonyl, 2-, 4- or 5-imidazolylcarbonyl, 1,2,3- or 1,2,4-triazolylcarbonyl, 1H- or 2H-tetrazolylcarbonyl, 2- or 3-furylcarbonyl, 2- or 3-thienylcarbonyl, 2-, 4- or 5-oxazolylcarbonyl, 3-, 4- or 5-isoxazolylcarbonyl, 1,2,3-oxadiazol-4- or 5-ylcarbonyl, 1,2,4-oxadiazol-3- or 5-ylcarbonyl, 1,2,5- or 1,3,4-oxadiazolylcarbonyl, 2-, 4- or 5-thiazolylcarbonyl, 2-amino-4-thiazolylcarbonyl, 3-, 4- or 5-isothiazolylcarbonyl, 1,2,3-thiadiazol-4- or 5-ylcarbonyl, 1,2,4-thiadiazol-3- or 5-ylcarbonyl, 5-amino-1,2,4-thiadiazol-3-ylcarbonyl, 1,2,5- or 1,3,4-thiadiazolylcarbonyl, 2- or 3-pyrrolidinylcarbonyl, 2-, 3- or 4-pyridylcarbonyl, 2-, 3- or 4-pyridylcarbonyl-N-oxide, 3- or 4-pyridazinylcarbonyl, 3- or 4-pyridazinylcarbonyl-N-oxide, 2-, 4- or 5-pyrimidinylcarbonyl, 2-, 4- or 5-pyrimidinylcarbonyl-N-oxide, pyrazinylcarbonyl, 2-, 3- or 4-piperidinylcarbonyl, piperazinylcarbonyl, 3H-indol-2- or 3-ylcarbonyl, 2-, 3- or 4-pyranylcarbonyl, 2-, 3- or 4-thiopyranylcarbonyl, benzopyranylcarbonyl, quinolylcarbonyl, pyrido[2,3-d]pyrimidylcarbonyl, 1,5-, 1,6-, 1,7-, 1,8-, 2,6- or 2,7-naphthylidylcarbonyl, thieno[2,3-b]pyridylcarbonyl, pyrimidopyridylcarbonyl, pyrazinoquinolylcarbonyl, or 3-(2,6-dichlorophenyl)-5-methylisoxazol-4-ylcarbonyl.

As the esterified carboxyl groups (hereinafter sometimes denoted as the symbol $R^c$) included in the substituents $R^o$, the substituted oxycarbonyl groups mentioned above as protective groups of optionally protected amino groups shown by $R^1$ can be applied also here as they are. Hence, the afore-mentioned methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl or cyclohexyloxycarbonyl can be mentioned here also.

The substituent $R^4$ in the compounds [I] of this invention stands for hydrogen atom, methoxy group or formamido group (HCONH—).

The substituent $R^{13}$ in the compounds [I] of this invention stands for hydrogen atom, methyl group, hydroxyl group or halogen atom. The halogen atom means here fluorine, chlorine, bromine or iodine.

In the compounds [I] of this invention, the substituent A stands for imidazol-1-yl group which forms a condensed ring at the 2,3- or 3,4-position. The condensed ring means the imidazole ring having a 5- to 6-membered aromatic heterocyclic ring condensed therewith, and it may optionally be further condensed with another aromatic ring or aromatic heterocyclic ring. The mark ⊕ attached to the right shoulder of the substituent A means that A has a monovalent positive electric charge. The optionally substituted imidazol-1-yl group ($A^⊕$) forming the condensed ring at 2,3- or 3,4-position is shown by the general formula [$A^1$] or [$A^2$];

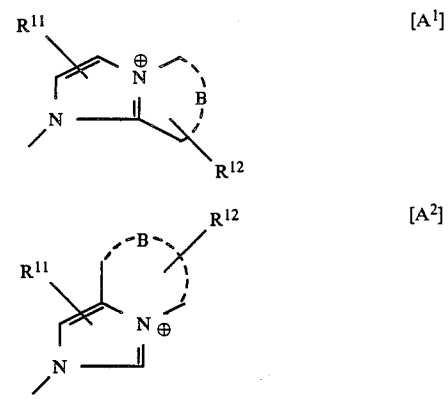

wherein B stands for a group forming a 5- to 6-membered aromatic heterocyclic ring which may be condensed with another aromatic ring or aromatic heterocyclic ring, $R^{11}$ stands for hydrogen atom or a substituent (or substituents) on the imidazole ring and $R^{12}$ stands for hydrogen atom or a substituent (or substituents) on the ring which may be condensed with the imidazole ring. B consists of carbon atom, nitrogen atom, oxygen atom and/or sulfur atom, and, among them, carbon atom combines with one hydrogen atom or one substituent, or forms another condensed ring together with adjacent carbon atom. The $A^1$ group may be embodied as follows, for example;

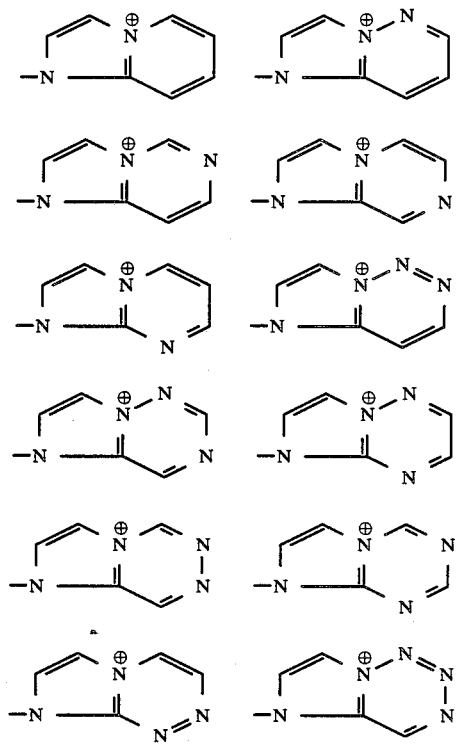

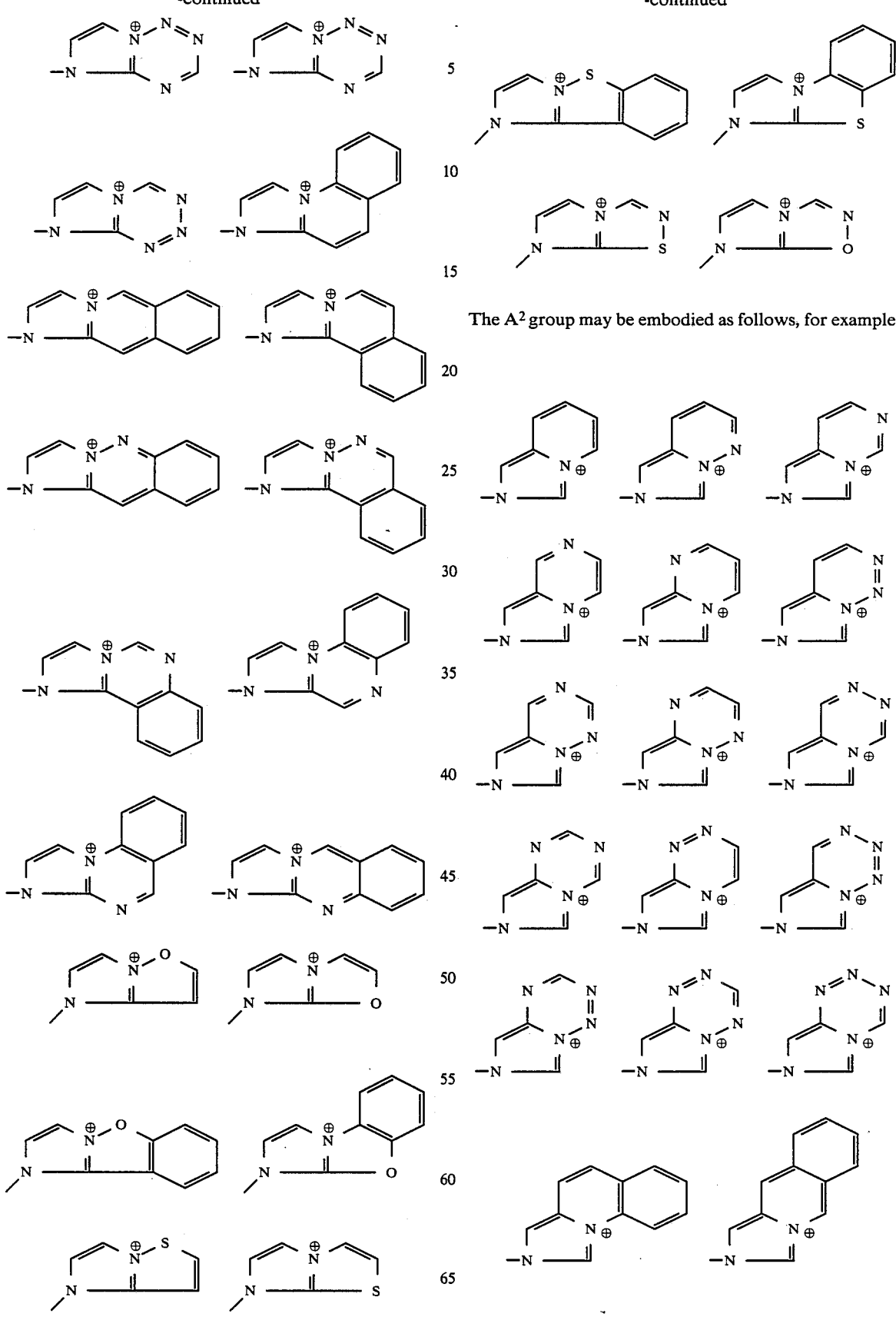
The A² group may be embodied as follows, for example;

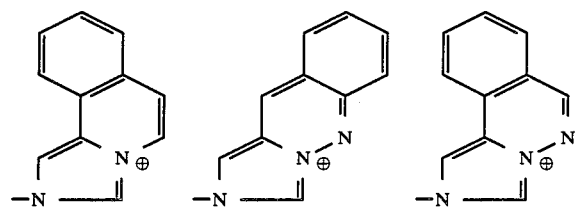

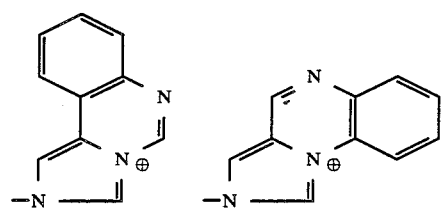

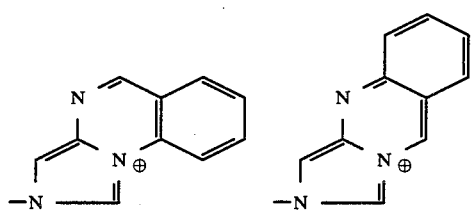

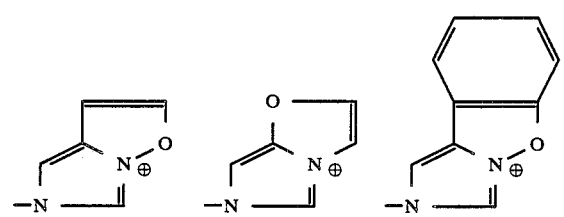

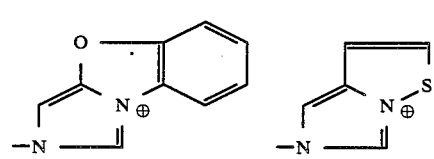

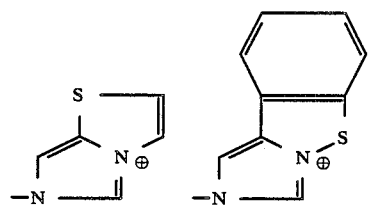

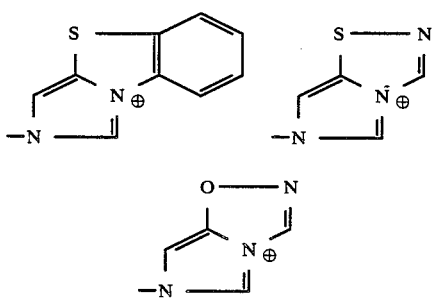

Among these groups, especially preferable are imidazo[1,2-a]pyridinium-1-yl( 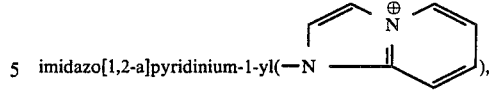 ), imidazo[1,2-b]pyridazinium-1-yl( 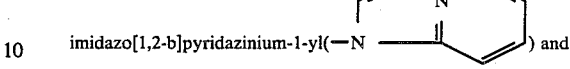 ) and imidazo[1,5-a]pyridinium-2-yl( 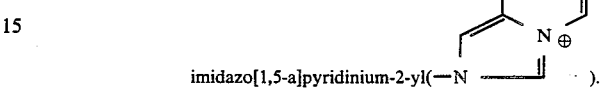 ).

In the above-mentioned formulae [A$^1$] and [A$^2$] as well as A$^1$ groups and A$^2$ groups embodied as above, the positive electric charge A⊕ is applied, for convenience sake, to the nitrogen atom at the 3-position of imidazole, but there may be a case where the said quaternary nitrogen is that of the nitrogen atom at the 1-position. Further, there may be cases where the monovalent positive electric charge is delocalized at the imidazole ring, or even delocalized on the entire condensed ring. Therefore, the above

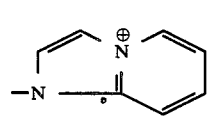

may include

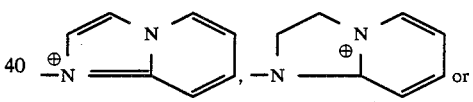

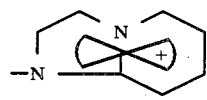

The position which this positive electric charge takes varies with, among others, the state (solid or in solution) of the compound [I], kinds of solvents, pH, temperature or kinds of substituents. Accordingly, the present invention includes all the cases where the positive electric charge is localized at a nitrogen atom or is delocalized on the entire condensed ring. The substituents R$^{11}$ and R$^{12}$ on the condensed ring A may be exemplified by a hydroxyl group, hydroxy C$_{1-6}$ alkyl group, C$_{1-6}$ alkyl group, C$_{2-6}$ alkenyl group, C$_{2-6}$ alkynyl group, C$_{4-6}$ alkadienyl group, C$_{3-10}$ cycloalkyl group, C$_{5-6}$ cycloalkenyl group, C$_{3-10}$ cycloalkyl C$_{1-6}$ alkyl group, C$_{6-10}$ aryl group, C$_{7-12}$ aralkyl group, di-C$_{6-10}$ arylmethyl group, tri-C$_{6-10}$ arylmethyl group, heterocyclic group, C$_{1-6}$ alkoxy group, C$_{1-6}$ alkoxy C$_{1-6}$ alkyl group, C$_{3-10}$ cycloalkyloxy group, C$_{6-10}$ aryloxy group, C$_{7-19}$ aralkyloxy group, mercapto group, mercapto C$_{1-6}$ alkyl group, sulfo group, sulfo C$_{1-6}$ alkyl group, C$_{1-6}$ alkylthio group, C$_{1-6}$ alkylthio C$_{1-6}$ alkyl group, C$_{3-10}$ cycloalkylthio group, C$_{6-10}$ arylthio group, C$_{7-19}$ aralkylthio group, amino group, amino C$_{1-6}$ alkyl group, mono-$C_{1-6}$ alkylamino group, di-$C_{1-6}$ alkylamino group, mono-$C_{1-6}$ alkylamino $C_{1-6}$ alkyl group, di-$C_{1-6}$ alkylamino $C_{1-6}$ alkyl group, $C_{3-10}$ cycloalkylamino group, $C_{6-10}$ arylamino group, $C_{7-19}$ aralkylamino group, cyclic amino group, cyclic amino $C_{1-6}$ alkyl group, cyclic amino $C_{1-6}$ alkylamino group, azido group, nitro group, halogen atom, halogeno $C_{1-6}$ alkyl group, cyano group, cyano $C_{1-6}$ alkyl group, carboxyl group, carboxy $C_{1-6}$ alkyl group, $C_{1-10}$ alkoxy-carbonyl group, $C_{1-10}$ alkoxy-carbonyl $C_{1-6}$ alkyl group, $C_{6-10}$ aryloxycarbonyl group, $C_{7-19}$ aralkyloxy-carbonyl group, $C_{6-10}$ arylacyl$^{30}$ group, $C_{1-6}$ alkanoyl group, $C_{2-6}$ alkanoyl $C_{1-6}$ alkyl group, $C_{3-5}$ alkenoyl group, $C_{6-10}$ arylacyl$^+$oxy group, $C_{2-6}$ alkanoyloxy group, $C_{2-6}$ alkanoyloxy $C_{1-6}$ alkyl group, $C_{3-5}$ alkenoyloxy group, carbamoyl $C_{1-6}$ alkyl group, carbamoyl* group, thiocarbamoyl* group, carbamoyl*oxy group, carbamoyloxy $C_{1-6}$ alkyl group, $C_{1-6}$ alkanoylamino group, $C_{6-10}$ aryl-acyl$^+$amino group, sulfonamido group, carboxyamino group, $C_{1-10}$ alkoxy-carboxamido group, $C_{6-10}$ aryloxy-carboxamido group or $C_{7-19}$ aralkyloxy-carboxamido group. Among the above-mentioned substituents, "$C_{4-6}$ alkadienyl group" is exemplified by 1,3-butadienyl, "$C_{3-10}$ cycloalkyl $C_{1-6}$ alkyl group" is exemplified by cyclopentylmethyl or cyclohexylmethyl, and halogen atom means here fluorine, chlorine or bromine. All the groups other than the above may be exemplified as in the foregoing.

These substituents may occur singly or in plurarity with the same or different ones. And, in $A^1$, the 5,6-position or imidazole ring may be condensed with an alicyclic ring, aromatic ring or heterocyclic ring. As the examples, the following may be counted:

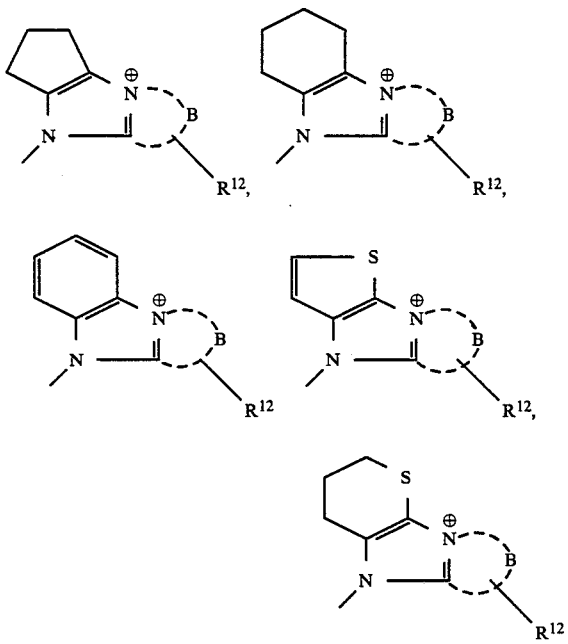

In the above, B and $R^{12}$ are of the same significance as afore-defined. The above-mentioned $R^{11}$ and $R^{12}$ may be further substituted.

In the above compound [I], the mark ⊖ attached to the right shoulder of the carboxyl substituent (—COO) means that the said carboxyl group is a carboxylate anion and forms an internal salt by making a pair with the positive electric charge on the substituent A. On the other hand, the compound [I] may be physiologically or pharmaceutically acceptable salts or esters. As the physiologically or pharmaceutically acceptable salts, there may be mentioned, among others, inorganic base salts, ammonium salt, organic base salts, inorganic acid addition salts, organic acid addition salts and basic amino acid salts. There may be exemplified an alkali metal (e.g. sodium, potassium, etc.) or an alkaline earth metal (e.g. calcium) as an inorganic base capable of giving the inorganic base salts; procaine, 2-phenylethylbenzylamine, dibenzylethylenediamine, ethanolamine, diethanolamine, tris-hydroxymethylaminomethane, poly-hydroxyalkylamine of N-methylglucosamine as an organic base capable of giving the organic base salts; hydrochloric acid, hydrobromic acid, sulfuric acid, nitric acid or phosphoric acid as an inorganic acid capable of giving the inorganic acid addition salts; p-toluenesulfonic acid, methanesulfonic acid, formic acid, trifluoroacetic acid or maleic acid as an organic acid capable of giving the organic acid addition salts; and lysine, arginine, ornithine or histidine as a basic amino acid capable of giving the basic amino acid salts.

Among these salts, basic salts (i.e. inorganic base salts, ammonium salt, organic base salts and basic amino acid salts) mean salts derivable in case there is (are) acidic group(s) e.g. carboxyl group, sulfo group etc. on the substituent $R^o$ or A of the compound [I], and acid addition salts (i.e. inorganic acid addition salts and organic acid addition salts) means salts derivable in case there is (are) basic group(s) e.g. amino group, monoalkylamino group, dialkylamino group, cycloalkylamino group, arylamino group, aralkylamino group, cyclic amino group, nitrogen-containing heterocyclic group etc. on the substituent $R^o$ or A of the compound [I]. Incidentally, the acid addition salt also includes an intramolecular salt of the compound [I], i.e. a salt having carboxyl(COOH) group at the 4-position and $CH_2A^{\oplus}.M^{\ominus}$ group [wherein $M^{\ominus}$ denotes an anion formed by removal of a proton ($H^{\oplus}$) from inorganic acid or organic acid; such an anion is exemplified by chloride ion, bromide ion, sulfate ion, p-toluenesulfonate ion, methanesulfonate ion, trifluoroacetate ion] at the 3-position, which is formed through addition of one mole of acid to carboxylate($COO^{\ominus}$) group of the 4-position and $CH_2A^{\oplus}$ group of the 3-position of the compound [I]. The ester derivatives of the compound [I] means esters derivable by esterifying the carboxyl group contained in the molecule, which include esters usable as synthetic intermediates and bioavailably unstable non-toxic esters. The esters usable as synthetic intermediates are exemplified by $C_{1-6}$ alkyl* ester, $C_{2-6}$ alkenyl ester, $C_{3-10}$ cycloalkyl ester, $C_{3-10}$ cycloalkyl $C_{1-6}$ alkyl ester, $C_{6-10}$ aryl* ester, $C_{7-12}$ aralkyl* ester, di-$C_{6-10}$ arylmethyl ester, tri-$C_{6-10}$ aryl-methyl ester or substituted silyl ester. There may be exemplified, as "$C_{1-6}$ alkyl* group" capable of giving $C_{1-6}$ alkyl* ester, methyl, ethyl, n-propyl, isopropyl, n-butyl, isobutyl, sec-butyl, tert-butyl, n-pentyl, n-hexyl, benzyloxymethyl, 2-methylsulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridine-1-oxido-2-methyl, methylsulfinylmethyl, of 2-cyano-1,1-dimethylethyl; as $C_{2-6}$ alkenyl group capable of giving $C_{2-6}$ alkenyl ester, the afore-mentioned ones, i.e. vinyl, allyl, 1-propenyl, isopropenyl, 1-butenyl, 2-butenyl, 3-butenyl, methallyl, 1,1-dimethylallyl or 3-methyl-3-butenyl; as $C_{3-10}$ cycloalkyl group capable of giving $C_{3-10}$ cycloalkyl ester, the afore-mentioned ones, i.e. cyclopropyl, cyclobutyl, cyclopentyl, cyclohexyl, cycloheptyl, norbornyl or adamantyl; as $C_{3-10}$ cycloalkyl $C_{1-6}$ alkyl group capable of giving $C_{3-10}$ cycloalkyl $C_{1-6}$ alkyl ester, the afore-mentioned ones, i.e. cyclopropylmethyl, cyclopentylmethyl or cyclohexylmethyl; as "$C_{6-10}$ aryl* group" capable of giving $C_{6-10}$ aryl* ester, phenyl, α-naphthyl, β-naphthyl, biphenylyl, p-nitrophenyl or p-chlorophenyl; as "$C_{7-12}$ aralkyl* group" capable of giving $C_{7-12}$ ;l aralkyl* ester, benzyl, 1-phenylethyl, 2-phenylethyl, phenylpropyl, naphthylmethyl, p-nitrobenzyl, p-methoxybenzyl, 1-indanyl, phenacyl or 3,5-di-tert-butyl-4-hydroxybenzyl; as di-$C_{6-10}$ aryl-methyl group capable of giving di-$C_{6-10}$ aryl-methyl ester, the afore-mentioned ones, i.e. benzhydryl or bis(p-methoxyphenyl)methyl; as tri-$C_{6-10}$ aryl-methyl group capable of giving tri-$C_{6-10}$ aryl-methyl ester, the afore-mentioned ones, i.e. trityl; and as substituted silyl group capable of giving substituted silyl ester, the afore-mentioned ones, i.e. trimethylsilyl, tert-butyldimethylsilyl or —Si(CH$_3$)$_2$CH$_2$CH$_2$Si(CH$_3$)$_2$—. The above esters include ester at the 4-position. Such compound having above ester group at the 4-position forms an intramolecular salt of CH$_2$A$^\oplus$·M$^\ominus$ [wherein M$^\ominus$ has the same meaning as defined above] at the 3-position.

As the bioavailably unstable and non-toxic esters, those which have been confirmed as employable in the fields of penicillin and cephalosporin can conveniently be employed also in the present invention, which may be exemplified by $C_{2-6}$ alkanoyloxy $C_{1-6}$ alkyl ester, 1-($C_{1-6}$ alkoxy)$C_{1-6}$ alkyl ester or 1-($C_{1-6}$ alkylthio)$C_{1-6}$ alkyl ester. The $C_{2-6}$ alkanoyloxy $C_{1-6}$ alkyl ester is exemplified by acetoxymethyl ester, 1-acetoxyethyl ester, 1-acetoxybutyl ester, 2-acetoxyethyl ester, propionyloxymethyl ester, pivaloyloxymethyl ester. The 1-($C_{1-6}$ alkoxy)$C_{1-6}$ alkyl ester is exemplified by methoxymethyl ester, ethoxymethyl ester, isopropoxymethyl ester, 1-methoxyethyl ester or 1-ethoxyethyl ester. The 1-($C_{1-6}$ alkylthio)$C_{1-6}$ alkyl ester is exemplified by methylthiomethyl ester or ethylthiomethyl ester. The present invention includes, besides the above-mentioned ester derivatives, physiologically or pharmaceutically acceptable compounds which are convertible in vivo to the compound [I]. The above-mentioned esters usable as synthetic intermediates and bioavailably unstable non-toxic esters include esters at the 4-position. Such esters at the 4-position usually form an intramolecular salt of CH$_2$A$^\oplus$·M$^\ominus$ [wherein M$^\ominus$ has the same meaning as defined above] at the 3-position.

When a compound [I] has a hydroxyl group, the hydroxyl group may be protected. Groups usable for protecting hydroxyl group include those which are usually employed for protecting hydroxyl group in the field of β-lactam and organic chemistry, which may be exemplified by, besides the afore-mentioned $C_{2-6}$ alkanoyl groups, substituted oxycarbonyl group, tert-butyl group, $C_{7-12}$ aralkyl* group, di-$C_{6-10}$ aryl-methyl group, tri-$C_{6-10}$ aryl-methyl group, 1-($C_{1-6}$ alkoxy)$C_{1-6}$ alkyl group, 1-($C_{1-6}$ alkylthio)$C_{1-6}$ alkyl group and substituted silyl group, acetal residues e.g. 2-tetrahydropyranyl or 4-methoxy-4-tetrahydropyranyl.

When a compound [I] additionally has an amino group other than those mentioned above, the amino group may also be protected. Grops employable for protecting those amino groups are exemplified also here by those referred to in the protection of the afore-mentioned amino groups.

Among the compounds [I] of this invention, one in which the substituent $R^o$ is nitrogen-containing heterocyclic group ($R^a$) or acyl group ($R^b$) has a broad antibacterial spectrum and can be used for prophylaxis and therapy of various diseases of men and animals caused by pathogenic bacteria, for example, infections of respiratory tract or of urinary passages. Characteristic features of the antibacterial spectrum of the antibacterial compound [I] ($R^o=R^a$ or $R^b$) are mentioned as follows:

(1) remarkably strong activity against a variety of gram-negative bacteria;

(2) strong activity against gram-positive bacteria (e.g. *Staphylococcus aureus* or *Cornyebacterium diphtheriae*);

(3) remarkably effective against *Pseudomonas aeruginosa* which are not sensitive to therapy with conventional cephalosporin-type antibiotics; and (4) Strong activity against a variety of β-lactamase-producing gram-negative bacteria (e.g. the genera Escherichia, Enterobacter, Serratia or Proteus). Especially against bacteria belonging to the genus Pseudomonas, to which aminoglycoside antibiotics such as Amikacin or Gentamicin have been used, the antibacterial compound [I] shows antibacterial activity comparable to these aminoglycosides with remarkably lower toxicity to men and animals, which is counted as one of the great advantages.

Besides, the antibacterial compound [I] ($R^o=R^a$ or $R^b$) of this invention has the following characteristic features, i.e. excellent stability, high concentration in blood, long duration of effect and remarkably high concentration in tissue.

How to make the compound [I] of this invention, its salts or esters will be described in detail as follows. These compound [I] or its salt or ester can be produced by a conventional method or an analogous one thereto.

Production Method (1): Synthesis of Compound [II]

([I], $R^0$=hydrogen atom)

For example, 7-amino compound [II] ([I], $R^0$=hydrogen atom) can be synthesized by allowing a compound representable by the general formula;

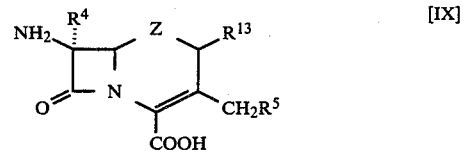

[wherein the symbol $R^5$ stands for hydroxyl group, acyloxy group, carbamoyloxy group, substituted carbamoyloxy or halogen atom, and other symbols are of respectively the same meanings as defined above] or a salt or ester thereof to react with an imidazole compound representable by the general formula A' [A' means optionally substituted imidazole forming a condensed ring at 2,3- or 3,4-position] or a salt thereof.

The reaction scheme is as follows:

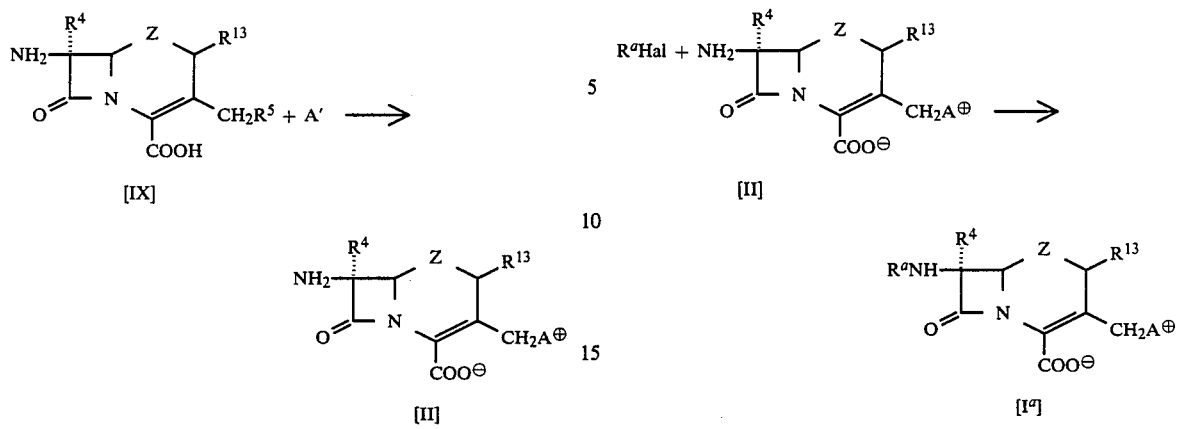

([II], $R^0$ = hydrogen atom)

[wherein Z, $R^4$, $R^{13}$, $R^5$ and A are of the same meaning as defined above].

The starting compound [IX] or a salt or ester thereof is a compound which can be easily produced by a conventional method or an analogous one thereto. As salts and esters of the compound [IX] can be also mentioned here the same ones described hereafter as those of the compound [II].

As the acyloxy group representable by the symbol $R^5$, the above-mentioned acyl+oxy group can be employed also here, especially preferable being acetoxy, chloroacetoxy, propionyloxy, butyryloxy, pivaloyloxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, o-carboxybenzoyloxy, o-(ethoxycarbonylcarbamoyl)benzoyloxy and o-(ethoxycarbonylsulfamoyl)benzoyloxy. As the substituted carbamoyloxy group representable by the symbol $R^5$, the above-mentioned ones can be employed also here, especially preferable being methylcarbamoyloxy and N,N-dimethylcarbamoyloxy. Halogen atoms representable by the symbol $R^5$ are preferably chlorine, bromine and iodine. As to the imidazole compound A' and its salts, detailed description will be given hereafter.

Even in case where the amino group at 7-position is protected, the above reaction proceeds likewise. When necessary, the protecting group may be removed after the reaction to thereby give a 7-amino compound [II] ([II], $R^0$=hydrogen atom).

Production Method (2): Synthesis of Compound [$I^a$]

($R^0=R^a$; $R^a$ denotes nitrogen-containing heterocyclic group)

For example, (2-1): By allowing the 7-amino compound [II] obtained in the preceding section (1) or a salt or ester thereof (description about the salt and ester will be made hereafter) to react with a compound representable by the general formula $R^a$Hal [$R^a$ stands for a nitrogen-containing heterocyclic group and Hal stands for a halogen atom e.g. fluorine, chlorine, bromine or iodine] or its salt, a compound [$I^a$] ($R^0=R^a$) can be synthesized.

The reaction scheme is as follows:

[wherein the symbol $R^a$ stands for nitrogen containing heterocyclic group, and Z, $R^4$, $R^{13}$, A and Hal are of the same meaning as defined above].

As the halogen atom (Hal) of the compound $R^a$Hal, use is most often made of fluorine. As salts of the compound $R^a$Hal are exemplified inorganic acid addition salts such as hydrochloride, hydrobromide, sulfate, nitrate or phosphate, or organic acid addition salts such as formate, acetate, trifluoroacetate, methanesulfonate or p-toluenesulfonate. The reaction is generally conducted by mixing a compound $R^a$Hal or its salt with a 7-amino compound [II] or a salt or ester thereof in water or an aqueous solvent at room temperature (about 15°-30° C.). For preventing hydrolysis of the compound $R^a$Hal prior to its reaction with the 7-amino compound [II], it is necessary to control the pH of the reaction solution. Optimal pH ranges from 6 to 8.5. For the purpose of eliminating from the reaction system hydrogen halogenide formed during the reaction, use may be made of a deacidifying agent, for example, inorganic bases such as sodium carbonate, potassium carbonate, calcium carbonate or sodium hydrogen carbonate; tertiary amines such as triethylamine, tri-(n-propyl)amine, tri-(n-butyl)amine, diisoproplethylamine, cyclohexyldimethylamine, pyridine, lutidine, γ-collidine, N,N-dimethylaniline, N-methylpiperidine, N-methylpyrrolidine or N-methylmorpholine; or alkylene oxides such as propylene oxide or epichlorohydrin. For preventing the pH to shift to alkali side too far, an inorganic acid such as hydrochloric acid, hydrobromic acid, sulfuric acid, nitric acid or phosphoric acid may sometimes be employed. When an aqueous solvent is employed, as the organic solvent to be mixed with water, there may be exemplified by dimethylsulfoxide, sulfolane, or hexamethyl phosphoramide, besides ethers such as dioxane, tetrahydrofuran, diethyl ether, tert-butyl methyl ether or diisopropyl ether, amides such as formamide, N,N-dimethylformamide or N,N-dimethylacetamide and ketones such as acetone, methyl ethyl ketone or methyl isobutyl ketone. Amount of the compound $R^a$Hal is usually 1-3 mol., preferably 1-2 mol., relative to 1 mol. of the 7-amino compound [II]. While the reaction time varies with kinds of 7-amino compound [II] and the compound $R^a$Hal, kinds of the solvent employed and reaction temperatures, it usually ranges from one minute to 48 hours, preferably from 15 minutes to 3 hours.

The compound $R^a$Hal and its salt can be easily produced by a conventional method or an analogous one thereto.

According to the method mentioned above, compounds having the following general formula can be synthesized, for example.

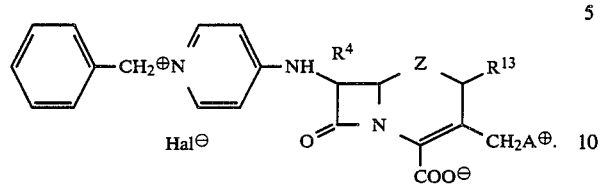

When the compound R$^a$Hal is too reactive and liable to be hydrolyzed, the reaction may be conducted in e.g. anhydrous dimethylsulfoxide in the presence of an organic base e.g. anhydrous triethylamine. According to this method, compounds of the following general formula can be synthesized, for example.

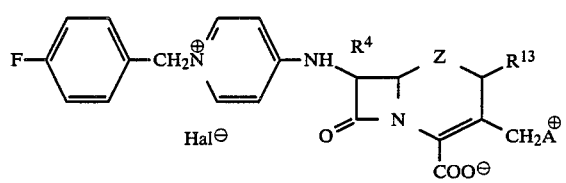

The above reaction is sometimes conducted in the presence of an organic acid e.g. p-toluenesulfonic acid, methanesulfonic acid, ethanesulfonic acid, acetic acid or butyric acid, or an inorganic acid e.g. hydrochloric acid, sulfuric acid or carbonic acid. In this case also, as the halogen atom (Hal) of R$^a$Hal, fluorine is most frequently employed. The reaction is usually conducted in a solvent such as dimethylformamide, tetrahydrofuran, dioxane, chloroform, methanol, acetonitrile, benzene, acetone or water, or an optional mixture thereof. The reaction temperature ranges from 0° C. to 150° C., preferably 20° C. to 80° C. The reaction time usually ranges from 30 minutes to 20 hours. According to this method, compounds of the following general formula can be synthesized, for example.

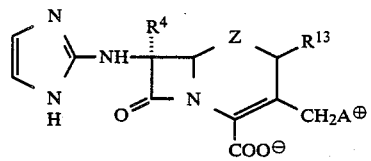

(2-2): After allowing the starting compound [IX] employed in the preceding section(1) or a salt or ester thereof to react with the compound R$^a$Hal or a salt thereof, imidazole compound A' [A' is of the same meaning as defined above] is further allowed to react with the reaction product to synthesize a corresponding compound [I$^a$] (R$^0$=R$^a$).

The reaction is shown by the following scheme:

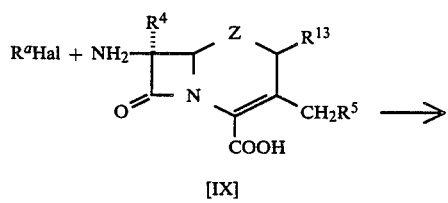

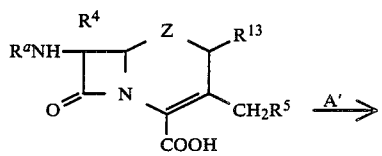

(including salts.esters)

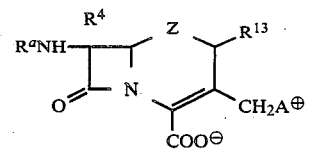

[wherein the symbol R$^a$ stands for nitrogen-containing heterocyclic group, and the symbols Z, R$^4$, R$^{13}$, R$^5$, A and Hal are of the same meaning as defined above].

The starting compound [IX], its salts and esters, and the compound R$^a$Hal and its salts can be exemplified also here by those mentioned in the foregoing. About the imidazole compound A' and its salts, detailed description will be given later. The reactions of Production Method (2-1) and (1) can be applied as they are.

Production Method (3): Synthesis of compound [I$^b$]

(R$^0$=R$^b$; R$^b$ denotes acyl group)

For example.

(3-1):

By allowing the 7-amino compound [II] obtained in the section (1) or a salt or ester thereof to react with a carboxylic acid representable by the general formula R$^b$OH [wherein R$^b$ denotes acyl group or a salt or reactive derivative thereof, a compound [I$^b$] (R$^0$=R$^b$) can be synthesized. The reaction is shown by the following scheme:

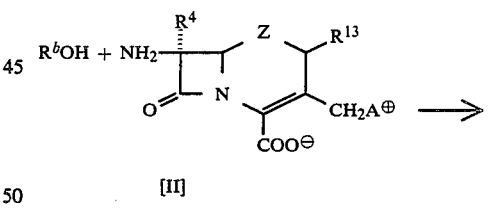

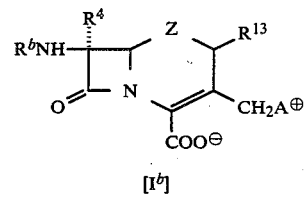

[wherein the symbol R$^b$ stands for acyl group, and the symbols Z, R$^4$, R$^{13}$, and A are of the same meaning as defined above].

This is a method of subjecting a 7-amino compound [II] to acylation with carboxylic acid R$^b$OH or a salt or reactive derivative thereof. In this method, the carboxylic acid R$^b$OH in the free form, a salt or reactive derivative thereof is used as the acylating agent of the 7-amino group of the 7-amino compound [II]. More concretely, the free acid $R^bOH$ or a reactive derivative of the free acid $R^bOH$, such as inorganic salt, organic salt, acid halide, acid azide, acid anhydride, mixed acid anhydride, active amide, active ester or active thioester is used for the acylation. There may be mentioned, among others, as inorganic salts, alkali metal salts (e.g. sodium salt, potassium salt, etc.) or alkaline earth metal salts (e.g. calcium salt, etc.); as organic salts, trimethylamine salt, triethylamine salt, tert-butyldimethylamine salt, dibenzylmethylamine salt, benzyldimethylamine salt, N,N-dimethylaniline salt, pyridine salt or quinoline salt; as acid halide, acid chloride or acid bromide; as mixed acid anhydride, mono-$C_{1-6}$ alkyl carbonic acid mixed anhydride (e.g. mixed acid anhydride of the free acid $R^bOH$ with, for example, monomethyl carbonic acid, monoethyl carbonic acid, monoisopropyl carbonic acid, monoisobutyl carbonic acid, mono-tert-butyl carbonic acid, monobenzyl carbonic acid, mono(p-nitrobenzyl)-carbonic acid, or monoallyl carbonic acid), $C_{1-6}$ aliphatic carboxylic acid mixed anhydride (e.g. mixed acid anhydride of the free acid $R^bOH$ with, for example, acetic acid, trichloroacetic acid, cyanoacetic acid, propionic acid, butyric acid, isobutyric acid, valeric acid, isovaleric acid, pivalic acid, trifluoroacetic acid, trichloroacetic acid or acetoacetic acid), $C_{7-12}$ aromatic carboxylic acid mixed anhydride (e.g. mixed acid anhydride of the free acid $R^bOH$ with, for example, benzoic acid, p-toluic acid or p-chlorobenzoic acid), organic sulfonic acid mixed anhydride (e.g. mixed acid anhydride of the free acid $R^bOH$ with, for example, methanesulfonic acid, ethanesulfonic acid, benzenesulfonic acid or p-toluenesulfonic acid); as active amide, an amide with a nitrogen-containing heterocyclic compound (e.g. acid amide of the free acid $R^bOH$ with, for example, pyrazole, imidazole or benzotriazole, these nitrogen-containing heterocyclic compounds being optionally substituted with aforementioned $C_{1-6}$ alkyl group, $C_{1-6}$ alkoxy group, halogen atom, oxo group, thioxo group or $C_{1-6}$ alkylthio group). As the active ester, those which can be used for the same purpose in the fields of β-lactam and peptide synthesis can all be used, which are exemplified by, -besides organic phosphoric acid ester (e.g. diethoxy phosphoric acid ester or diphenoxy phosphoric acid)-, p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyridone ester. The active thioester can be exemplified by esters with aromatic heterocyclic thiol compounds (e.g. 2-pyridylthiol ester, 2-benzothiazolylthiol ester, these heterocyclic rings being substituted with aforementioned $C_{1-6}$ alkyl group, $C_{1-6}$ alkoxy group, halogen atom or $C_{1-6}$ alkylthio group). On the other hand, the 7-amino compound [II] can be used as free, a salt or ester thereof. Salts of the 7-amino compound [II] are exemplified by inorganic base salts, ammonium salt, organic base salts, inorganic acid addition salts or organic acid addition salts. There may be mentioned, as inorganic base salts, alkali metal salts (e.g. sodium salts or potassium salts) and alkaline earth metal salts (e.g. calcium salts); as organic base salts, for example triethylamine salts, triethylamine salts, tert-butyldimethylamine salts, dibenzylmethylamine salts, benzyldimethylamine salts, N,N-dimethylaniline salts, pyridine salts or quinoline salts; as inorganic acid addition salts, for example hydrochlorides, hydrobromides, sulfates, nitrates or phosphates; and as organic acid addition salts, formates, acetates, trifluoroacetates, methanesulfonates, or p-toluenesulfonates. As the esters of the 7-amino compound [II], esters already referred to as ester derivatives of the compound [I] can also be counted, more concretely, $C_{1-6}$ alkyl* ester, $C_{2-6}$ alkenyl ester, $C_{3-10}$ cycloalkyl ester, $C_{3-6}$ cyclalkyl $C_{1-6}$ alkyl ester, $C_{6-10}$ aryl* ester, $C_{7-12}$ aralkyl* ester, di-$C_{6-10}$ aryl-methyl ester, tri-$C_{6-10}$ aryl-methyl ester or $C_{2-6}$ alkanoyloxy $C_{1-6}$ alkyl ester. The starting material $R^bOH$ as well as salts and reactive derivatives thereof can be easily be prepared by known methods or analogous methods thereto. A reactive derivative of the compound $R^bOH$, after isolation from the reaction mixture, can be allowed to react with a 7-amino compound [II], or as the reaction mixture containing the reactive derivative of the compound $R^bOH$ before the isolation, it can be allowed to react with a 7-amino compound [II]. When the carboxylic acid $R^bOH$ is used in the state of its free acid or salt, a suitable condensing agent is employed. As the condensing agents, there may be counted N,N'-di-substituted carbodiimides e.g. N,N'-di-cyclohexylcarbodiimide; azolides e.g. N,N'-carbonyldiimidazole or N,N'-thiocarbonyldiimidazole; dehydrating agents e.g. N-ethoxycarbonyl-2-ethoxy-1,2-dihydroquinoline, phosphorus oxychloride or alkoxyacetylene; 2-halogenopyridinium salts e.g. 2-chloropyridinium methyl iodide or 2-fluoropyridinium methyl iodide. The reactions where these condensing agents are employed are considered to proceed via reactive derivatives of the carboxylic acid $R^bOH$. These reactions are generally conducted in a solvent which does not hamper the reaction. These solvents may be exemplified by ethers such as dioxane, tetrahydrofuran, diethyl ether, tert-butyl methyl ether, diisopropyl ether or ethylene glycol dimethyl ether; esters such as ethyl formate, ethyl acetate or n-butyl acetate; halogenated hydrocarbons such as dichloromethane, chloroform, carbon tetrachloride, trichlene or 1,2-dichloroethane; hydrocarbons such as n-hexane, benzene or toluene; amides such as formamide, N,N-dimethylformamide or N,N-dimethylacetamide; ketones such as acetone, methyl ethyl ketone or methyl isobutyl ketone; or nitriles such as acetonitrile or propionitrile, and, besides, dimethyl sulfoxide, sulfolane, hexamethylphosphoramide or water, singly or in combination. The amount of acylating agent ($R^bOH$) is usually 1–5 mol., preferably 1–2 mol., relative to 1 mol. of the 7-amino compound [II]. The reaction is conducted within the temperature range of $-80° \sim 80°$ C., preferably $-40° \sim 50°$ C., most preferably $-30° \sim 30°$ C. The reaction time varies with kinds of the 7-amino compound [II] and carboxylic acid $R^bOH$, kinds of the solvent (mixture ratio as well when mixture solvents are used) and reaction temperatures, but it is usually within the range from one minute to 72 hours, preferably from 15 minutes to three hours. When an acid halide is employed as the acylating agent, the reaction can be conducted in the presence of a deacidifying agent for the purpose of eliminating from the reaction system the hydrogen halogenide to be liberated. The deacidifying agent may be exemplified by inorganic bases such as sodium carbonate, potassium carbonate, calcium carbonate or sodium hydrogen carbonate; tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine; or alkylene oxides such as propylene oxide or epichlorohydrin.

By the method mentioned above, the compound [VII] described in the foregoing can be synthesized. The reaction scheme is as follows:

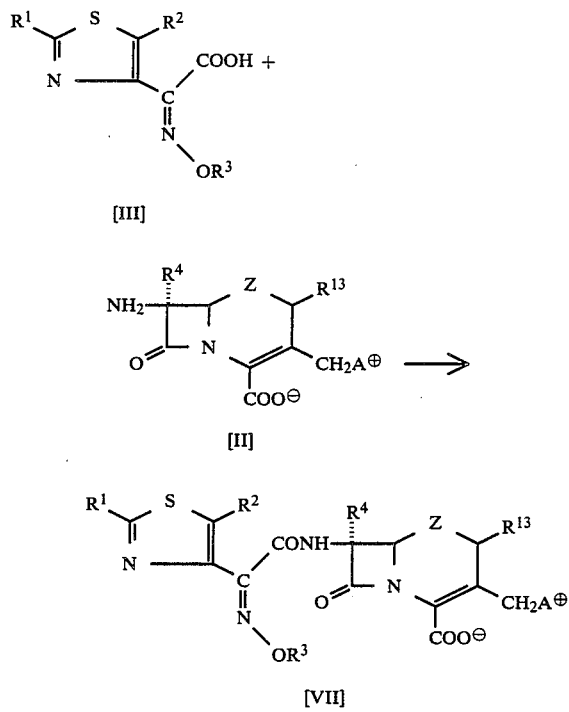

The carboxylic acid [III] can be easily prepared by a known process or a process analogous thereto.

(3-2):

By allowing a compound representable by the general formula:

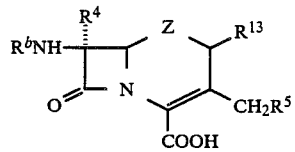

[wherein $R^b$ stands for acyl group, and other symbols are of the same meaning as defined above] or a salt or ester thereof to react with a imidazole compound of the general formula A' [A' is of the same meaning as defined above] or a salt thereof, a compound [$I^b$] ($R^0=R^b$) can be synthesized, which is shown by the following reaction scheme:

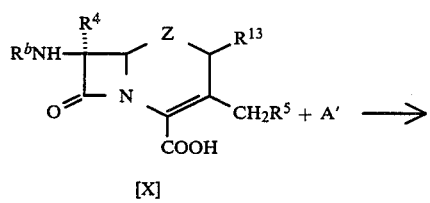

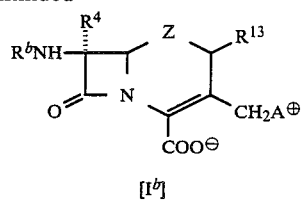

[wherein the symbol $R^b$ stands for acyl group and the symbols Z, $R^4$, $R^{13}$, $R^5$ and A are of the same meaning as defined above].

This reaction is substantially the same as that mentioned in the Production Method (1) above, namely, imidazole compound A' or a salt thereof is allowed to react with a compound [X] or a salt or ester thereof to cause nucleophilic substitution to thereby synthesize a compound [$I^b$] ($R^0=R^b$). In the compound [X], $R^5$ stands for, also here, hydroxyl group, acyloxy group, carbamoyloxy group, substituted carbamoyloxy group or halogen atom. The compound [X] can be used in the free state, or salts or esters thereof. The salts and esters of the compound [X] are those mentioned as salts and esters of the 7-amino compound [II] in the above Production Method (3-1). The compound [X], salts and esters thereof can be easily prepared by known methods or analogous ones thereto. On the other hand, the imidazole compound A' stands for an optionally substituted imidazole forming a condensed ring at the 2,3-position or the 3,4-position. The condensed ring means a form of condensation between the imidazole ring and the 5- and 6-membered aromatic heterocyclic ring. Thus-condensed ring may be further condensed with another aromatic ring or aromatic heterocyclic ring. The optionally substituted imidazole (A') forming a condensed ring at the 2,3-position or the 3,4-position may be represented by the general formula [$A^{1'}$] or [$A^{2'}$];

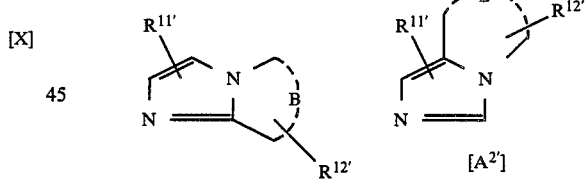

and the $A^\oplus$ group of the end-product [$I^b$] ($R^0=R^b$) to be synthesized by allowing the compound [X] to react with the compound [$A^{1'}$] stands for the afore-mentioned $A^1$ group, and the $A^\oplus$ group of the end-product [$I^b$] ($R^0=R^b$) to be synthesized by allowing the compound [X] to react with the compound [$A^{2'}$], stands for the afore-mentioned $A^2$ group. The symbol B in the formulae of condensed imidazole [$A^{1'}$] and [$A^{2'}$] is of the same meaning as that of symbol B in the [$A^1$] and [$A^2$] groups defined in the above. Hence, the compound [$A^{1'}$] is exemplified by

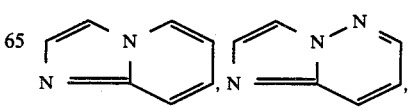

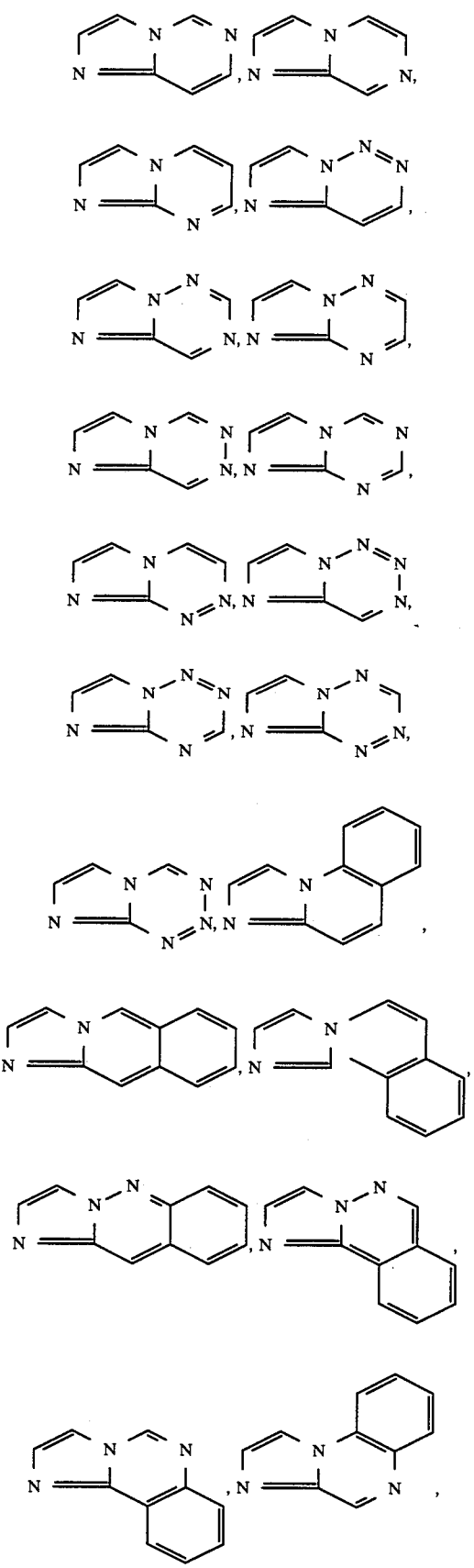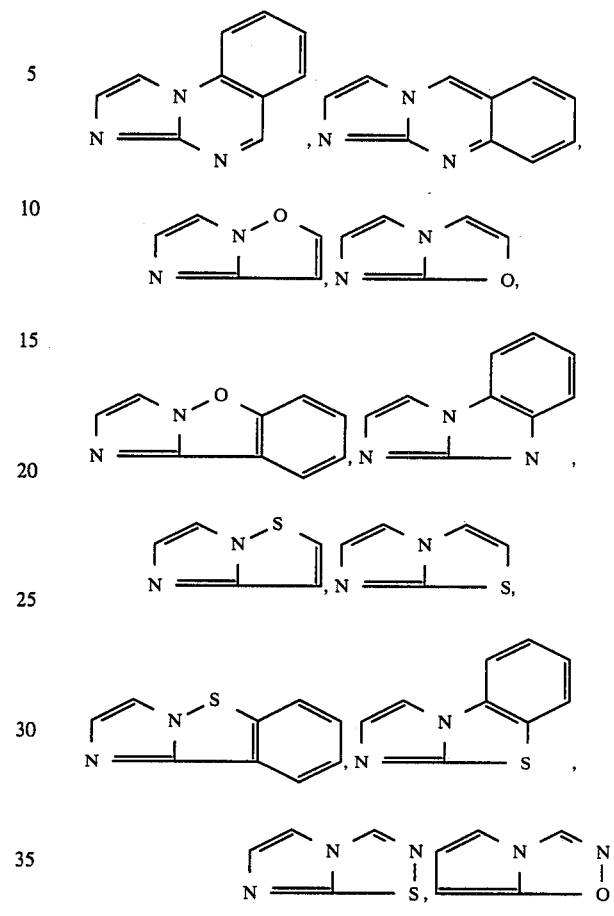
and the compound [A²'] is exemplified by
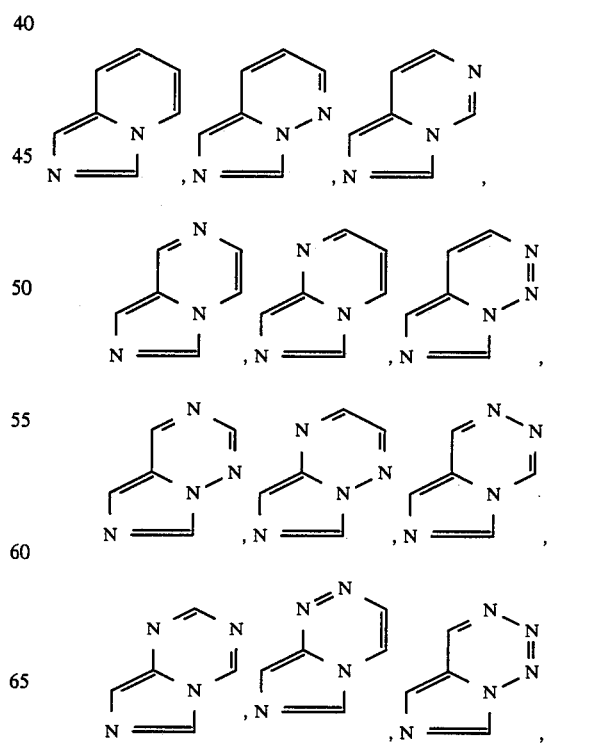

-continued

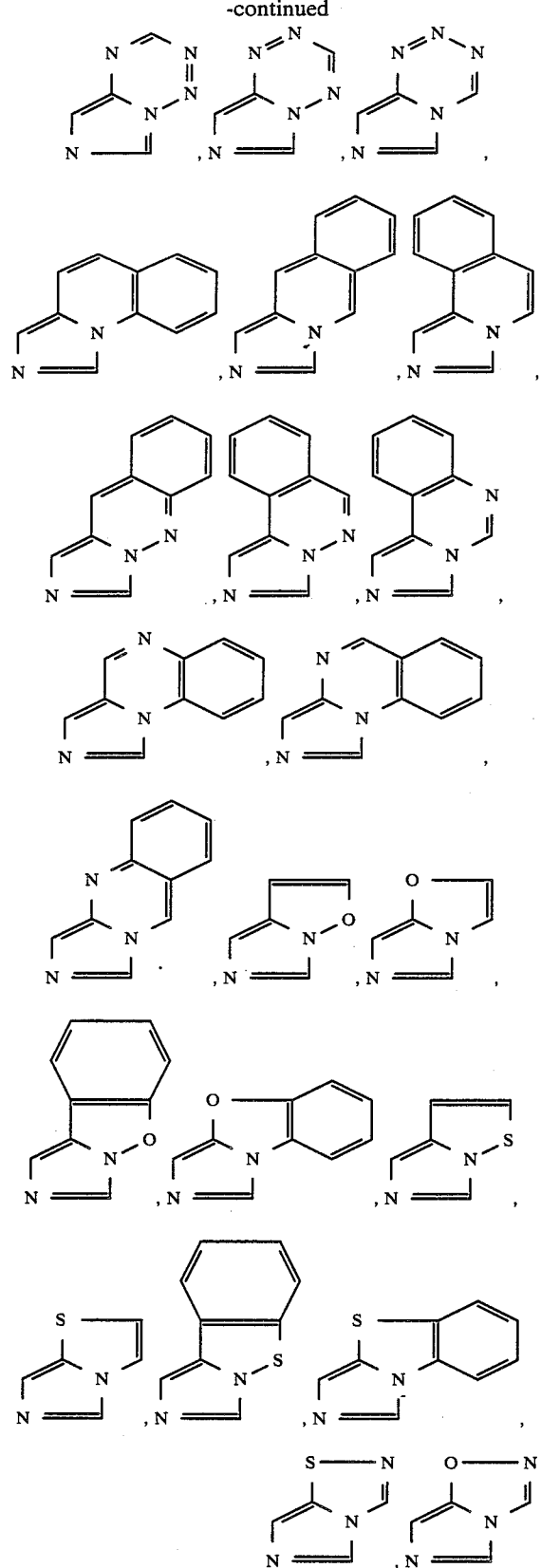

The substituents $R^{11'}$ and $R^{12'}$ on the imidazole compound A' are those mentioned as the substituents $R^{11}$ and $R^{12}$ of the group A. And, in the compound [A1'], the 5,6-position of the imidazole ring may be condensed with an alicyclic ring, aromatic ring or heterocyclic ring, which may be exemplified by

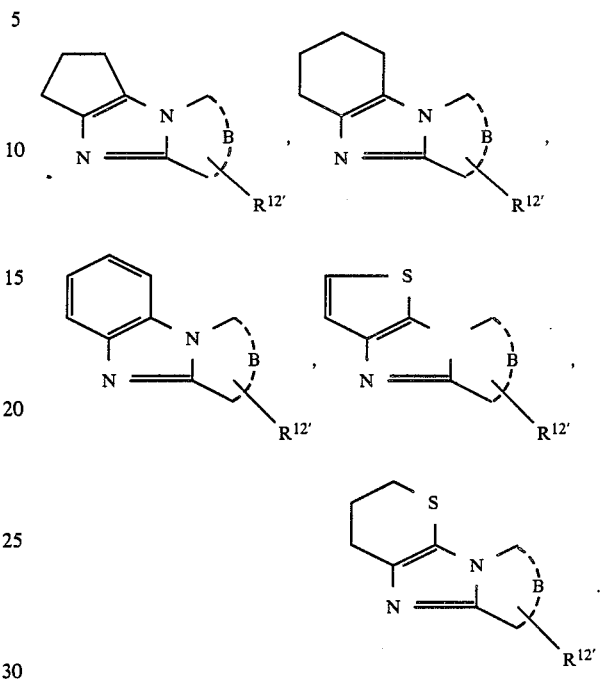

In the above, B and $R^{12'}$ are of the same meaning as defined in the foregoing. The above-mentioned substituents $R^{11'}$ and $R^{12'}$ may be further substituted. The imidazole compound A' may be used as salts thereof, which may be exemplified by inorganic acid addition salts e.g. hydrochloride, hydrobromide, sulfate, nitrate or phosphate, or organic acid addition salts e.g. formate, acetate, trifluoroacetate, methanesulfonate or p-toluenesulfonate. The imidazole compound A' and its salt may be synthesized, in general, by known methods described in literature references or by analogous methods thereto. The nucleophilic substitution to the compound [X] with the imidazole compound A' is a per se well known reaction, which is usually conducted in a solvent, for example, ethers, esters, halogenated hydrocarbons, hydrocarbons, amides, ketones, nitriles or water, which are used in the Production Method (3-1). Besides, alcohols such as methanol, ethanol, n-propanol, isopropanol, ethylene glycol or 2-methoxyethanol may be used as well. When the imidazole compound A' is in liquid state, it may be sometimes used in a large excess amount (e.g. 10–200 mol.) relative to the compound [X] to allow it to act as also the solvent. In this case, use of the above-mentioned solvents is unnecessary, or the imidazole A' may be used as a mixture solvent with any of the above-mentioned solvents.

(3-2-1): The case where $R^5$ stands for acyloxy group, carbamoyloxy group or a substituted carbamoyloxy group Preferable solvents are water and mixture solvents of water-miscible organic solvents and water. Among the water-miscible organic solvents, preferable ones are exemplified by acetone, methyl ethyl ketone and acetonitrile. The amount of the nucleophilic reagent A' is usually 1–5 mole, preferably 1–3 moles, relative to 1 mole of the compound [X]. The reaction is conducted within a temperature ranging from 10° C. to 100° C., preferably from 30° C. to 80° C. The reaction time depends on the kinds of the compound [X] and the compound A', kinds of solvents (mixture ratios when mixture solvents are used), or reaction temperature, and ranges usually from 30 minutes to five days, preferably from one hour to five hours. The reaction is advantageously conducted at pH 2–8, preferably near neutral pH, i.e., pH 5–8. The reaction readily proceeds usually in the presence of 2–30 equivalents of an iodide or thiocyanate. These salts are exemplified by sodium iodide, potassium iodide, sodium thiocyanate and potassium thiocyanate. In addition to the above exemplified salts, a surface-active quaternary ammonium salt such as trimethylbenzylammonium bromide, triethylbenzylammonium bromide or triethylbenzylammonium hydroxide may be sometimes used for allowing the reaction to proceed smoothly.

(3-2-2): The case where $R^5$ stands for hydroxyl group

The reaction is conducted in the presence of an organic phosphorus compound according to the manner described in, for example, Publication of Unexamined Patent Application (Kokai) in Japan, No. Sho 58-43979. The organic phosphorus compound is exemplified by o-phenylene phosphorochloridate, o-phenylene phosphorofluoridate, methyl o-phenylene phosphate, ethyl o-phenylene phosphate, propyl o-phenylene phosphate, isopropyl o-phenylene phosphate, butyl o-phenylene phosphate, isobutyl o-phenylene phosphate, sec.-butyl o-phenylene phosphate, cyclohexyl o-phenylene phosphate, phenyl o-phenylene phosphate, p-chlorophenyl o-phenylene phosphate, p-acetylphenyl o-phenylene phosphate, 2-chloroethyl o-phenylene phosphate, 2,2,2-trichloroethyl o-phenylene phosphate, ethoxycarbonylmethyl o-phenylene phosphate, carbamoylmethyl o-phenylene phosphate, 2-cyanoethyl o-phenylene phosphate, 2-methylsulfonylethyl o-phenylene phosphate, benzyl o-phenylene phosphate, 1,1-dimethyl-2-propenyl o-phenylene phosphate, 2-propenyl o-phenylene phosphate, 3-methyl-2-butenyl o-phenylene phosphate, 2-thienylmethyl o-phenylene phosphate, 2-furfurylmethyl o-phenylene phosphate, bis-o-phenylene pyrophosphate, 2-phenyl-1,3,2-benzodioxaphosphole-2-oxide, 2-(p-chlorophenyl)-1,3,2-benzodioxaphosphole-2-oxide, 2-butyl-1,3,2-benzodioxaphosphole-2-oxide, 2-anilino-1,3,2-benzodioxaphosphole-2-oxide, 2-phenylthio-1,3,2-benzodioxaphosphole-2-oxide, 2-methoxy-5-methyl-1,3,2-benzodioxaphosphole-2-oxide, 2-chloro-5-ethoxycarbonyl-1,3,2-benzodioxaphosphole-2-oxide, 2-methoxy-5-ethoxycarbonyl-1,3,2-benzodioxaphosphole-2-oxide, 5-ethoxycarbonyl-2-phenyl-1,3,2-benzodioxaphosphole-2-oxide, 2,5-dichloro-1,3,2-benzodioxaphosphole-2-oxide, 4-chloro-2-methoxy-1,3,2-benzodioxaphosphole-2-oxide, 2-methoxy-4-methyl-1,3,2-benzodioxaphosphole-2-oxide, 2,3-naphthalene methyl phosphate, 5,6-dimethyl-2-methyoxy-1,3,2-benzodioxaphosphole-2-oxide, 2,2-dihydro-4,5,6,7-tetrachloro-2,2,2-trimethoxy-1,3,2-benzodioxaphosphole, 2,2-dihydro-4,5,6,7-tetrachloro-2,2,2-triphenoxy-1,3,2-benzodioxaphosphole, 2,2-dihydro-2,2-ethylenedioxy-2-methoxy-1,3,2-benzodioxaphosphole, 2,2-dihydro-benzyl-1,2,2-dimethoxy-1,3,2-benzodioxaphosphole, 2,2-dihydro-4,5-benzo-2,2,2-trimethoxy-1,3,2-benzodioxaphosphole, 2,2-dihydro-2,2,2-triphenoxy-1,3,2-benzodioxaphosphole, 2,2-dihydro-2,2,-(o-phenylenedioxy)-2-phenoxy-1,3,2-benzodioxaphosphole, 2-chloro-2,2-dihydro-2,2-(o-phenylenedioxy)-1,3,2-benzodioxaphosphole 2,2-dihydro-2-methoxy-2,2-(o-phenylenedioxy)-1,3,2-benzodioxaphosphole, 2,2,-dihydro-2,2,2-trichloro-1,3,2-benzodioxaphosphole, 9,10-phenanthrenedioxytrimethoxyphosphorus, o-phenylen phosphorochloridite, o-phenylene phosphorobromidite, o-phenylene phosphorofluoridite, methyl o-phenylene phoshite, butyl o-phenylene phosphite methoxycarbonylmethyl o-phenylene phosphite, phenyl o-phenylene phosphite, p-chloro (or p-nitro)phenyl o-phenylene phosphite, 2-phenyl-1,3,2-benzodioxaphosphole, bis-o-phenylene pyrophosphite, 2-methoxy-5-methyl-1,3,2-benzodioxaphosphole, 5-acetyl-2-phenoxy-1,3,2-benzodioxaphosphole, 9,10-phenanthrene phosphorochloridite, 2-chloro-4-methyl-1,3,2-benzodioxaphosphole, 5-ethoxycarbonyl-2-phenyl-1,3,2-benzodioxaphosphole, 2-chloro-2-thioxo-1,3,2-benzodioxaphosphole, 2-phenoxy-2-oxo-1,3,2-benzodiazaphosphole, 2-phenoxy-1,3,2-benzodioxaazaphosphole, 2,2-dihydro-2-oxo-2-methoxy-4,5-dimethyl-1,3,2-dioxaphosphole, 2,2-dihydro-2-oxo-2-chloro-4,5-dimethyl-1,3,2-dioxaphosphole, 2,2-dihydro-2-oxo-2-(1-imidazolyl)-4,5-dimethyl-1,3,2-dioxaphosphole, 2,2-dihydro-2,2-ethylenedioxy-2-methoxy-4,5-dimethyl-1,3,2-dioxaphosphole, 2,2-dihydro-2,2-dimethoxy-2-phenoxy-4,5-dimethyl-1,3,2-dioxaphosphole, 2,2-dihydro-2,2,2-trimethoxy-4,5-dimethyl-1,3,2-dioxaphosphole, 2,2-dihydro-2,2,2-triphenoxy-4,5-dimethyl-1,3,2-dioxaphosphole, 2,2-dihydro-2,2,2-triethoxy-4,5-diphenyl-1,3,2-dioxaphosphole, 2,2-dihydro-2,2,2-trimethoxy-4,5-diphenyl-1,3,2-dioxaphosphole, 2,2-dihydro-2-oxo-2-methoxy-4,5-diphenyl-1,3,2-dioxaphosphole, 2,2-dihydro-2,2,2-trimethoxy-1,3,2-dixoaphosphole, 2,2-dihydro-2,2,2-trimethoxy-4-phenyl-1,3,2-dioxaphosphole, 2,2-dihydro-2,2,2-trimethoxy-4-methyl-1,3,2-dioxaphosphole, 2,2-dihydro-2,2,2-trimethoxy-4-methyl-5-phenylcarbamoyl-1,3,2-dioxaphosphole, 2,2,4,5,6,7-hexahydro-2,2,2-trimethoxy-1,3,2-benzodioxaphosphole, 2,2'-oxybis(4,5-dimethyl-2,2-dihydro-1,3,2-dixoaphosphole) and 2,2'-oxybis(4,5-dimethyl-2,2-dihydro-1,3,2-dioxaphosphole-2-oxide).

For the reaction, any solvent can be employed if only it does not hamper the reaction, and, preferably, the afore-mentioned ethers, esters, halogenated hydrocarbons, hydrocarbons, amides, ketones and nitriles may be used singly or in a mixture thereof. Especially, use of dichloromethane, acetonitrile, formamide, a mixture of formamide and aceonitrile, or a dichloromethane and acetonitrile brings about a preferable result. The amounts of the nucleophilic reagent A' and the organic phosphorus compound are respectively, relative to 1 mole of the compound [X], 1–5 moles and 1–10 moles, more preferably 1–3 moles and 1–6 moles. The reaction is conducted within the temperature range from −80° C. to 50° C., preferably from −40° C. to 40° C. The reaction time is usually within the range of one minute to 15 hours, preferably five minutes to two hours. To the reaction system may be added an organic base. As the organic base may be exemplified amines such as triethylamine, tri-(n-butyl)amine, di-(n-butyl)amine, diisobutylamine, dicyclohexylamine or 2,6-lutidine. The amount of the base to be added is preferably 1–5 moles relative to 1 mole of the compound [X].

(3-2-3): The case where $R^5$ stands for halogen atom

Preferable solvents are the afore-mentioned ethers, esters, halogenated hydrocarbons, hydrocarbons, amides, ketones, nitriles, alcohols and water. The amount of the nucleophilic reagent A' to be used is usually, relative to one mole of the compound [X], 1–5 moles, preferably 1–3 moles. The reaction is conducted within a temperature range of 0°–80° C., preferably 20°–60° C.

The reaction time is usually 30 minutes to 15 hours, preferably 1–5 hours. For accelerating the reaction, the reaction may be conducted in the presence of a dehalogenating agent. As such dehalogenating agents, there may be counted deacidifying agents such as inorganic bases, tertiary amines and alkylene oxides mentioned in the Production Method (3-1), while the nucleophilic reagent A' itself may be allowed to act as the dehalogenating agent also. In this case, the compound A' is used in an amount of two moles or more relative to one mole of the compound [X]. The halogen atom shown by $R^5$ is exemplified by chlorine, bromine and iodine, and preferably iodine. The compound [X] wherein $R^5$ stands for iodine can be easily produced in accordance with the method described in, for example, Publication of Unexamined Patent Application (Kokai) in Japan, No. Sho 58-57390 or a method analogous thereto.

By the method described here, the afore-mentioned compound [VII] or [VIII] for example can be synthesized. The reaction schemes are as follows:

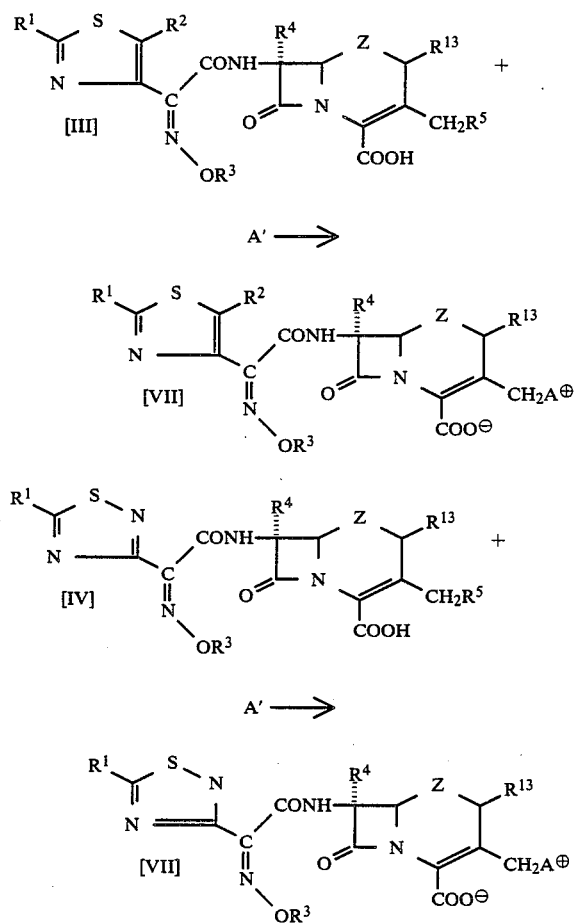

The compounds [III] and [IV] can be easily prepared by a known method or a method analogous thereto.

The following compound [XI] including the compounds [VII] and [VIII] can also be prepared by, besides the above-mentioned Production Method (3-1) or (3-2), the Production Method (3-3) to be described later. The compound [VII] can also be prepared by, besides the Production Method (3-1), (3-2) or (3-3), the Production Method (3-4) to be described later.

(3-3):

The reaction scheme is as follows:

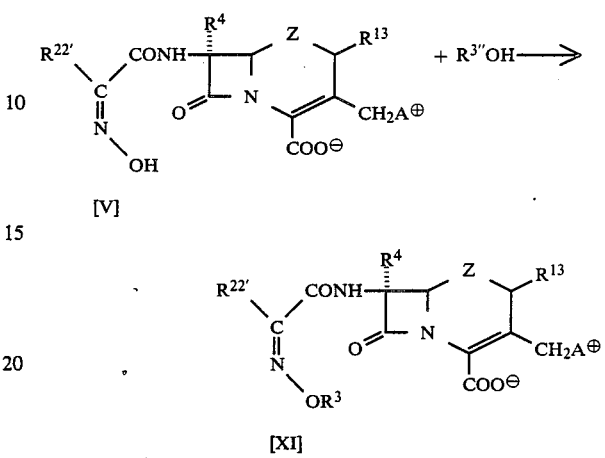

[wherein the symbol $R^{22'}$ stands for an optionally substituted heterocyclic group, and the symbols Z, $R^4$, $R^{13}$, A and $R^3$ are of the same meaning as defined above].

This is a method of synthesizing the compound [XI] by allowing a compound representable by the general formula of $R^{3''}$ OH or a reactive derivative thereof to react with a hydroxyimino compound [V], which is a well-known etherifying reaction provided that, when $R^{22'}$ stands for

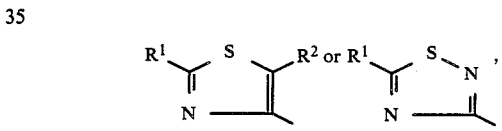

the resultant compounds [XI] are respectively [VII] or [VIII]. $R^{3''}$ stands for an optionally substituted hydrocarbon residue which is the same as that referred to in $R^3$. $R^{3''}$OH may be employed as it is or as a reactive derivative thereof. Reactive derivatives of $R^{3''}$OH are representable by the general formula $R^{3''}$Y, having a group to be liberated together with the hydrogen atom of the hydroxyimino compound [V]. The group Y to be liberated together with hydrogen atom may be exemplified by halogen atom, sulfo group or mono-substituted sulfonyloxy group. The halogen atom may be exemplified by chlorine, bromine or iodine. The mono-substituted sulfonyloxy group may be exemplified by $C_{1-6}$ alkylsulfonyloxy and $C_{6-10}$ arylsulfonyloxy groups e.g. methanesulfonyloxy, ethanesulfonyloxy, benzenesulfonyloxy or p-toluenesulfonyloxy. When a $C_{1-4}$ alkylether derivative of the compound [V] is intended, there may be used, besides the above-mentioned reaction derivatives, $C_{1-4}$ diazoalkane such as diazomethane or diazoethane, and di-$C_{1-4}$ alkyl sulfate such as dimethyl sulfate or diethyl sulfate.

The compound [V] can be prepared by the acylation as mentioned above in The Production Method (3-1) or the nucleophilic substitution as mentioned above in the Production Method (3-2). The reaction schemes are as follows, respectively:

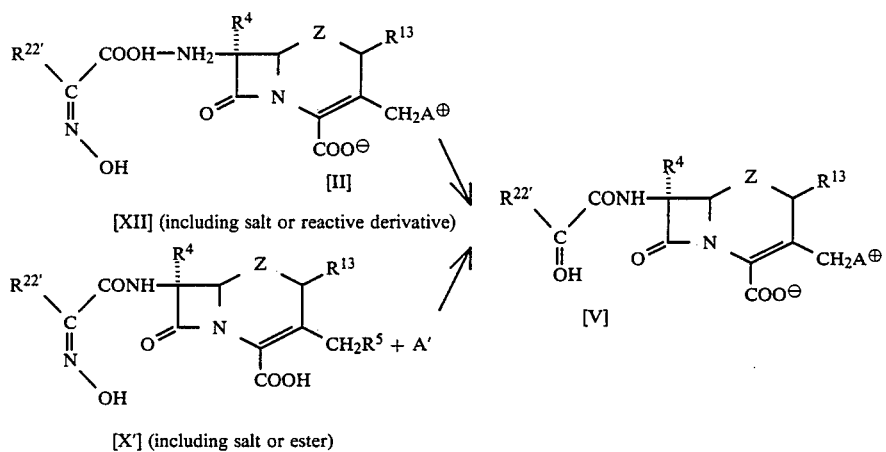

[XII] (including salt or reactive derivative)

[X'] (including salt or ester)

[V]

The starting materials [XII] and [X'] can be easily prepared by a known method or an analogous one thereto. The compound $R^{3''}OH$ and the reactive derivative thereof can also be easily prepared by a known method or an analogous one thereto.

(3-3-1): The case where $R^{3''}OH$ is used

A suitable dehydrating agent is allowed to react with a hydroxyimino compound [V] to synthesize a compound [XI]. The dehydrating agent may be exemplified by phosphorus oxychloride, thionyl chloride, dialkyl azodicarboxylate (usally used in the presence of phosphine) or N,N-dicyclohexylcarbodiimide, and preferably diethyl azodicarboxylate in the presence of triphenyl phosphine. The reaction in which diethyl azodicarboxylate is used in the presence of triphenyl phosphine is usually conducted in an anhydrous solvent such as ethers or hydrocarbons mentioned above. Relative to 1 mole of the compound [V], 1-1.5 mole each of the compound $R^{3''}OH$, ethyl azodicarboxylate and triphenyl phosphine is employed. The reaction requires 1-4 days at a temperature range of 0°-50° C.

(3-3-2): The case where $R^{3''}Y$ is used

The reaction between $R^{3''}Y$ and a hydroxyimino compound [V] is a conventional etherification reaction, which is conducted in a solvent. The solvent is exemplified also here by those as mentioned in the Production Method (3-1) above, i.e., ethers, esters, hydrogenated hydrocarbons, hydrocarbons, amides, ketones, nitriles, alcohols, water or a mixture of any of them, preferably a mixture solvent of a water-miscible solvent and water (e.g. aqueous methanol, aqueous ethanol, aqueous acetone and aqueous dimethyl sulfoxide). The reaction may also be allowed to proceed smoothly in the presence of a suitable base. The base may be exemplified by inorganic bases such as alkali metal salts e.g. sodium carbonate, sodium hydrogencarbonate or potassium carbonate, or alkali metal hydroxides e.g. sodium hydroxide or potassium hydroxide. This reaction may be conducted in a buffer solution of pH 7.5-8.5. The mole numbers of a reagent $R^{3''}Y$ and the base relative to 1 mole of the starting compound [V] are respectively 1-5 and 1-10, preferably 1-3 and 1-5, respectively. The reaction temperature is in the range from −30° C. to 100° C., preferably, 0° C. to 80° C. The reaction time ranges from 10 minutes to 15 hours, preferably from 30 minutes to 5 hours.

(3-3-3): The case where $C_{1-4}$ diazoalkane is used

The reaction is usually conducted in a solvent. As the solvent are employed, the afore-mentioned ethers and hydrocarbons. A hydroxyimino compound [V] is dissolved in a solvent, to which is then added a solution of a diazoalkane compound, whereupon the reaction proceeds. The reagent is used, relative to 1 mole of the compound [V], in an amount of 1-10 moles, preferably 1-5 moles. The reaction is conducted at a relatively low temperature range of from −50° C. to 20° C., preferably from −30° C. to 0° C. The reaction time ranges from 1 minute to 5 hours, preferably 10 minutes to one hour.

(3-3-4): The case where di-$C_{1-4}$ alkylsulfate is used

The reaction is conducted usually in water or a mixture solvent of a water-miscible solvent and water. As the mixture solvent are mentioned those mentioned in the Production Method (3-3-2). This reaction is usually conducted in the presence of an inorganic base, for example, an alkali metal hydroxide such as sodium hydroxide and potassium hydroxide. The reagent is used in an amount of 0.5-10 moles, preferably 1-2 moles, relative to 1 mole of the compound [V]. The reaction temperature ranges from 20° C. to 100° C., preferably 50°-100° C. The reaction time ranges from 10 minutes to 5 hours, preferably from 30 minutes to 3 hours.

(3-4):

The reaction scheme is as follows:

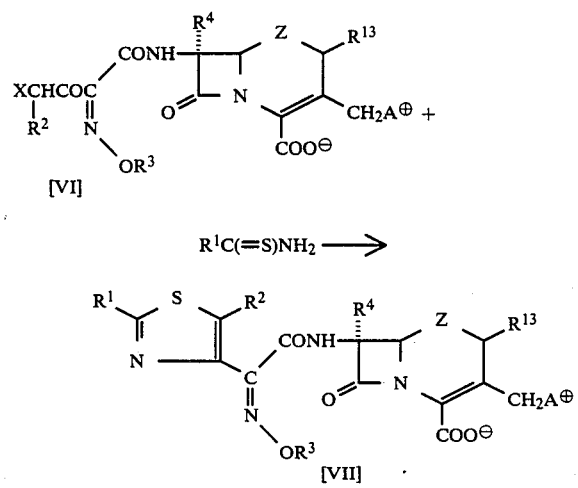

[wherein the symbols Z, $R^4$, $R^{13}$, A, $R^1$, $R^2$ and $R^3$ are of the same meaning as defined above].

This is a method of synthesizing the end product [VII] by allowing a compound [VI] to react with thiourea representable by the general formula $R^1C(=S)NH_2$ or a derivative thereof. The compound [VI] is employed in its free state or as a salt or ester thereof. X in the compound [VI] stands for a halogen atom e.g. chlorine, bromine or iodine. As salts of the compound [VI] are mentioned those (inorganic base salts, ammonium salt, organic base salts, inorganic acid addition salts or organic acid addition salts, for example) of the 7-amino compound [II] exemplified in the Production Method (3-1). As esters of the compound [VI] as well, are mentioned those of the 7-amino compound [II] exemplified in the Production Method (3-1) ($C_{1-6}$ alkyl* ester, $C_{2-6}$ alkenyl ester, $C_{3-10}$ cycloalkyl ester, $C_{3-6}$ cycloalkyl $C_{1-6}$ alkyl ester, $C_{6-10}$ aryl* ester, $C_{7-12}$ aralkyl* ester, di-$C_{6-10}$ aryl-methyl ester, tri-$C_{6-10}$ arylmethyl ester and $c_{2-6}$ alkanoyloxy $C_{1-6}$ alkyl ester). The starting compound [VI] can be prepared by allowing a compound representable by the general formula:

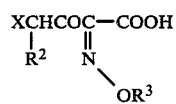

wherein the symbols are of the same meaning as defined above or a salt or reactive derivative thereof to react with the afore-mentioned 7-amino compound [II] or a salt or ester thereof according to the manner as described in the Production Method (3-1) above. Compounds representable by the general formula;

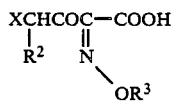

or reactive derivatives thereof can be easily prepared by a per se conventional process or an analogous one thereto. The reaction between a compound [VI] and $R^1C(=S)NH_2$ is usually conducted in a solvent. The solvent may be exemplified by ethers such as dioxane, tetrahydrofuran and diethyl ether, alcohols such as methanol, ethanol and n-propanol, or amides such as dimethylformamide and dimethylacetamide. The amount of thiourea or a reactive derivative thereof representable by $R^1C(=S)NH_2$ is usually, relative to the compound [VI], 1-5 moles, preferably 1-3 moles. The reaction is conducted at temperatures ranging from 0° C. to 100° C., preferably 20°-60° C. The reaction time usually ranges from 30 minutes to 15 hours, preferably 1-5 hours.

When the compounds [$I^b$] produced by the above-mentioned Production Methods (3-1) to (3-4) have hydroxyimino (or substituted hydroxyimino) group in the substituent $R^b$, e.g. in the case of the compounds [VII], [VIII] and so on, there may sometimes be the cases where the compounds [$I^b$] are obtained as a mixture of syn[Z]- and anti[E]-isomers.

In the above-mentioned Production Method (3-1)-(3-4), there may sometimes be the cases where the compound [XI] including the compounds [VII] and [VIII] are obtained as a mixture of syn[Z]- and anti[E]-isomers. For isolating the desired syn-isomer from the mixture, a per se known process or analogous ones thereto may be employed. These processes may be exemplified by fractionation by utilizing the differences in, for example, solubilities or crystallizability, isolation by means of chromatography, or isolation utilizing the differences in hydrolysis rates between the respective ester derivatives.

Production Method (4): Compound [I] ($R^0=R^c$; $R^c$ denotes esterified carboxyl group)

For example, (4-1): By allowing the 7-amino compound [II] ([I], $R^0$=hydrogen atom) obtained by the above Production Method (1) or a salt or ester thereof to react with an oxycarbonylation reagent, a compound [I] ($R^0=R^c$) can be synthesized. The oxycarbonylation reagent

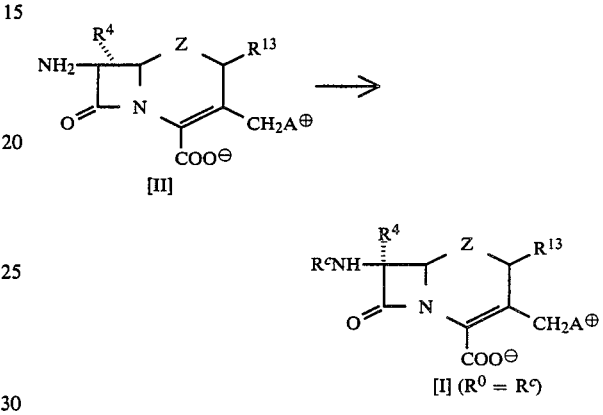

is exemplified by substituted oxycarbonyl halide (e.g. chlorine, bromine or iodine as halogen), substituted oxycarbonyl azide, substituted oxycarbonic anhydride, substituted oxycarbonyl sulfide or substituted oxycarbonyl azolide (e.g. imidazole, N-methylimidazole, triazole, 2-thiooxazolidine or 2-oxoxazolidine as azole). The reaction is conducted usually in a solvent, preferably an anhydrous solvent. As such solvents, use is often made of ethers, e.g. dioxane, tetrahydrofuran, diethyl ether, tert-butyl methyl ether, diisopropyl ether or ethylene glycol dimethyl ether, halogenated hydrocarbons e.g. dichloroethane, chloroform, carbon tetrachloride, trichlene or 1,2-dichloroethane, nitriles, e.g. acetonitrile, alcohols e.g. methanol, ethanol, propanol or butanol, hydrocarbons, e.g. n-hexane, benzene or toluene, amides e.g. dimethylformamide, dimethylacetamide or hexamethylphosphorus triamide, or sulfoxides e.g. dimethyl sulfoxide, singly or as a mixture solvent. The amount of the oxycarbonylation reagent is usually, relative to 1 mole of the 7-amino compound [II], 1-5 moles, preferably 1-2 moles. The reaction is conducted within the temperature range of from −80° C. to 80° C., preferably from −40° C. to 50° C., most preferably from −30° C. to 30° C. While the reaction time varies with kinds of the 7-amino compound [II] and the oxycarbonylation reagents, kinds of solvents and reaction temperatures, it ranges from one minute to 48 hours, preferably from ten minutes to two hours. When a substituted oxycarbonyl halide is employed as the oxycarbonylation reagents, the reaction may be conducted in the presence of a deacidifying agent for the purpose of eliminating from the reaction system the hydrogen halogenide to be liberated. The deacidifying agent may be exemplified by inorganic bases such as sodium carbonate, potassium carbonate, calcium carbonate or sodium hydrogencarbonate; tertiary amines such as triethylamine, tri-(n-propyl)amine, tri-(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine; or alkylene oxides such as propylene oxide or epichlorohydrin.

(4-2): By following the compound [XII] or a salt or ester thereof to react with the imidazole compound A' [A' is of the same meaning as defined above] or a salt thereof, a compound [I$^c$] (R$^0$=R$^c$) can also be synthesized.

The reaction is shown by the following scheme:

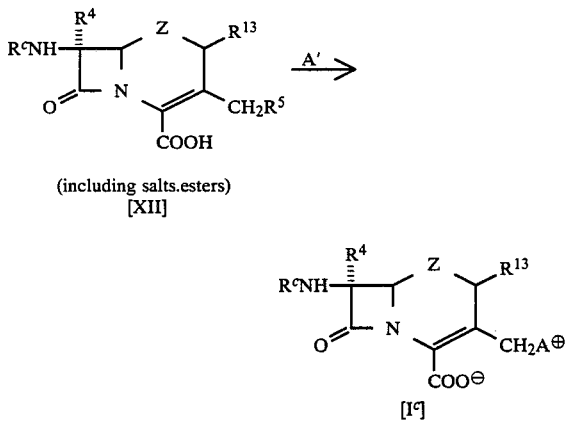

(including salts.esters)
[XII]

[I$^c$]

[wherein the symbols are of the same meaning as defined above].

This reaction substantially the same as that mentioned in the Production Methods (1) and (3-2). The starting compound [XII], salts and esters thereof can be easily prepared by the same procedure as described in the production Method (4-1) above, namely, the oxycarbonylation reagent is allowed to react with a compound [IX] or a salt or ester thereof to synthesized the compound [XII].

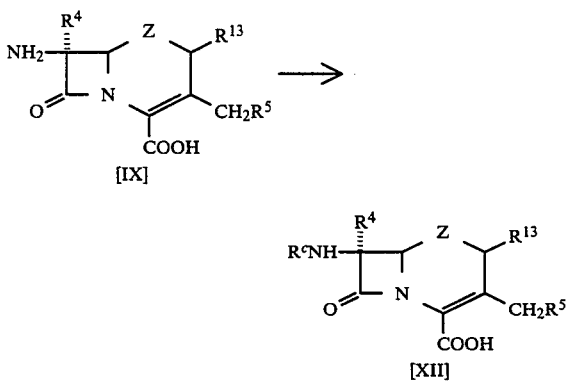

[IX]

[XII]

After the above-mentioned Production Method (1)–(4), when required, removal of protecting groups and purification are conducted to obtain the end product [I] of this invention. Methods of removing protecting groups and purification are described as follows:

Process of removing protecting group: As aforementioned, in the fields of β-lactam and peptide syntheses, amino-protecting groups have been sufficiently studied, and the method of protecting amino groups has been established. The method of removing the amino-protecting group has also been established, and, in the present invention as well, for removing protecting groups, conventional technique can be used as such. For example, monohalogenoacetyl group (chloroacetyl, bromoacetyl, etc.) can be removed by using thiourea; alkoxycarbonyl group (methoxycarbonyl, ethoxycarbonyl, tert-butoxycarbonyl, etc.) can be removed by using an acid (e.g. hydrochloric acid); aralkyloxycarbonyl group (e.g. benzyloxycarbonyl, p-methylbenzyloxycarbonyl or p-nitrobenzyloxycarbonyl) can be removed by means catalytic reduction; and 2,2,2-trichloroethoxycarbonyl can be removed by using zinc and an acid (e.g. acetic acid). On the other hand, in the case when the compound [I] as the intermediate has been esterified, the ester residue can be removed by a per se known process or an analogous one thereto. For example, 2-methylsulfonylethyl ester can be removed by using an alkali; aralkyl ester (benzyl ester, p-methyoxybenzyl ester, p-nitrobenzyl ester, etc.) can be removed by using an acid (e.g. trifluoroacetic acid) or by means of catalytic reduction; 2,2,2-trichloroethyl ester can be removed by using zinc and an acid (e.g. acetic acid); and silyl ester (e.g. trimethylsilyl ester or tert-butyldimethylsilyl ester) can be removed by using only water.

Process of purifying the compound [I]: The compound [I] produced in the reaction mixture by any of the processes described in detail in the foregoing Production Methods (1)–(4) and, upon necessity, followed by removal of protecting groups by conducting the above-mentioned process, can be isolated and purified by a known process such as extraction, column-chromatography, precipitation and recrystallization. On the other hand, the compound [I] thus isolated can be converted into then desired physiologically acceptable ssalts or bioavailably unstable non-toxic esters.

Sulfoxide ([I], Z=S→O) of the cephem compound ([I], Z=S) can be prepared by subjecting the compound ([I], Z=S) to a conventional oxidation. Oxidizing agents suitable for oxidation of sulfur atom of the cephem ring are exemplified by oxygen, peracid, hydroperoxide, or hydrogen peroxide, and the peracid may be given by mixing an acid with a peroxide in the reaction system of the oxidation. As such peracids, use is often made of peracetic acid, perbenzoic acid or p-chloroperbenzoic acid. The reaction is usually conducted in a solvent which is exemplified by ethers such as dioxane or tetrahydrofuran; halogenated hydrocarbons such as dichloromethane, chloroform or chlorobenzene; organic acids such as formic acid, acetic acid trifluoroacetic acid; or amides such as dimethylformamide or dimethylacetamide. The reaction temperature ranges from −20° C. to 80° C., and preferably a temperature as low as possible, i.e. ranging from −20° C. to 20° C. It is generally known that, when the cephem compound ([I], Z=S) is subjected to oxidation, sulfoxide having an S-configuration is produced. The R- and S-sulfoxide can be separated by utilizing the difference in solubility between them or the difference in travelling rate in chromatography. The above-mentioned oxidation to give sulfoxide can be conducted before or after the afore-mentioned Production Methods (1)–(4).

The compound [I] including compounds [VII] and [VIII] of this invention can be administered orally or non-orally as injections, capsules, tablets or granules, like known penicillin and cephalosporin preparations. The dosage is 0.5–80 mg/day, preferably 1–20 mg/day in 3–4 doses relative to one kilogram of the body weight of men and animals infected with pathogenic bacteria as set forth above. Carriers of injectable preparations are exemplified by distilled water or physiological saline. When used as capsule, powder, granule or tablet, the compound [I] is mixed with conventional pharmaceutically acceptable excipients (e.g. starch, maltose, sucrose, calcium carbonate or calcium phosphate), binders (e.g. starch, gum-arabica, carboxymethylcellulose, hydroxypropylcellulose or crystalline cellulose), lubricants (e.g. magnesium stearate or talc) and disintegrators (e.g. carboxymethyl calcium or talc).

A pharmaceutical composition containing the compound [I] is made by a known procedure. The composition is usually produced by mixing at least one of the compounds [I] or their salts or esters with the above carriers or excipients. The ratio of the compound [I] to the whole composition is usually 5 to 100%(w/w), preferably 20 to 100%(w/w) in solid composition such as capsules, tablets and granules, 5 to 30%(w/w) in liquid composition such as injections etc.

The compound [I] or its physiologically or pharmaceutically acceptable salt or ester is preferably administered as an injection for example for combatting against urinary tract infections caused by *Escherichia coli*. In this case, the dosage amount is in the range of from 1 to 20 mg/kg in 3 to 4 divided doses relative to one kilogrum of the body weight of adult human. The injection is easily prepared by dissolving or suspending the compound [I], its salt or ester into physiological saline.

The present invention will be further explained by the following Reference Examples and Working Examples, but those Examples are mere examples and not to restrict the present invention in any manner, including variations to such extent as not deviating the scope of this invention.

Elution in column-chromatography in the Reference Examples and Working Examples was conducted under observation by means of TLC (Thin-Layer Chromatography), wherein were employed $BOF_{254}$ (manufactured by E. Merck) as TLC plate, the solvent for elution in the column-chromatography as developing solvent, and a UV detector as detecting means. As silica-gel for the column, Kieselgel 60 (230-400 mesh) manufactured by E. Merck was employed. "Cephadex" is a product of Pharmacia Fine Chemicals. XAD-2 resin is a product of Rohm & Haas Co. NMR spectrum was determined by XL-100A (100 MHz)-, EM390 (90 MHz)-, EM360 (60 MHz)- or $T_{60}$(60 MHz)-type spectrometer using tetramethylsilane as internal or external standard, and all the δ values were shown by ppm. The numeral values parenthesized for mixture solvents mean the ratio by volume of each solvent mixed. "%" for solvents means number of grams in 100 ml of each solution. Symbols in the Reference Examples and Working Examples have respectively the meanings as follows:

s: singlet
d: doublet
t: triplet
q: quartet
Abq: AB type quartet
d.d: double doublet
m: multiplet
br: broad
J: coupling constant
Hz: Herz
mg: milligram
g: gram
ml: milliliter
l: liter
%: percent
DMSO: dimethylsulfoxide
$D_2O$: deuterium oxide
$CDCl_3$: deuterochloroform

REFERENCE EXAMPLE 1

7β-[2-(2-Chloroacetamidothiazol-4-yl)-2(Z)-methoxyiminoacetamido]-3-(3-oxobutyryloxymethyl)-3-cephem-4-carboxylic acid In a mixture of 500 ml of tetrahydrofuran and 500 ml of water is suspended 157 g of 7β-amino-3-(3-oxobutyryloxymethyl)-3-cephem-4-carboxylic acid. To the suspension is added little by little 141 g of sodium hydrogen carbonate with stirring. To the mixture is added 150 g of 2-(2-chloroacetamidothiazol-4-yl)-2(Z)-methoxyiminoacetyl chloride hydrochloride at 5° C., during 20 minutes with stirring, and the mixture is stirred for further one hour. After completion of the reaction, the reaction mixture is adjusted to pH 3.0 with 10% hydrochloric acid, and extracted twice with 1 l portions of a mixture is ethyl acetate-tetrahydrofuran (1:1). The extract is dried over anhydrous magnesium sulfate, and then the solvent is evaporated off under reduced pressure to leave colorless power, which is triturated with 200 ml of ethyl acetate and collected by filtration to afford 253 g of the above-identified compound.

Elemental analysis for $C_{20}H_{20}ClN_5O_9S_2$: Calcd. (%): C, 41.85; H, 3.51; N, 12.20. Found (%): C, 41.39; H, 3.57; N, 11.94.

IR spectrum $\nu_{max}^{KBr}cm^{-1}$; 1780, 1740, 1655, 1540, 1410.

NMR spectrum ($d_6$-DMSO)δ: 2.20(2H, s), 3.45 and 3.68(2H, ABq, J=18 Hz), 3.65(2H, s), 3.92(3H, s), 4.38(2H, s), 4.79 & 5.09(2H, ABq, J=13 Hz), 5.18(1H, d, J=5 Hz), 5.85(1H, d.d, J=5 Hz & 8 Hz), 7.44(1H, s), 9.66(1H, d, J=8 Hz), 12.85(1H, br.s).

REFERENCE EXAMPLE 2

7β-[2-(2-Aminothiazol-4-yl)-2(Z)-methoxyiminoacetamido]-3-(3-oxobutyryloxymethyl)-3-cephem-4-carboxylic acid In 500 ml of a mixture of tetrahydrofuran-water (1:1) is dissolved 150 g of 7β-2-[2-(chloroacetamidothiazol-4-yl)-2(Z)-methoxyiminoacetamido]-3-(3-oxobutyryloxymethyl)-3-cephem-4-carboxylic acid. To the solution is added 51 g of sodium N-methyldithiocarbamate, and the mixture is stirred at 20° C. for three hours. To the reaction mixture is added 200 ml of ethyl acetate. The organic layer is removed, and the aqueous layer is adjusted to pH 4 with 10% hydrochloric acid to bring about precipitation of an oily substance, which is extracted with one liter of a mixture of tetrahyrofuran-ethyl acetate (1:1). The aqueous layer is further extracted with 200 ml of 1-butanol. The extracts are combined and dried over anhydrous sodium sulfate, and the solvent is evaporated off under reduced pressure. To the residue is added 200 ml of ethyl acetate, and the mixture is stirred. The precipitating crystals are collected by filtration to give 90 g of the above-identified compound.

Elemental analysis for $C_{18}H_{19}N_5O_8S_2$: Calcd. (%): C, 42.19; H, 4.30; N, 13.55. Found (%): C, 41.94; H, 4.11; N, 13.59.

IR spectrum $\nu_{max}^{KBr}cm^{-1}$: 1770, 1710, 1620, 1520.

NMR spectrum ($d_6$-DMSO)δ: 2.20(3H, s), 3.43 and 3.65 (2H, ABq, J=18 Hz), 3.63(2H, s), 3.86(3H, s), 4.78 and 5.06 (2H, ABq, J=13 Hz), 5.14(1H, d, J=5 Hz), 5.79(1H, d.d, J=5 Hz and 8 Hz), 6.73(1H, s), 7.17 (2H, br.), 9.56(1H, d, J=8 Hz).

REFERENCE EXAMPLE 3

7β-[2-(2-Aminothiazol-4-yl)-2(Z)-ethoxyiminoacetamido]-3-(3-oxobutyryloxymethyl)-3-cephem-4-carboxylic acid In 100 ml of dimethylformamide is dissolved 23 g of 2-(2-aminothiazol-4-yl)-2(Z)-ethoxyiminoacetic acid. To the solution are added 15 g of 1-hydroxybenzotriazole and 20.6 g of dicyclohexylcarbodiimide, and the mixture is stirred at 20° C. for 1.5 hours. The insolubles are filtered off. The filtrate added, under ice-cooling, to a solution of 31 g of 7β-amino-3-(3-oxobutyryloxymethyl)-3-cephem-4-carboxylic acid and 28 ml of triethylamine in 100 ml of dimethylformamide. The reaction mixture was stirred at 20° C. for three hours. To the mixture is added 500 ml of ether, are resulting precipitates are collected by filtration and then dissolved in 100 ml of water. The resulting aqueous solution is adjusted to pH 3.0 with 10% hydrochloric acid and extracted twice with 200 ml portions of methyl ethyl ketone. The extract is washed with water and dried over anhydrous sodium sulfate. The solvent is evaporated under reduced pressure to leave a solid which is washed with ethyl acetate to give 31 g of the above-identified compound.

IR spectrum $\nu_{max}^{KBr}$cm$^{-1}$: 1780, 1720, 1660.

NMR spectrum (d$_6$-DMSO)δ: 1.30 (3H, t, J=7.5 Hz), 2.25(3H, s), 3.45–3.65(4H, m), 4.20(2H, q, J=7.5 Hz), 4.70 & 5.10(2H, ABq, J=18 Hz), 5.25(2H, d, J=5 Hz), 5.90(1H, d.d, J=5 Hz & 8 Hz), 6.90(1H, s), 7.20–7.80(2H, br.), 9.80(1H, d, J=7.5 Hz).

REFERENCE EXAMPLE 4

7β-[2-(2-Aminothiazol-4-yl)-2(Z)-propoxyiminoacetamido]-3-(3-oxobutyryloxymethyl)-3-cephem-4-carboxylic acid In 10 ml of dimethylformamide is dissolved 1.7 g of 2-(2-aminothiazol-4-yl)-2(Z)-propoxyiminoacetic acid. To the solution are added 1.5 g of 1-hydroxybenzotriazole and 1.73 g of dicyclohexylcarbodiimide, and the mixture is stirred at 20° C. for 1.5 hours. Insoluble precipitate is filtered off and the filtrate is added to a solution of 2.7 g or 7β-amino-3-(3-oxobutyryloxymethyl)-3-cephem-4-carboxylic acid and 3.2 ml of triethylamine in 10 ml of dimethylformamide. The reaction mixture is stirred at 20° C. for three hours, followed by addition of 100 ml of diethyl ether. Precipitated solid substance is collected by filtration and dissolved in 50 ml of water. The resulting aqueous solution is adjusted to pH 3.0 and then extracted three times with 50 ml portions of 1-butanol. The combined extract is washed with water and dried over anhydrous magnesium sulfate. The solvent is evaporated under reduced pressure to leave a solid substance, which is washed with ethyl acetate to give 1.7 g of the above-identified compound.

IR spectrum $\nu_{max}^{KBr}$cm$^{-1}$: 1790, 1750, 1720, 1680, 1640, 1555.

NMR spectrum (d$_6$-DMSO)δ: 0.91(3H, t, J=7 Hz), 1.4–1.85(2H, m), 2.18(3H, s), 3.45 and 3.70(2H, ABq, J=16 Hz), 3.64(2H, s), 4.10(2H, t, J=7 Hz), 4.76–5.08(2H, ABq, J=13 Hz), 5.04(1H, d, J=4.5 Hz), 5.80 (1H, d.d, J=4.5 Hz & 8 Hz), 6.87(1H, s), 7.13(2H, br.s), 9.70(1H, d, J=8 Hz).

REFERENCE EXAMPLE 5

7β-[2-(2-Aminothiazol-4-yl)-2(Z)-isopropoxyiminoacetamido]-3-(3-oxobutyryloxymethyl)-3-cephem-4-carboxylic acid Starting from 2-(2-aminothiazol-4-yl)-2(Z)-isopropoxyiminoacetic acid and 7β-amino-3-(3-oxobutyryloxymethyl)-3-cephem-4-carboxylic acid, the titled compound is obtained by the procedure of Reference Example 3.

IR spectrum $\nu_{max}^{KBr}$cm$^{-1}$: 1780, 1745, 1720, 1670, 1620, 1530.

NMR spectrum (d$_6$-DMSO)δ: 1.18(6H, d, J=6 Hz), 2.20(3H, s), 3.46 & 3.66(2H, ABq, J=18 Hz), 3.64(2H, s), 4.93& 5.21(2H, ABq, J=13 Hz), 5.03(1H, d, J=4.5 Hz), 5.6–5.9(1H, m), 6.69(1H, s), 7.20(2H, br.s), 9.46(1H, d, J=8 Hz).

REFERENCE EXAMPLE 6

7β-[2-(2-Aminothiazol-4-yl)-2(Z)-butoxyiminoacetamido]-3-(3-oxobutyryloxymethyl)-3-cephem-4-carboxylic acid Starting from 2-(2-aminothiazol-4-yl)-2(Z)-butoxyiminoacetic acid, the above-identified compound is obtained by the procedure of Reference Example 3.

IR spectrum $\nu_{max}^{KBr}$cm$^{-1}$: 1780, 1750, 1720, 1660, 1620.

NMR spectrum (d$_6$-DMSO)δ: 0.92(3H, t, J=7 Hz), 1.1–1.8(4H, m), 2.22(3H, s), 3.44 and 3.65(2H, ABq, J=17 Hz), 3.63(2H, s), 4.08(2H, t, J=7 Hz), 4.81 and 5.08(2H, ABq, J=14 Hz), 5.14(1H, d, J=4.5 Hz), 5.78(1H, d.d, J=4.5 Hz & 8 Hz), 6.69(1H, s), 7.12(2H, br.s), 9.48(1H, d, J=8 Hz).

REFERENCE EXAMPLE 7

7β-[2-(2-Aminothiazol-4-yl)-2(Z)-hexyloxyiminoacetamido]-3-(3-oxobutyryloxymethyl)-3-cephem-4-carboxylic acid Starting from 2-(2-aminothiazol-4-yl)-2(Z)-hexyloxyiminoacetic acid, the above-identified compound is obtained by the procedure of Reference Example 3.

NMR spectrum (d$_6$-DMSO)δ: 0.87(3H, t), 1.28(8H, br.s), 2.20(3H, s), 3.38 and 3.61(2H, ABq, J=18 Hz), 3.63(2H, s), 4.06(2H, t, J=7 Hz), 4.77 and 5.05(2H, ABq, J=13 Hz), 5.10(1H, d, J=4.5 Hz), 5.74(1H, d.d, J=4.5 Hz & 8 Hz), 6.70(1H, s), 7.14(2H, br.s), 9.48(1H, d, J=8 Hz).

REFERENCE EXAMPLE 8

7β-[2-(2-Aminothiazol-4-yl)-2(Z)-allyloxyiminoacetamide]-3-(3-oxobutylyloxymethyl)-3-cephem-4-carboxylic acid In 50 ml of dimethylformamide is dissolved 13 g of 2-(2-aminothiazol-4-yl)-2(Z)-allyloxyiminoacetic acid. To the solution are added 8 g of 1-hydroxybenzotriazole and 10.3 g of dicyclohexylcarbodiimide, and the mixture is stirred at 20° C. for three hours. Insoluble substance is removed by filtration, and the filtrate is added, under ice-cooling, to 50 ml of dimethylformamide dissolving 16 g of 7β-amino-3-(3-oxobutyryloxymethyl)-3-cephem-4-carboxylic acid and 10 g of triethylamine. The reaction mixture is stirred at 20° C. for three hours, to which is added 500 ml of diethyl ether, followed by removal of the ether layer to leave insoluble substance. The insoluble substance is dissolved in 50 ml of water, and the aqueous solution is adjusted to pH 3.0 to give the titled compound in crude state, which is dissolved in 500 ml of a mixture of ethyl acetate and tetrahydrofuran (1:1), dried over anhydrous magnesium sulfate, treated with activated carbon, followed by removal of the solvent by evaporation under reduced pressure to leave 25 g of the title compound as amorphous powder.

IR spectrum $\nu_{max}^{KBr}$cm$^{-1}$: 1780, 1720, 1660, 1620.

NMR spectrum (d$_6$-DMSO)δ: 2.30 (3H, s), 3.45–3.66(4H, m), 4.64 (2H, d, J=6 Hz), 4.80–5.10 (2H, ABq, J=18 Hz), 5.23 (2H, d, J=9 Hz), 5.26 (2H, d, J=5 Hz), 5.90 (1H, d.d, J=5 Hz & 9 Hz), 5.90–6.20 (1H, m), 6.80(1H, s), 7.20–8.00 (2H, br.), 9.83 (1H, d, J=9 Hz).

REFERENCE EXAMPLE 9

7β-[2-(2-Aminothiazol-4-yl)-2(Z)-(2-hydroxyethoxyimino)acetamido]-3-(3-oxobutyryloxymethyl)-3-cephem-4-carboxylic acid Starting from 2-(2-aminothiazol-4-yl)-2(Z)-(2-hydroxyethoxyimino)acetic acid and 7β-amino-3-(3-oxobutyryloxymethyl)-3-cephem-4-carboxylic acid, the titled compound is obtained by the procedure of Reference Example 3.

IR spectrum $\nu_{max}^{KBr}$cm$^{-1}$: 1780, 1750, 1720, 1670, 1630, 1550.

NMR spectrum (d$_6$-DMSO)δ: 2.20(3H, s), 2.9–3.2(2H, m), 3.4–3.7(2H, m), 3.65(3H, s), 4.32(2H, t, J=6 Hz), 4.95 & 5.12(2H, ABq, J=13 Hz), 5.04(1H, d, J=4.5 Hz), 5.6–5.9(1H, m), 6.70(1H, s), 7.20(2H, br.s), 9.46(1H, d, J=8 Hz).

REFERENCE 10

7β-[2-(2-Aminothiazol-4-yl)-2(Z)-cyclopropylmethoxyiminoacetamido]-3-(3-oxobutyryloxymethyl)-3-cephem-4-carboxylic acid Starting from 2-(2-aminothiazol-4-yl)-2(Z)-cyclopropylmethoxyiminoacetic acid and 7β-amino-3-(3-oxobutyryloxymethyl)-3-cephem-4-carboxylic acid, the titled compound is obtained by the procedure of Reference Example 3.

IR spectrum $\nu_{max}^{KBr}$cm$^{-1}$: 1760, 1635, 1540, 1400, 1365, 1270, 1150.

NMR spectrum (d$_6$-DMSO)δ: 0.1–0.6(4H, m), 0.7–1.5(1H, m), 2.20(3H, s), 3.42 & 3.66(2H, ABq, J=18 Hz), 3.64(2H, s), 3.91(2H, d, J=7 Hz), 4.80 & 5.08(2H, ABq, J=14 Hz), 5.15(1H, d, J=5 Hz), 5.78(1H, d.d, J=5 Hz & J=8 Hz), 6.70(1H, s), 7.22(2H, br.s), 9.52(1H, d, J=8 Hz).

REFERENCE EXAMPLE 11

7β-[2-(2-Aminothiazol-4-yl)-2(Z)-carbamoylmethoxyiminoacetamido]-3-(3-oxobutyryloxymethyl)-3-cephem-4-carboxylic acid (a) In 100 ml of dimethylformamide is dissolved 24 g of 2-(2-chloroacetamidothiazol-4-yl)-2(Z)-carbamoylmethoxyiminoacetic acid. To the solution are added 11.4 g of 1-hydroxybenzotriazole and 22 g of dicyclohexylcarbodiimide, and the mixture is stirred at 20° C. for two hours. Insoluble substance is filtered off, and then the filtrate is added at 0° C. to 70 ml of dimethylformamide dissolving 22 g of 7β-amino-3-(3-oxobutyryloxymethyl)-3-cephem-4-carboxylic acid and 21 ml of triethylamine. The reaction mixture is stirred at 20° C. for one hour, to which are added 500 ml of methyl ethyl ketone, 60 ml of phosphoric acid and one liter of saturated saline solution. The mixture is stirred. The organic layer is taken and washed with water, which is then dried over anhydrous magnesium sulfate. The solvent is evaporated off under reduced pressure. To the residue is added 200 ml of ethyl acetate, and then the precipitating solid material is collected by filtration to yield 19 g of 7β-[2-(2-chloroacetamidothiazol-4-yl)-2(Z)-carbamoylmethoxyiminoacetamido]-3-(3-oxobutyryloxymethyl)-3-cephem-4-carboxylic acid.

IR spectrum $\nu_{max}^{KBr}$cm$^{-1}$: 1770, 1720, 1640, 1530.

(b) Into 150 ml of water is dissolved 19 g of 7β-[2-(2-chloroacetamidothiazol-4-yl)-2-(Z)-carbamoylmethoxyiminoacetamido]-3-(3-oxobutyryloxymethyl)-3-cephem-4-carboxylic acid which is obtained in the above (a). To the solution are added 20 g of sodium methyldithiocarbamate and 150 ml of ethylacetate. The mixture is stirred at 20° C. for eight hours, to which is added acetic acid to adjust the pH thereof to 4.0. Then, the aqueous layer is taken, concentrated under reduced pressure. The concentrate is lyophilized. The resulting solid material is dissolved in 100 ml of water, which is subjected to extraction with a mixture of 100 ml of tetrahydrofuran and 200 ml of methyl ethyl ketone. The extract is dried over anhydrous magnesium sulfate, followed by removal of the solvent by evaporation under reduced pressure to give 6.0 g of the titled compound.

IR spectrum $\nu_{max}^{KBr}$cm$^{-1}$: 1780, 1720, 1660.

NMR spectrum (d$_6$-DMSO)δ: 2.10(3H, s), 3.40 & 3.65(2H, ABq, J=18 Hz), 3.63(2H, s), 4.40(2H, s), 4.80 & 5.06(2H, ABq, J=13 Hz), 5.16(1H, d, J=5 Hz), 5.80(1H, d.d, J=5 Hz & 8 Hz), 6.74(1H, s), 7.05–7.40(4H, m), 9.60(1H, d, J=8 Hz).

REFERENCE EXAMPLE 12

7β-[2-(2-Aminothiazol-4-yl)-2(Z)-benzyloxyiminoacetamido]-3-(3-oxobutyryloxymethyl)-3-cephem-4-carboxylic acid Starting from 2-(2-aminothiazol-4-yl)-2(Z)-benzyloxyiminoacetic acid, the above-identified compound is obtained by the procedure of Reference Example 3.

IR spectrum $\nu_{max}^{KBr}$ cm$^{-1}$: 1770, 1730, 1700, 1640, 1520.

NMR spectrum (d$_6$-DMSO)δ: 2.21(3H, s), 3.2–3.8(4H, m), 4.82 and 5.12(2H, ABq, J=13 Hz), 5.10(1H, d, J=4.5 Hz), 5.18(2H, s), 5.84(1H, d.d, J=4.5 Hz and 8 Hz), 7.22(2H, br.s), 7.38(5H, s), 9.65(1H, d, J=8 Hz).

REFERENCE EXAMPLE 13

7β-[2-(Aminothiazol-4-yl)-2(Z)-(2-methoxyethoxyimino)acetamido]-3-(3-oxobutyryloxymethyl)-3-cephem-4-carboxylic acid Starting from 2-(2-aminothiazol-4-yl)-2(Z)-(2-methoxyethoxyimino)acetic acid, the above-identified compound is obtained by the procedure of Reference Example 3.

IR spectrum $\nu_{max}^{KBr}$ cm$^{-1}$: 1770, 1750, 1670, 1630, 1540.

NMR spectrum (d$_6$-DMSO)δ: 2.20(3H, s), 3.28(3H, s), 3.4–3.7(4H, m), 4.19(4H, t, J=7 Hz), 4.81 and 5.08 (2H, ABq, J=13 Hz), 5.77(1H, d.d, J=4.5 Hz and 8 Hz), 6.73(1H, s), 7.13(2H, br.s), 9.51(1H, d, J=8 Hz).

REFERENCE EXAMPLE 14

7β-[2-(2-Aminothiazol-4-yl)-2(Z)-(2-chloroethoxyimino)acetamido]-3-(3-oxobutyryloxymethyl)-3-cephem-4-carboxylic acid From 2-(2-aminothiazol-4-yl)-2(Z)-(2-chloroethoxyimino)acetic acid and 7β-amino-3-(3-oxobutyryloxymethyl)-3-cephem-4-carboxylic acid, the above-identified compound is obtained by a similar procedure to that of Reference Example 3.

IR spectrum $\nu_{max}^{KBr}$ cm$^{-1}$: 1770, 1705, 1660, 1630, 1520.

NMR spectrum (d$_6$-DMSO)δ: 2.20(3H, s), 3.05 and 3.50(2H, ABq, J=18Hz), 3.60(2H, s), 3.73–3.90(2H, m), 4.20–4.50(2H, m), 4.76 and 5.06(2H, ABq, J=14 Hz), 5.16(1H, d, J=5 Hz), 5.80(1H, d.d, J=5 Hz and 8 Hz), 6.76(1H, s), 7.20(2H, br.s), 9.60(1H, d, J=8 Hz).

REFERENCE EXAMPLE 15

7β-[2-(2-Aminothiazol-4-yl)-2(Z)-(2-fluoroethoxyimino)actamido]-3-(3-oxobutyryloxymethyl)-3-cephem-4-carboxylic acid Starting from 2-(2-aminothiazol-4-yl)-2(Z)-(2-fluoroethoxyimino)acetic acid and 7β-amino-3-(3-oxobutyryloxymethyl)-3-cephem-4-carboxylic acid, the above-identified compound is obtained by the procedure of Reference Example 3.

IR spectrum $\nu_{max}^{KBr}$ cm$^{-1}$: 1770, 1740, 1680, 1620, 1540.

NMR spectrum (d$_6$-DMSO)δ: 2.20(3H, s), 3.50–3.70(2H, m), 3.66(2H, s), 4.10–4.30(1H, m), 4.43–4.66(3H, m), 4.80–5.03(2H, m), 5.20(1H, d, J=4.5 Hz), 5.86(1H, d.d, J=4.5 Hz and 8 Hz), 6.80(1H, s), 7.13(2H, br.s), 9.70(1H, d, J=8 Hz).

REFERENCE EXAMPLE 16

2-Methylthioethyl 2-(2-aminothiazol-4-yl)-2(Z)-(1-tert-butoxycarbonylpropoxyimino)acetate A mixture of 10 g of 2-methylthioethyl 2-(2-aminothiazol-4-yl)-2(Z)-hydroxyiminoacetate, 10 g of tertbutyl 2-bromobutyrate and 7 g of anhydrous potassium carbonate in 250 ml of acetone is kept at 60°–70° C. for 20 hours with stirring. Insolubles are filtered off and the filtrate is concentrated under reduced pressure. The residue is dissolved in ethyl acetate, and the solution is washed with water, then with saturated aqueous sodium chloride and dried over anhydrous magnesium sulfate. The solvent is then evaporated off to give the above-identified compound as a viscous liquid, which, upon standing, solidifies. Yield: 12.6 g.

NMR spectrum (CDCl$_3$)δ: 0.98(3H, t, J=7 Hz), 1.48(9H, s), 1.65–2.15(2H, m), 2.18(3H, s), 2.82(2H, t, J=7 Hz), 4.1–4.65(3H, m), 6.27(2H, br.s), 6.72(1H, s).

REFERENCE EXAMPLE 17

2-(2-Aminothiazol-4-yl)-2(Z)-(1-tert-butoxycarbonylpropoxyimino)acetic acid

To a mixture of 100 ml of acetone and 25 ml of water are added 10 g of the ester compound obtained in Reference Example 11 and 0.1 g of ammonium molybdate. To the resulting mixture is added 10 ml of 30% hydrogen peroxide, and the mixture is stirred at room temperature overnight. After addition of an aqueous solution of sodium sulfite, the mixture is neutralized and then extracted with 120 ml of ethyl acetate. The organic layer is diluted with 170 ml of acetone and 170 ml of water and the solution is adjusted to pH 10–11 with 30% aqueous potassium carbonate and stirred at 30°–40° C. for 2 hours. After neutralization with 1N HCl, the organic layer is separated and extracted with 5% aqueous sodium chloride. The aqueous layers are combined, acidified with 1N HCl and extracted with methyl ethyl ketone. The organic layer is washed with saturated aqueous sodium chloride and dried over anhydrous magnesium sulfate. The solvent is then evaporated off to give 3.2 g of the above-identified compound as crystals.

mp 121.5°–124° C.

Elemental analysis for C$_{13}$H$_{19}$N$_3$O$_5$S.3/2H$_2$O: Calcd. (%): C, 42.14; H, 5.64; N, 11.15. Found (%): C, 42.37; H, 6.02; N, 11.40.

REFERENCE EXAMPLE 18

2-Methylthioethyl 2-(2-aminothiazol-4-yl)-2(Z)-(1-tert-butoxycarbonylbutoxyimino)acetate Starting from 2-methylthioethyl 2-(2-aminothiazol-4-yl)-2(Z)-hydroxyiminoacetate and tert-butyl 2-bromovalerate, the above-identified compound is obtained by the procedure of Reference Example 16.

mp 102°–105° C.

Elemental analysis for C$_{17}$H$_{27}$N$_3$O$_5$S$_2$: Calcd. (%): C, 48.90; H, 6.52; N, 10.01. Found (%): C, 48.74; H, 6.46; N, 10.04.

REFERENCE EXAMPLE 19

2-(2-Aminothiazol-4-yl)-2(Z)-(1-tert-butoxycarbonylbutoxyimino)acetic acid

From the ester compound obtained in Reference Example 3, the above-identified compound is obtained by the procedure of Reference Example 17.

mp 138°–139° C.

Elemental analysis for C$_{14}$H$_{21}$N$_3$O$_5$S.3/2H$_2$O: Calcd. (%): C, 45.27; H, 6.51; N, 11.31. Found (%): C, 45.26; H, 6.09; N, 11.15.

REFERENCE EXAMPLE 20

7β-[2-(2-Aminothiazol-4-yl)-2(Z)-(tert-butoxycarbonylmethoxyimino)acetamido]-3-(3-oxobutyryloxymethyl)-3-cephem-4-carboxylic acid In 20 ml of dimethylformamide is dissolved 6.0 g of 2-(2-aminothiazol-4-yl)-2-(Z)-tert-butoxycarbonylmethoxyiminoacetic acid. To the solution are added 3.5 g of 1-hydroxybenzotriazole and 4.4 g of dicyclohexylcarbodiimide, and the mixture is stirred at 20° C. for three hours. Insoluble substance is removed by filtration, and the filtrate is added, under ice-cooling, to 20 ml of dimethylformamide dissolving 6.2 g of 7β-amino-3-(3-oxobutyryloxymethyl)-3-cephem-4-carboxylic acid and 4.0 g of triethylamine. The reaction solution is stirred at 20° C. for eight hours. To 200 ml of diethyl ether is added the reaction mixture and the ether layer is removed. The residue is dissolved in 50 ml of water. The aqueous solution is adjusted to pH 4 with 10% hydrochloric acid to cause precipitation of crystals. The crystals are collected by filtration, washed with water then with diethyl ether, followed by drying to give 10 g of the titled compound.

IR spectrum $\nu_{max}^{KBr}$ cm$^{-1}$: 1790, 1730, 1710, 1660, 1530.

NMR spectrum (d$_6$-DMSO)δ: 1.50(9H, s), 2.20(3H, s), 3.40–3.60(4H, m), 4.40(2H, s), 4.80 & 5.10(2H, ABq, J=14 Hz), 5.20(1H, d, J=5 Hz), 5.80(1H, d.d, J=5 Hz & 8 Hz), 6.70(1H, s), 7.20–7.80(2H, br.), 9.30(1H, d, J=8 Hz).

REFERENCE EXAMPLE 21

7β-[2-(2-Aminothiazol-4-yl)-2(Z)-(1-tert-butoxycarbonylethoxyimino)acetamido]-3-(3-oxobutyryloxymethyl)-3-cephem-4-carboxylic acid In 20 ml of N,N-dimethylformamide is dissolved 3 g of 2-(2-aminothiazol-4-yl)-2(Z)-(1-tert-butoxycarbonylethoxyimino)acetic acid. To the solution are added 1.5 g of 1-hydroxybenzotriazole and 2.1 g of dicyclohexylcarbodiimide, and the mixture is stirred at room temperature for 1 hour. Insoluble substance is filtered off and the filtrate is added to a suspension of 3.1 g of 7β-amino-3-(3-oxobutyryloxymethyl)-3-cephem-4-carboxylic acid and 2 g of triethylamine in 20 ml of dimethylformamide. The mixture is stirred at room temperature for 6 hours. Insoluble substance is removed by filtration and 500 ml of diethyl ether is added to the filtrate. The ether layer is removed and the residue is dissolved in water. The mixture is adjusted to pH 3–4 with 1N HCl and extracted with methyl ethyl ketone. The organic layer is washed with saturated aqueous sodium chloride solution and dried over anhydrous magnesium sulfate. The solvent is then evaporated off under reduced pressure. The residue solidifies on addition of hexane. The powder obtained is collected by filtration to give 3.9 of the above-identified compound.

NMR spectrum (d$_6$-DMSO)δ:0.88 and 0.95(3H, 2 t, J=7 Hz), 1.42(9H, s), 2.20(3H, s), 3.44 and 3.68(2H, ABq, J=18 Hz), 3.64(2H, s), 4.5–4.7(1H, m), 4.80 and 5.11(2H, ABq, J=14 Hz), 5.18(1H, d, J=4.5 Hz), 5.84(1H, d.d, J=4.5 Hz and 8 Hz), 6.77(1 H, s), 7.18 (2H, br.s), 9.40(1H, d, J=8 Hz).

REFERENCE EXAMPLE 22

7β-[2-(2-Aminothiazol-4-yl)-2(Z)-(1-tert-butoxycarbonylpropoxyimino)acetamido]-3-(3-oxobutylryoxymethyl)-3-cephem-4-carboxylic acid Starting from 2-(2-aminothiazol-4-yl)-2(Z)-(1-tert-butoxycarbonylpropoxyimino)acetic acid, the above-identified compound is obtained by the procedure of Reference Example 21.

NMR spectrum (d$_6$-DMSO)δ: 0.90 and 0.93(3H, 2d, J=7 Hz), 1.42(9H, s), 1.45–1.9(2H, m), 2.20(3H, s), 3.22 and 3.51(2H, ABq, J=18 Hz), 4.3–4.6(1H, m), 4.77 and 5.12(2H, ABq, J=14 Hz), 5.16(1H, d, J=4.5 Hz), 5.75–5.95(1H, m), 6.77(1H, s), 9.46(1H, d, J=8 Hz).

REFERENCE EXAMPLE 23

7β-[2-(2-Aminothiazol-4-yl)-2-(Z)-(1-tert-butoxycarboylbutoxyimino)acetamido]-3-(3-oxobutyryloxymethyl)-3-cephem-4-carboxylic acid Starting from 2-(2-aminothiazol-4-yl)-2(Z)-(1-tert-butoxycarbonylbutoxyimino)acetic acid, the above-identified compound is obtained by the procedure of Reference Example 21.

NMR spectrum (d$_6$-DMSO)δ: 0.91 and 0.92 (total 3H, each t, J=7 Hz), 1.43(9H, s), 1.2–1.9(4H, m), 2.20(3H, s), 3.26 and 3.50(2H, ABq, J=18 Hz), 4.4–4.6(1H, m), 4.80 and 5.10(2H, ABq, J=13 Hz), 5.18(1H, d, J=4.5 Hz), 5.7–5.95(1H, m), 6.78(1H, s), 9.44(1H, d, J=8 Hz).

REFERENCE EXAMPLE 24

3-(3-Oxobutyryloxymethyl)-7β-[2-(2-tritylaminothiazol-4-yl)-2(Z)-(1-methyl-1-tert-butoxycarbonyl)ethoxyiminoacetamido]-3-cephem-4-carboxylic acid.

In 20 ml of dimethylformamide is dissolved 12 g of 2-[(2-tritylaminothiazol-4-yl)-2(Z)-(1-methyl-1-tert-butoxycabonyl)ethoxyiminoacetic acid. To the solution are added 3.5 g of 1-hydroxybenzotriazole and 4.4 g of dicyclohexylcarbodiimide, and the mixture is stirred at 20° C. for 20 hours. Insoluble substance is removed by filtration, and the filtrate is added, under ice-cooling, to 20 ml of dimethylformamide dissolving 6.2 g of 7β-amino-3-(3-oxobutyryloxymethyl)-3-cephem-4-carboxylic acid and 4.0 g of triethylamine. The reaction mixture is stirred at 20° C. for 24 hours, to which is added 200 ml of a mixture of diethyl ether and petroleum ether (1:1). The ether layer is removed. To the residue is added 50 ml of water, followed by adjusting the pH to 4.0 to cause precipitation of crystalline powder. The powder is collected by filtration and washed with water then with diethyl ehter, followed by drying to give 13 g of the titled compound.

IR spectrum $\nu_{max}^{KBr}$ cm$^{-1}$: 1780, 1730, 1700, 1680, 1530, 1150.

NMR spectrum (d$_6$-DMSO)δ: 1.35(15H, s), 2.25(3H, s), 3.40–3.60(4H, m), 5.80 & 5.10(2H, ABq, J=14 Hz), 5.25(1H, d, J=5 Hz), 5.80(1H, d.d, J=5 Hz & 8 Hz), 6.70(1H, s), 7.20–7.80(2H, br.), 7.30(15H, s), 9.30(1H, d, J=8 Hz).

REFERENCE EXAMPLE 25

7β-[2-(2-Aminothiazol-4-yl)-2(Z)-(1-tert-butoxycarbonyl-1-methylethoxyimino)acetamido]-3-(3-oxobutyryloxymethyl)-3-cephem-4-carboxylic acid Starting from 2-(2-aminothiazol-4-yl)-2(Z)-(1-tert-butoxycarbonyl-1-methylethoxyimino)acetic acid, the above-identified compound is obtained by the procedure of Reference Example 21.

IR spectrum $\nu_{max}^{KBr}$ cm$^{-1}$: 1780, 1720, 1660, 1530.

NMR spectrum (d$_6$-DMSO)δ: 1.42(15H, s), 2.20(3H, s), 3.4–3.7(4H, m), 4.70 and 5.10(2H, ABq, J=14 Hz), 5.19(1H, d, J=4.5 Hz), 5.82(1H, d.d, J=4.5 Hz and 8 Hz), 6.73(1H, s), 7.19(2H, br.s), 9.29 (1H, d, J=8 Hz).

REFERENCE EXAMPLE 26

7β-[2-(2-Aminothiazol-4-yl)-2(Z)-(1-carbamoyl-1-methylethoxyimino)acetamido]-3-(3-oxobutyryloxymethyl)-3-cephem-4-carboxylic acid Starting from 2-2-(2-aminothiazol-4-yl)-2(Z)-(1-carbamoyl-1-methylethoxyimino)acetic acid, the above-identified compound is obtained by the procedure of Reference Example 3.

IR spectrum $\nu_{max}^{KBr}$ cm$^{-1}$: 1770, 1730, 1670, 1610, 1540.

NMR spectrum (d$_6$-DMSO)δ: 1.39 and 1.42 (total 6H, each s), 2.25(3H s), 3.11 and 3.72(2H, ABq, J=18 Hz), 3.60(2H, s), 4.80 and 5.12(2H, ABq, J=16 Hz), 4.92(1H, d, J=5 Hz), 5.60(1H, d.d, J=5 Hz and 8 Hz), 6.7–7.1(2H, m), 6.70(1H, s), 7.20(2H, br.s), 9.38(1H, d, J=8 Hz).

REFERENCE EXAMPLE 27

7β-[2-(5-tert-Butoxycarbonylamino-1,2,4-thiadiazol-3-yl)-2(Z)-methoxyiminoacetamido]-3-(3-oxobutyryloxymethyl)-3-cephem-4-carboxylic acid To 4 ml of dichlormethane is added 302 mg of 2-(5-tert-butoxycarbonylamino-1,2,4-thiadiazol-3-yl)-2(Z)-methoxyiminoacetic acid, followed by addition of 208 mg of phosphorus pentachloride. The mixture is stirred with ice-cooling for 15 minutes. The solvent is then evaporated off under reduced pressure and hexane is added to the residue. The mixture is evaporated to dryness under reduced pressure and the residue is dissolved in dichloromethane. The resulting solution is added to a solution of 300 mg of 7β-amino-3-(3-oxobutyloxymethyl)-3-cephem-4-carboxylic acid and 0.6 ml of triethylamine in 5 ml of dimethylacetamide, and the mixture is stirred with ice-cooling for 30 minutes. To the reaction mixture is added a solution of 1 g of phosphoric acid in 10 ml of water and the resulting mixture is extracted with methyl ethyl ketone (10 ml). The extract is washed with water and dried over magnesium sulfate. The solvent is then evaporated off under reduced pressure. Ethyl acetate is added to the residue and the solvent is evaporated again to give 390 mg of the above-identified compound.

IR spectrum $\nu_{max}^{KBr}$ cm$^{-1}$: 2980, 2940, 1780, 1715, 1540, 1370, 1245, 1150, 1040, 855.

NMR spectrum (d$_6$-DMSO)δ: 1.56(9H, s), 2.20(3H, s), 3.43 and 3.70(2H, ABq, J=18 Hz), 3.65(2H, s), 4.00(3H, s), 4.80 and 5.12(2H, ABq, J=12 Hz), 5.18(1H, d, J=4.5 Hz), 5.88(1H, d.d, J=9 Hz and 4.5 Hz), 9.63(1H, d, J=9 Hz).

REFERENCE EXAMPLE 28

7β-[2-(5-Amino-1,2,4-thiadiazol-3-yl)-2(Z)-ethoxyiminoacetamido]-3-(3-oxobutyryloxymethyl)-3-cephem-4-carboxylic acid In 200 ml of dichloromethane is suspended 11 g of 7β-amino-3(3-oxobutyryloxymethyl)-3-cephem-4-carboxylic acid. To the suspension is added 14 g of bis-trimethylsilylacetamide and the mixture is stirred at room temperature until complete dissolution and cooled in an ice-water bath. To this solution, 14 g of 2-(5-amino-1,2,4-thiadiazol-3-yl)-2(Z)-ethoxyiminoacetyl chloride is added and the mixture is stirred for a while, to which 6 g of dimethylacetamide is added. The whole mixture is stirred with ice-cooling for 60 minutes. The dichloromethane is evaporated off and the residue is dissolved in methyl ethyl ketone. The solution is washed with water and dried. The solvent is then evaporated off and diethyl ether is added to the residue to give a fine precipitate, which is collected by filtration, giving 12.5 g of the above-identified compound.

IR spectrum $\nu_{max}^{KBr}$ cm$^{-1}$: 3300, 3000, 1780, 1720, 1620, 1520, 1410, 1260, 1150, 1040.

NMR spectrum (d$_6$-DMSO)δ: 1.25(3H, t, J=7 Hz), 2.18(3H, s), 3.41 and 3.63(2H, ABq, J=18 Hz), 3.62(2H, s), 4.18(2H, q, J=7 Hz), 4.76 and 5.06(2H, ABq, J=13 Hz), 5.14(1H, d, J=4.8 Hz), 5.82(1H, d.d, J=8 Hz and 4.8 Hz), 8.00(2H, br.), 9.48(1H, d, J=8 Hz).

REFERENCE EXAMPLE 29

(i)

7β-[2-(5-Chloro-2-chloroacetamidothiazol-4-yl)-2(Z)-methoxyiminoacetamido]-3-(3-oxobutyryloxymethyl)-3-cephem-4-carboxylic acid To 50 ml of dichloromethane is added 2.39 g of 2-(5-chloro-2-chloroacetamidothiazol-4-yl)-2(Z)-methoxyiminoacetic acid and, while cooling at −5° C. to −8° C., 2.13 g of phosphorus pentachloride is added and the mixture is stirred for 45 minutes. To the reaction mixture is added 150 ml (in 30-ml portions) of hexane, and the dark oily precipitate is separated and washed with hexane to give the corresponding crude chloride. Separately, a solution of 2.06 g of 7β-amino-3-(3-oxobutyryloxymethyl)-3-cephem-4-carboxylic acid in 15 ml of tetrahydrofuran is added to a solution of 2.06 g of sodium hydrogen carbonate in 15 ml of water, and to the resulting mixture, the chloride obtained above is added while maintaining the inside temperature at 0°-3° C. Thereafter, the mixture is stirred at the temperature not exceeding 5° C. for 1 hour and then at room temperature for further 1 hour. Fifty ml of methyl ethyl ketone is added to the reaction mixture and the mixture is acidified with concentrated hydrochloric acid. The organic layer is separated and the aqueous layer is extracted with methyl ethyl ketone. The organic layer and the extract are combined and dried over anhydrous sodium sulfate. The solvent is then evaporated off under reduced pressure to give 2.94 g of the above-identified compound as light-orange powder.

NMR spectrum (CDCl$_3$+d$_6$-DMSO)δ: 2.23(3H, s), 3.24–3.73(2H, m), 3.50(2H, s), 4.01(3H, s), 4.21(2H, s), 4.91 and 5.18(2H, ABq, J=13 Hz), 5.05(1H, d, J=4.5 Hz), 5.88(1H, d.d, J=4.5 Hz & 9 Hz). 6.43(2H, br.), 8.79(1H, d, J=9 Hz).

(ii)

7β-[2-(2-Amino-5-chlorothiazol-4-yl)-2(Z)-methoxyiminoacetamido]-3-(3-oxobutyryloxymethyl)-3-cephem-4-carboxylic acid To a mixture of 13 ml of water and 13 ml of tetrahydrofuran is dissolved 2.94 g of 7β-[2-(5-chloro-2-chloroacetamidothiazol-4-yl)-2(Z)-methoxyiminoacetamido]-3-(3-oxobutyryloxymethyl)-3-cephem-4-carboxylic acid. To the mixture is added 1.15 g of sodium N-methyldithiocarbamate in 3 portions with stirring at room temperature for 3 hours. Ethyl acetate is added to the reaction mixture and the ethyl acetate layer is separated and discarded. The aqueous layer is acidified with concentrated hydrochloric acid and extracted with 200 ml of methyl ethyl ketone. The extract is washed with aqueous sodium chloride solution and dried over anhydrous sodium sulfate. The solvent is then evaporated off to give 2.28 g of the above-identified compound.

NMR spectrum (d$_6$-DMSO+CDCl$_3$)δ: 2.21(3H, s), 3.3–3.75 (2H, m), 3.57(2H, s), 3.90(2H, s), 4.81 and 5.09(2H, ABq, J=13 Hz), 5.07(1H, d, J=5 Hz), 5.77(1H, d.d, J=5 Hz & 9 Hz), 7.10(2H, br.), 9.46(1H, d, J=9 Hz).

REFERENCE EXAMPLE 30

Methyl (2-chloroacetamidothiazol-4-yl-3-oxido)2(Z)-ethoxyiminoacetate

To an ice-cooled solution of 18 g of maleic anhydride in 300 ml of methylene chloride is added 42 ml of 30% aqueous hydrogen peroxide, and the mixture is stirred at 0° C. for 2 hours. To this solution is added 40 g of methyl (2-chloroacetamidothiazol-4-yl)-2(Z)-ethoxyiminoacetate and the mixture is stirred at room temperature for 16 hours. To the mixture is added 300 ml of 2% aqueous solution of sodium hydrogen carbonate. The organic layer is separated and washed with two 300-ml portions of saturated aqueous sodium chloride and dried over anhydrous magnesium sulfate. The solvent is then evaporated off and the residue is crystallized from 95% ethanol to give 20 g (48% yield) of the above-identified compound.

mp 166°–168° C.

Elemental analysis for $C_{10}H_{12}ClN_3O_5S$: Calcd. (%): C, 37.33; H, 3.76; N, 13.06. Found (%): C, 37.32; H, 3.56; N, 12.88.

IR spectrum $\nu_{max}^{KBr}$ cm$^{-1}$: 1740, 1690, 1560, 1430, 1355, 1280, 1200.

NMR spectrum (d$_6$-DMSO)δ: 1.28(3H, t, J=7 Hz), 3.78(3H, s), 4.26(2H, q, J=7 Hz), 4.48(2H, s), 5.82(1H, br.s), 7.62(1H, s).

REFERENCE EXAMPLE 31

2-(2-Chloroacetamidothiazol-4-yl-3-oxido)-2(Z)-ethoxyiminoacetic acid

In 131 ml of ethanol is suspended 20 g of methyl 2-(2-chloroacetamidothiazol-4-yl-3-oxido)-2(Z)-ethoxyiminoacetate. To the suspension is added dropwise 11.3 ml of 35% aqueous sodium hydroxide solution while maintaining the inside temperature at 15°–20° C. by ice-cooling. The mixture is stirred at room temperature for 7 hours and then concentrated. The residue is dissolved in 150 ml of water and with ice-cooling, the solution is adjusted to pH 3 with concentrated hydrochloric acid. Colorless crystalline precipitate separated is collected by filtration, washed with a small amount of cold water and dried to give 15.5 g (81% yield) of the above-identified compound.

mp 154°–156° C.

Elemental analysis for $C_9H_{10}ClN_3O_5S$: Calcd. (%): C, 35.13; H, 3.28; N, 13.66. Found (%): C, 35.10; H, 3.10; N, 13.82.

IR spectrum $\nu_{max}^{KBr}$ cm$^{-1}$: 1720, 1550, 1360, 1290, 1205.

NMR spectrum (d$_6$-DMSO)δ: 1.26(3H, t, J=7 Hz), 4.25(2H, q, J=7 Hz), 4.49(2H, s), 7.55(1H, s), 9.19(2H, br.).

REFERENCE EXAMPLE 32

7β-tert-Butoxycarbonylamino-3-(3-oxobutyryloxymethyl)-3-cephem-4-carboxylic acid To 500 ml of dimethyl sulfoxide is added 200 g of 7β-amino-3-(3-oxobutyryloxymethyl)-3-cephem-4-carboxylic acid. To this 200 g of di-tert-butyl carbonate is added at room temperature and the mixture is stirred for 16 hours. To the reaction mixture are added 200 g of ice, 2 liters of water and 1 liter of ethyl acetate, and the mixture is stirred. After phase separation, the upper layer is discarded. To the aqueous layer is added 1 liter of ethyl acetate, and 129 g of phosphoric acid is added dropwise thereto while stirring (pH 4). After thorough mixing, the upper layer is separated and the lower layer is extracted with 1 liter of ethyl acetate. The organic layers are combined, washed with two 2-liter portions of ice-water and then with 1 liter of saturated aqueous sodium chloride, dried over anhydrous magnesium sulfate and then concentrated. To the residue is added 100 ml of methylene chloride, and the resulting mixture is concentrated and dried to give 194 g (74% yield) of the above-identified compound as a glassy solid.

Elemental analysis for $C_{17}H_{22}N_2O_8S \cdot \frac{1}{2}H_2O$: Calcd. (%): C, 48.22; H, 5.47; N, 6.62. Found (%): C, 48.16; H, 5.30; N, 6.32.

IR spectrum $\nu_{max}^{KBr}$ cm$^{-1}$: 1780, 1720, 1520, 1370, 1320.

NMR spectrum (d$_6$-DMSO)δ: 1.42(9H, s), 2.18(3H, s), 3.41 and 3.62(2H, ABq, J=18 Hz), 3.62(2H, s), 4.78 and 5.06(2H, ABq, J=14 Hz), 5.03(1H, d, J=5 Hz), 5.45(1H, d.d, J=5 Hz and 8 Hz), 7.83(1H, d, J=8 Hz).

REFERENCE EXAMPLE 33

7β-Formamido-3-(3-oxobutyryloxymethyl)-3-cephem-4-carboxylic acid

In 60 ml of formic acid is dissolved 3.2 g of 7β-amino-3-(3-oxobutyryloxymethyl)-3-cephem-4-carboxylic acid and the solution is cooled to 0°–5° C. With stirring, 20 ml of acetic anhydride is added dropwise to the solution during 30 minutes. The mixture is stirred at the same temperature for 30 minutes and then at room temperature for 1 hour. The solvent is evaporated off under reduced pressure and the residue is dissolved in methyl ethyl ketone. The solution is washed with water and saturated aqueous sodium chloride solution and dried over anhydrous magnesium sulfate. The solvent is then evaporated off under reduced pressure and a diisopropylether-hexane mixture is added to the residue to bring about solidification. The solid is then collected by filtration to give 3.1 g of the above-identified compound as a light-yellow powder. IR spectrum $\nu_{max}^{KBr}$ cm$^{-1}$: 3380, 1780, 1720, 1660, 1625, 1510.

NMR spectrum (d$_6$-DMSO)δ: 2.20(3H, s), 3.45 and 3.68(2H, ABq, J=18 Hz), 3.63(2H, s), 4.79 and 5.09(2H, ABq, J=13 Hz), 5.11 (1H, d, J=4.5 Hz), 5.79(1H, d.d, J=4.5 Hz and 8 Hz), 8.15(1H, br.), 9.00(1H, d, J=8 Hz).

REFERENCE EXAMPLE 34

2-(2-Amino-5-chlorothiazol-4-yl)-2(Z)-[1-(tert-butoxycarbonyl)-1-methylethoxyimino]acetic and In 50 ml of methanol is dissolved 6.0 g of 2-(2-aminothiazol-4-yl)-2(Z)-[1-(tert-butoxycarbonyl)-1-methylethoxyimino]acetic acid, and 2.4 g of N-chlorosuccinimide is added to the solution with stirring at room temperature. The mixture is stirred at room temperature for 6 hours and the solvent is evaporated off under reduced pressure. The residue is dissolved in ethyl acetate and the solution is washed with water and saturated aqueous sodium chloride solution and dried over anhydrous magnesium sulfate. The solvent is then evaporated off under reduced pressure to give 5.5 g of the above-identified compound as light-yellow cyrstals.

IR spectrum $\nu_{max}^{KBr}$ cm$^{-1}$: 3325, 3200, 1720, 1635, 1540, 1140.

NMR spectrum (CDCl$_3$-d$_6$-DMSO)δ: 1.42(9H, s), 1.46(6H, s), 6.80–7.80(3H, m).

REFERENCE EXAMPLE 35

2-(2-Amino-5-bromothiazol-4-yl)-2(Z)-(tert-butoxycarbonylmethoxyimino)acetic acid A mixture of 12 g of 2-(2-aminothiazol-4-yl)-2(Z)-(tert-butoxycarbonylmethoxyimino)acetic acid and 9.54 g of N-bromosuccinimide in 100 ml of methanol is stirred at 60° C. for 2 hours.

The solvent is evaporated off under reduced pressure and the residue is partitioned between 200 ml of tetrahydrofuran and an aqueous phase consisting of 200 ml of saturated aqueous sodium chloride solution and 50 ml of 5% aqueous sodium thiosulfate solution. The organic phase is separated, washed twice with 100 ml portions of saturated aqueous sodium chloride solution and dried over anhydrous magnesium sulfate. The solvent is removed and the residue is crystallized from methanol to give 8.48 g (56% yield) of the above-identified compound as colorless crystals.

M.p.: 155°–160° C. (decomposition)

Elemental analysis for $C_{11}H_{14}BrN_3O_5S$: Calcd. (%): C, 34.75; H, 3.71; N, 11.05. Found (%): C, 34.60; H, 3.99; N, 10.76.

IR spectrum $\nu_{max}^{KBr}cm^{-1}$: 1730, 1700, 1605, 1535, 1415, 1370.

NMR spectrum (d$_6$-DMSO)δ: 1.42(9H, s), 4.56(2H, s), 6.6–8.0(2H, br. s).

REFERENCE EXAMPLE 36

2-(2-Amino-5-chlorothiazol-4-yl)-2(Z)-(tert-butoxycarbonylmethoxyimino)acetic acid Six grams of 2-(2-aminothiazol-4-yl)-2(Z)-(tert-butoxycarbonylmethoxyimino)acetic acid and 3.2 g of N-chlorosuccinimide are reacted in the manner of Reference Example 35 and the product obtained is solidified by treating hexane to give 6.5 g of the above-identified compound as a powder.

IR spectrum $\nu_{max}^{KBr}cm^{-1}$: 1735, 1630, 1540, 1370, 1300, 1240.

NMR spectrum (d$_6$-DMSO)δ: 1.41(9H, 2), 4.57(2H, s), 6–8(2H, br. s).

REFERENCE EXAMPLE 37

2-(2-Chloroacetamido-5-bromothiazol-4-yl)-2(Z)-methoxyiminoacetic acid

In 30 ml of dimethylacetamide is dissolved 13.9 g of 2-(2-chloroacetamidothiazol-4-yl)-2(Z)-methoxyiminoacetic acid. To this solution, 10.8 g of N-bromosuccinimide is added and the mixture is stirred at room temperature for 6 hours.

To the reaction mixture are added 300 ml of water, 100 ml of ethyl acetate, 300 ml of methyl ethyl ketone and 50 ml of 5% aqueous sodium thiosulfate solution and the mixture is shaken. The organic layer is separated, washed with 100 ml of saturated aqueous sodium chloride solution, dried over anhydrous magnesium sulfate, then concentrated. The residue is crystallized from ethyl acetate to give 13.5 g (76% yield) of the above-identified compound.

M.p.: 176°–180° C. (decomposition)

Elemental analysis for $C_8H_7BrClN_3O_4S$: Calcd. (%): C, 26.94; H, 1.98; N, 11.78. Found (%): C, 26.90; H, 2.09; N, 11.52.

IR spectrum $\nu_{max}^{KBr}cm^{-1}$: 1720, 1670, 1535, 1315, 1280, 1260.

NMR spectrum (d$_6$-DMSO)δ: 3.95(3H, s), 4.36(2H, s), 12.90(1H, br. s).

REFERENCE EXAMPLE 38

2-(2-Chloroacetamido-5-iodothiazol-4-yl)-2(Z)-methoxyiminoacetic acid

To a solution of 13.9 g of 2-(2-chloroacetamidothiazol-4-yl)-2(Z)-methoxyiminoacetic acid in 30 ml of dimethylacetamide, 17.0 g of N-iodosuccinimide is added and the mixture is stirred at 60° C. for 1 hour. Then, the reaction mixture is processed as in Reference Example 37 to give 19.6 g (97% yield) of the above-identified compound as colorless crystals.

M.p.: 190°–195° C. (decomposition)

Elemental analysis for $C_8H_7ClIN_3O_4S$: Calcd. (%): C, 23.81; H, 1.75; N, 10.41. Found (%): C, 23.60; H, 2.05; N, 10.19.

IR spectrum $\nu_{max}^{KBr}cm^{-1}$: 1720, 1660, 1535, 1310, 1290, 1270.

NMR spectrum (d$_6$-DMSO)δ: 3.96(3H, s), 4.35(2H, s), 12.91(1H, br. s).

REFERENCE EXAMPLE 39

7β-[2-(2-Amino-5-chlorothiazol-4-yl)-2(Z)-[1-(tert-butoxycarbonyl)-1-methylethoxyimino]acetamido]-3-(3-oxobutyryloxymethyl)-3-cephem-4-carboxylic acid 2-(2-Amino-5-chlorothiazol-4-yl)-2(Z)-[1-(tert-butyoxycarbonyl)-1-methylethoxyimino]acetic acid is reacted with 7β-amino-3-(3-oxobutyryloxymethyl)-4-carboxylic acid in the manner of Reference Example 3 to give the above-identified compound.

IR spectrum $\nu_{max}^{KBr}cm^{-1}$: 1780, 1720, 1660, 1530, 1140.

REFERENCE EXAMPLE 40

7β-[2-(2-Amino-5-chlorothiazol-4-yl)-2(Z)-(tert-butoxycarbonylmethoxyimino)acetamido]-3-(3-oxobutyryloxymethyl)-3-cephem-4-carboxylic acid Six grams of 2-(2-amino-5-chlorothiazol-4-yl)-2(Z)-(tert-butoxycarbonylmethoxyimino)acetic acid, 3.8 g of 1-hydroxy-1H-benzotriazole monohydrate and 4.4 g of dicyclohexylcarbodiimide are dissolved in dimethylformamide under ice-cooling. This mixture is stirred at the same temperature for 5 minutes and then at room temperature for 30 minutes further. To the resulting mixture is added a suspension composite of 5.61 g of 7β-amino-3-(3-oxobutyryloxy)methyl-3-cephem-4-carboxylic acid, 7.5 ml of triethylamine and 20 ml of dimethylformamide and the mixture is stirred at room temperature for 16 hours.

To the reaction mixture, 500 ml of diethyl ether is added and the upper layer is removed by decantation. To the lower layer, 300 ml of diethyl ether is added and the upper layer is removed again by decantation. The lower layer is mixed with 100 ml of water, 200 ml of ethyl acetate and 200 ml of methyl ethyl ketone, and then adjusted to pH 2.5. Insoluble substance is removed by filtration and the organic layer is separated, washed twice with 100 ml portions of saturated aqueous sodium chloride solution and dried over anhydrous magnesium sulfate. The solvent is evaporated under reduced pressure to give 10.1 g (89% yield) of the above-identified compound.

IR spectrum $\nu_{max}^{KBr}cm^{-1}$: 1780, 1740, 1620, 1530, 1445, 1370, 1310.

NMR spectrum (d$_6$-DMSO)δ: 1.44(9H, s), 2.10(3H, s), 3.42 and 3.64(2H, Abq, J=18 Hz), 3.64(2H, s), 4.57(2H, s), 4.79 and 5.08(2H, Abq, J=13 Hz), 5.14(1H, d, J=5 Hz), 5.84(1H, d.d, J=5 and 8 Hz), 7–8(2H, br.), 9.41(1H, d, J=8 Hz).

REFERENCE EXAMPLE 41

7β-[2-(2-Amino-5-bromothiazol-4-yl)-2-(Z)-(tert-butoxycarbonylmethoxyimino)acetamido]-3-(3-oxobutyryloxymethyl)-3-cephem-4-carboxylic acid 2-(2-Amino-5-bromothiazol-4-yl)-2-(Z)-(tert-butoxycarbonylmethoxyimino)acetic acid and 7β-amino-3-(3-oxobutyryloxymethyl)-3-cephem-4-carboxylic acid are reacted and worked up in the manner Reference Example 40 to give the above-identified compound (99% yield).

IR spectrum $\nu_{max}^{KBr}$cm$^{-1}$: 1780, 1630, 1620, 1530, 1450, 1370, 1310.

NMR spectrum (d$_6$-DMSO)δ: 1.44(9H, s), 2.20(3H, s), 3.42 and 3.65(2H, Abq, J=18 Hz), 3.64(2H, s), 4.58(2H, s), 4.79 and 5.09(2H, Abq, J=14 Hz), 5.13(1H, d, J=5 Hz), 5.85(1H, d.d, J=5 and 8 Hz), 9.38(1H, d, J=8 Hz).

REFERENCE EXAMPLE 42

7β-[2-(5-Amino-1,2,4-thiadiazol-3-yl)-2-(Z)-(cyanomethoxyimino)acetamido]-3-(3-oxobutyryloxymethyl)-3-cephem-4-carboxylic acid A mixture of 13 g of 2-(5-amino-1,2,4-thiadiazol-3-yl)acetic acid, 10.7 g of selenium dioxide and 200 ml of dioxane is heated in an oil bath kept at 90° C. for 40 minutes with stirring. After cooling, dioxane is evaporated off. To the residue is added 150 ml of ethyl acetate and, after filtration, ethyl acetate is evaporated off under reduced pressure. To the residue are added 100 ml of ethanol and then, with stirring, 3.6 g of O-cyanomethylhydroxylamine. The mixture is then stirred at room temperature for 40 minutes and ethanol is evaporated off under reduced pressure. The residue is dissolved in 150 ml of ethyl acetate. The ethyl acetate solution is washed once with water and then shaken with 100 ml of 5% aqueous sodium bicarbonate solution. The aqueous phase is separated, covered with 150 ml of ethyl acetate and acidified with phosphoric acid with efficient stirring. The ethyl acetate layer is separated and dried over anhydrous magnesium sulfate. Ethyl acetate is evaporated off under reduced pressure and the residue is dissolved in 30 ml of dichloromethane. To the resulting solution, is added 2.2 g of phosphorus pentachloride under ice-cooling. After 20 minutes' stirring at the same temperature, dichloromethane is evaporated off. The residue is redissolved in 5 ml of dichloromethane and the solution is added all at once to a solution composite of 3.1 g of 7β-amino-3-(3-oxobutyryloxymethyl)-3-cephem-4-carboxylic acid, 6 ml of bistrimethylsilylacetamide and 60 ml of dichloromethane and the mixture is stirred under ice-cooling for 30 minutes. Dichloromethane is then evaporated off and the residue is dissolved in 100 ml of ethyl acetate. The resulting solution is washed with water and dried over anhydrous magnesium sulfate and ethyl acetate is then evaporated off under reduced pressure. To the residue is added 10 ml of ice-cooled trifluoroacetic acid and the mixture is stirred at room temperature for 30 minutes. To the reaction mixture is added 50 ml of ethyl acetate and the solvent is then evaporated under reduced pressure. The residue is triturated with ethyl acetate and the insoluble substance is collected by filtration giving 2 g of crude above-identified compound. The filtrate is then concentrated, the residue treated with diethyl ether and insoluble substance is collected by filtration to give 1.4 g of the above-identified compound.

IR spectrum $\nu_{max}^{KBr}$cm$^{-1}$: 1780, 1700, 1620, 1520, 1400, 1360, 1310, 1140, 1040.

NMR spectrum (d$_6$-DMSO)δ: 2.21(3H, s), 3.44 and 3.68(2H, Abq, J=18 Hz), 3.65(2H, s), 4.79 and 5.10(2H, Abq, J=14 Hz), 5.11(2H, s), 5.17(1H, d, J=4.8 Hz), 5.85(1H, d.d, J=4.8 and 8 Hz), 8.16(2H, br.), 9.74(1H, d, J=8 Hz).

REFERENCE EXAMPLE 43

Imidazo[1,2-a]pyridine derivatives and imidazo[1,5-a]pyridine derivatives are synthesized according to known methods, e.g. W. W. Paudler and H. L. Blewitt H. Org. Chem. 30, 4081 (1965), J. P. Paolini and R. K. Robius J. Org. Chem., 30, 4085 (1965), J. P. Paolini and K. Robius J. Heterocyclic Chem., 2, 53 (1965).

Synthesis of novel imidazo[1,2-a]pyridine derivatives is described below.

(43-1) 6-Carbamoylimidazo[1,2-a]pyridine

To 100 ml of ethanol are added 10 g of 6-aminonicotinamide, 11 g of 40% chloroacetaldehyde and 12.5 g of sodium hydrogen carbonate and the mixture is heated under reflux for 4 hours. Ethanol is evaporated off and 100 ml of water is added to the residue. The mixture is adjusted to pH 10 by adding 10% aqueous sodium hydroxide solution and then extracted four times with 50 ml portions of a mixture solvent of tetrahydrofuran-ethyl acetate (1:1). The extracts are combined, dried over anhydrous sodium sulfate and concentrated under reduced pressure. The resulting residue is recrystallized from a mixture solvent of methanol-diethyl ether to give 3.5 g of the above-identified compound as colorless needles.

M.P.: 202°–204° C.

IR spectrum $\nu_{max}^{KBr}$cm$^{-1}$: 3350, 3120, 1670, 1620, 1420, 1320.

NMR spectrum (d$_6$-DMSO-D$_2$O)δ: 7.65(3H, s), 8.03(1H, s), 9.10(1H, s).

(43-2) 5-Methylthioimidazo[1,2-a]pyridine

Into 100 ml of dimethylformamide are suspended 5 g of 5-chloroimidazo[1,2-a]pyridine and 5 g of sodium methanethiolate and the mixture is stirred at 20° C. for 1 hour. The solvent is evaporated off under reduced pressure and the residue is dissolved in 200 ml of dichloromethane. The mixture is washed with aqueous saturated sodium chloride solution, dried over anhydrous magnesium sulfate and purified by silica-gel column chromatography to give 3 g of the above-identified compound as an oil.

NMR spectrum (CDCl$_3$)δ: 2.55(3H, s), 6.63(1H, d, J=7 Hz), 7.07(1H, d.d, J=7 Hz and 9 Hz), 7.43(1H, d, J=9 Hz), 7.61(2H, s).

(43-3) 5-Acetamidoimidazo[1,2-a]pyridine acetate

To 200 ml of 1N sodium hydroxide is dissolved 10 g of 5-aminoimidazo[1,2-a]pyridine hydrobromide and the mixture is extracted with 500 ml of dichloromethane. The extract is evaporated to dryness and the residue is suspended into 50 ml of acetic anhydride. The mixture is heated under reflux for 6 hours. The solvent is evaporated off under reduced pressure and then ethyl acetate is added to the residue to give 3.6 g of the above-identified compound as crystals.

M.p.: 110°–112° C.

NMR spectrum (CDCl₃)δ: 2.33(6H, s), 6.73(1H, d, J=7 Hz), 7.05–7.4(2H, m), 7.6–8.8(3H, m).

(43-4) 6-Cyanoimidazo[1,2-a]pyridine

A mixture of 2.6 g of 6-carbamoylimidazo[1,2-a]pyridine and 30 ml of phosphorus oxychloride is heated under reflux for 16 hours. The excess phosphorus oxychloride is removed under reduced pressure and the residue is poured onto ice. The mixture is neutralized with sodium carbonate and extracted with ethyl acetate. The organic layer is washed with saturated aqueous sodium chloride solution and dried over anhydrous magnesium sulfate. The solvent is then evaporated off under reduced pressure to give 2.0 g of the above-identified compound as colorless crystals.

M.p.: 166°–167° C.

Elemental analysis for $C_8H_5N_3$: Calcd. (%): C, 67.13; H, 3.52; N, 29.35. Found (%): C, 67.37; H, 3.62; N, 28.99.

(43-5) 8-Hydroxyimidazo[1,2-a]-pyridine hydrochloride

In 80 ml of concentrated hydrochloric acid is dissolved 5 g of 8-benzyloxyimidazo[1,2-a]pyridine, and the solution is stirred at room temperature for 24 hours and then concentrated. After addition of 1-butanol, water is azeotropically removed by distillation, and the residue is crystallized from diethyl ether to give 3.8 g of the above-identified compound.

M.p.: 153°–156° C.

IR spectrum $\nu_{max}^{KBr}$ cm$^{-1}$: 1670, 1580, 1520, 1410, 1320, 1300.

NMR spectrum (d₆-DMSO)δ: 7.2–7.4(2H, m), 8.25(1H, d), 8.3–8.5(2H, m).

(43-6) 8-Benzyloxyimidazo[1,2-a]pyridine

2-Amino-3-benzyloxypyridine is reacted with bromoacetaldehye in aqueous tetrahydrofuran in the presence of sodium hydrogen carbonate, whereby the above-identified compound is obtained.

M.p.: 97°–98° C.

Elemental analysis for $C_{14}H_{12}N_2O$: Calcd. (%): C, 74.98; H, 5.39; N, 12.49. Found (%): C, 74.86; H, 5.40; N, 12.37.

IR spectrum $\nu_{max}^{KBr}$ cm$^{-1}$: 1540, 1500, 1330, 1315, 1280, 1115.

NMR spectrum (CDCl₃)δ: 5.31(2H, s), 6.3–6.8(2H, m), 7.2–7.8(8H, m).

(43-7) 8-Fluoroimidazo[1,2-a]pyridine

2-Amino-3-fluoropyridine (21.1 g) is added to a solution of bromoacetaldehyde prepared from 74 g of bromoacetaldehyde diethylacetal, 18.5 ml of aqueous hydrogen bromide solution and 18.5 ml of water and made to react in the presence of sodium bicarbonate in aqueous ethanolic solution giving 12 g of the above-identified compound, bp. 91°–100° C./1–1.5 mmHg, which solidifies at room temperature.

NMR spectrum (CDCl₃)δ: 6.53–7.33(2H, m), 7.60–7.70(2H, m), 7.88–8.03(1H, m).

EXAMPLE 1

7β-[2-(2-Aminothiazol-4-yl)-2(Z)-methoxyiminoacetamido]-3-[(imidazo[1,2-a]pyridinium-1-yl)methyl]-3-cephem-4-carboxylate

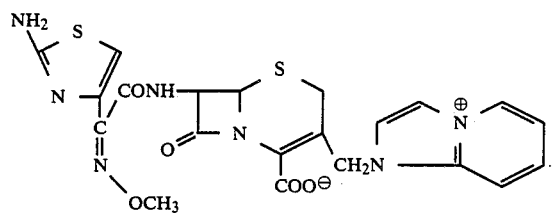

In 40 ml of a 1:1 mixture of acetonitrile and water are dissolved 4 g of 7β-[2-(2-aminothiazol-4-yl)-2(Z)-methoxyiminoacetamido]-3-(3-oxobutyryloxymethyl)-3-cephem-4-carboxylic acid, 4 g of imidazo[1,2-a]pyridine and 4 g of potassium iodide, and the mixture is stirred at 70° C. for 2 hours. The solvent is evaporated off under reduced pressure and the residue is solidified by addition of 100 ml of acetonitrile. The resulting powder is collected by filtration and subjected to silica gel column chromatography using a mixture of acetonitrile and water (4:1) as an eluent. The eluted fraction is concentrated under reduced pressure and the residue is lyophilized. A solid obtained is dissolved in 5 ml of water and chromatographed on an XAD-2 column using 10% aqueous ethanol as an eluent. The fractions containing the objective compound are combined and concentrated under reduced pressure, and the residue is lyophilized to give 1.0 g of the above-identified compound.

Element analysis for: $C_{21}H_{19}N_7O_5S_2 \cdot 7/2H_2O$: Calcd. (%): C 43.74; H, 4.54; N, 17.00. Found (%): C 44.00; H, 4.29; N, 17.23.

IR spectrum $\nu_{max}^{KBr}$ cm$^{-1}$: 1765, 1670, 1605, 1520, 1030.

NMR spectrum (d₆-DMSO)δ: 2.95 & 3.44 (2H, ABq, J=18 Hz), 3.80 (3H, s), 4.99 (1H, d, J=4.5 Hz), 5.27 & 5.74 (2H, ABq, J=14 Hz), 5.59 (1H, d. d, J=4.5 Hz & 8 Hz), 6.68 (1H, s), 7.16 (2H, br. s), 7.4–7.6 (1H, m), 7.85–8.15 (1H, m), 8.4–8.9 (2H, m), 8.9 (1H, d, J=7 Hz), 9.46 (1H, d, J=8 Hz).

EXAMPLE 2

7β-[2-(2-Aminothiazol-4-yl)-2(Z)-ethoxyiminoacetamido]-3-[(imidazo[1,2-a]pyridinium-1-yl)methyl]-3-cephem-4-carboxylate

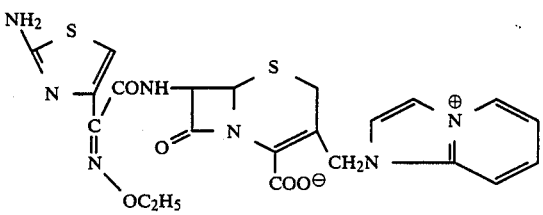

In a 1:1 mixture of acetonitrile and water are dissolved 5.0 g of 7β-[2-(2-aminothiazol-4-yl)-2(Z)-ethoxyiminoacetamido]-3-(3-oxobutyryloxymethyl)-3-cephem-4-carboxylic acid, 5.0 g of imidazo[1,2-a]pyridine and 5.0 g of potassium iodide, and the mixture is stirred at 70° C. for 2 hours. The solvent is evaporated off under reduced pressure, and the residue is dissolved in 20 ml of water and extracted twice with 20 ml portions of ethyl acetate. The organic layer is discarded and the aqueous layer is subjected to XAD-2 column chromatography using 20% aqueous ethanol as an eluent. The fractions containing the objective compound are combined and concentrated under reduced pressure, and the residue is lyophilized. A solid obtained is dissolved in 10 ml of water and chromatographed on a column of Cephadex LH-20 using water as an eluent. The fractions containing the objective compound are combined and concentrated under reduced pressure, and the residue is lyophilized to give 0.5 g of the above-identified compound.

Elemental analysis for: $C_{22}H_{21}N_7O_5S_2.3H_2O$: Calcd. (%): C, 45.43; H, 4.68, N, 16.86. Found (%): C, 45.64; H, 4.26; N, 16.78.

IR spectrum $\nu_{max}^{KBr}$ cm$^{-1}$: 1770, 1610, 1530, 1200, 1030.

NMR spectrum (d$_6$-DMSO)δ: 1.19 (3H, t, J=7 Hz), 3.00 and 3.45 (2H, ABq, J=18 Hz), 4.06 (2H, q, J=7 Hz), 5.01 (1H, d, J=4.8 Hz), 5.28 & 5.48 (2H, ABq, J=14 Hz), 5.63 (1H, d. d, J=4.8 Hz & 8 Hz), 6.66 (1H, s), 7.15 (1H, br. s), 7.40–7.64 (1H, m), 7.86–8.10 (1H, m), 8.36–8.70 (3H, m), 8.88–9.00 (1H, d, J=7 Hz), 9.42 (1H, d, J=8 Hz).

EXAMPLE 3

7β-[2-(2-Aminothiazol-4-yl)-2(Z)-allyloxyiminoacetamido]-3-[(imidazo[1,2-a]pyridinium-1-yl)methyl]-3-cephem-4-carboxylate

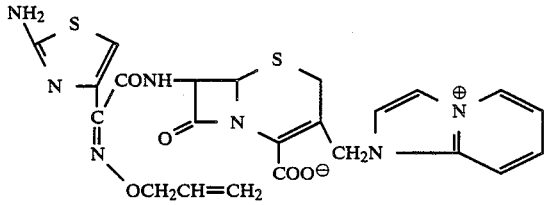

In 40 ml of a 1:1 mixture of acetonitrile and water are dissolved 2.0 g of 7β-[2-(2-aminothiazol-4-yl)-2(Z)-allyloxyiminoacetamido]-3-(3-oxobutyryloxymethyl)-3-cephem-4-carboxylic acid, 2.0 g of imidazo[1,2-a]pyridine and 2.0 g of potassium iodide, and the mixture is stirred at 70° C. for 1.5 hours. The mixture is concentrated under reduced pressure and the residue is solidified by addition of 50 ml of acetonitrile. The resulting powder is collected by filtration, dissolved in 10 ml of water and subjected to XAD-2 column chromatography using 10% aqueous ethanol as an eluent. The fractions containing the objective compound are combined and concentrated under reduced pressure, and the residue is lyophilized to give the crude solid compound. This solid is dissolved in 3 ml of water and chromatographed on a silica gel column using acetonitrile-water (4:1) as an eluent. The fractions containing the objective compound are combined and concentrated under reduced pressure, and the residue lyophilized to give 0.25 g of the above-identified compound.

Elemental analysis for: $C_{23}H_{21}N_7O_5S_2.3H_2O$: Calcd. (%): C, 46.53; H, 4.59; N, 16.52. Found (%): C, 46.70; H, 4.41; N, 16.75.

IR spectrum $\nu_{max}^{KBr}$ cm$^{-1}$: 1770, 1670, 1610, 1530, 1390.

NMR spectrum (d$_6$-DMSO-D$_2$O) δ: 3.00 & 3.50 (2H, ABq, J=18 Hz), 4.60 (2H, d, J=4.5 Hz), 5.05 (1H, d, J=5Hz), 5.23 (2H, d, J=15 Hz), 5.40 (2H, s), 5.70 (1H, d, J=5 Hz), 6.80–6.10 (1H, m), 6.73 (1H, s), 7.50–7.60 (1H, m), 7.90–8.10 (1H, m), 8.30–8.46 (3H, m), 8.83 (1H, d, J=6 Hz).

EXAMPLE 4

7β-[2-(2-Aminothiazol-4-yl)-2(Z)-carboxymethoxyiminoacetamido]-3-[(imidazo[1,2-a]pyridinium-1-yl)methyl]-3-cephem-4-carboxylate monosodium salt

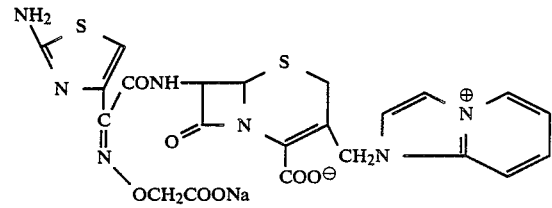

(a) In 60 ml of a 1:1 mixture of acetonitrile and water are dissolved 3.0 g of 7β-[2-(2-aminothiazol-4-yl)-2(Z)-tert-butoxycarbonylmethoxyiminoacetamido]-3-(3-oxobutyryloxymethyl)-3-cephem-4-carboxylic acid, 3.0 g of imidazo[1,2-a]pyridine and 3.0 g of potassium iodide, and the mixture is stirred at 70° C. for 2 hours. The mixture is concentrated under reduced pressure and to the residue is added 20 ml of water. The mixture is extracted twice with 20 ml portions of ethyl acetate and the insoluble substance is removed off. The aqueous layer is subjected to XAD-2 column chromatography using 20% aqueous ethanol as an eluent. The fractions containing the objective compound is combined and concentrated under reduced pressure, and the residue is lyophilized to give 0.9 g of 7β-[2-(2-aminothiazol-4-yl)-2(Z)-tert-butoxycarbonylmethoxyiminoacetamido]-3-[(imidazol[1,2-a]-pyridinium-1-yl)methyl]-3-cephem-4-carboxylate.

(b) In 4 ml of trifluoroacetic acid is dissolved 0.8 g of 7β-[2-(2-aminothiazol-4-yl)-2(Z)-tert-butoxycarbonylmethoxyiminoacetamido]-3-[(imidazo[1,2-a]pyridinium-1-yl)methyl]-3-cephem-4-carboxylate and the mixture is stirred at 20° C. for 2 hours. The mixture is concentrated under reduced pressure and the residue is dissolved in 5 ml of water. Then, the mixture is adjusted to pH 8.0 by adding sodium hydrogen carbonate and subjected to XAD-2 column chromatography using water as an eluent. The fractions containing the objective compound are combined and concentrated under reduced pressure, and then the residue is lyophilized to give 0.4 g of the above-identified compound.

Element analysis for: $C_{22}H_{18}N_7O_7S_2Na.4H_2O$: Calcd. (%): C, 40.56; H, 4.02; N, 15.05. Found (%): C, 40.39; H, 3.75; N, 15.22.

IR spectrum $\nu_{max}^{KBr}$ cm$^{-1}$: 1770, 1660, 1605, 1530.

NMR spectrum (d$_6$-DMSO-H$_2$O) δ: 3.03 & 3.45 (2H, ABq, J=18 Hz), 4.30 (2H, s), 5.03 (1H, d, J=4.5 Hz), 5.33 (2H, s), 5.66 (1H, d, J=4.5 Hz), 6.80 (1H, s), 7.46–7.60 (1H, m), 7.95–8.10 (1H, m), 8.30–8.50 (3H, m), 8.86 (1H, d, J=6 Hz).

EXAMPLE 5%

7β-[2-(2-Aminothiazol-4-yl)-2(Z)-(1-carboxy-1-methylethoxyimino)acetamido]-3-[(imidazo[1,2-a]pyridinium-1-yl)methyl]-3-cephem-4-carboxylate monosodium salt

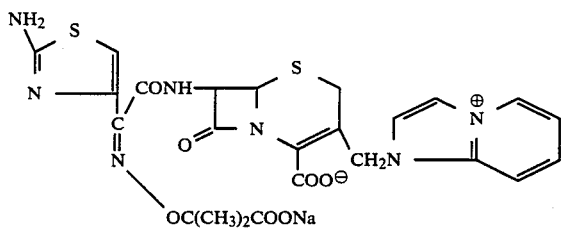

(a) In 60 ml of a 1:1 mixture of acetonitrile and water are dissolved 4.0 g of 3-(3-oxobutyryloxymethyl)-7β-[2-(2-tritylaminothiazol-4-yl)-2(Z)-(1-methyl-1-tert-butoxycarbonyl)-ethoxyiminoacetamido]-3-cephem-4-carboxylic acid, 4.0 g of imidazo[1,2-a]pyridine and 4.0 g of potassium iodide, and the mixture is stirred at 70° C. for 2 hours. The mixture is concentrated under reduced pressure and the residue is extracted four times with 50 ml portions of a 1:1 mixture of tetrahydrofuran and ethyl acetate. The extracts are combined and dried over anhydrous magnesium sulfate, and the solvent is evaporated off under reduced pressure. The residue is subjected to silica gel column chromatography using a 9:1 mixture of acetonitrile and water as an eluent to give 1.2 g of 3-[(imidazo[1,2-a]pyridinium-1-yl)methyl]-7β-[2-(2-tritylaminothiazol-4-yl)-2(Z)-(1-methyl-1-tert-butoxycarbonyl)-ethoxyiminoacetamido]-3-cephem-4-carboxylate.

(b) To 6 ml of trifluoroacetic acid is dissolved 1.2 g of 3-[(imidazo[1,2-a]pyridinium-1-yl)methyl]-7β-[2-(2-tritylaminothiazol-4-yl)-2(Z)-(1-methyl-1-tert-butoxycarbonyl)ethoxyiminoacetamido]-3-cephem-4-carboxylate and the mixture is stirred at 20° C. for 2 hr. The mixture is concentrated under reduced pressure and the residue is dissolved in 5 ml of water. Then, the mixture is adjusted to pH 8.0 by adding sodium hydrogen carbonate and subjected to XAD-2 column chromatography using 5% aqueous ethanol as an eluent. The fractions containing the objective compound are combined, concentrated under reduced pressure, and then the residue is lyophilized to give 0.3 g of the above-identified compound.

Elemental analysis for: $C_{24}H_{22}N_7O_7S_2Na.3H_2O$: Calcd. (%): C, 43.44; H, 4.56; N, 14.78. Found (%): C, 43.67; H, 4.39; N, 14.60.

IR spectrum $\nu_{max}^{KBr}$ cm$^{-1}$: 1765, 1670, 1600, 1530.

NMR spectrum (d$_6$-DMSO-H$_2$O) δ: 1.50 (6H, s), 3.10 & 3.55 (2H, ABq, J=18 Hz), 5.06 (1H, d, J=5 Hz), 5.43 (2H, s), 5.75 (1H, d, J=5 Hz), 6.73 (1H, s), 7.45–7.65 (1H, m), 7.96–8.15 (1H, m), 8.40–8.55 (3H, m), 8.96 (1H, d, J=8 Hz).

7β-[2-(2-Aminothiazol-4-yl)-2(Z)-(substituted oxyimino)acetamido]-3-(3-oxobutyryloxymethyl)-3-cephem-4-carboxylic acid is reacted with various imidazole compounds in the same manner as described in Example 1 to give the compounds of Examples 6–22, which have the following general formula:

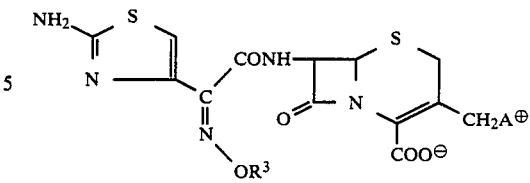

EXAMPLE 6

7β-[2-(2-Aminothiazol-4-yl)-2(Z)-methoxyiminoacetamido]-3-[(6-methylimidazo[1,2-a]pyridinium-1-yl)methyl]-3-cephem-4-carboxylate.

compound [VII′] (R$^3$=—CH$_3$, A$^\oplus$=

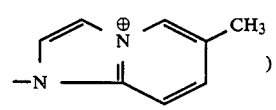

)

Elemental analysis for: $C_{22}H_{21}N_7O_5S_2.11/2H_2O$: Calcd. (%): C, 42.17; H, 5.15; N, 15.65. Found (%): C, 41.86; H, 4.21; N, 15.46.

IR spectrum $\nu_{max}^{KBr}$ cm$^{-1}$: 1765, 1610, 1535, 1035.

NMR spectrum (d$_6$-DMSO)δ: 2.41 (3H, s), 2.95 & 3.43 (2H, ABq, J=18 Hz), 3.78 (3H, s), 4.79 (1H, d, J=4.5 Hz), 5.20 & 5.41 (2H, ABq, J=14 Hz), 5.54 (1H, d. d, J=4.5 Hz & 8 Hz), 6.68 (1H, s), 7.14 (2H, br. s), 7.7–7.96 (1H, m), 8.2–8.65 (3H, m), 8.72 (1H, br. s), 9.45 (1H, d).

EXAMPLE 7

7β-[2-(2-Aminothiazol-4-yl)-2(Z)-methoxyiminoacetamido]-3-[(7-methylimidazo[1,2-a]pyridinium-1-yl)methyl]-3-cephem-4-carboxylate.

compound [VII′] (R$^3$=—CH$_3$, A$^\oplus$=

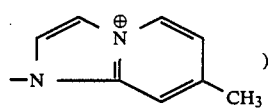

)

Elemental analysis for: $C_{22}H_{21}N_7O_5S_2.7/2H_2O$: Calcd. (%): C, 44.74; H, 4.78; N, 16.60. Found (%): C, 44.72; H, 4.40; N, 16.31.

IR spectrum $\nu_{max}^{KBr}$ cm$^{-1}$: 1770, 1660, 1615, 1535.

NMR spectrum (d$_6$-DMSO) δ: 2.52 (3H, s), 2.98 & 3.44 (2H, ABq, J=18 Hz), 3.80 (3H, s), 5.00 (1H, d, J=4.5 Hz), 5.20 & 5.37 (2H, ABq, J=14 Hz), 5.60 (1H, d. d, J=4.5 Hz & 8 Hz), 6.68 (1H, s), 7.12 (2H, br. s), 8.2–8.5 (1H, m), 8.1–8.5 (3H, m), 8.80 (1H, d, J=7 Hz), 9.45 (1H, d, J=8 Hz).

EXAMPLE 8

7β-[2-(2-Aminothiazol-4-yl)-2(Z)-methoxyiminoacetamido]-3-[(6-chloroimidazo[1,2-a]pyridinium-1-yl)methyl]-3-cephem-4-carboxylate compound [VII′] (R$^3$=—CH$_3$, A$^\oplus$=

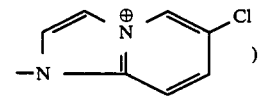

)

Elemental analysis: $C_{21}H_{18}N_7O_5S_2Cl.4H_2O$: Calcd. (%): C, 40.68; H, 4.23; N, 15.81. Found (%): C, 40.63; H, 3.96; N, 15.92.

IR spectrum $\nu_{max}^{KBr}$ cm$^{-1}$: 1765, 1660, 1610, 1520.

NMR spectrum (d$_6$-DMSO) δ: 2.96 & 3.34 (2H, ABq, J=18 Hz), 3.69 (3H, s), 4.98 (1H, d, J=4.5 Hz), 5.23 & 5.50 (2H, ABq, J=14 Hz), 5.60 (1H, d. d, J=4.5 Hz & 8 Hz), 6.67 (1H, s), 7.12 (2H, br. s), 8.0–8.2 (1H, m), 8.34 (1H, br. s), 8.58 (1H, br. s), 8.78 (1H, d, J=10 Hz), 9.28 (1H, s), 9.45 (1H, d, J=8 Hz).

EXAMPLE 9

7β-[2-(2-Aminothiazol-4-yl)-2(Z)-methoxyiminoacetamido]-3-[(3-chloroimidazo[1,2-a]pyridinium-1-yl)methyl]-3-cephem-4-carboxylate.

compound [VII'] (R$^3$=—CH$_3$, A$^⊕$=

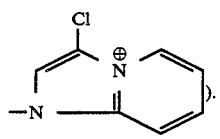

).

Elemental analysis for: $C_{21}H_{18}N_7O_5S_2Cl.5H_2O$: Calcd. (%): C, 39.53; H, 4.42; N, 15.37. Found (%): C, 39.87; H, 3.90; N, 15.61.

IR spectrum $\nu_{max}^{KBr}$ cm$^{-1}$: 1770, 1670, 1615, 1525.

NMR spectrum (d$_6$-DMSO) δ: 3.30 & 3.40 (2H, ABq, J=18 Hz), 3.80 (3H, s), 5.00 (1H, d, J=4.5 Hz), 5.25 & 5.50 (2H, ABq, J=14 Hz), 5.60 (1H, d. d, J=4.5 Hz & 8 Hz), 6.68 (1H, s), 7.12 (2H, br. s), 7.5–7.78 (2H, m), 7.95–8.25 (1H, m), 8.65–8.95 (2H, m), 9.44 (1H, d, J=8 Hz).

EXAMPLE 10

7β-[2-(2-Aminothiazol-4-yl)-2(Z)-methoxyiminoacetamido]-3-[(6-carbamoylimindazo[1,2-a]pyridinium-1-yl)methyl]-3-cephem-4-carboxylate compound [VII'] (R$^3$=—CH$_3$, A$^⊕$=

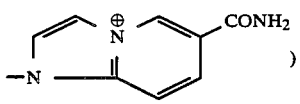

)

Elemental analysis for: $C_{22}H_{20}N_8O_6S_2.9/2H_2O$: Calcd. (%): C, 41.44; H, 4.58; N, 17.57. Found (%): C, 41.65; H, 4.36; N, 17.66.

IR spectrum $\nu_{max}^{KBR}$ cm$^{-1}$: 1770, 1680, 1620, 1520.

NMR spectrum (d$_6$-DMSO-D$_2$O) δ: 2.90 & 3.43 (2H, ABq, J=18 Hz), 3.65 (3H, s), 4.93 (1H, d, J=4.5 Hz), 5.30 (2H, br. s), 5.55 (1H, d, J=4.5 Hz), 6.60 (1H, s), 8.15–8.50 (4H, m), 9.30 (1H, s).

EXAMPLE 11

7β-[2(2-Aminothiazol-4-yl)-2(Z)-methoxyiminoacetamido]-3-[(3-methylimidazo[1,2-a]pyridinium-1-yl)methyl]-3-cephem-4-carboxylate compound [VII'] (R$^3$=—CH$_3$, A$^⊕$=

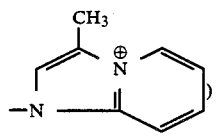

)

Elemental analysis for: $C_{22}H_{21}N_7O_5S_2.13/2H_2O$: Calcd. (%): C, 40.99; H, 5.32; N, 15.21. Found (%): C, 40.98; H, 5.42; N, 14.91.

IR spectrum $\nu_{max}^{KBr}$ cm$^{-1}$: 1770, 1660, 1620, 1530.

NMR spectrum (d$_6$-DMSO) δ: 2.57 (3H, s), 2.94 & 3.24 (2H, ABq, J=18 Hz), 3.84 (3H, s), 5.00 (1H, d, J=4.5 Hz), 5.23 & 5.48 (2H, ABq, J=14 Hz), 5.60 (1 H, d. d, J=4.5 Hz & 8 Hz), 6.68 (1H, s), 7.14 (2H, br. s), 7.4–7.7 (1H, m), 7.75–8.18 (2H, m), 8.28 (1H, s), 8.41–8.85 (1H, m), 9.43 (1H, d, J=8 Hz).

EXAMPLE 12

7β-[2-(2-Aminothiazol-4-yl)-2(Z)-methoxyiminoacetamido]-3-[(5,7-dimethylimidazo[1,2-a]pyridinium-1-yl)methyl]-3-cephem-4-carboxylate compound [VII'] (R$^3$=—CH$_3$, A$^⊕$=

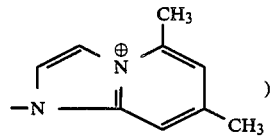

)

Elemental analysis for: $C_{23}H_{23}N_7O_5S_2.4H_2O$: Calcd. (%): C, 45.02; H, 5,09; N, 15.98. Found (%): C, 44.89; H, 4.69; N, 16.10.

IR spectrum $\nu_{max}^{KBr}$ cm$^{-1}$: 1765, 1660, 1605, 1520

NMR spectrum (d$_6$-DMSO) δ: 2.70 (3H, s), 2.71 (3H, s), 2.94 & 3.44 (2H, ABq, J=18 Hz), 3.78 (3H, s), 4.98 (1H, d, J=4.5 Hz), 5.20 & 5.40 (2H, ABq, J=14 Hz), 5.60 (1H, d. d, J=4.5 Hz & 8 Hz), 6.67 (1H, s), 7.13 (2H, br. s), 7.25 (1H, s), 8.12–8.4 (2H, m), 8.50 (1H, s), 9.44 (1H, d, J=8 Hz)

EXAMPLE 13

7β-[2-(2-Aminothiazol-4-yl)-2(Z)-methoxyiminoacetamido-3-[(5-acetamidoimidazo[1,2-a]pyridinium-1-yl)methyl]-3-cephem-4-carboxylate compound [VII'] (R$^3$=—CH$_3$, A$^⊕$=

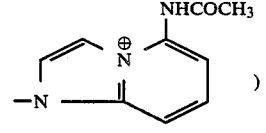

)

Elemental analysis for: $C_{23}H_{22}N_8O_6S_2.5H_2O$: Calcd. (%): C, 41.81; H, 4.88; N, 16.96. Found (%): C, 42.10; H, 4.63; N, 16.46.

IR spectrum $\nu_{max}^{KBr}$ cm$^{-1}$: 1765; 1650, 1610, 1520, 1370, 1280, 1170

NMR spectrum (d$_6$-DMSO) δ: 2.30 (3H, s), 3.03 & 3.48 (2H, ABq, J=18 Hz), 3.79 (3H, s), 5.00 (1H, d, J=4.5 Hz), 5.36 (2H, br. s), 5.62 (1H, d. d, J=4.5 Hz & 8 Hz), 6.68 (1H, s), 7.12 (2H, br. s), 7.5–8.6 (5H, m), 9.48 (1H, d, J=8 Hz)

EXAMPLE 14

7β-[2-(2-Aminothiazol-4-yl)-2(Z)-methoxyiminoacetamido]-3-[(6-bromoimidazo[1,2-a]pyridinium-1-yl)methyl]-3-cephem-4-carboxylate compound [VII'] ($R^3$=—$CH_3$, $A^\oplus$=

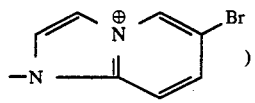)

Elemental analysis for: $C_{21}H_{18}N_7O_5S_2Br \cdot 2H_2O$: Calcd. (%): C, 40.13; H, 3.53; N, 15.60. Found (%): C, 40.30; H, 3.74; N, 15.29.

IR spectrum $\nu_{max}^{KBr}$ cm$^{-1}$: 1765, 1670, 1610, 1520

NMR spectrum (d$_6$-DMSO) δ: 2.95 & 3.31 (2H, ABq, J=18 Hz), 3.79 (3H, s), 4.98 (1H, d, J=4.5 Hz), 5.1–5.5 (2H, m), 5.60 (1H, d. d, J=4.5 Hz & 8 Hz), 6.67 (1H, s), 7.12 (2H, br. s), 8.04–8.44 (2H, m), 8.48–8.81 (1H, m), 9.32 (1H, s), 9.42 (1H, d, J=8 Hz)

EXAMPLE 15

7β-[2-(2-Aminothiazol-4-yl)-2(Z)-methoxyiminoacetamido]-3-[(8-methylimidazo[1,2-a]pyridinium-1-yl)methyl]-3-cephem-4-carboxylate compound [VII'] ($R^3$=—$CH_3$ $A^\oplus$=

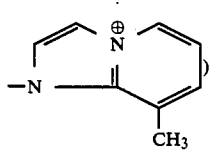)

Elemental analysis for: $C_{22}H_{21}N_7O_5S_2 \cdot 7/2H_2O$: Calcd. (%): C, 44.74 H, 4.78; N, 16.60. Found (%): C, 44.48; H, 4.43; N, 16.85.

IR spectrum $\nu_{max}^{KBr}$ cm$^{-1}$: 1780, 1665, 1615, 1540

NMR spectrum (d$_6$-DMSO) δ: 2.80 (3H, s), 3.11 & 3.49 (2H, ABq, J=18 Hz), 3.80 (3H, s), 5.01 (1H, d, J=4.5 Hz), 5.43 (2H, br. s), 5.63 (1H, d. d, J=4.5 Hz & 8 Hz), 6.69 (1H, s), 7.15 (2H, br. s), 7.37 (1H, t, J=7 Hz), 7.73 (1H, d, J=7 Hz), 8.38 (1H, d, J=2 Hz), 8.58 (1H, d, J=2 Hz), 8.64–8.97 (1H, m), 9.48 (1H, d, J=8 Hz)

EXAMPLE 16

7β-[2-(2-Aminothiazol-4-yl)-2(Z)-methoxyiminoacetamido]-3-[(5-methylimidazo[1,2-a]pyridinium-1-yl)methyl]-3-cephem-4-carboxylate compound [VII'] ($R^3$=—$CH_3$, $A^\oplus$=

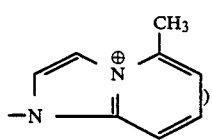)

Elemental analysis for: $C_{22}H_{21}N_7O_5S_2 \cdot 9/2H_2O$: Calcd. (%): C, 43.42; H, 4.96; N, 16.11. Found (%): C, 43.06; H, 4.73; N, 16.13.

IR spectrum $\nu_{ma}^{KBr}$ cm$^{-1}$: 1770, 1680, 1605, 1530.

NMR spectrum (d$_6$-DMSO) δ: 2.77 (3H, s), 2.94 & 3.44 (2H, ABq, J=18 Hz), 3.79 (3H, s), 4.99 (1H, d, J=4.5 Hz), 5.37 & 5.50 (2H, ABq, J=14 Hz), 5.60 (1H, d. d, J=4.5 Hz & 8 Hz), 6.68 (1H, s), 7.15 (2H, br. s) 7.25–7.50 (1H, m), 7.7–8.1 (1H, m), 8.28–8.68 (3H, m), 9.45 (1H, d, J=8 Hz)

EXAMPLE 17

7β-[2-(2-Aminothiazol-4-yl)-2(Z)-methoxyiminoacetamido]-3-[(5-chloroimidazo[1,2-a]pyridinium-1-yl)methoxy]-3-cephem-4-carboxylate compound [VII'] ($R^3$=—$CH_3$, $A^\oplus$=

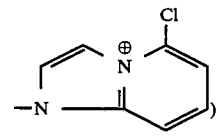)

Elemental analysis for: $C_{21}H_{18}N_7O_5S_2Cl \cdot 4H_2O$: Calcd. (%): C, 40.68; H, 4.23; N, 15.81. Found (%): C, 40.78; H, 3.93; N, 15.91.

IR spectrum $\nu_{max}^{KBr}$ cm$^{-1}$: 1770, 1670, 1610, 1535, 1510.

NMR spectrum (d$_6$-DMSO) δ: 2.97 & 3.40 (2H, ABq, J=18 Hz), 3.79 (3H, s), 4.90 (1H, d, J=4.5 Hz), 5.37 & 5.54 (2H, ABq, J=14 Hz), 5.60 (1H, d, d, J=4.5 Hz & 8 Hz), 6.68 (1H, s), 7.14 (2H, br. s), 7.62–8.18 (2H, m), 8.4–8.86 (3H, m), 9.46 (1H, d, J=8 Hz)

EXAMPLE 18

7β-[2-(2-Aminothiazol-4-yl)-2(Z)-methoxyiminoacetamido]-3-[(5-methoxyimidazo[1,2-a]pyridinium-1-yl)methyl]-3-cephem-4-carboxylate compound [VII'] ($R^3$=—$CH_3$, $A^\oplus$=

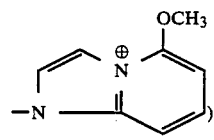)

Elemental analysis for: $C_{22}H_{21}N_7O_6S_2 \cdot 7/2H_2O$: Calcd. (%): C, 43.56; H, 4.65; N, 16.16. Found (%): C, 43.63; H, 4.57; N, 16.22.

IR spectrum $\nu_{max}^{KBr}$ cm$^{-1}$: 1765, 1650, 1620, 1530.

NMR spectrum (d$_6$-DMSO) δ: 2.96 & 3.45 (2H, ABq, J=18 Hz), 3.80 (3H, s), 4.25 (3H, s), 4.95 (1H, d, J=4.5 Hz), 5.24 & 5.44 (2H, ABq, J=14 Hz), 5.61 (1H, d. d, J=4.5 Hz & 8 Hz), 6.68 (1H, s), 6.9–7.3 (3H, m), 7.9–8.35 (3H, m), 8.4–8.62 (1H, m), 9.46 (1H, d, J=8 Hz)

EXAMPLE 19

7β-[2-(2-Aminothiazol-4-yl)-2(Z)-methoxyiminoacetamido]-3-[(5-methylthioimidazo[1,2-a]pyridinium-1-yl)methyl]-3-cephem-4-carboxylate compound [VII'] ($R^3$=—$CH_3$, $A^\oplus$

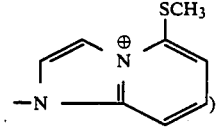)

Elemental analysis for: $C_{22}H_{21}N_7O_5S_3 \cdot 4H_2O$: Calcd. (%): C, 41.83; H, 4.63; N, 15.52. Found (%): C, 41.91; H, 4.40; N, 15.20.

IR spectrum $\nu_{max}^{KBr}$ cm$^{-1}$: 1770, 1660, 1620, 1530

NMR spectrum (d₆-DMSO) δ: 2.83 (3H, s), 3.16 (2H, ABq, J=18 Hz), 3.80 (3H, s), 4.99 (1H, d, J=4.5 Hz), 5.27 & 5.49 (2H, ABq, J=14 Hz), 5.61 (1H, d. d, J=4.5 Hz & 8 Hz), 6.68 (1H, s), 7.14 (2H, br. s), 7.32–7.58 (1H, m), 7.78–8.12 (1H, m), 8.34–8.36 (1H, m), 8.40–8.72 (2H, m), 9.46 (1H, d, J=8 Hz)

EXAMPLE 20

7β-[2-(2-Aminothiazol-4-yl)-2(Z)-methoxyiminoacetamido]-3-[(3-N,N-dimethylaminomethylimidazo[1,2-a]pyridinium-1-yl)methyl]-3-cephem-4-carboxylate compound [VII'] (R³=—CH₃, A⊕=

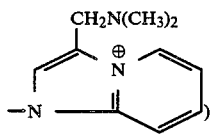

Elemental analysis for: C₂₄H₂₆N₇O₅S₂.4H₂O: Calcd. (%): C, 44.85; H, 5.33; N, 17.43. Found (%): C, 45.04; H, 4.81; N, 17.68.

IR spectrum $\nu_{max}^{KBr}$ cm⁻¹: 1770, 1660, 1610, 1520

NMR spectrum (d₆-DMSO) δ: 2.90 (3H, s), 2.98 (3H, s), 3.84 (3H, s), 5.06 (2H, bs), 5.19 (1H, d, J=4.5 Hz), 5.65 (1H, d. d, J=4.5 Hz & 8 Hz), 6.72 (1H, s), 7.16 (2H, br. s), 7.0–7.25 (1H, m), 7.27–7.52 (1H, m), 7.6–7.72 (1H, m), 7.93 (1H, s), 8.82–9.00 (1H, m), 9.53 (1H, d, J=8 Hz)

EXAMPLE 21

7β-[2-(2-Aminothiazol-4-yl)-2(Z)-methoxyiminoacetamido]-3-[(3-carbamoylimidazo[1,2-a]pyridinium-1-yl)methyl]-3-cephem-4-carboxylate compound [VII'] (R³=—CH₃, A⊕=

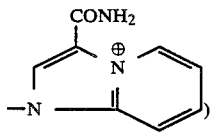

Elemental analysis for: C₂₂H₂₀N₈O₆S₂.9/2H₂O: Calcd. (%): C, 41.44; H, 4,58; N, 17.57. Found (%): C, 41.54; H, 4.32; N, 17.37.

IR spectrum $\nu_{max}^{KBr}$ cm⁻¹: 1775, 1680, 1620, 1520

NMR spectrum (d₆-DMSO) δ: 3.09 & 3.49 (2H, ABq, J=18 Hz), 3.80 (3H, s), 5.01 (1H, d, J=4.5 Hz), 5.37 & 5.67 (2H, ABq, J=14 Hz), 6.69 (1H, s), 7.14 (2H, br. s), 7.54–7.76 (1H, m), 7.92–8.28 (1H, m), 8.78–9.00 (1H, m), 9.16 (1H, s), 9.46 (1H, d, J=8 Hz), 9.76 (1H, d, J=7 Hz)

EXAMPLE 22

7β-[2-(2-Aminothiazol-4-yl)-2(Z)-methoxyiminoacetamido]-3-[(imidazo[1,5-a]pyridinium-2-yl)methyl]-3-cephem-4-carboxylate compound [VII'] (R³=—CH₃, A⊕=

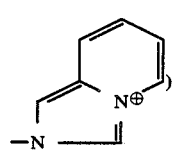

Elemental analysis for: C₂₁H₁₉N₇O₅S₂.7/2H₂O: Calcd. (%): C, 43.74; H, 4.54; N, 17.00. Found (%): C, 43.79; H, 4.30; N, 16.79.

IR spectrum $\nu_{max}^{KBr}$ cm⁻¹: 1770, 1660, 1615, 1515.

NMR spectrum (d₆-DMSO) δ: 3.15 & 3.56 (2H, ABq, J=18 Hz), 3.80 (3H, s), 5.03 (1H, d, J=4.5 Hz), 5.11 & 5.54 (2H, ABq, J=13 Hz), 5.64 (1H, d. d, J=4.5 Hz & 8 Hz), 6.68 (1H, s), 6.9–7.4 (4H, m), 7.24–7.45 (1H, m), 8.53 (1H, s), 8.68 (1H, d, J=6 Hz), 9.43 (1H, d, J=8 Hz), 10.03 (1H, br. s).

EXAMPLE 23

7β-[2-(2-Aminothiazol-4-yl)-2(Z)-ethoxyiminoacetamido]-3-[(6-chloroimidazo[1,2-a]pyridinium-1-yl)methyl]-3-cephem-4-carboxylate compound [VII'] (R³=—C₂H₅, A⊕=

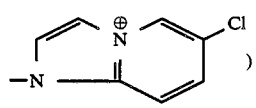

7β-[2-(2-Aminothiazol-4-yl)-2(Z)-ethoxyiminoacetamido]-3-(3-oxobutyryloxymethyl)-3-cephem-4-carboxylic acid is reacted with 6-chloroimidazo[1,2-a]pyridine in the same manner as described in Example 2 to give the above-identified compound Elemental analysis for: C₂₂H₂₀N₇O₅S₂Cl.4H₂O: Calcd. (%): C, 41.67; H, 4.45; N, 15.46. Found (%): C, 41.85; H, 4.09; N: 15.69.

IR spectrum $\nu_{max}^{KBr}$ cm⁻¹: 1760, 1660, 1615, 1520, 1380.

NMR spectrum (d₆-DMSO) δ: 1.19 (3H, t, J=7 Hz), 3.00 & 3.37 (2H, ABq, J=18 Hz), 4.06 (2H, q, J=7 Hz), 5.01 (1H, d, J=4.5 Hz), 5.27 & 5.50 (2H, ABq, J=14 Hz), 5.63 (1H, d. d, J=4.5 Hz & 8 Hz), 6.67 (1H, s), 7.16 (2H, br. s), 8.00–8.19 (1H, m), 8.26–8.44 (1H, m), 8.25–8.64 (1H, m), 8.66–8.86 (1H, m), 9.43 (1H, d, J=8 Hz).

EXAMPLE 24

7β-[2-(2-Aminothiazol-4-yl)-2(Z)-(1-carboxy-1-methylethoxyimino)acetamido]-3-[(6-chloroimidazo[1,2-a]pyridinium-1-yl)methyl]-3-cephem-4-carboxylate compound [VII'] (R³=—C(CH₃)₂COOH, A⊕=

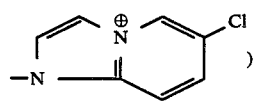

3-(3-Oxobutyryloxymethyl)-7β-[2-(2-tritylaminothiazol-4-yl)-2(Z)-(1-methyl-1tert-butoxycarbonylethoxyimino)acetamido]-3-cephem-4-carboxylic acid is reacted with 6-chloroimidazo[1,2-a]pyridine in the same manner as described in Example 5 to give the above-identified compound Elemental anslysis for: C₂₂H₂₀N₇O₅S₂Cl.4H₂O: Calcd. (%): C, 41.68; H, 4.45; N, 15.47. Found (%): C, 41.42; H, 4.67; N, 15.42.

IR spectrum $\nu_{max}^{KBr}$ cm⁻¹: 1760, 1610, 1520.

NMR spectrum (d₆-DMSO) δ: 1.38 (3H, s), 1.42 (3H, s), 3.01 (2H, ABq, J=18 Hz), 4.97 (1H, d, J=4.8 Hz), 5.20–5.52 (2H, m), 5.60–5.79 (1H, m), 6.67 (1H, s), 7.10

(2H, br. s), 7.96–8.16 (1H, m), 8.30–8.80 (3H, m), 9.32 (1H, s), 11.45 (1H, d, J=9 Hz).

EXAMPLE 25

7β-[2-(2-Aminothiazol-4-yl)-2(Z)-(1-carboxy-1-methylethoxyimino)acetamido]-3-[(6-methylimidazo[1,2-a]pyridinium-1-yl)methyl]-3-cephem-4-carboxylate monosodium salt compound [VII'] (R³=—C(CH₃)₂COONa, A⊕ =

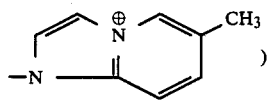

)

3-(3-Oxobutyryloxymethyl)-7β-[2-(2-tritylaminothiazol-4-yl)-2(Z)-(1-methyl-1-tert-butoxycarbonylethoxyimino)acetamido]-3-cephem-4-carboxylic acid is reacted with 6-methylimidazo[1,2-a]pyridine in the same manner as described in Example 5 to give the above-identified compound.

Elemental analysis for: $C_{25}H_{24}N_7O_7S_2Na.4H_2O$: Calcd. (%): C, 43.29; H, 4.65; N, 14.13. Found (%): C, 43.76, H, 4.55; N, 13.59.

IR spectrum $\nu_{max}^{KBr}$cm⁻¹: 1770, 1660, 1600, 1525.

NMR spectrum (d₆-DMSO) δ: 1.43 (6H, s), 2.43 (3H, s), 4.99 (1H, d, J=4.5 Hz), 5.33 (2H, br. s), 5.66 (1H, d. d, J=4.5 Hz & 8 Hz), 6.70 (1H, s), 7.13 (2H, br. s), 7.68–8.02 (1H, m), 8.06–8.6 (3H, m), 8.64–8.88 (1H, m), 11.54 (1H, d, J=8 Hz).

EXAMPLE 26

In 60 ml of a 1:1 mixture of acetonitrile and water are dissolved 3.0 g of 7β-[2-(2-aminothiazol-4-yl)-2(Z)-methoxyiminoacetamido]-3-acetoxymethyl-3-cephem-4-carboxylic acid, 3.0 g of imidazo[1,2-a]pyridine and 3.0 g of potassium iodide, and the mixture is stirred at 70° for 3 hours. The mixture is concentrated under reduced pressure and the residue is triturated with 20 ml of ethyl acetate. The residue is dissolved in 50 ml of water and subjected to XAD-2 column chromatography using 20% aqueous ethanol as an eluent. The fractions containing the objective compound are combined and concentrated under reduced pressure, and the residue is subjected to silica gel column chromatography using 4:1 mixture of acetonitrile and water. The fractions containing the objective compound are combined and concentrated under reduced pressure, and the residue is lyophilized to give 0.3 g of 7β-[2-(2-aminothiazol-4-yl)-2(Z)-methoxyiminoacetamido]-3-[(imidazo[1,2-a]pyridinium-1-yl)methyl]-3-cephem-4-carboxylate. This compound is found to be identical with that obtained in Example 1 in view of agreement in IR and NMR spectra.

EXAMPLE 27

Into a mixture of 20 ml acetonitrile and 20 ml of formamide is suspended 4.1 g of 7β-[2-(2-aminothiazol-4-yl)-2(Z)-methoxyiminoacetamido]-3-hydroxymethyl-3-cephem-4-carboxylic acid. To the mixture are added, under cooling at −30° C., successively 4.7 g of imidazo[1,2-a]pyridine and 20 ml of a solution (2 mmole/ml) of methyl o-phenylene phosphate in dichloromethane. The mixture is stirred for 2 hours. The solvent is evaporated off under reduced pressure and to the residue is added 20 ml of acetonitrile. The resulting solid is filtered and suspended in 20 ml of water. The mixture is adjusted to pH 8.0 and subjected to XAD-2 column chromatography using 10% aqueous ethanol as as eluent. The fractions containing the objective compound are combined and concentrated under reduced pressure, and the residue is lyophilized to give 3.0 g of 7β-[2-(2-aminothiazol-4-yl)-2(Z)-methoxyiminoacetamido]-3-[(imidazo[1,2-a]pyridinium-1-yl)methyl]-3-cephem-4-carboxylate. This compound is found to be identical with that obtained in Example 1 as the result of agreement in physical data.

EXAMPLE 28

Into 20 ml of chloroform is suspended 3.0 g of 7β-[2-(2-aminothiazol-4-yl)-2(Z)-methoxyiminoacetamido]-3-acetoxymethyl-3-cephem-4-carboxylic acid and 4 ml of N-methyl-N-trimethylsilyltrifluoroacetamide is added to the mixture. The resulting mixture is stirred at 20° C. until it becomes homogeneous. Then, 3.3 g of trimethylsilyl iodide is added to the mixture and the mixture is stirred at 20° C. for 10 minutes. The reaction mixture is concentrated under reduced pressure and 9 ml of acetonitrile is added to the residue. After addition of 0.8 ml of tetrahydrofuran, the mixture is stirred for 40 minutes. To the mixture is added 2 g of imidazo[1,2-a]pyridine and the mixture is stirred at 20° C. for 3 hr. The mixture is cooled under ice-cooling and 1 ml of water is added to it. The precipitated solid is filtered and subjected to silica gel column chromatography using a 4:1 mixture of acetonitrile and water as an eluent. The fractions containing the objective compound are combined and concentrated under reduced pressure, and the residue is lyophilized to give 0.3 g of 7β-[2-(2-aminothiazol-4-yl)-2(Z)-methoxyiminoacetamido]-3-[(imidazo[1,2-a]pyridinium-1-yl)methyl]-3-cephem-4-carboxylate. This compound is found to be identical with that obtained in Example 1 as the result of agreement in physical data.

EXAMPLE 29

(a) In 120 ml of a 1:1 mixture of acetonitrile and water are dissolved 6.2 g of 7β-amino-3-(3-oxo-butyryloxymethyl)-3-cephem-4-carboxylic acid, 6.0 g of imidazo[1,2-a]pyridine and 6.0 g of potassium iodide, and the mixture is stirred at 70° C. for 1 hour. The solvent is removed under reduced pressure and the residue is triturated three times with each 30 ml of ethyl acetate. After the solid is filtered and dissolved in 30 ml of water, it is subjected to XAD-2 column chromatography using water as an eluent. The fractions containing the objective compound are combined and concentrated under reduced pressure, and the residue is lyophilized to give 1.3 g of 7β-amino-3-[(imidazo[1,2-a]pyridinium-1-yl)methyl]-3-cephem-4-carboxylate.

(b) In a solution of 0.94 g 2-(2-aminothiazol-4-yl)-2(Z)-methoxyiminoacetic acid and 0.64 g of 1-hydroxybenzotriazole in 20 ml of dimethylformamide is added 1.0 g of dicyclohexylcarbodiimide, and the mixture is stirred at 20° C. for 2 hr. The precipitated insolubles are filtered off and the filtrate is added to 20 ml of dimethylformamide solution of 1.3 g of 7β-amino-3-[(imidazo[1,2-a]pyridinium-1-yl)methyl]-3-cephem-4-carboxylate obtained in the above (a), and the mixture is stirred at 20° C. for 3 hr. After 200 ml of diethyl ether is added to the mixture, the ether layer is removed off. The residue is dissolved in 20 ml of water and subjected to XAD-2 column chromatography using 10% aqueous ethanol as an eluent. The fractions containing the objective compound are combined and concentrated under reduced pressure. The residue is lyophilized to give 0.25 g of 7β-[2-(2-aminothiazol-4-yl)-2(Z)-methoxyiminoacetamido]-3-[(imidazo[1,2-a]pyridinium-1-yl)methyl]-3-cephem-4-carboxylate. The physical data of this compound is in agreement with those of the compound obtained in Example 1.

EXAMPLE 30

7β-[2-(2-Aminothiazol-4-yl)-2(Z)-propoxyiminoacetamido]-3-[(imidazo[1,2-a]pyridinium-1-yl)methyl]-3-cephem-4-carboxylate compound [VII'] ($R^3$=—n—$C_3H_7$, $A^\oplus$=

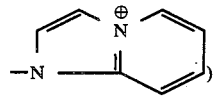

In a 1:1 mixture of acetonitrile and water are added 1.5 g of 7β-[2-(2-aminothiazol-4-yl)-2(Z)-propoxyiminoacetamido]-3-(3-oxobutyryloxymethyl)-3-cephem-4-carboxylic acid, 1.5 g of imidazo[1,2-a]pyridine and 1.5 g of potassium iodide, and the mixture is stirred at 70° C. for 2 hours. The solvent is evaporated off under reduced pressure and the residue is subjected to silica gel column chromatography using a 4:1 mixture of acetonitrile and water as an eluent. The eluted fractions are combined and concentrated under reduced pressure, and the residue is lyophilized. The resulting solid is dissolved in 5 ml of water and subjected to 20% aqueous ethanol as an eluent. The fractions containing the objective compound are combined and concentrated under reduced pressure, and the residue is lyophilized to give 0.25 g of the above-identified compound.

Elemental analysis for: $C_{23}H_{23}N_7O_5S_2.4H_2O$: Calcd.: C, 45.02; H, 5.09; N, 15.98. Found: C, 44.95; H, 4.66; N, 15.80.

IR spectrum $\nu_{max}^{KBr}$cm$^{-1}$: 1775, 1650, 1610, 1530.

NMR spectrum (d$_6$-DMSO) δ: 0.86 (3H, t, J=7 Hz), 1.36–1.80 (2H, m), 2.97 & 3.37 (2H, ABq, J=18 Hz), 3.96 (2H, t, J=7 Hz), 4.99 (1H, d, J=5 Hz), 5.27 & 5.45 (2H, ABq, J=13 Hz), 5.61 (1H, d. d, J=5 Hz & 8 Hz), 6.65 (1H, s), 7.13 (2H, br. s), 7.35–7.66 (1H, m), 7.84–8.14 (1H, m), 8.3–8.76 (3H, m), 8.8–9.05 (1H, m), 9.40 (1H, d, J=8 Hz).

7β-[2-(2-Aminothiazol-4-yl)-2(Z)-(substituted-oxyimino)acetamido]-3-(3-oxobutyryloxymethyl)-3-cephem-4-carboxylic acid is reacted with various imidazole compounds in the same manner as described in Example 30 to give the following compounds [VII'] (Example 31–41).

EXAMPLE 31

7β-[2-(2-Aminothiazol-4-yl)-2(Z)-(2-fluoroethoxyimino)acetamido]-3-[(imidazo[1,2-a]pyridinium-1-yl)methyl]-3-cephem-4-carboxylate Compound [VII'] ($R^3$=—$CH_2CH_2F$, $A^\oplus$=

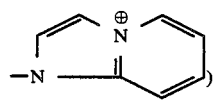

Elemental analysis for: $C_{22}H_{20}N_7O_5S_2F.4H_2O$: Calcd. (%) C, 42.78; H, 4.57; N, 15.87. Found (%) C, 42.57; H, 4.27; N, 15.71.

IR spectrum $\nu_{max}^{KBr}$cm$^{-1}$: 1760, 1610, 1525.

NMR spectrum (d$_6$-DMSO) δ: 2.96 & 3.43 (2H, ABq, J=18 Hz), 4.0–4.2 (1H, m), 4.2–4.5 (2H, m), 4.7–5.0 (1H, m), 5.00 (1H, d, J=5 Hz), 5.2–5.6 (2H, m), 5.61 (1H, d. d, J=4 Hz & 8 Hz), 6.70 (1H, s), 7.16 (2H, br. s), 7.4–7.7 (2H, m), 7.8–8.2 (2H, m), 8.3–8.8 (3H, m), 8.97 (1H, d, J=7 Hz), 9.50 (1H, d, J=8 Hz).

EXAMPLE 32

7β-[2-(2-Aminothiazol-4-yl)-2(Z)-(2-chloroethoxyimino)acetamido]-3-[(imidazo[1,2-a]pyridinium-1-yl)methyl]-3-cephem-4-carboxylate Compound [VII'] ($R^3$=—$CH_2CH_2Cl$, $A^\oplus$=

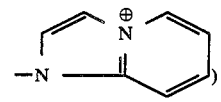

Elemental analysis for: $C_{22}H_{20}N_7O_5S_2Cl.5/2H_2O$: Calcd.: C, 43.53; H, 4.15; N, 16.15. Found: C, 43.25; H, 4.03; N, 15.94.

IR spectrum $\nu_{max}^{KBr}$cm$^{-1}$: 1760, 1605, 1520.

NMR spectrum (d$_6$-DMSO) δ: 2.98 & 3.43 (2H, ABq, J=18 Hz), 3.7–3.9 (2H, m), 4.1–4.4 (2H, m), 5.00 (1H, d, J=5 Hz), 5.25 & 5.47 (2H, ABq, J=16 Hz), 5.62 (1H, d. d, J=5 Hz & 8 Hz), 6.74 (1H, s), 7.16 (2H, br. s), 7.4–7.6 (2H, m), 7.9–8.2 (2H, m), 8.3–8.8 (3H, m), 8.93 (1H, d, J=7 Hz), 9.45 (1H, d, J=8 Hz).

EXAMPLE 33

7β-[2-(2-Aminothiazol-4-yl)-2(Z)-isopropoxyiminoacetamido]-3-[(imidazo[1,2-a]pyridinium-1-yl)methyl]-3-cephem-4-carboxylate Compound [VII'] ($R^3$=—$CH(CH_3)_2$, $A^\oplus$=

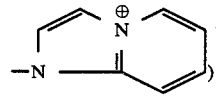

Elemental analysis for: $C_{23}H_{23}N_7O_5S_2.11/2H_2O$: Calcd.: C, 43.11; H, 5.35; N, 15.30. Found: C, 42.81; H, 4.86; N, 15.00.

IR spectrum $\nu_{max}^{KBr}$cm$^{-1}$: 1770, 1650, 1610, 1530.

NMR spectrum (d$_6$-DMSO) δ: 1.18 (6H, d, J=6 Hz), 5.00 (1H, d, J=4.5 Hz), 5.28 & 5.48 (2H, ABq, J=13 Hz), 5.46 (1H, d. d, J=4.5 Hz & 8 Hz), 6.64 (1H, s), 7.13 (2H, br. s), 7.3–7.6 (1H, m), 7.8–8.15 (1H, m), 8.28–8.75 (3H, m), 8.8–9.15 (1H, m), 9.35 (1H, d, J=8 Hz).

EXAMPLE 34

7β-[2-(2-Aminothiazol-4-yl)-2(Z)-(2-hydroxyethoxyimino)acetamido]-3-[(imidazo[1,2-a]pyridinium-1-yl)methyl]-3-cephem-4-carboxylate Compound [VII'] ($R^3$=—$CH_2CH_2OH$, $A^\oplus$=

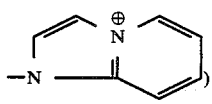

Elemental analysis for: $C_{22}H_{21}N_7O_6S_2.4H_2O$: Calcd.: C, 42.92; H, 4.75; N, 15.93. Found: C, 42.86; H, 4.54; N, 15.70.

IR spectrum $\nu_{max}^{KBr}$cm$^{-1}$: 1770, 1650, 1610, 1530.

NMR spectrum (d$_6$-DMSO) δ: 2.97 & 3.43 (2H, ABq, J=18 Hz), 3.44–3.72 (2H, m), 4.02 (2H, t, J=6 Hz), 4.50 (1H, br.s), 4.98 (1H, d, J=4.5 Hz), 5.26 & 5.46 (2H, ABq, J=13 Hz), 5.60 (1H, d. d, J=4.5 Hz & 8 Hz), 6.67 (1H, s), 7.15 (2H, br. s), 7.36–7.60 (1H, m), 7.80–8.12 (1H, m), 8.30–8.76 (3H, m), 8.84–9.04 (1H, m), 9.36 (1H, d, J=8 Hz).

EXAMPLE 35

7β-[2-(2-Aminothiazol-4-yl)-2(Z)-cyclopropylmethyloxyiminoacetamido]-3-[(imidazo[1,2-a]pyridinium-1-yl)methyl]-3-cephem-4-carboxylate Compound [VII'] (R$^3$=

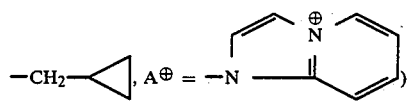

Elemental analysis for: C$_{24}$H$_{23}$N$_7$O$_5$S$_2$13/2H$_2$O: Calcd.: C, 42.98; H, 5.41; N, 14.62. Found C, 43.09; H, 5.60; N, 14.74.

IR spectrum $\nu_{max}^{KBr}$cm$^{-1}$: 1770, 1620, 1530.

NMR spectrum (d$_6$-DMSO) δ: 0.1–0.6 (4H, m), 0.7–1.3 (1H, m), 2.95 (1H, ABq, J=18 Hz), 3.84 (2H, d, J=14 Hz), 4.99 (1H, d, J=5 Hz), 5.28 & 5.46 (2H, ABq, J=18 Hz), 5.62 (1H, d. d, J=5 Hz & 8 Hz), 6.64 (1H, s), 7.12 (2H, br. s), 7.30–7.60 (1H, m), 7.86–8.20 (1H, m), 8.20–8.80 (3H, m), 8.80–9.02 (1H, m), 9.40 (1H, d, J=8 Hz).

EXAMPLE 36

7β-[2-(2-Aminothiazol-4-yl)-2(Z)-carbamoylmethyloxyiminoacetamido]-3-[(imidazo[1,2-a]pyridinium-1-yl)methyl]-3-cephem-4-carboxylate Compound [VII'] (R$^3$=—CH$_2$CONH$_2$, A$^\oplus$=

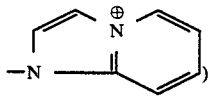

Elemental analysis for: C$_{22}$H$_{20}$N$_8$O$_6$S$_2$.11/2H$_2$O: Calcd.: C, 40.30; H, 4.77; N, 17.09. Found: C, 40.54; H, 4.15; N, 17.09.

IR spectrum $\nu_{max}^{KBr}$cm$^{-1}$: 1770, 1675, 1610, 1530.

NMR spectrum (d$_6$-DMSO) δ: 3.00 & 3.44 (2H, ABq, J=18 Hz), 4.36 (2H, s), 5.02 (1H, d, J=4.8 Hz), 5.28 & 5.47 (2H, ABq, J=14 Hz), 5.66 (1H, d. d, J=4.8 Hz & J=8 Hz), 6.78 (1H, s), 7.00–7.60 (5H, m), 7.86–8.10 (1H, m), 8.28–8.70 (3H, m), 8.86–9.00 (1H, m), 9.70 (1H, d, J=8 Hz).

EXAMPLE 37

7β-[2-(2-Aminothiazol-4-yl)-2(Z)-(2,2,2-trifluoroethyloxyimino)acetamido]-3-[(imidazo[1,2-a]pyridinium-1-yl)methyl]-3-cephem-4-carboxylate Compound [VII'] (R$^3$=—CH$_2$CF$_3$, A$^\oplus$=

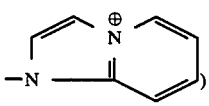

Elemental analysis for: C$_{22}$H$_{18}$N$_7$O$_5$S$_2$F$_3$.3H$_2$O: Calcd. (%): C, 41.58; H, 3.81; N, 15.43. Found (%): C, 41.30; H, 3.99; N, 15.25.

IR spectrum $\nu_{max}^{KBr}$cm$^{-1}$: 1770, 1620, 1530, 1380, 1280, 1060.

NMR spectrum (D$_2$O) δ: 3.15 & 3.56(2H, ABq, J=18 Hz), 5.20–5.50(3H, m), 5.80(1H, d, J=4.5 Hz), 6.93(1H, s), 7.40–7.60(1H, m), 7.90–8.20(4H, m), 8.66(1H, d J=6 Hz).

EXAMPLE 38

7β-[2-(2-Aminothiazol-4-yl)-2(Z)-ethoxyiminoacetamido]-3-[(imidazo[1,5-a]pyridinium-2-yl)methyl]-3-cephem-4-carboxylate Compound [VII'] (R$^3$=—CH$_2$CH$_3$, A$^\oplus$=

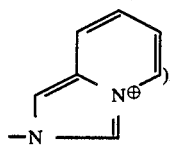

Elemental Analysis for: C$_{22}$H$_{21}$N$_7$O$_5$S$_2$.9/2H$_2$O: Calcd. (%): C, 43.42; H, 4.97; N, 16.11. Found (%): C, 43.72; H, 4.47; N, 16.00.

IR spectrum $\nu_{max}^{KBr}$cm$^{-1}$: 1760, 1600, 1520, 1380.

NMR spectrum (d$_6$-DMSO) δ: 1.18(3H, t, J=7 Hz), 3.12 & 3.55(2H, ABq, J=18 Hz), 4.05(2H, q, J=7 Hz), 5.02(1H, d, J=5 Hz), 5.07 & 5.53(2H, ABq, J=14 Hz), 5.63(1H, d.d, J=5 Hz & 8 Hz), 6.67(1H, s), 7.0–7.2 (5H, m), 7.8–7.9(1H, m), 8.5–8.8(2H, m), 9.37(1H, d, J=8 Hz).

EXAMPLE 39

7β-[2-(2-Aminothiazol-4-yl)-2(Z)-(2-fluoroethoxyimino)acetamido]-3-[(6-chloroimidazo[1,2-a]pyridinium-1-yl)methyl]-3-cephem-4-carboxylate Compound [VII'] (R$^3$=—CH$_2$CH$_2$F, A$^\oplus$=

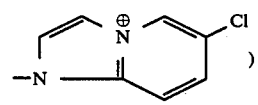

Elemental Analysis for: C$_{22}$H$_{19}$N$_7$O$_5$S$_2$ClF.3H$_2$O: Calcd. (%): C, 41.68; H, 3.98; N, 15.47. Found (%): C, 41.49; H, 4.26; N, 15.31.

IR spectrum $\nu_{max}^{KBr}$cm$^{-1}$: 1765, 1670, 1610, 1530.

NMR spectrum (d$_6$-DMSO) δ: 2.95 & 3.20(2H, ABq, J=18 Hz), 4.00–4.25(1H, m), 4.30–4.53(2H, m), 4.65–5.01(2H, m), 5.06(1H, d, J=5 Hz), 5.30–5.56(1H, m), 5.66(1H, d.d, J=4.5 Hz & 8 Hz), 6.73(1H, s), 7.20(2H, br.s), 8.10(1H, d, J=9 Hz), 8.30(1H, s), 8.60(1H, s), 8.76(1H, d, J=9 Hz), 9.30(1H, s), 9.55(1H, d, J=8 Hz).

EXAMPLE 40

7β-[2-(2-Aminothiazol-4-yl)-2(Z)-methoxyiminoacetamido]-3-[(imidazo[2,1-b]thiazolium-7-yl)methyl]-3-cephem-4-carboxylate Compound [VII'] (R$^3$=CH$_3$, A$^\oplus$=

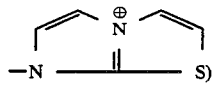

Elemental Analysis for: C₁₉H₁₇N₇O₅S₃.3H₂O: Calcd. (%): C, 39.80; H, 4.04; N, 17.10. Found (%): C, 39.65; H, 3.99; N, 16.73.

IR spectrum $\nu_{max}^{KBr}$cm⁻¹: 1770, 1660, 1610, 1530.

NMR spectrum (d₆-DMSO) δ: 2.90 & 3.26(2H, ABq, J=18 Hz), 3.76(3H, s), 4.85 & 5.20(2H, ABq, J=13 Hz), 5.66(1H, d.d, J=5 Hz & J=8 Hz), 6.15(1H, d, J=5 Hz), 6.70(1H, s), 7.20(2H, br.s), 7.80-7.90(2H, m), 9.50 (1H, d, J=8 Hz).

EXAMPLE 41

7β-[2-(2-Aminothiazol-4-yl)-2(Z)-methoxyiminoacetamido]-3-[(2,6-dimethylimidazo[2,1-b][1,3,4]thiadiazolium-7-yl)methyl]-3-cephem-4-carboxylate Compound [VII'] (R³=CH₃, A⊕ =

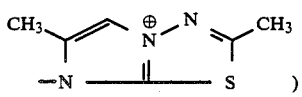

Elemental Analysis for: C₂₀H₂₀N₈O₅S₃.9/2 H₂O: Calcd. (%): C, 38.15; H, 4.64; H, 17.80. Found (%): C, 38.18; H, 4.23; H, 18.02.

IR spectrum $\nu_{max}^{KBr}$cm⁻¹: 1770, 1670, 1610, 1530.

NMR spectrum (d₆-DMSO) δ: 2.52(3H, s), 2.78(3H, s), 3.09 & 3.52(2H, ABq, J=18 Hz), 3.84(3H, s), 4.86 & 5.26(2H, ABq, J=5 Hz & 8 Hz), 6.72(1H, s), 7.16(2H, br.s), 8.39(1H, s), 9.46(1H, d, J=8 Hz).

EXAMPLE 42

7β-[2-(2-Aminothiazol-4-yl)-2(Z)-methoxyiminoacetamido]-3-[(6-cyanoimidazo[1,2-a]pyridinium-1-yl)methyl]-3-cephem-4-carboxylate compound [VII'] (R³=—CH₃, A⊕ =

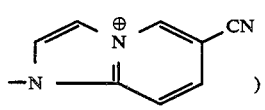

In 30 ml of a 1:1 mixture of acetonitrile and water are dissolved 2.3 g of 7β-[2-aminothiazol-4-yl)-2(Z)-methoxyiminoacetamido]-3-(3-oxobutyryloxymethyl)-3-cephem-4-carboxylic acid, 1.79 g of 6-cyanoimidazo[1,2-a]pyridine and 2.2 g of potassium iodide, and the mixture is stirred at 60°-70° C. for 1.5 hours. The solvent is then evaporated off under reduced pressure and the residue is solidified by addition of 100 ml of acetonitrile. The resulting powder is collected by filtration and then subjected to silica gel column chromatography. The acetonitrile-water (7:3)-eluated fraction is concentrated under reduced pressure and the residue is lyophilized. A solid obtained is dissolved in 5 ml of water and chromatographed on a column of MCI GEL CHP20P (150-300 meshes; Mitsubishi Chemical Industries, Ltd., Japan) with water-ethanol. The water-ethanol (85:15)-eluated fraction is concentrated under reduced pressure and the residue lyophilized to give 0.27 g of the above-identified compound.

Elemental analysis for: C₂₂H₁₈N₈O₅S₂.5H₂O: Calcd. (%): C, 42.03; H, 4.49; N, 17.83. Found (%): C, 42.28; H, 4.12; N, 17.65.

IR spectrum $\nu_{max}^{KBr}$cm⁻¹: 2250, 1770, 1670, 1610, 1530.

NMR spectrum (d₆-DMSO) δ: 2.97(½×2H, ABq, J=18 Hz), 3.79(3H, s), 5.00(1H, d, J=4.5 Hz), 5.27 & 5.53(2H, ABq, J=14 Hz), 5.61(1H, d, d.J=4.5 Hz & 8 Hz), 6.68(1H, s), 7.14(2H, br.s), 8.25-8.55(2H, m), 8.65-9.00(2H, m), 9.46(1H, d, J=8 Hz), 9.67(1H, s).

7β-[2-(2-Aminothiazol-4-yl)-2(Z)-(substituted oxyimino)acetamido]-3-(3-oxobutyryloxymethyl)-3-cephem-4-carboxylic acid is reacted with various imidazole compounds in the same manner as described in Example 42 to give the following compounds [VII'] (Examples 43-83).

EXAMPLE 43

7β-[2-(2-Aminothiazol-4-yl)-2(Z)-butoxyiminoacetamido]-3-[(imidazo[1,2-a]pyridinium-1-yl)methyl]-3-cephem-4-carboxylate Compound [VII'] (R³=n—C₄H₉, A⊕ =

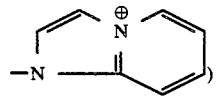

Elemental analysis for: C₂₄H₂₅N₇O₅S₂.7/2H₂O: Calcd. (%): C, 46.59; H, 5.21; N, 15.85. Found (%): C, 46.87; H, 5.10; N. 15.65.

IR spectrum $\nu_{max}^{KBr}$cm⁻¹: 1770, 1670, 1610, 1530.

NMR spectrum (d₆-DMSO) δ: 0.84(3H, t, J=7 Hz), 1.1-1.8 (4H, m), 2.96 & 3.43(2H, ABq, J=17 Hz), 4.00(2H, t, J=7 Hz), 4.98 (1H, d, J=4.5 Hz), 5.29 & 5.48(2H, ABq, J=14 Hz), 5.60(1H, d.d, J=4.5 Hz & 8 Hz), 6.64(1H, s), 7.11(2H, br.s), 7.4-7.6(1H, m), 7.84 8.1(1H, m), 7.35-7.78(3H, m), 7.88-8.02(1H, m), 9.39(1H, d, J=8 Hz).

EXAMPLE 44

7β-[2-(2-Aminothiazol-4-yl)-2(Z)-hexyloxyiminoacetamido]-3-[(imidazo[1,2-a]pyridinium-1-yl)methyl]-3-cephem-4-carboxylate Compound [VII'] (R³=n—C₆H₁₃, A⊕ =

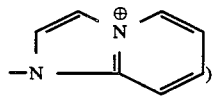

Elemental analysis for: C₂₆H₂₉N₇O₅S₂.5/2H₂O: Calcd. (%): C, 49.67; H, 5.45; N, 15.60. Found (%): C, 49.53; H, 5.53; N, 15.23.

IR spectrum $\mu_{max}^{KBr}$cm⁻¹: 1770, 1670, 1610.

NMR spectrum (d₆-DMSO) δ: 0.78(3H, t, J=7 Hz), 1.0-1.7 (8H, m), 2.92 & 3.43(2H, ABq, J=18 Hz), 3.98(2H, t, J=7 Hz), 4.98 (1H, d, J=4.5 Hz), 5.25 & 5.44(2H, ABq, J=14 Hz), 5.60(1H, d.d, J=4.5 Hz & 8 Hz), 6.63(1H, s), 7.10(2H, br.s) 7.36-7.60(1H, m), 7.80-8.10(1H, m), 8.30-8.64(2H, m), 8.54-8.76(1H, m), 8.84-9.00 (1H, m), 9.38(1H, d, J=8 Hz).

EXAMPLE 45

7β-[2-(2-Aminothiazol-4-yl)-2(Z)-benzyloxyiminoacetamido]-3-[(imidazo[1,2-a]pyridinium-1-yl)methyl]-3-cephem-4-carboxylate Compound [VII'] ($R^3$=—$CH_2C_6H_5$, $A^\oplus$=

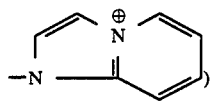

Elemental analysis for: $C_{27}H_{23}N_7O_5S_2.7/2H_2O$: Calcd. (%): C, 49.69; H, 4.63; N, 15.02. Found (%): C, 49.77; H, 4.38; N, 14.92.

IR spectrum $\nu_{max}^{KBr}cm^{-1}$: 1765, 1680, 1640, 1610, 1515.

NMR spectrum (d6-DMSO) δ: 2.91(½×2H, ABq, J=18 Hz), 4.99(1H, d, J=4.5 Hz), 5.09(2H, s), 5.26 & 5.48(2H, ABq, J=14 Hz), 5.62(1H, d,d, J=4.5 Hz & 8 Hz), 6.67(1H, s), 7.13(2H, br.s), 7.00-7.66(7H, m), 7.78-8.2(1H, m), 8.30-8.78(2H, m), 8.82-9.04(1H, m), 9.55(1H, d, J=8 Hz).

EXAMPLE 46

7β-[2-(2-Aminothiazol-4-yl)-2(Z)-(2-methoxyethoxyimino)acetamido]-3-[(imidazo[1,2-a]pyridinium-1-yl)methyl]-3-cephem-4-carboxylate Compound [VII'] ($R^3$=—$CH_2CH_2OCH_3$, $A^\oplus$=

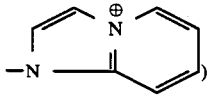

Elemental analysis for: $C_{23}H_{23}N_7O_6S_2.7/2H_2O$: Calcd. (%): C, 44.51; H, 4.87; N, 15.80. Found (%): C, 44.67; H, 4.75; N, 15.25.

IR spectrum $\nu_{max}^{KBr}cm^{-1}$: 1775, 1670, 1610, 1530.

NMR spectrum (d6-DMSO) δ: 3.00 & 3.46(2H, ABq, J=18 Hz), 3.24(3H, s), 4.13(4H, t, J=7 Hz), 5.03(1H, d, J=4.5 Hz), 5.29 and 5.47(2H, ABq, J=13 Hz), 5.64(1H, d,d, J=4.5 Hz & 8 Hz), 6.69(1H, s), 7.15(2H, br.s), 7.38-7.64(1H, m), 7.86-8.12(1H, m), 8.30-8.72(3H, m), 8.82-9.04(1H, m), 9.43(1H, d, J=8 Hz).

EXAMPLE 47

7β-[2-(2-Aminothiazol-4-yl)-2(Z)-propargyloxyiminoacetamido]-3-[(imidazo[1,2-a]pyridinium-1-yl)methyl]-3-cephem-4-carboxylate Compound [VII'] ($R^3$=—$CH_2C\equiv CH$, $A^\oplus$=

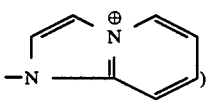

Elemental analysis for: $C_{23}H_{19}N_7O_5S_2.7/2H_2O$ : Calcd. (%): C, 46.00; H, 4.36; N, 16.33. Found (%): C, 46.07; H, 4.51; N, 16.18.

IR spectrum $\nu_{max}^{KBr}cm^{-1}$: 1770, 1665, 1610, 1530.

NMR spectrum (d6-DMSO) δ: 3.06(½×2H, ABq, J=18 Hz), 5.00(1H, d, J=4.5 Hz), 5.22-5.56(4H, m), 5.64(1H, d.d, J=4.5 Hz and 8 Hz), 6.74(1H, s), 7.20(2H, br.s), 7.50-7.64(1H, m), 7.86-8.10(1H, m), 8.34-8.60(3H, m), 8.92(1H, d, J=6 Hz), 9.58(1H, d, J=7 Hz).

EXAMPLE 48

7β-[2-(2-Aminothiazol-4-yl)-2(Z)-cyclopentyloxyiminoacetamido]-3-[(imidazo[1,2-a]pyridinium-1-yl)methyl]-3-cephem-4-carboxylate Compound [VII']

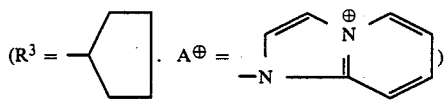

Elemental analysis for: $C_{25}H_{25}N_7O_5S_2.4H_2O$: Calcd. (%): C, 33.26; H, 5.20; N, 15.33. Found (%): C, 33.49; H, 5.46; N, 15.15.

IR spectrum $\nu_{max}^{KBr}cm^{-1}$: 1770, 1665, 1610, 1530.

NMR spectrum (d6-DMSO) δ: 1.30-1.90(8H, m), 3.02 and 3.30(2H, ABq, J=18 Hz), 4.80(1H, m), 5.06(1H, d, J=4.5 Hz), 5.20-5.44(2H, m), 5.60(1H, d.d, J=4.5 Hz & 8 Hz), 6.68(1H, s), 7.20(2H, br.s), 7.46-7.60(1H, m), 7.85-7.90(1H, m), 8.22-8.70(3H, m), 8.90(1H, d, J=7 Hz), 9.35(1H, d, J=8 Hz).

EXAMPLE 49

7β-[2-(2-Aminothiazol-4-yl)-2(Z)-methoxyiminoacetamido]-3-[(6-nitroimidazo[1,2-a]pyridinium-1-yl)methyl]-3-cephem-4-carboxylate Compound [VII'] ($R^3$=—$CH_3$, $A^\oplus$=

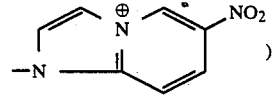

Elemental analysis for: $C_{21}H_{18}N_8OP_7S_2.3H_2O$: Calcd. (%): C, 41.18; H, 3.95; N, 18.30. Found (%): C, 41.50; H, 4.09; N, 17.98.

IR spectrum $\nu_{max}^{KBr}cm^{-1}$: 1775, 1665, 1620, 1530.

NMR spectrum (d6-DMSO) δ: 3.02 & 3.50(2H, ABq, J=18 Hz), 3.80(3H, s), 5.06(1H, d, J=4.5 Hz), 5.30 & 5.50(2H, Abq, J=14 Hz), 5.68(1H, d.d, J=4.5 Hz & 8 Hz), 6.70(1H, s), 7.16(2H, br.s), 7.74-8.0(2H, m), 8.56-8.78(2H, m), 9.48(1H, d, J=8 Hz), 9.96(1H, d, J=2 Hz).

EXAMPLE 50

7β-[2-(2-Aminothiazol-1-yl)-2(Z)-methoxyiminoacetamido]-3-[(8-ethoxycarbonylimidazo[1,2-a]pyridinium-1-yl)methyl]-3-cephem-4-carboxylate Compound [VII'] ($R^3$=—$CH_3$, $A^\oplus$=

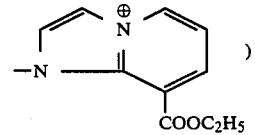

Elemental analysis for: $C_{24}H_{23}N_7O_7S_2.2H_2O$: Calcd. (%): C, 46.38; H, 4.38; N, 15.78. Found (%): C, 46.25; H, 4.61; N, 15.54.

IR spectrum $\nu_{max}^{KBr}cm^{-1}$: 1765, 1710, 1620, 1530.

NMR spectrum (d6-DMSO) δ: 1.34(3H, t, J=7 Hz), 3.00 and 3.45(2H, ABq, J=18 Hz), 3.82(3H, s); 4.48(2H, q, J=7 Hz), 5.08 (1H, d, J=4.5 Hz), 5.20-5.42(2H, m), 5.70(1H, d.d, J=4.5 Hz & 8 Hz), 6.72(1H, s), 7.10(2H, br.s), 7.80-8.0(1H, m), 8.34-8.60(3H, m), 9.10-9.22(1H, m), 9.52(1H, d, J=8 Hz).

EXAMPLE 51

7β-[2-(2-Aminothiazol-4-yl)-2(Z)-methoxyiminoacetamido]-3-[(6,8-dichloroimidazo[1,2-a]pyridinium-1-yl)methyl]-3-cephem-4-carboxylate Compound [VII'] ($R^3$=—$CH_3$, $A^\oplus$=

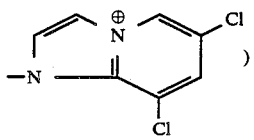
)

Elemental analysis for: $C_{21}H_{17}N_7O_5S_2Cl_2.4H_2O$: Calcd. (%): C, 38.54; H, 3.85; N, 14.99. Found (%): C, 38.77; H, 4.01; N, 14.67.

IR spectrum $_{max}{}^{KBr}cm^{-1}$: 1760, 1660, 1610, 1530.

NMR spectrum (d$_6$-DMSO) δ: 2.94 & 3.46(2H, ABq, J=18 Hz), 3.80(3H, s), 5.06(1H, d, J=4.5 Hz), 5.20 & 5.45(2H, ABq, J=14 Hz), 5.60(1H, d.d, J=4.5 Hz & 8 Hz), 6.66(1H, s), 7.14(2H, br.s), 7.70 (1H, s), 8.30-8.50(2H, m), 9.26(1H, s), 9.50(1H, d, J=8 Hz).

EXAMPLE 52

7β-[2-(2-Aminothiazol-4-yl)-2(Z)-methoxyiminoacetamido]-3-[[3-(morpholinomethyl)imidazo[1,2-a]pyridinium-1-yl]methyl]-3-cephem-4-carboxylate Compound [VII'] ($R^3$=—$CH_3$, $A^\oplus$=

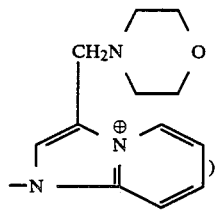
)

Elemental analysis for: $C_{26}H_{28}N_8O_6S_2.11/2H_2O$: Calcd. (%): C, 43.88; H, 5.52; N, 15.74. Found (%): C, 43.50; H, 5.03; N, 15.46.

IR spectrum $v_{max}{}^{KBr}cm^{-1}$: 1775, 1670, 1610, 1530.

NMR spectrum (d$_6$-DMSO) δ: 2.3-2.55(4H, m), 3.01 & 3.45 (2H, ABq, J=18 Hz), 3.74-4.05(4H, m), 3.80(3H, s), 4.95(1H, d, J=4.5 Hz), 5.26 & 5.46(2H, ABq, J=14 Hz), 5.60(1H, d.d, J=4.5 Hz and 8 Hz), 6.69(1H, s), 7.14(2H, br.s), 7.40-7.68(2H, m), 7.92-8.16(1H, m), 8.6-8.78(1H, m), 8.8-8.98(1H, m), 9.44(1H, d, J=8 Hz).

EXAMPLE 53

7β-[2-(2-Aminothiazol-4-yl)-2(Z)-methoxyiminoacetamido]-3[[3-(hydroxyiminomethyl)imidazo[1,2-a]pyridinium-1-yl]methyl]-3-cephem-4-carboxylate Compound [VII'] ($R^3$=—$CH_3$, $A^\oplus$=

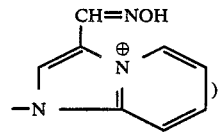
)

Elemental analysis for: $C_{22}H_{20}N_8O_6S_2.4H_2O$: Calcd. (%): C, 42.03; H, 4.48; N, 17.83. Found (%): C, 41.99; H, 4.70; N, 17.54.

IR spectrum $v_{max}{}^{KBr}cm^{-1}$: 1770, 1690, 1670, 1610, 1520.

NMR spectrum (d$_6$-DMSO) δ: 3.08 & 3.49(2H, ABq, J=18 Hz), 3.79(3H, s), 4.99(1H, d, J=5 Hz), 5.2-5.8(3H, m), 6.69(1H, s), 7.15(2H, br.s), 7.51-7.76(2H, m), 8.00-8.25(2H, m), 8.80-9.00(1H, m), 9.17(1H, s), 9.47(1H, d, J=9 Hz), 9.75(1H, d, J=7 Hz).

EXAMPLE 54

7β-[2-(2-Aminothiazol-4-yl)-2(Z)-methoxyiminoacetamido]-3-[(2-ethoxycarbonylimidazo[1,2-a]pyridinium-1-yl)methyl]-3-cephem-4-carboxylate Compound [VII'] ($R^3$=—$CH_3$, $A^\oplus$=

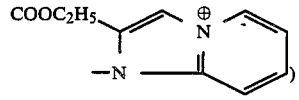
)

Elemental analysis for: $C_{24}H_{23}N_7O_7S_2.5H_2O$: Calcd. (%): C, 40.88; H, 4.92; N, 14.51. Found (%): C, 41.07; H, 4.56; N, 14.57.

IR spectrum $v_{max}{}^{KBr}cm^{-1}$: 1770, 1670, 1600, 1530.

NMR spectrum (d$_6$-DMSO) δ: 1.39(3H, t, J=7 Hz), 2.96 & 3.37 (2H, ABq, J=18 Hz), 3.78(3H, s), 4.48(2H, q, J=7 Hz), 4.99(1H, d, J=4.5 Hz), 5.46-5.85(3H, m), 6.67(1H, s), 7.14(2H, br.s), 7.5-7.75(1H, m), 8.00-8.26(1H, m), 8.8-9.05(1H, m), 9.14(1H, s), 9.2-9.38(1H, m), 9.47(1H, d, J=9 Hz).

EXAMPLE 55

7β-[2-(2-Aminothiazol-4-yl)-2(Z)-propoxyiminoacetamido]-3-[(6-cyanoimidazo[1,2-a]pyridinium-1-yl)methyl]-3-cephem-4-carboxylate Compound [VII'] ($R^3$=—$CH_2CH_2CH_3$, $A^\oplus$=

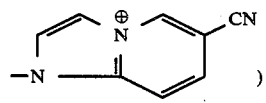
)

Elemental analysis for: $C_{24}H_{22}N_8O_4S_2.5H_2O$: Calcd. (%): C, 44.99; H, 5.03; N, 17.49. Found (%): C, 45.06; H, 4.71; N, 17.21.

IR spectrum $v_{max}{}^{KBr}cm^{-1}$: 2250, 1770, 1670, 1610, 1530.

NMR spectrum (d$_6$-DMSO) δ: 0.86(3H, t, J=7 Hz), 1.35-1.80(2H, m), 2.98 & 3.32(2H, ABq, J=18 Hz), 3.96(2H, t, J=7 Hz), 5.00(1H, d, J=7 Hz), 5.25-5.52(2H, ABq, J=14 Hz), 5.55-5.75 (1H, m), 6.65(1H, s), 7.12(2H, br.s), 8.20-8.55(2H, m), 8.6-8.75(1H, m), 8.80-9.00(1H, m), 9.40(1H, d, J=8 Hz), 9.74(1H, s).

EXAMPLE 56

7β-[2-(2-Aminothiazol-4-yl)-2(Z)-methoxyiminoacetamido]-3-[(6-methylimidazo[1,2-b]pyridazinium-1-yl)methyl]-3-cephem-4-carboxylate Compound [VII'] ($R^3$=—$CH_3$, $A^\oplus$=

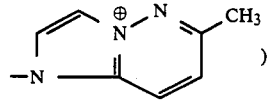)

Elemental analysis for: $C_{21}H_{20}N_8O_5S_2.9/2H_2O$: Calcd. (%): C, 41.37; H, 4.79; N, 18.38. Found (%): C, 41.50; H, 4.86; N, 17.91.

IR spectrum $\nu_{max}^{KBr}$ cm$^{-1}$: 1770, 1670, 1630, 1550.

NMR spectrum (d$_6$-DMSO) δ: 2.67(3H, s), 3.03 & 3.46(2H, ABq, J=18 Hz), 3.79(3H, s), 5.00(1H, d, J=4.5 Hz), 5.25 & 5.50 (2H, ABq, J=14 Hz), 5.61(1H, d.d, J=4.5 Hz), 6.68(1H, s), 7.15(2H, br.s), 7.87(1H, d, J=10 Hz), 8.55–8.74(2H, m), 9.19(1H, d, J=10 Hz), 9.47(1H, d, J=8 Hz).

EXAMPLE 57

7β-[2-(2-Aminothiazol-4-yl)-2(Z)-methoxyiminoacetamido]-3-[(6-chloroimidazo[1,2-b]pyridazinium-1-yl)methyl]-3-cephem-4-carboxylate compound [VII'] ($R^3$=—$CH_3$, $A^\oplus$=

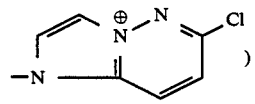)

Elemental analysis for $C_{20}H_{17}N_8O_5S_2Cl.3H_2O$: calcd. (%): C, 39.84; H, 3.84; N, 18.58. Found (%): C, 39.62; H, 3.69; N, 18.42.

IR spectrum $\nu_{max}^{KBr}$ cm$^{-1}$: 1780, 1670, 1610, 1530.

NMR spectrum (d$_6$-DMSO)δ: 2.97 & 3.43(2H, ABq, J=18 Hz), 3.77(3H, s), 4.97(1H, d, J=4.5 Hz), 5.21 & 5.54(2H, ABq, J=14 Hz), 5.60(1H, d. d, J=4.5 Hz & 8 Hz), 6.66(1H, s), 7.09(2H, br. s), 8.13 (1H, d, J=10 Hz), 8.71–8.84(2H, m), 9.34–9.54(2H, m).

EXAMPLE 58

7β-[2-(2-Aminothiazol-4-yl)-2(Z)-methoxyiminoacetamido]-3-[(6-methoxyimidazo[1,2-b]pyridazinium-1-yl)methyl]-3-cephem-4-carboxylate Compound [VII'] ($R^3$=—$CH_3$, $A^\oplus$=

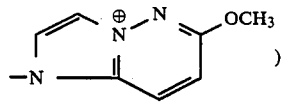)

Elemental analysis for $C_{21}H_{20}N_8O_6S_2.9/2H_2O$: Calcd. (%): C, 40.32; H, 4.67; N, 17.91. Found (%): C, 40.34; H, 4.71; N, 17.42.

IR spectrum $\nu_{max}^{KBr}$ cm$^{-1}$: 1775, 1670, 1620, 1510.

NMR spectrum (d$_6$-DMSO)δ: 2.99 & 3.44(2H, ABq, J=18 Hz), 3.80(3H, s), 4.06(3H, s), 5.01(1H, d, J=4.5 Hz), 5.21 & 5.49(2H, ABq, J=14 Hz), 5.61(1H, d. d, J=4.5 Hz & 8 Hz), 6.70(1H, s), 7.15 (2H, br. s), 7.62(1H, d, J=10 Hz), 8.48–8.66(2H, m), 9.21(1H, d, J=10 Hz), 9.48(1H, d, J=8 Hz).

EXAMPLE 59

7β-[2-(2-Aminothiazol-4-yl)-2(Z)-ethoxyiminoacetamido]-3-[(6-methoxyimidazo[1,2-b]pyridazinium-1-yl)methyl]-3-cephem-4-carboxylate Compound [VII'] ($R^3$=—$CH_2CH_3$, $A^\oplus$=

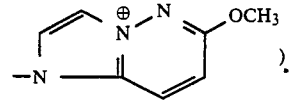).

Elemental analysis for $C_{22}H_{22}N_8O_6S_2.5H_2O$: Calcd. (%): C, 40.73; H, 4.97; N, 17.27. Found (%): C, 41.00; H, 4.52; N, 17.62.

IR spectrum $\nu_{max}^{KBr}$ cm$^{-1}$: 1770, 1660, 1620, 1530.

NMR spectrum (d$_6$-DMSO)δ: 1.19(3H, t, J=6 Hz), 2.99 and 3.44(2H, ABq, J=18 Hz), 4.05(3H, s), 4.06(2H, q, J=6 Hz), 4.99 (1H, d, J=4.5 Hz), 5.19 & 5.50(2H, ABq, J=14 Hz), 5.62(1H, d. d, J=4.5 Hz & 8 Hz), 6.65(1H, s), 7.14(2H, br. s), 7.62(1H, d, J=10 Hz), 8.45–8.68(2H, m), 9.24(1H, d, J=10 Hz), 9.43(1H, d, J=8 Hz).

EXAMPLE 60

7β-[2-(2-Aminothiazol-4-yl)-2(Z)-methoxyiminoacetamido]-3-[(2-methylimidazo[1,2-a]pyridinium-1-yl)methyl]-3-cephem-4-carboxylate Compound [VII'] ($R^3$=—$CH_3$, $A^\oplus$=

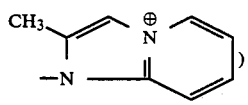)

Elemental analysis $C_{22}H_{21}N_7O_5S_2.4H_2O$: Calcd. (%): C, 44.06; H, 3.52; N, 16.35. Found (%): C, 44.50; H, 3.77; N, 17.01.

IR spectrum $\nu_{max}^{KBr}$ cm$^{-1}$: 1770, 1660, 1610, 1530.

NMR spectrum (d$_6$-DMSO)δ: 2.95 & 3.47(2H, ABq, J=18 Hz), 3.78(3H, s), 3.80(3H, s), 5.08(1H, d, J=4.5 Hz), 5.44(2H, br. s), 5.62(1H, d. d, J=4.5 Hz & 8 Hz), 6.68(1H, s), 7.15(2H, br. s), 7.55–8.15(5H, m), 9.48(1H, d, J=8 Hz).

EXAMPLE 61

7β-[2-(2-Aminothiazol-4-yl)-2(Z)-methoxyiminoacetamido]-3-[(2-carbamoylimidazo[1,2-a]pyridinium-1-yl)methyl]-3-cephem-4-carboxylate Compound [VII'] ($R^3$=—$CH_3$, $A^\oplus$=

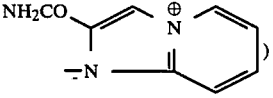)

Elemental analysis for $C_{22}H_{20}N_8O_6S_2.17/2H_2O$: Calcd. (%): C, 37.23; H, 5.25; N, 15.78. Found (%): C, 37.37; H, 5.43; N, 15.29.

IR spectrum $\nu_{max}^{KBr}$ cm$^{-1}$: 1765, 1750, 1690, 1610, 1530.

NMR spectrum (d$_6$-DMSO-D$_2$O)δ: 3.01 & 3.34(2H, ABq, J=18 Hz), 3.80(3H, s), 4.98(1H, d, J=5 Hz), 5.20–5.50(2H, m), 5.60(1H, d), 6.71(1H, s), 7.3–7.7(2H, m), 7.95–8.28(1H, m), 8.68–9.05(2H, m).

EXAMPLE 62

7β-[2-(2-Aminothiazol-4-yl)-2(Z)-methoxyiminoacetamido]-3-[(3-ethoxycarbonyl-2-methylimidazo[1,2-a]pyridinium-1-yl)methyl]-3-cephem-4-carboxylate Compound [VII'] ($R^3$=—$CH_3$, $A^\oplus$=

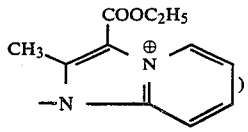

Elemental analysis for $C_{25}H_{25}N_7O_7S_2.7/2H_2O$: Calcd. (%): C, 45.31; H, 4.87; N, 14.80. Found (%): C, 45.90; H, 4.65; N, 14.73.

IR spectrum $\nu_{max}^{KBr}$ cm$^{-1}$: 1760, 1710, 1670, 1600.

NMR spectrum (d$_6$-DMSO)δ: 1.41(3H, t, J=7 Hz), 2.88(3H, s), 3.18(½×2H, ABq, J=18 Hz), 3.78(3H, s), 4.49(2H, q, J=7 Hz), 4.95(1H, d, J=4.5 Hz), 5.21 & 5.52(2H, ABq, J=14 Hz), 5.50-5.78(1H, m), 6.67(1H, s), 7.15(2H, br. s), 7.58-7.84(1H, m), 8.00-8.30 (1H, m), 9.10-9.30(1H, m), 9.35-9.60(2H, m).

EXAMPLE 63

7β-[2-(2-Aminothiazol-4-yl)-2(Z)-(1-carbamoyl-1-methylethoxyimino)acetamido]-3-[(imidazo[1,2-a]pyridinium-1-yl)methyl]-3-cephem-4-carboxylate Compound [VII'] ($R^3$=—$C(CH_3)_2CONH_2$, $A^\oplus$=

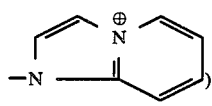

Elemental analysis for $C_{24}H_{24}N_8O_6S_2.4H_2O$: Calcd. (%): C, 43.90; H, 4.91; N, 17.06. Found (%): C, 43.94; H, 5.03; N, 16.90.

IR spectrum $\nu_{max}^{KBr}$ cm$^{-1}$: 1780, 1725, 1670, 1610, 1540.

NMR spectrum (d$_6$-DMSO)δ: 1.36(6H, br. s), 3.02 & 3.42 (2H, ABq, J=15 Hz), 5.01(1H, d, J=5 Hz), 5.2-5.3(2H, m), 5.68 (1H, d. d, J=5 Hz & 8 Hz), 6.71(1H, s), 6.7-7.1(2H, m), 7.21(2H, br. s), 7.4-7.6(1H, m), 7.8-8.1(1H, m), 8.3-8.7(3H, m), 8.8-9.0(1H, m), 9.58(1H, d, J=8 Hz).

EXAMPLE 64

7β-[2-(2-Aminothiazol-4-yl)-2(Z)-ethoxyiminoacetamido]-3-[(6-carbamoylimidazo[1,2-a]pyridinium-1-yl)methyl]-3-cephem-4-carboxylate Compound [VII'] ($R^3$=—$CH_2CH_3$, $A^\oplus$=

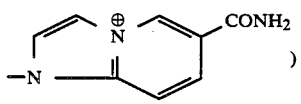

Elemental analysis for $C_{23}H_{22}N_8O_6S_2.4H_2O$: Calcd. (%): C, 42.99; H, 4.70; N, 17.44. Found (%): C, 43.19; H, 4.41; N, 17.23.

IR spectrum $\nu_{max}^{KBr}$ cm$^{-1}$: 1770, 1680, 1610, 1535.

NMR spectrum (d$_6$-DMSO)δ: 1.18(3H, t, J=7 Hz), 3.04 and 3.48(2H, ABq, J=16 Hz), 4.05(2H, q, J=7 Hz), 5.02(1H, d, J=5 Hz), 5.30 & 5.52(2H, ABq, J=16 Hz), 5.64(1H, d. d, J=5 Hz & 8 Hz), 6.67 (1H, s), 7.15(2H, br. s), 7.5-8.2(2H, m), 8.2-8.9(4H, m), 9.44 (1H, d, J=8 Hz), 9.60(1H, br. s).

EXAMPLE 65

7β-[2-(2-Aminothiazol-4-yl)-2(Z)-ethoxyiminoacetamido]-3-[(6-cyanoimidazo[1,2-a]pyridinium-1-yl)methyl]-3-cephem-4-carboxylate Compound [VII'] ($R^3$=—$CH_2CH_3$, $A^\oplus$=

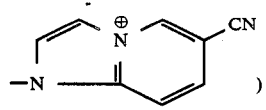

Elemental analysis for $C_{23}H_{20}N_8O_5S_2.5H_2O$: Calcd. (%): C, 42.99; H, 4.70; N, 17.44. Found (%): C, 42.82; H, 4.39; N, 16.98.

IR spectrum $\nu_{max}^{KBr}$ cm$^{-1}$: 2250, 1770, 1610, 1530.

NMR spectrum (d$_6$-DMSO)δ: 1.18(3H, t, J=7 Hz), 2.99 and 3.44(2H, ABq, J=18 Hz), 4.05(2H, q, J=7 Hz), 5.01(1H, d, J=5 Hz), 5.28 & 5.53(2H, ABq, J=14 Hz), 5.64(1H, d. d, J=5 Hz & 8 Hz), 6.66 (1H, s), 7.14(2H, br. s), 8.2-9.0(4H, m), 9.42(1H, d, J=8 Hz), 9.77(1H, br. s).

EXAMPLE 66

7β-[2-(2-Aminothiazol-4-yl)-2(Z)-(2-chloroethoxyimino)acetamido]-3-[(6-cyanoimidazo[1,2-a]pyridinium-1-yl)methyl]-3-cephem-4-carboxylate Compound [VII'] ($R^3$=—$CH_2CH_2Cl$, $A^\oplus$=

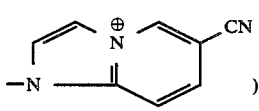

Elemental analysis for $C_{23}H_{19}N_8O_5S_2Cl.7/2H_2O$: Calcd. (%): C, 42.50; H, 4.03; N, 17.24. Found (%): C, 42.54; H, 3.93; N, 16.97.

IR spectrum $\nu_{max}^{KBr}$ cm$^{-1}$: 2250, 1770, 1650, 1610, 1530.

NMR spectrum (d$_6$-DMSO)δ: 2.99 & 3.47(2H, ABq, J=18 Hz), 3.6-3.9(2H, m), 4.1-4.4(2H, m), 5.12 & 5.27(2H, ABq, J=13 Hz), 5.64(1H, d. d, J=5 Hz & 8 Hz), 6.72(1H, s), 7.19(2H, br. s), 8.2-9.0(4H, m), 9.50(1H, d, J=8 Hz), 9.78(1H, br. s).

EXAMPLE 67

7β-[2-(2-Aminothiazol-4-yl)-2(Z)-methoxyiminoacetamido]-3-[(8-hydroxyimidazo[1,2-a]pyridinium-1-yl)methyl]-3-cephem-4-carboxylate Compound [VII'] ($R^3$=—$CH_3$, $A^\oplus$=

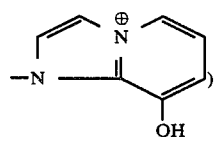

Elemental analysis for $C_{21}H_{19}N_7O_6S_2.6H_2O$: Calcd. (%): C, 39.55; H, 4.90; N, 15.38. Found (%): C, 39.39; H, 5.22; N, 14.98.

IR spectrum $\nu_{max}^{KBr}$ cm$^{-1}$: 1760, 1670, 1620, 1530, 1370.

NMR spectrum (d₆-DMSO)δ: 3.13 & 3.49(2H, ABq, J=18 Hz), 3.79(1H, s), 5.02(1H, d, J=5 Hz), 5.26 & 5.45(2H, ABq, J=13 Hz), 5.63(1H, d. d, J=5 Hz & 8 Hz), 6.70(1H, s), 7.13(2H, br. s), 6.0-8.4(6H, m), 9.46(1H, d, J=8 Hz).

EXAMPLE 68

7β-[2-(2-Aminothiazol-4-yl)-2(Z)-methox-yiminoacetamido]-3-[(8-benzyloxyimidazo[1,2-a]pyridinium-1-yl)methyl]-3-cephem-4-carboxylate Compound [VII'] (R³=—CH₃, A⊕=

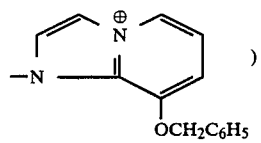

Elemental analysis for C₂₆H₂₅N₇O₆S₂.9/2H₂O: Calcd. (%): C, 47.99; H, 4.89; N, 13.99. Found (%): C, 47.89; H, 4.60; N, 13.99.

IR spectrum $\nu_{max}^{KBr}$ cm⁻¹: 1770, 1670, 1610, 1570, 1520.

NMR spectrum (d₆-DMSO)δ: 2.93 & 3.31(2H, ABq, J=18 Hz), 3.80(3H, s), 4.96(1H, d, J=5 Hz), 5.18 & 5.44(2H, ABq, J=13 Hz), 5.47(2H, s), 5.59(1H, d. d, J=5 Hz & 8 Hz), 6.70(1H, s), 7.13(2H, br. s), 7.2-7.7(7H, m), 8.17(1H, d, J=2 Hz), 8.50(1H, d, J=7 Hz), 8.79(1H, d, J=2 Hz), 9.43(1H, d, J=8 Hz).

EXAMPLE 69

7β-[2-(2-Aminothiazol-4-yl)-2(Z)-methox-yiminoacetamido]-3-[(imidazo[1,2-a]quinolinium-1-yl)methyl]-3-cephem-4-carboxylate Compound [VII'] (R³=—CH₃, A⊕=

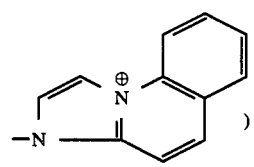

Elemental analysis for C₂₅H₂₁N₇O₅S₂.11/2H₂O: Calcd. (%): C, 45.31; H, 4.87; N, 14.80. Found (%): C, 45.32; H, 4.64; N, 14.71.

IR spectrum $\nu_{max}^{KBr}$ cm⁻¹: 1770, 1670, 1620, 1550, 1530, 1455.

NMR spectrum (d₆-DMSO)δ: 3.05 & 3.50(2H, ABq, J=18 Hz), 3.80(3H, s), 5.00(1H, d, J=5 Hz), 5.37 & 5.58(2H, ABq, J=13 Hz), 5.60(1H, d. d, J=5 Hz & 8 Hz), 6.67(1H, s), 7.12(2H, br. s), 7.4-8.8(7H, m), 9.18(1H, m), 9.47(1H, d, J=8 Hz).

EXAMPLE 70

7β-[2-(2-Aminothiazol-4-yl)-2(Z)-methox-yiminoacetamido]-3-[(3-methylthiazolo[3,2-a]benzimidazolium-1-yl)methyl]-3-cephem-4-carboxylate Compound [VII'] (R³=—CH₃, A⊕=

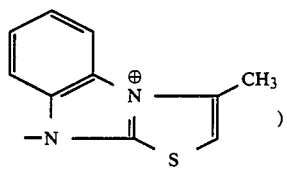

Elemental analysis for C₂₄H₂₁N₇O₅S₃.8H₂O: Calcd. (%): C, 39.61; H, 5.12; N, 13.47. Found (%): C, 39.56; H, 4.97; N, 13.46.

IR spectrum $\nu_{max}^{KBr}$ cm⁻¹: 1770, 1670, 1625, 1530, 1480, 1440.

NMR spectrum (d₆-DMSO)δ: 2.85(3H, s), 3.11 & 3.50(2H, ABq, J=18 Hz), 5.04(1H, d, J=5 Hz), 5.29 & 5.53(2H, ABq, J=13 Hz), 5.67(1H, d. d, J=5 Hz & 8 Hz), 6.70(1H, s), 7.12(2H, br. s), 7.62(1H, s), 6.8-7.9(2H, m), 8.0-8.5(2H, m), 9.50(1H, d, J=8 Hz).

EXAMPLE 71

7β-[2-(2-Aminothiazol-4-yl)-2(Z)-methox-yiminoacetamido]-3-[(imidazo[1,2-a]pyrimidinium-1-yl)methyl]-3-cephem-4-carboxylate Compound [VII'] (R³=—CH₃, A⊕=

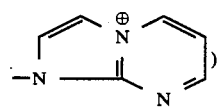

Elemental analysis for C₂₀H₁₈N₈O₅S₂.7/2H₂O: Calcd. (%): C, 41.59; H, 4.36; N, 19.40. Found (%): C, 41.63; H, 4.26; N, 19.13.

IR spectrum $\nu_{max}^{KBr}$ cm⁻¹: 1775, 1670, 1630, 1610, 1540.

NMR spectrum (d₆-DMSO)δ: 3.12 & 3.54(2H, ABq, J=18 Hz), 3.79(3H, s), 5.00(1H, d, J=4.5 Hz), 5.15 & 5.31(2H, ABq, J=13.5 Hz), 5.62(1H, d. d, J=4.5 Hz & 8 Hz), 6.68(1H, s), 7.14(2H, br. s), 7.6-7.8(1H, m), 8.36(1H, d, J=2.5 Hz), 8.89(1H, d, J=2.5 Hz), 9.00-9.18(1H, m), 9.30-9.55(1H, m), 9.43(1H, d, J=8 Hz).

EXAMPLE 72

7β-[2-(2-Aminothiazol-4-yl)-2(Z)-ethox-yiminoacetamido]-3-[(6-chloroimidazo[1,2-b]pyridazinium-1-yl)methyl]-3-cephem-4-carboxylate Compound [VII'] (R³=—C₂H₅, A⊕=

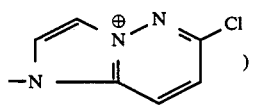

Elemental analysis for C₂₁H₁₉ClN₈O₅S₂.7/2H₂O: Calcd. (%): C, 40.29; H, 4.19; N, 17.90. Found (%): C, 40.46; H, 3.94; N, 17.54.

IR spectrum $\nu_{max}^{KBr}$ cm⁻¹: 1780, 1770, 1670, 1610, 1530.

NMR spectrum (d₆-DMSO)δ: 1.19(3H, t, J=7 Hz), 3.01 and 3.47(2H, ABq, J=18 Hz), 4.06(2H, q, J=7 Hz), 5.00(1H, d, J=4.5 Hz), 5.26 & 5.56(2H, ABq, J=14 Hz), 5.64(1H, d. d, J=4.5 Hz & 8 Hz), 6.67 (1H, s), 7.14(2H, br. s), 8.17(1H, d, J=10 Hz), 8.78-8.90(2H, m), 9.44(1H, d, J=8 Hz), 9.48(1H, d, J=10 Hz).

EXAMPLE 73

7β-[2-(2-Aminothiazol-4-yl)-2(Z)-methoxyiminoacetamido]-3-[(5,7-dimethylimidazo[1,2-c]pyrimidinium-1-yl)methyl]-3-cephem-4-carboxylate Compound [VII′] (R³=—CH₃, A⊕=

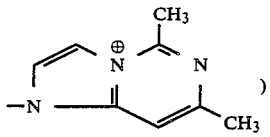
)

Elemental analysis for C₂₂H₂₂N₈O₅S₂.5H₂O: Calcd. (%): C, 41.77; H, 5.10; N, 17.71. Found (%): C, 41.87; H, 4.69; N, 17.24.

IR spectrum ν$_{max}^{KBr}$ cm⁻¹: 1775, 1670, 1615, 1535.

NMR spectrum (d₆-DMSO)δ: 2.60(3H, s), 2.90(3H, s), 3.26 (½×2H, ABq, J=18 Hz), 3.79(3H, s), 4.97(1H, d, J=4.5 Hz), 5.11 and 5.36(2H, ABq, J=14 Hz), 5.58(1H, d. d, J=4.5 Hz & 8 Hz), 6.67 (1H, s), 7.12(2H, br. s), 8.3–8.65(3H, s), 9.43(1H, d, J=8 Hz).

EXAMPLE 74

7β-[2-(2-Aminothiazol-4-yl)-2(Z)-(2-fluoroethoxyimino)acetamido]-3-[(imidazo[1,5-a]pyridinium-2-yl)methyl]-3-cephem-4-carboxylate Compound [VII′] (R³=—CH₂CH₂F, A⊕=

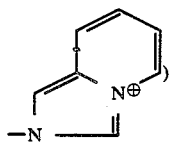
)

Elemental analysis for C₂₂H₂₀N₇O₅S₂F.7/2H₂O: Calcd. (%): C, 43.42; H, 4.47; N, 16.11. Found (%): C, 43.58; H, 4.29; N, 15.85.

IR spectrum ν$_{max}^{KBr}$ cm⁻¹: 1770, 1660, 1610, 1535, 1390, 1360.

NMR spectrum (d₆-DMSO)δ: 3.12 & 3.57(2H, ABq, J=18 Hz), 4.0–4.2(1H, m), 4.2–4.5(2H, m), 4.7–4.9(1H, m), 5.04(1H, d, J=5 Hz), 5.53 & 5.51(2H, ABq, J=13 Hz), 5.64(1H, d. d, J=5 Hz & 8 Hz), 6.71(1H, s), 6.9–7.2(5H, m), 7.7–8.0(1H, m), 8.4–8.8(2H, m), 9.45(1H, d, J=8 Hz).

EXAMPLE 75

7β-[2-(2-Aminothiazol-4-yl)-2(Z)-methoxyiminoacetamido]-3-[(3-carboxy-2-methylimidazo[1,2-a]pyridinium-1-yl)methyl-3-cephem-4-carboxylate monosodium salt Compound [VII′] (R³=—CH₃, A⊕=

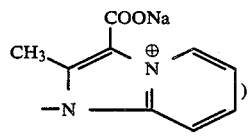
)

Elemental analysis for C₂₃H₂₀N₇O₆S₂Na.6H₂O: Calcd. (%): C, 40.29; H, 4.70; N, 14.29. Found (%): C, 40.66; H, 4.59; N, 13.79.

IR spectrum ν$_{max}^{KBr}$ cm⁻¹: 1770, 1610, 1535, 1390.

NMR spectrum (d₆-DMSO)δ: 2.86(3H, s), 2.87 & 3.31 (2H, ABq, J=18 Hz), 3.78(3H, s), 4.97(1H, d, J=4.5 Hz), 5.2–5.48(2H, m), 5.52–5.70(1H, m), 6.67(1H, s), 7.12(2H, br. s), 7.3–7.56(1H, m), 7.76–8.00(1H, m), 8.66–8.89(1H, m), 9.48 (1H, d, J=8 Hz), 10.08–10.24(1H, m).

EXAMPLE 76

7β-[2-(2-Aminothiazol-4-yl)-2(Z)-methoxyiminoacetamido]-3-[(2-carboxyimidazo[1,2-a]pyridinium-1-yl)methyl]-3-cephem-4-carboxylate monosodium salt Compound [VII′] (R³=—CH₃, A⊕=

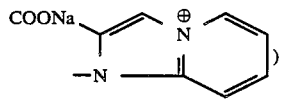
)

Elemental analysis for C₂₂H₁₈N₇O₇S₂Na.4H₂O: Calcd. (%): C, 40.55; H, 4.02; N, 15.05. Found (%): C, 40.59; H, 3.71; N, 14.57.

IR spectrum ν$_{max}^{KBr}$ cm⁻¹: 1765, 1620, 1520.

NMR spectrum (d₆-DMSO)δ: 3.02 & 3.29(2H, ABq, J=18 Hz), 3.80(3H, s), 4.95(1H, d, J=4.5 Hz), 5.56(1H, d. d, J=4.5 Hz & 8 Hz), 6.07 & 6.25(2H, ABq, J=14 Hz), 6.67(1H, s), 7.15(2H, br. s), 7.3–7.6(1H, m), 7.72–8.00(1H, m), 8.44(1H, s), 8.78–9.00(2H, m), 9.45(1H, d, J=8 Hz).

EXAMPLE 77

7β-[2-(2-Aminothiazol-4-yl)-2(Z)-methoxyiminoacetamido]-3-[(3-cyanoimidazo[1,2-a]pyridinium-1-yl)methyl]-3-cephem-4-carboxylate Compound [VII′] (R³=—CH₃, A⊕=

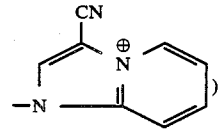
)

Elemental analysis for C₂₂H₁₈N₈O₅S₂.4H₂O: Calcd. (%): C, 43.27; H, 4.29; N, 18.35. Found (%): C, 43.63; H, 4.29; N, 18.16.

IR spectrum ν$_{max}^{KBr}$ cm⁻¹ 2245, 1770, 1660, 1610.

NMR spectrum (d₆-DMSO)δ: 3.02 & 3.47(2H, ABq, J=18 Hz), 3.79(3H, s), 4.99(1H, d, J=5 Hz), 5.20–5.79(3H, m), 6.68(1H, s), 7.14(2H, br. s), 7.62–7.84(1H, m), 8.10–8.45(1H, m), 8.9–9.14 (2H, m), 9.46(1H, d, J=8 Hz), 9.50(1H, s).

EXAMPLE 78

7β-[2-(2-Aminothiazol-4-yl)-2(Z)-ethoxyiminoacetamido]-3-[(3-cyanoimidazo[1,2-a]pyridinium-1-yl)methyl]-3-cephem-4-carboxylate Compound [VII′] (R³=—C₂H₅, A⊕=

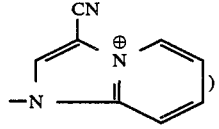
)

Elemental analysis for $C_{23}H_{20}N_8O_5S_2 \cdot 3H_2O$: Calcd. (%): C, 45.54; H, 4.32; N, 18.47. Found (%): C, 45.33; H, 4.44; N, 17.76.

IR spectrum $\nu_{max}^{KBr}$ cm$^{-1}$: 2240, 1770, 1670, 1610, 1530, 1510.

NMR spectrum (d$_6$-DMSO)δ: 1.19(3H, t, J=7 Hz), 3.03 and 3.47(2H, ABq, J=18 Hz), 4.05(2H, q, J=7 Hz), 5.00(1H, d, J=4.5 Hz), 5.32 & 5.59(2H, ABq, J=14 Hz), 5.64(1H, d. d, J=4.5 Hz & 8 Hz), 6.66 (1H, s), 7.14(2H, br. s), 7.64–7.86(1H, m), 8.17–8.40(1H, m), 8.90–9.15(2H, m), 9.43(1H, d, J=8 Hz), 9.50(1H, s).

EXAMPLE 79

7β-[2-(2-Aminothiazol-4-yl)-2(Z)-(2-hydroxyethoxyimino)acetamido]-3-[(6-cyanoimidazo[1,2-a]pyridinium-1-yl)methyl]-3-cephem-4-carboxylate Compound [VII'] (R$^3$=—CH$_2$CH$_2$OH, A$^\oplus$=

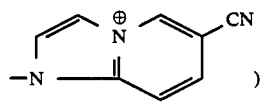

Elemental analysis for $C_{23}H_{20}N_8O_6S_2 \cdot 4H_2O$: Calcd. (%): C, 43.04; H, 4.41; N, 17.49. Found (%): C, 43.24; H, 3.64; N, 16.86.

IR spectrum $\nu_{max}^{KBr}$ cm$^{-1}$: 2250, 1765, 1650, 1610.

NMR spectrum (d$_6$-DMSO)δ: 2.97 & 3.14 (2H, ABq, J=18 Hz), 3.9–4.2 (4H, m), 5.01 (1H, d, J=4.5 Hz), 5.34 (2H, br. s), 5.62 (1H, d, d, J=4.5 Hz & 8 Hz), 6.68 (1H, s), 7.15 (2H, br. s), 8.28–8.58 (2H, m), 8.6–9.00 (2H, m), 9.38 (1H, d, J=8 Hz), 9.76 (1H, br. s).

EXAMPLE 80

7β-[2-(2-Aminothiazol-4-yl)-2-(Z)-methoxyiminoacetamido]-3-[[3-(cyanomethyl)imidazo[1,2-a]pyridinium-1-yl]methyl]-3-cephem-4-carboxylate Compound [VII'](R$^3$=—CH$_3$, A$^\oplus$=

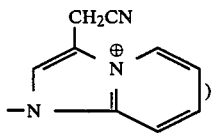

Elemental analysis for $C_{23}H_{20}N_8O_5S_2 \cdot 4H_2O$: Calcd. (%): C, 44.23; H, 4.51; N, 17.93. Found (%): C, 44.16; H, 4.63; N, 17.93.

IR spectrum $\nu_{max}^{KBr}$ cm$^{31}$ $^1$: 2260, 1765, 1650, 1605.

NMR spectrum (d$_6$-DMSO)δ: 3.0 & 3.45 (2H, ABq, J=18 Hz), 3.79 (3H, s), 4.70 (2H, s), 4.99 (1H, d, J=4.5 Hz), 5.25 & 5.51 (2H, ABq, J=14 Hz), 5.60 (1H, d. d, J=4.5 Hz & 8 Hz), 6.68 (1H, s), 7.15 (2H, br. s), 7.5–7.78 (1H, m), 7.95–8.25 (1H, m), 8.6–9.0 (3H, m), 9.45 (1H, d, J=8 Hz).

EXAMPLE 81

7β-[2-(2-Aminothiazol-4-yl)-2(Z)-methoxyiminoacetamido]-3-[(6-carboxyimidazo[1,2-a]pyridinium-1-yl)methyl]-3-cephem-4-carboxylate monosodium salt Compound [VII'](R$^3$=—CH$_3$, A$^{61}$ =

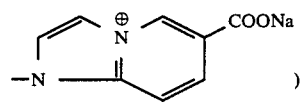

Elemental analysis for $C_{22}H_{18}N_7O_7S_2Na \cdot 5H_2O$: Calcd. (%): C, 39.46; H, 4.21; N, 14.64. Found (%): C, 39.39; H, 4.11; N, 14.53.

IR spectrum $\nu_{max}^{KBr}$cm$^{-1}$: 3400, 1765, 1665, 1610, 1530, 1390.

NMR spectrum (d$_6$-DMSO)δ: 2.53 (3H, s), 3.12 & 3.58 (2H, ABq, J=16 Hz), 5.00 (1H, d, J=5 Hz), 5.1–5.4 (2H, m), 5.71 (1H, d. d, J=5 Hz & 8 Hz), 6.57 (1H, s), 7.20 (2H, br. s), 8.0–8.7 (4H, m), 9.25 (1H, d, J=8 Hz), 9.45 (1H, br. s).

EXAMPLE 82

7β-[2-(2-Aminothiazol-4-yl)-2(Z)-(2-fluoroethoxyimino)acetamido]-3-[(6-cyanoimidazo[1,2-a]pyridinium-1-yl)methyl]-3-cephem-4-carboxylate Compound [VII'](R$^3$=—CH$_2$CH$_2$F, A$^{61}$ =

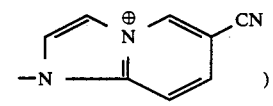

Elemental analysis for $C_{23}H_{19}N_8O_5S_2F \cdot 7/2H_2O$: Calcd. (%): C, 43.60; H, 4.14; N, 17.68. Found (%): C, 43.42; H, 3.94; N, 17.42.

IR spectrum $\nu_{max}^{KBr}$cm$^{-1}$: 3400, 2250, 1760, 1610, 1520.

NMR spectrum (d$_6$-DMSO)δ: 2.99 & 3.62 (2H, ABq, J=17 Hz), 4.0–4.2 (1H, m), 4.2–4.6 (2H, m), 4.7–5.0 (1H, m), 5.02 (1H, d, J=5 Hz), 5.28 & 5.54 (2H, ABq, J=15 Hz), 5.64 (1H, d. d, J=5 Hz & 8 Hz), 6.71 (1H, s), 7.17 (2H, br. s), 8.2–9.0 (1H, d, J=8 Hz), 9.77 (1H, br. s).

EXAMPLE 83

7β-[2-(2-Aminothiazol-4-yl)-2(Z)-methoxyiminoacetamido]-3-[[6-(trichloromethyl)imidazo[1,2-a]pyridinium]methyl]-3-cephem-4-carboxylate Compound [VII'](R$^3$=—CH$_3$, A$^{61}$=

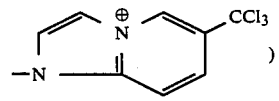

Elemental analysis for $C_{22}H_{18}N_7O_5S_2Cl_3 \cdot 5H_2O$: Calcd. (%): C, 36.65; H, 3.91; N, 13.60. Found (%): C, 36.52; H, 3.65; N, 13.35.

IR spectrum $\nu_{max}^{KBr}$cm$^{-1}$: 3400, 1755, 1605, 1520.

EXAMPLE 84

7β-[2-(2-Aminothiazol-4-yl)-2-(Z)-(1-carboxyethoxyimino)acetamido]-3-[(imidazo[1,2-a]pyridinium-1-yl)methyl]-3-cephem-4-carboxylate monosodium salt

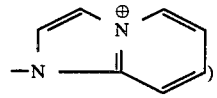

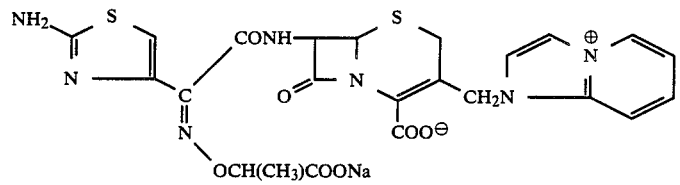

In 50% aqueous acetonitrile are dissolved 3 g of 7β-[2-(2-aminothiazol-4-yl)-2(Z)-(1-tert-butoxycarbonylethoxyimino)acetamido]-3-(3-oxobutyryloxymethyl)-3-cephem-4-carboxylic acid, 3 g of imidazo[1,2-a]pyridine and 3 g of potassium iodide. The solution is stirred at 60°–70° C. for 2 hours, and, then, subjected to silica gel column chromatography using aqueous acetone as the eluent. Fractions eluated with 80% aqueous acetone are combined and concentrated under reduced pressure and the residue is lyophilized. A powder thus-obtained is dissolved in water and the solution is subjected to chromatography on a MCI GEL CHP20P column using aqueous alcohol as the eluent. Fractions eluated with 30% aqueous alcohol are combined and concentrated under reduced pressure, and the residue is lyophilized to leave 0.2 g of a powder, which is dissolved in 2 ml of trifluoroacetic acid. The solution is stirred at room temperature for 2 hours and the solvent is removed under reduced pressure. To the residue are added water and sodium carbonate. The resulting solution is subjected to MCI GEL CHP20P column chromatography using water and then 5% aqueous ethanol as the eluent. Fractions containing the desired product are combined and concentrated under reduced pressure. Lyophilization of the residue gives 0.14 g of the above-identified compound.

Elemental analysis for $C_{23}H_{20}N_7O_7S_2Na.6H_2O$: Calcd. (%): C, 39.37; H, 4.60; N, 13.97. Found (%): C, 39.65; H, 4.20; N, 13.30.

IR spectrum $\nu_{max}^{KBr}$cm$^{-1}$: 1780, 1670, 1610, 1530.

NMR spectrum (d$_6$-DMSO)δ: 1.32 (3H, d, J=7 Hz), 3.01 and 3.38 (2H, ABq, J=18 Hz), 4.25–4.56 (1H, m), 4.96 & 5.00 (total 1H, each d, J=4.5 Hz), 5.2–5.5 (2H, m), 5.55–5.84 (1H, m), 6.72 & 6.78 (total 1H, 2s), 7.12 (2H, br. s), 7.36–7.60 (1H, m), 7.76–8.10 (1H, m), 8.25–8.65 (3H, m), 8.85–9.05 (1H, m), 11.56 & 11.71 (total 1H, each d, J=8 Hz).

By the procedure of Example 84, compounds of the following Examples 85–90 of the above general formula [VII'] can be prepared by reacting 7β-[2-(2-aminothiazol-4-yl)-2(Z)-(substituted oxyimino)acetamido]3-(3-oxobutyryloxymethyl)-3-cephem-4-carboxylic acid with various imidazole compounds.

EXAMPLE 85

7β-[2-(2-Aminothiazol-4-yl)-2(Z)-(1-carboxypropoxyimino)acetamido]-3-[(imidazo[1,2-a]pyridinium-1-yl)methyl]-3-cephem-4-carboxylate monosodium salt Compound [VII'](R$^3$=—CH(C$_2$H$_5$)COONa, A$^⊕$=

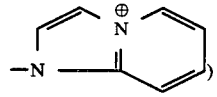

Elemental analysis for $C_{24}H_{22}N_7O_7S_2Na.9/2H_2O$: Calcd. (%): C, 41.86; H, 4.54; N, 14.24. Found (%): C, 41.67; H, 4.38; N, 14.58.

IR spectrum $\nu_{max}^{KBr}$cm$^{-1}$: 1780, 1765, 1670, 1600, 1530.

NMR spectrum (d$_6$-DMSO)δ: 0.90 & 0.92 (total 3H, each d, J=7 Hz), 1.50–1.95 (2H, m), 3.02 (½×2H, ABq, J=18 Hz), 4.00–4.34 (1H, m), 4.96 & 5.00 (total 1H, each d, j=4.5 Hz), 5.18–5.75 (3H, m), 6.71 & 6.80 (total 1H, each s), 7.11 (2H, br, s), 7.35–7.65 (1H, m), 7.75–8.15 (1H, m), 8.25–8.76 (3H, m), 8.80–9.10 (1H, m), 11.6–12.0 (1H, m).

EXAMPLE 86

7β-[2-(2-Aminothiazol-4-yl)-2(Z)-(1-carboxybutoxyimino)acetamido]-3-[(imidazo[1,2-a]pyridinium-1-yl)methyl]-3-cephem-4-carboxylate monosodium salt Compound A$^{61}$= [VII'](R$^3$=—CH(n—C$_3$H$_7$)COONa,

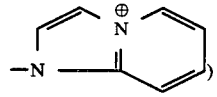

Elemental analysis for $C_{25}H_{24}N_7O_7S_2Na.5H_2O$: Calcd. (%): C, 42.19; H, 4.81; N, 13.77. Found (%): C, 42.15; H, 4.63; N, 13.61.

IR spectrum $\nu_{max}^{KBr}$cm$^{-1}$: 1770, 1670, 1610, 1530.

NMR spectrum (d$_6$-DMSO)δ: 0.74 & 0.82 (total 3H, each t, J=7 Hz), 1.1–1.9 (4H, m), 2.97 & 3.30 (2H, ABq, J=18 Hz), 4.1–4.42 (1H, m), 4.95 & 5.00 (total 1H, each d, J=5 Hz), 5,39 (2H, br. s), 5.6–5.7 (1H, m), 6.70 & 6.77 (total 1H, each s), 7.11 (2H, br. s), 7.35–7.60 (1H, m), 7.75–8.06 (1H, m), 8.3–8.7 (3H, m), 8.86–9.08 (1H, m), 11.62–11.90 (1H, m).

EXAMPLE 87

7β-[2-(2-Aminothiazol-4-yl)-2(Z)-(1-carboxy-1-methylethoxyimino)acetamido]-3-[(6-methylimidazo[1,2-b]pyridazinium-1-yl)methyl]-3-cephem-4-carboxylate monosodium salt Compound [VII'](R$^3$=—C(CH$_3$)$_2$COONa, A$^{61}$=

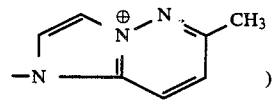

Elemental analysis for $C_{24}H_{23}N_8O_7S_2Na.5H_2O$:
Calcd. (%): C, 40.45; H, 4.67 N, 15.72. Found (%): C, 40.46; H, 4.21; N, 15.33.

IR spectrum $\nu_{max}^{KBr}cm^{-1}$: 1770, 1610, 1530.

NMR spectrum ($d_6$-DMSO)δ: 1.36 (3H, s), 1.41 (3H, s), 2.66 (3H, s), 3.04 & 3.22 (2H, ABq, J=18 Hz), 4.98 (1H, d, J=4.5 Hz), 5.22-5.50 (2H, m), 5.56-5.60 (1H, m), 6.67 (1H, s), 7.13 (2H, br. s), 7.78 (1H, d, J=10 Hz), 8.5-8.72 (2H, d, J=10 Hz), 11.50 (1H, d, J=8 Hz).

EXAMPLE 88

7β-[2-(2-Aminothiazol-4-yl)-2(Z)-(1-carboxy-1-methylethoxyimino)acetamido]-3-[(imidazo[1,5-a]pyridinium-2-yl)methyl]-3-cephem-4-carboxylate monosodium salt Compound [VII'](R³=—C(CH₃)₂COONa, A⊕=

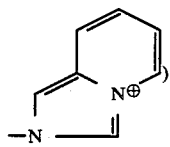

Elemental analysis for $C_{24}H_{22}N_7O_5S_2Na.9/2H_2O$:
Calcd. (%): C, 41.86; H, 4.54; N, 14.24. Found (%): C, 42.08; H, 4.26; N, 13.89.

IR spectrum $\nu_{max}^{KBr}cm^{-1}$: 1780, 1660, 1610, 1520.

NMR spectrum ($d_6$-DMSO)δ: 1.39 (3H, s), 1.42 (3H, s), 3.16 & 3.56 (2H, ABq, J=18 Hz), 5.05 (1H, d, J=4.5 Hz), 5.15-5.60 (2H, m), 5.65-5.85 (1H, m), 6.69 (1H, s), 7.13 (2H, br. s), 7.8-7.9 (2H, m), 8.2-8.5 (2H, m), 8.55-8.81 (1H, m), 10.44 (1H, br. s), 11.92 (1H, d, J=8 Hz).

EXAMPLE 89

7β-[2-(2-Aminothiazol-4-yl)-2(Z)-(1-carboxy-1-methylethoxyimino)acetamido]-3-[(6-cyanoimidazo[1,2-a]pyridinium-1-yl)methyl]-3-cephem-4-carboxylate monosodium salt Compound [VII'](R³=—C(CH₃)₂COONa, A⁶¹ =

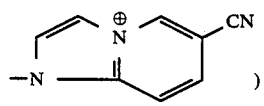

Elemental analysis for $C_{22}H_{21}N_8O_7S_2Na.5H_2O$:
Calcd. (%): C, 41.55; H, 4.32; N, 15.51. Found (%): C, 41.47; H, 4.16; N, 15.30.

IR spectrum $\nu_{max}^{KBr}cm^{-1}$: 2250, 1780, 1610, 1530.

NMR spectrum ($d_6$-DMSO)δ: 1.38 (3H, s), 1.42 (3H, s), 3.02 & 3.71 (2H, ABq, J=18 Hz), 4.99 (1H, d, J=5 Hz), 5.2-5.5 (2H, m), 5.68 (1H, d. d, J=5 Hz & 8 Hz), 6.68 (1H, s), 7.10 (2H, br. s), 8.2-8.8 (4H, m), 9.81 (1H, br. s), 11.44 (1H, d, J=8 Hz).

EXAMPLE 90

7β-[2-(2-Aminothiazol-4-yl)-2(Z)-(1-carboxy-1-methylethoxyimino)acetamido]-3-[(3-cyanoimidazo[1,2-a]pyridinium-1-yl)methyl]-3-cephem-4-carboxylate monosodium salt Compound [VII'](R³=—C(CH₃)₂COONa, A⊕=

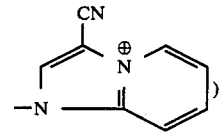

Elemental analysis for $C_{25}H_{21}N_8O_7S_2Na.5H_2O$:
Calcd. (%): C, 41.55; H, 4.32; N, 15.50. Found (%): C, 41.84; H, 4.14; N, 15.39.

IR spectrum $\nu_{max}^{KBr}cm^{-1}$: 2240, 1765, 1670, 1600, 1530.

NMR spectrum ($d_6$-DMSO)δ: 1.40 (6H, br. s), 3.12 & 3.49 (2H, ABq, J=18 Hz), 5.01 (1H, d, J=4.5 Hz), 5.40 (2H, br. s), 5.71 (1H, d, J=5 Hz), 6.73 (1H, s), 7.55-7.90 (1H, m), 8.00-8.80 (3H, m), 9.00 (1H, s).

EXAMPLE 91

7β-[2-(2-Amino-5-chlorothiazol-4-yl)-2(Z)-methoxyiminoacetamido]-3-[(imidazo[1,2-a]pyridinium-1-yl)methyl]-3-cephem-4-carboxylate

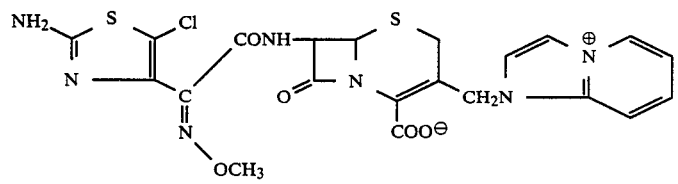

Starting from 2.0 g of 7β-[2-(2-amino-5-chlorothiazol-4-yl)-2(Z)-methoxyiminoacetamido]-3-(3-oxobutyryloxymethyl)-3-cephem-4-carboxylic acid, 2 g of imidazo[1,2-a]pyridine and 2 g of potassium iodide, 329 mg of the above-identified compound is obtained by the procedure of Example 42.

Elemental analysis for $C_{21}H_{18}ClN_7O_5S_2.2H_2O$:
Calcd. (%): C, 43.19; H, 3.80; N, 16.79. Found (%): C, 43.16; H, 3.39; N, 15.50.

IR spectrum $\nu_{max}^{KBr}cm^{-1}$: 3400, 1765, 1665, 1605, 1520, 1450.

NMR spectrum ($d_6$-DMSO)δ: 2.96 & 3.44 (2H, ABq, J=18 Hz), 3.80 (3H, s), 4.97 (1H, d, J=4.5 Hz), 5.2-5.5 (2H, m), 5.61 (1H, d. d, J=4.5 Hz & 8 Hz), 7.32 (2H, br. s), 7.5-9.0 (6H, m), 9.44 (1H, d, J=8 Hz).

EXAMPLE 92

7β-[2-[2-Amino-5-chlorothiazol-4-yl)-2(Z)-(1-carboxy-1-methylethoxyimino)acetamido]-3-[(imidazo[1,2-a]pyridinium-1-yl)methyl]-3-cephem-4-carboxylate monosodium salt

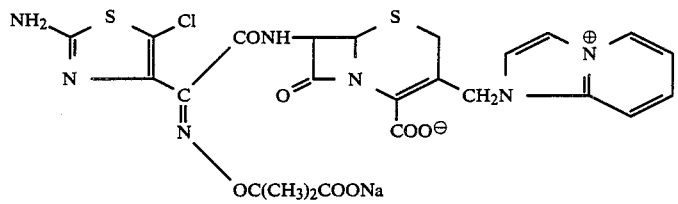

7β-[2-(2-Amino-5-chlorothiazol-4-yl)-2(Z)-(1-tert-butoxycarbonyl-1-methylethoxyimino)acetamido]-3-(3-oxobutyryloxymethyl)-3-cephem-4-carboxylic acid is reacted with imidazo[1,2-a]pyridine, by the procedure of Example 84 to give the above-identified compound.

Elemental analysis for $C_{24}H_{21}N_7O_7S_2ClNa \cdot 4H_2O$: Calcd. (%): C, 40.37; H, 4.09; N, 13.73. Found (%): C, 40.52; H, 3.76; N, 13.55.

IR spectrum $\nu_{max}^{KBr}cm^{-1}$: 1765, 1600, 1520.

EXAMPLE 93

7β-[2-(5-Amino-1,2,4-thiadiazol-3-yl)-2(Z)-ethoxyiminoacetamido]-3-[(6-cyanoimidazo[1,2-a]pyridinium-1-yl)methyl]-3-cephem-4-carboxylate

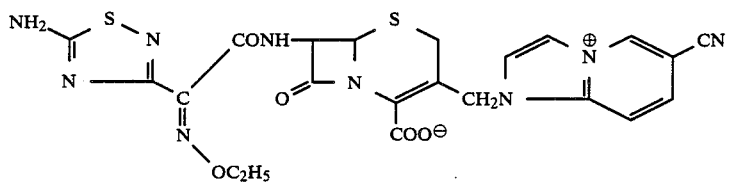

The compound obtained in Reference Example 28 is reacted with 6-cyanoimidazo[1,2-a]pyridine in the procedure of Example 42 to give the above-identified compound.

Elemental analysis for $C_{22}H_{19}N_9O_5S_2 \cdot 4H_2O$: Calcd. (%): C, 42.24; H, 4.35; N, 20.15. Found (%): C, 42.12; H, 3.90; N, 19.97.

IR spectrum $\nu_{max}^{KBr}cm^{-1}$: 2250, 1760, 1620, 1525.

NMR spectrum (d6-DMSO)δ: 1.19(3H, t, J=7 Hz), 2.98 and 3.44 (2H, ABq, J=18 Hz), 4.12 (2H, q, J=7 Hz), 5.00 (1H, d, J=5 Hz), 5.1–5.6 (2H, m), 5.66 (1H, d. d, J=5 Hz & 8 Hz), 8.10 (2H, br. s), 8.2–9.0 (4H, m), 9.42 (1H, d, J=8 Hz), 9.76 (1H, br. s).

EXAMPLE 94

7β-[2-(5-Amino-1,2,4-thiadiazol-3-yl)-2(Z)-methoxyiminoacetamido]-3-[(imidazo[1,2-a]pyridinium-1-yl)methyl]-3-cephem-4-carboxylate

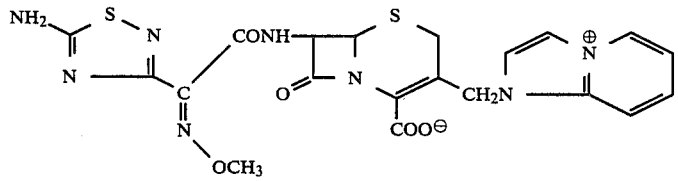

(i) Three grams of 7β-[2-(5-tert-butoxycarbonylamino-1,2,4-thiadiazol-3-yl)-2(Z)-methoxyiminoacetamido]-3-(3-oxobutyryloxymethyl)-3-cephem-4-carboxylic acid, 3 g of potassium iodide and 3 g of imidazo[1,2-a]pyridine, as reacted as in Example 42. The reaction mixture is then washed with ethyl acetate, and the aqueous layer is separated and subjected to XAD-2 column chromatography using water as eluent.

The reaction product eluted is subjected to silica gel column chromatography [silica gel: 40 g; eluent: acetone-water (6:4)] to give 290 mg of the above-identified compound.

Elemental analysis for $C_{20}H_{18}N_8O_5S_2 \cdot 4H_2O$: Calcd. (%): C, 40.95; H, 4.47; N, 19.10. Found (%): C, 41.15; H, 4.23; N, 18.54.

IR spectrum $\nu_{max}^{KBr}cm^{-1}$: 1770, 1620, 1530, 1390, 1045, 770.

NMR spectrum (d6-DMSO)δ: 2.96 & 3.42 (2H, ABq, J=18 Hz), 3.86 (3H, s), 4.98 (1H, d, J=4.8 Hz), 5.26 & 5.48 (2H, ABq, J=14 Hz), 5.62 (1H, d. d, J=8 Hz & 4.8 Hz), 7.40–7.60 (1H, t), 7.86–8.20 (3H, m), 8.34–8.76 (3H, m), 8.86–9.00 (1H, d), 9.43 (1H, d, J=8 Hz).

Further, another reaction product eluted from the XAD-2 column chromatography using 50% ethanol as eluent is again subjected to silica gel column chromatography [silica gel: 40 g; eluent: acetone-water (6:4)] to give 240 mg of 7β-[2-(5-tert-butoxycarbonylamino-1,2,4-thiadiazol-3-yl)-2(Z)-methoxyiminoacetamido]-3-[(imidazo[1,2-a]pyridinium-1-yl)methyl]-3-cephem-4-carboxylate.

IR spectrum $\nu_{max}^{KBr}cm^{-1}$: 1775, 1620, 1530, 1380, 1160, 1045, 770.

NMR spectrum (D2O)δ: 1.50 (9H, s), 3.15 & 3.55 (2H, ABq, J=18 Hz), 4.08 (3H, s), 5.23 (1H, d, J=4.8 Hz), 5.32 (2H, s), 5.86 (1H, d, J=4,8 Hz), 7.09–8.20 (7H, m), 8.66 (1H, d, J=8 Hz).

(ii) 7β-[2-(5-tert-Butoxycarbonylamino-1,2,4-thiadiazol-3-yl)-2(Z)-methoxyiminoacetamido]-3-[(imidazo[1,2-a]pyridinium-1-yl)methyl]-3-cephem-4-carboxylate (240 mg) obtained in the above procedure (i) is treated with 2 ml of trifluoroacetic acid under ice-cooling. Then, the cooling bath is removed and the reaction mixture is stirred at room temperature for 40 minutes, followed by the addition of ethyl acetate. The mixture is evaporated to dryness under reduced pressure. The residue is dissolved in water, and the solution is neutralized with sodium hydrogen carbonate under ice-cooling and then subjected to XAD-2 column chromatography using 20% EtOH as the eluent. The eluted fraction is further subjected to silica gel column chromatography [silica gel: 40 g; eluent: acetone-water (6:4)]. Fractions containing the desired product is concentrated and lyophilized to give 310 mg of the above-identified compound.

EXAMPLE 95

7β-[2-(5-Amino-1,2,4-thiadiazol-3-yl)-2(Z)-ethoxyiminoacetamido]-3-[(imidazo[1,2-a]pyridinium-1-yl)methyl]-3-cephem-4-carboxylate

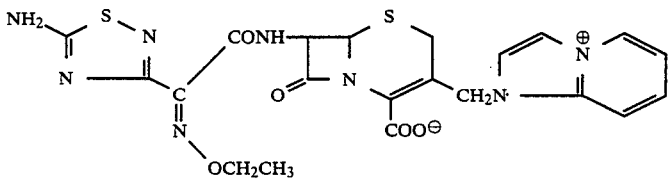

7β-[2-(5-Amino-1,2,4-thiadiazol-3-yl)-2(Z)-ethoxyiminoacetamido]-3-(3-oxobutyryloxymethyl)-3-cephem-4-carboxylic acid and imidazo[1,2-a]pyridine, are reacted in the procedure of Example 42 to give the above-identified compound.

Elemental analysis for $C_{21}H_{20}N_8O_5S_2 \cdot 4H_2O$: Calcd. (%): C, 42.00; H, 4.70; N, 18.66. Found (%): C, 42.25; H, 4.25; N, 18.44.

IR spectrum $\nu_{max}^{KBr}\text{cm}^{-1}$: 1770, 1610, 1530, 1390, 1360, 1040, 765.

NMR spectrum (d$_6$-DMSO)δ: 1.20(3H, t, J=7 Hz), 3.02 and 3.44(2H, ABq, J=18 Hz), 4.12(2H, q, J=7 Hz), 5.01(1H, d, J=4.8 Hz), 5.42(2H, br.s), 5.66(1H, d.d, J=8 Hz & 4.8 Hz), 7.50(t, J=7 Hz), 8.00(t, J=7 Hz), 8.40-7.00(m) and 8.98(d, J=7 Hz) (total 6H), 9.42(1H, d, J=8 Hz), 8.16(2H, s).

EXAMPLE 96

7β-[2-(5-Amino-1,2,4-thiadiazol-3-yl)-2(Z)-ethoxyiminoacetamido]-3-[(6-chloroimidazo[1,2-a]pyridinium-1-yl)methyl]-3-cephem-4-carboxylate

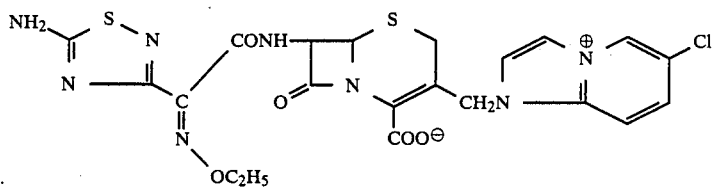

7β-[2-(5-Amino-1,2,4-thiadiazol-3-yl)-2(Z)-ethoxyiminoacetamido]-3-(3-oxybutyryloxymethyl)-3-cephem-4-carboxylic acid and 6-chloroimidazo[1,2-a]pyridine are reacted in the manner of Example 42 to give the above-identified compound.

Elemental analysis for $C_{21}H_{19}ClN_8O_5S_2 \cdot 3H_2O$: Calcd. (%): C, 40.88; H, 4.08; N, 18.16. Found (%): C, 40.85; H, 3.97; N, 18.01.

IR spectrum $\nu_{max}^{KBr}\text{cm}^{-1}$: 3300, 3150, 1780, 1680, 1620, 1520, 1390, 1040.

NMR spectrum (d$_6$-DMSO)δ: 1.11(3H, t, J=7 Hz), 2.99 and 3.44(2H, ABq, J=18 Hz), 4.13(2H, q, J=7 Hz), 5.00(1H, d, J=4.8 Hz), 5.27 & 5.49(2H, ABq, J=14 Hz), 5.66(1H, d.d, J=8 Hz & 4.8 Hz), 8.00-8.86(m) and 9.30(s) (total 5H), 9.42(1H, d, j=8 Hz).

EXAMPLE 97

7β-[2-(5-Amino-1,2,4-thiadiazol-3-yl)-2(Z)-ethoxyiminoacetamido]-3-[3-(dimethylaminoethyl)imidazo[1,2-a]pyridinium-1-yl)methyl]-3-cephem-4-carboxylate

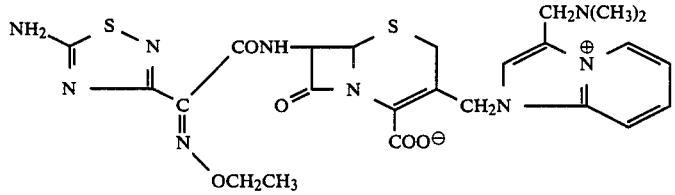

7β-[2-(5-Amino-1,2,4-thiadiazol-3-yl)-2(Z)-ethoxyiminoacetamido]-3-(3-oxobutyryloxymethyl)-3-cephem-4-carboxylic acid and 3-(dimethylaminomethyl)imidazo[1,2-a]pyridine are reacted in the procedure of Example 42 to give the above-identified compound.

Elemental analysis for $C_{24}H_{27}N_9O_5S_2 \cdot 3H_2O$: Calcd. (%): C, 45.06; H, 5.20; N, 19.71. Found: (%): C, 45.18; H, 4.68; N, 19.57.

IR spectrum $\nu_{max}^{KBr}\text{cm}^{-1}$: 1770, 1660, 1615, 1530.

NMR spectrum (d$_6$-DMSO)δ: 1.26(3H, t, J=7 Hz), 2.90(3H, s), 2.98(3H, s), 4.17(2H, q, J=7 Hz), 5.06(2H, br.s), 5.19(1H, d, J=4.5 Hz), 5.68(1H, d.d, J=4.5 Hz & 8 Hz), 6.96-7.56(2H, m), 7.54-7.76(1H, m), 7.84–8.00(1H, m), 8.10(2H, br.s), 8.76–9.00(1H, m), 9.48(1H, d, J=8 Hz).

EXAMPLE 98

7β-[2-(2-Aminothiazol-4-yl-2(Z)-ethoxyiminoacetamido]-3-[(imidazol[1,2-a]pyridinium-1-yl)methyl]-3-cephem-4-carboxylate 1-β-sulfoxide

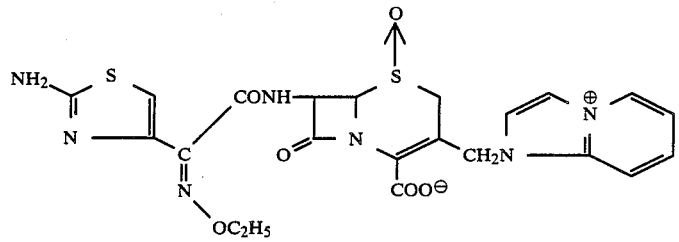

In 10 ml of acetic acid is dissolved 246 mg of 7β-[2-(2-aminothiazol-4-yl)-2(Z)-ethoxyiminoacetamido]-3-[(imidazo[1,2-a]pyridinium)methyl]-3-cephem-4-carboxylate and, under cooling at 10°–15° C., 86 mg of m-chloroperbenzoic acid is added thereto. The mixture is stirred at the same temperature for 1 hour. The solvent is then evaporated off under reduced pressure and the residue is dissolved in water. The solution is subjected to chromatography on a column of highporous polymer (MCI GEL CHP20P Mitsubishi Chemical Industries, Ltd.) using 15% ethanol as the eluent. The eluate is concentrated and lyophilized to give 1400 mg of the above identified compound.

Elemental analysis for $C_{22}H_{21}N_7O_6S_2.7/2H_2O$: Calcd. (%): C, 43.61; H, 4.64; N, 16.18. Found (%): C, 43.67; H, 4.42; N, 15.98.

IR spectrum $\nu_{max}^{KBr}$cm$^{-1}$: 1780, 1670, 1620, 1525, 1450, 1385, 1350, 1280, 1200, 1040, 770.

NMR spectrum (d$_6$-DMSO)δ: 1.22(3H, t, J=7 Hz), 2.10(2H, q, J=7 Hz), 4.86(1H, d, J=5 Hz), 5.44(2H, br.s), 5.76(1H, d.d, J=5 Hz & 8 Hz), 6.80(1H, s), 7.16(2H, br.s), 7.52(1H, t, J=b 7 Hz), 7.99(1H, t, J=7 Hz), 8.3–8.8(3H, t, J=7 Hz), 8.96(1H, d, J=6 Hz).

EXAMPLE 99

7β-[2-(2-Aminothiazol-4-yl)-2-formamidoacetamido]-3-[(imidazo[1,2-a]pyridinium-1-yl)methyl]-3-cephem-4-carboxylate

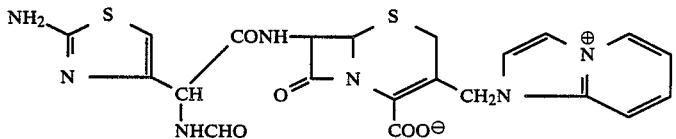

(i) In 100 ml of formic acid is dissolved 4 g of 7β-[2-(2-aminothiazol-4-yl)-2(Z)-methoxyiminoacetamido]-3-(3-oxobutyryloxymethyl)-3-cephem-4-carboxylate and, under ice-cooling, 20 g of zinc powder is added little by little with stirring in the course of 30 minutes. The mixture is stirred at room temperature for 1 hour, and insoluble substance is filtered off.

The filtrate contains 7β-[2-amino-2-(2-aminothiazol-4-yl)acetamido]-3-(3-oxobutyryloxymethyl)-3-cephem-4-carboxylic acid.

TLC [acetonitrile-water (4:1); Merck, Silica Gel Art. 5715), Rf 0.37

(ii) A mixture of 10 ml of formic acid and 10 ml of acetic anhydride is warmed at 50° C. for 40 minutes, and the resulting mixed acid anhydride solution is cooled and added to the ice-cooled solution of 7β-[2-amino-2-(2-aminothiazol-4-yl)acetamido]-3-(3-oxobutyryloxymethyl)-3-cephem-4-carboxylic acid obtained in the above procedure (i). The mixture is stirred for 2 hours, and 50 ml of water is added thereto, followed by concentration. The concentrate is adjusted to pH 5.5 with sodium hydrogen carbonate to give a solution containing 7β-[2-(2-aminothiazol-4-yl)-2-formamidoacetamido]-3-(3-oxobutyryloxymethyl)-3-cephem-4-carboxylic acid.

TLC [acetonitrile-water (4:1); Merck, Silica Gel Art. 5715), Rf 0.76

(iii) The solution of 7β-[2-(2-aminothiazol-4-yl)-2-formamidoacetamido]-3-(3-oxobutyryloxymethyl)-3-cephem-4-carboxylic acid obtained in the above procedure (ii) is concentrated. To the residue, 10 g of potassium iodide, 5 g of imidazo[1,2-a]pyridine, 50 ml of water and 50 ml of acetonitrile are added and the mixture is stirred at 70° C. for 2 hours.

After cooling to room temperature, 300 ml of ethyl acetate is added to the reaction mixture. The mixture is stirred and then allowed to stand and the upper layer is removed by decantation. This procedure is repeated three times, and the lower layer is subjected to silica gel column chromatography; the column is washed with acetone-water (8:1) and elution is carried out with acetone-water (3:1). Fractions containing the desired product are combined and concentrated, then subjected to chromatography on a column of highporous polymer (MCI GEL CHP20P, Mitsubishi Chemical Industries, Ltd.); the column is washed with water, and elution is carried out with 10% ethanol. Fractions containing the desired product are concentrated and the concentrate is subjected to chromatography on a Sephadex (LH-20, Pharmacia) column using water as the developing solvent and eluent. Lyophilization of fractions containing the desired product gives the above-identified compound.

Elemental analysis for $C_{21}H_{19}N_7O_5S_2.4H_2O$: Calcd. (%): C, 43.07; H, 4.65; N, 16.74. Found (%): C, 43.26; H, 4.36; N, 16.61.

IR spectrum $\nu_{max}^{KBr}$cm$^{-1}$: 1770, 1680, 1615, 1520, 1450.

NMR spectrum (D$_2$O+CD$_3$COCD$_3$)δ: 3.05 & 3.43, 3.11 & 3.48(total 2H, each ABq, J=18 Hz), 5.03, 5.07(total 1H, each d, J=5 Hz), 5.28(2H, bs), 5.44(1H, s), 5.56, 5.66(total 1H, each d, J=5 Hz), 6.62, 6.64(1H, each S), 7.3–7.6(1H, m), 7.8–8.3(4H, m), 8.68(1H, d, J=6 Hz).

EXAMPLE 100

7β-[2-(5-Amino-1,2,4-thiadiazol-3-yl)-2-formamidoacetamido]-3-[(imidazo[1,2-a]pyridinium-1-yl)methyl]-3-cephem-4-carboxylate

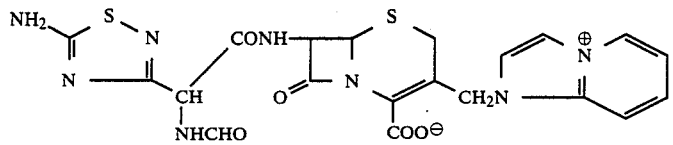

(i) In 50 ml of formic acid is dissolved 2 g of 7β-[2-(5-amino-1,2,4-thiadiazol-3-yl)-2(Z)-ethoxyiminoacetamido]-3-(3-oxobutyryloxmethyl)-3-cephem-4-carboxylic acid. To this solution, under ice-cooling, 10 g of zinc powder is added little by little with stirring in the course of 30 minutes. The mixture is stirred at room temperature for 1 hour and insoluble substance is removed by filtration.

The filtrate contains 7β-[2-amino-2-(5-amino-1,2,4-thiadiazol-3-yl)acetamido]-3-(3-oxobutyryloxymethyl)-3-cephem-4-carboxylic acid.

TLC [acetonitrile-water (4:1), Merck, Silica Gel Art. 5715), Rf 0.25

(ii) A mixture of 10 ml of formic acid and 10 ml acetic anhydride is heated at 50° C. for 30 minutes, and the resulting mixed acid anhydride solution is cooled and added to a solution of 7β-[2-amino-2-(5-amino-1,2,4-thiadiazol-3-yl)acetamido]-3-(3-oxobutyryloxymethyl)-3-cephem-4-carboxylic acid obtained in the above procedure (i) under ice-cooling. The mixture is stirred for 2 hours, followed by addition of 50 ml of water. The mixture is concentrated and the concentrate is adjusted to pH 5.5 with sodium hydrogen carbonate to give a solution containing 7β-[2-(5-amino-1,2,4-thiadiazol-3-yl)-2-formamidoacetamido]-3-(oxobutyryloxymethyl)-3-cephem-4-carboxylic acid.

TLC [acetonitrile-water (4:1), Merck, Silica Gel Art. 5715), Rf 0.50

(iii) The solution of 7β-[2-(5-amino-1,2,4-thiadiazol-3-yl)-2-formamidoacetamido]-3-(3-oxobutyryloxymethyl-3-cephem-4-carboxylic acid obtained in the above procedure (ii) is concentrated. To the residue, are added 4 g of sodium iodide, 4 g of imidazo[1,2-a]pyridine, 50 ml of water and 50 ml of acetonitrile and the mixture is stirred at 70° C. for 90 minutes. After cooling to room temperature, 200 ml of ethyl acetate is added, and the mixture is stirred and then allowed to stand, followed by removal of the upper layer by decantation. This procedure is repeated three times, and the lower layer is subjected to silica gel column chromatography; the column is washed with acetone-water (8:1) and elution is carried out with acetone-water (3:1). Fractions containing the desired product are combined and concentrated, and the concentrate is subjected to chromatography on a column of highporous polymer (MCI GEL CHP20P), Mitsubishi Chemical Industries, Ltd.); the column is washed with water and elution is carried out with 15% ethanol. Fractions containing the desired product are concentrated and the concentrate is subjected to chromatography on a Sephadex (LH-20, Pharmacia) column using water as the developing solvent and eluent. Lyophilization of fractions containing the desired product gives above-identified compound.

Elemental analysis for $C_{20}H_{18}N_8O_5S_2.4H_2O$: Calcd. (%): C, 40.95; H, 4.47; N, 19.10. Found (%): C, 40.20; H, 4.17; N, 18.95.

IR spectrum $\nu_{max}^{KBr}$cm$^{-1}$: 1765, 1680, 1615, 1530.

NMR spectrum (D$_2$O)δ: 3.11 & 3.49, 3.15 & 3.51(total 2H, each ABq, J=18 H), 5.10, 5.14(total 1H, each d, J=5 Hz), 5.32, 5.34(2H, each br,s), 5.63, 5.72(total 1H, each d, J=5 Hz), 7.3–7.7(1H, m), 7.8–8.4(4H, m), 8.71(1H, d, J=6 Hz), 8.24(1H, s).

EXAMPLE 101

7β-[2-Acetamido-2-(2-aminothiazol-4-yl)acetamido]-3-[(imidazo[1,2-a]pyridinium-1-yl)methyl]-3-cephem-4-carboxylate

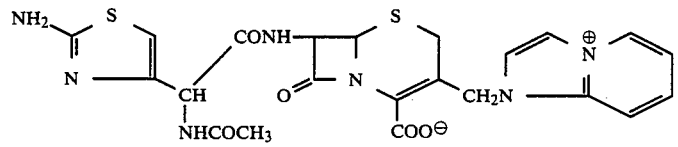

In 20 ml of acetic acid is dissolved 500 mg of 7β-[2-(2-aminothiazol-4-yl)-2(Z)-methoxyiminoacetamido]-3-[(imidazo[1,2-a]pyridinium-1-yl)methyl]-3-cephem-4-carboxylate, and cooled to the inside temperature of 15° C., followed by addition of 3 ml of acetic anhydride. With vigorous stirring, 1 g of zinc powder is added little by little in the course of 30 minutes, maintaining the inside temperature in the range of 15° to 25° C. The mixture is stirred at room temperature for 1 hour and insoluble substance is filtered off. The filtrate is concentrated and the concentrate is subjected to chromatography on a column of highporous polymer (MCI GEL CHP20P), Mitsubishi Chemical Industries, Ltd.); the column is washed with water and elution is carried out with 10% ethanol. Fractions containing the desired product are concentrated and the concentrate is subjected to chromatography on a Sephadex (LH-20, Pharmacia) column using water as the eluent. The eluate is concentrated and lyophilized to give the above-identified compound.

Elemental analysis for $C_{22}H_{21}N_7O_5S_2.4H_2O$: Calcd. (%): C, 44.07; H, 4.87; N, 16.35. Found (%) C, 44.22; H, 4.69; n, 16.49.

IR spectrum $\nu_{max}^{KBr}$cm$^{-1}$: 1760, 1660sh, 1605, 1520, 1440.

NMR spectrum (D$_2$O)δ: 2.08(3H, s), 3.16 & 3.52, 3.12 & 3.50(total 2H, each ABq, J=18 Hz), 5.10, 5.13(total 1H, each d, J=5 Hz), 5.30,5.33(total 2H, each br.s), 5.39 (1H, s), 5.62, 5.71(total 1H, each d, J=5 Hz), 6.68

6.70(1H, s), 7.3–7.7(1H, m), 7.8–8.3(4H, m), 8.69(1H, d, J=6 Hz).

EXAMPLE 102

7β-tert-Butoxycarbonylamino-3-[(imidoazo[1,2-a]pyridinium-1-yl)methyl]-3-cephem-4-carboxylate

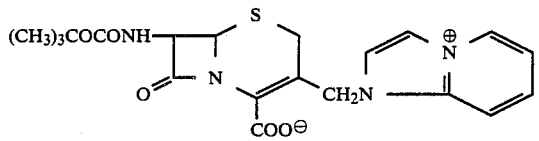

In a mixture of 50 ml of acetonitrile and 50 ml of water are dissolved 20 g of 7β-tert-butoxycarbonylamino-3-(3-oxobutyryloxymethyl)-3-cephem-4-carboxylic acid, 20 g of imidazo[1,2-a]pyridine and 10 g of sodium iodide, and the solution is stirred at 70° C. for 2 hours.

Thereafter, 200 ml of ethyl acetate is added to the solution. The mixture is stirred and then allowed to stand. The upper layer is removed by decantation. To the lower layer is added 200 ml of ethyl acetate and the same procedure as above is repeated.

The lower layer (aqueous layer) is subjected to chromatography using 150 g of silica gel; the column is washed with 1 liter of acetone and then with 1.8 liters of acetone-water (8:1), and then elution is carried out with acetonitrile-water (3:1). Fractions containing the desired product are concentrated and lyophilized to give 8.0 g (41% yield) of the above-identified compound.

Elemental analysis for $C_{20}H_{22}N_4O_5S.2H_2O$: Calcd. (%): C, 51.49; H, 5.62; N, 12.01. Found (%): C, 51.60; H, 5.84; N, 12.10.

IR spectrum $\nu_{max}^{KBr}cm^{-1}$: 1765, 1710, 1610, 1525, 1365.

NMR spectrum (d$_6$-DMSO)δ: 1.38(9H, s), 3.03 & 3.44(2H, ABq, J=18 Hz), 4.91(1H, d, J=5 Hz), 5.31(1H, d.d, J=5 Hz & 8 Hz), 5.41(2H, br.s), 7.50(1H, t, J=6 Hz), 7.77(1H, d, J=8 Hz), 8.00(1H, t, J=7 Hz), 8.3–8.7(3H, m), 9.00(1H, d, J=6 Hz).

EXAMPLE 103

7β-Amino-3-[(imidazo[1,2-a]pyridinium-1-yl)methyl]-3-cephem-4-carboxylate trifluoroacetate

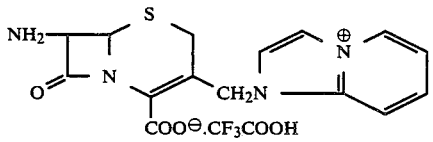

Under ice-cooling, 2 g of 7β-tert-butoxycarbonylamino-3-[(imidazo[1,2-a]pyridinium-1-yl)methyl]-3-cephem-4-carboxylate is suspended in 20 ml of methylene chloride, and 20 ml of trifluoroacetic acid is added to the suspension. The mixture is stirred for 30 minutes.

The solvent is then evaporated off under reduced pressure and, to the residue, 100 ml of ether is added and the mixture is stirred. The resulting precipitate is collected by filtration, washed with two 20-ml portions of ether and 20 ml of n-hexane and dried to give 1.15 g (60% yield) of the above-identified compound as a light-yellow powder.

Elemental analysis for $C_{15}H_{14}N_4O_3S.CF_3COOH.2H_2O$: Calcd. (%): C, 38.14; H, 3.80; N, 11.12. Found (%): C, 37.74; H, 3.60; N, 10.83.

IR spectrum $\nu_{max}^{KBr}cm^{-1}$: 1780, 1675, 1525, 1380, 1200.

NMR spectrum (d$_6$-DMSO)δ: 3.37 & 3.62(2H, ABq, J=18 Hz), 5.16(2H, br.s), 5.47(2H, br.s), 5.47(2H, br.s), 7.58(1H, t, J=6 Hz), 7.8–8.6(4H, m), 9.00(1H, d, J=7 Hz).

EXAMPLE 104

7β-[2-(2-Chloroacetamidothiazol-4-yl-3-oxido)-2(Z)-ethoxyiminoacetamido]-3-[(imidazo[1,2-a]pyridinium-1-yl)methyl]-3-cephem-4-carboxylate

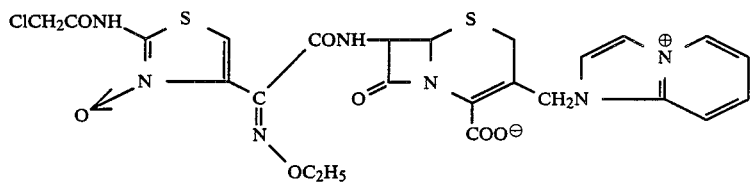

To 50 ml of methylene chloride is added 3.08 g of 2-(chloroacetamidothiazol-4-yl-3-oxido)-2(Z)-ethoxyiminoacetic acid. To this, under ice-cooling, 2.08 g of phosphorus pentachloride is added and the mixture is stirred for 15 minutes. To the reaction mixture is added 150 ml of hexane, and the resulting mixture is stirred for 15 minutes further. Crystals separated are collected by filtration and washed with methylene chloride-hexane (1:3) to give the corresponding acid chloride as hydrochloride.

Under ice-cooling, 4.0 g of 7β-amino-3-(3-imidazo[1,2-a]pyridinium-1-yl)methyl-3-cephem-4-carboxylate trifluoroacetate is suspended in 30 ml of dimethylformamide. To this suspension, 5.17 g of diisopropylethylamine and then the above acid chloride are added and the mixture is stirred for 30 minutes.

To the mixture is added 200 ml of ether, and the resulting precipitate is collected by filtration and dissolved in a mixture of 20 ml of water and 2 g of sodium hydrogen carbonate. The solution is subjected to chromatography on a column of highporous polymer (MCI GEL CHP20P Mitsubishi Chemical Industries, Ltd.); the column is washed with water and elution is carried out 10% ethanol. Lyophilization of fractions containing the desired product gives 2.9 g (47% yield) of the above-identified compound.

Elemental analysis for $C_{24}H_{22}ClN_7O_7S_2.3H_2O$: Calcd. (%): C, 42.76; H, 4.19; N, 14.55. Found (%): C, 43.05; H, 4.39; N, 14.26.

IR spectrum $\nu_{max}^{KBr}$ cm$^{-1}$: 1770, 1610, 1525, 1470, 1380, 1350, 1310, 1270, 1200.

NMR spectrum (d$_6$-DMSO)δ: 1.25(3H, t, J=7 Hz), 4.14(2H, q, J=7 Hz), 4.08 & 4.32(2H, ABq, J=18 Hz), 5.00(1H, d, J=5 Hz), 5.38(2H, br.s), 5.63(1H, d.d, J=5

Hz & 8 Hz), 7.18(1H, s), 7.50(1H, t, J=6 Hz), 7.88(1H, t, J=7 Hz), 8.2–8.7(3H, m), 8.99(1H, d, J=7 Hz).

EXAMPLE 105

7β-[2-(2-Aminothiazol-4-yl-3-oxido)-2(Z)-ethoxyiminoacetamido]-3-[(imidazo[1,2-a]pyridinium-1-yl)methyl]-3-cephem-4-carboxylate

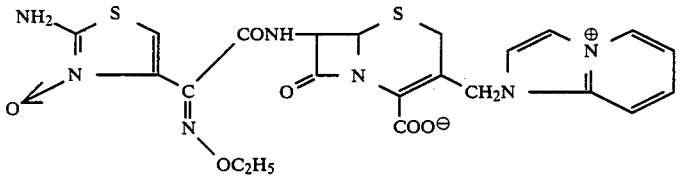

In 20 ml of water are dissolved 2.7 g of 7β-[2-(2-chloroacetamidothiazol-4-yl-3-oxido)-2(Z)-ethoxyiminoacetamido-3-[(imidazo[1,2-a]pyridinium-1-yl)methyl]-3- cephem-4-carboxylate and 1.0 g of sodium N-methyldithiocarbamate, and the solution is stirred at room temperature for 2 hours.

To the solution is added 20 ml of ethyl acetate and, after phase separation, the organic layer is discarded. The aqueous layer is washed with two 20-ml portions of ethyl acetate and subjected to chromatography on a column of MCI GEL CHP20P (Mitsubishi Chemical Industries, Ltd.); the column is washed with water, and elution is carried out with 10% ethanol. Fractions containing the desired product are concentrated and the concentrate is subjected to chromatography on a Sephadex (LH-20, Pharmacia) column using water as the developing solvent and eluent. Fractions containing the desired product are concentrated and lyophilized to give 830 mg (35% yield) of the above-identified compound.

Elemental analysis for $C_{22}H_{21}N_7O_6S_2.3H_2O$: Calcd. (%): C, 44.21; H, 4.55; N, 16.41. Found (%): C, 43.98; H, 4.29; N, 16.20.

IR spectrum $\nu_{max}^{KBr}$ cm$^{-1}$: 1760, 1610, 1525, 1440, 1380, 1350, 1270, 1200.

NMR spectrum (d$_6$-DMSO)δ: 1.22(3H, t, J=7Hz), 3.02 & 3.41(2H, ABq, J=18 Hz), 4.17(2H, q, =7 Hz), 4.96(1H, d, J=5 Hz), 5.39(2H, br.s), 5.60(1H, d.d, J=5 Hz & 8 Hz), 7.00(1H, s), 7.50(1H, t, J=6 Hz), 8.00(1H, t, J=7 Hz), 8.3–8.7(3H, m), 8.97(1H, d, J=7 Hz), 11.63(1H, d, J=8 Hz).

NMR(D$_2$O)δ: 1.35(t, 3H, J=7 Hz), 3.20 & 3.55(2H, ABq, J=18 Hz), 4.33(2H, q, J=7 Hz), 5.20(1H, d, J=5 Hz), 5.26 & 5.44(2H, ABq, J=14 Hz), 5.85(1H, d, J=5 Hz), 7.12(1H, s), 7.42–7.62(1H, m), 7.85–8.20(3H, m), 8.73(1H, d, J=7 Hz).

EXAMPLE 106

7β-Amino-3-[(imidazo[1,2-a]pyridinium-1-yl)methyl]-3-cephem-4-carboxylate

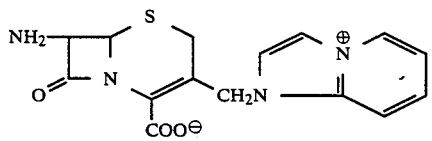

7δ-Amino-3-(3-oxobutyryloxymethyl)-3-cephem-4-carboxylic acid and imidazo[1,2-a]pyridine, are reacted in the procedure of Example 42 to give the above-identified compound.

IR spectrum $\nu_{max}^{KBr}$ cm$^{-1}$: 1760, 1610, 1535.

NMR spectrum (d$_6$-DMSO-DCl)δ: 3.35 & 3.64(2H, ABq, J=18 Hz), 4.94–4.44(4H, m), 7.42–7.67(1H, m), 7.80–8.50(4H, m), 8.85–9.05(1H, m).

EXAMPLE 107

7β-Formamido-3-[(imidazo[1,2a]pyridinium-1-yl)methyl]-3-cephem-4-carboxylate

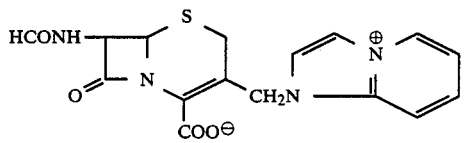

7β-Formamido-3-(3-oxobutyryloxy)methyl-3-cephem-4-carboxylic acid and imidazo[1,2-a]pyridine, are reacted in the procedure of Example 42 to give the above-identified compound.

Elemental analysis for $C_{16}H_{14}N_4O_4S.2H_2O$: Calcd. (%): C, 48.73; H, 4.60; N, 14.21. Found (%): C, 47.02; H, 4.63; N, 13.85.

IR spectrum $\nu_{max}^{KBr}$ cm$^{-1}$: 1770, 1670, 1600, 1520.

NMR spectrum (d$_6$-DMSO)δ: 3.01 & 3.46(2H, ABq, J=18 Hz), 4.96(1H, d, J=5 Hz), 5.30 & 5.48(2H, ABq, J=15 Hz), 5.60(1H, d.d, J=5 Hz & 8 Hz), 7.4–7.66(1H, m), 7.84–8.20(2H, m), 8.34–8.80(3H, m), 8.85–9.20(2H, m).

EXAMPLE 108

7β-[2-(2-Amino-5-chlorothiazol-4-yl)-2(Z)-(tert-butoxycarbonylmethoxyimino)acetamido]-3-[(imidazo[1,2-a]pyridinium-1-yl)methyl]-3-cephem-4-carboxylate

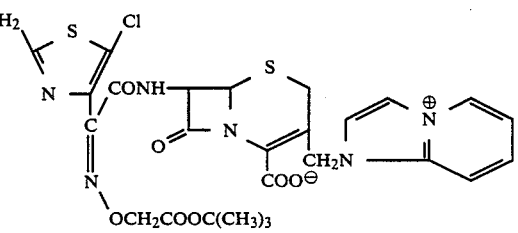

A mixture of 3.0 g of 7β-[2-(2-amino-5-chlorothiazol-4-yl)-2(Z)-(tert-butoxycarbonylmethoxyimino)acetamido]-3-(3-oxobutyryloxymethyl)-3-cephem-4-carboxylic acid, 3.0 g of imidazo[1,2-a]pyridine and 3.0 g of sodium iodide in 20 ml of 50% aqueous acetonitrile is stirred at 70° C. for 90 minutes.

After being cooled to room temperature, the reaction mixture is chromatographed on a silica gel (50 g) column. The column is washed with 0.2 l of acetone and then with 1 l of acetone:water=20:1. The product is then eluted with acetone:water=3:1. Fractions containing the objective product are concentrated and subjected to chromatography on a column of Sephadex ® LH-20 (Pharmacia Inc., Sweden) with water as eluent. Fractions containing the objective product are concentrated and the residue is lyophilized to give the above-identified compound.

Elemental analysis for $C_{26}H_{25}ClN_7O_7S_2 \cdot 2H_2O$: Calcd.(%): C, 47.96; H, 4.50; H, 15.06. Found (%): C, 47.70; H, 4.88; N, 14.77.

IR spectrum $\nu_{max}^{KBr}$ cm$^{-1}$: 1760, 1670, 1610, 1530, 1440, 1370, 1310.

NMR spectrum (d$_6$-DMSO)δ: 1.38(9H, s), 2.90(1H, ABq×½, J=18 Hz), 4.48(2H, s), 4.97(1H, d, J=5 Hz), 5.25 and 5.49(2H, ABq, J=14 Hz), 5.58(1H, d.d, J=5 Hz and 8 Hz), 7.34(2H, br.s), 7.52(1H, t, J=8 Hz), 8.00(1H, t, J=8 Hz), 8.40 (1H, br.s), 8.52(1H, br.s), 8.70(1H, d, J=9 Hz), 8.94(1H, d, J=6 Hz), 9.27(1H, d, J=8 Hz).

EXAMPLE 109

7β-[2-(2-Amino-5-chlorothiazol-4-yl)-2(Z)-(carboxymethoxyimino)acetamido]-3-[(imidazo[1,2-a]pyridinium-1-yl)methyl]-3-cephem-4-carboxylate monosodium salt

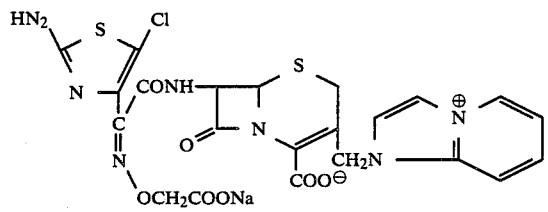

To 10 ml of trifluoroacetic acid is added 0.28 g of 7β-[2-(2-amino-5-chlorothiazol-4-yl)-2(Z)-(tert-butoxycarbonylmethoxyimino)acetamido]-3-[(imidazo[1,2-a]pyridinium-1-yl)methyl]-3-cephem-4-carboxylate and the mixture is stirred at room temperature for 1 hour. The reaction mixture is concentrated and the residue is dissolved in a mixture of 2 g of sodium bicarbonate in 15 ml of water and then subjected to column chromatography on a column of MCI GEL CHP20P (150-300; mesh; Mitsubishi Chemical Industries, Ltd., Japan). The column is washed with 0.8 l of water and the product is then eluted with 7.5% ethanol in water. Fractions containing the objective compound are concentrated and the residue is lyophilized to give the above-identified compound.

Elemental analysis for $C_{22}H_{17}ClN_7NaO_7S_2 \cdot 3H_2O$: Calcd.(%): C, 39.55; H, 3.47; N, 14.68. Found (%): C, 39.26; H, 3.70; N, 14.39.

IR spectrum $\nu_{max}^{KBr}$ cm$^{-1}$: 1760, 1610, 1530, 1400, 1360, 1310.

NMR spectrum (d$_6$-DMSO)δ: 3.02(1H, ABq×½, J=18 Hz), 4.22(2H, br.s), 4.97(1H, d, J=5 Hz), 5.38(2H, br.s), 5.64(1H, d.d, J=5 Hz, and 8 Hz), 7.35(2H, br.s) 7.49(1H, t, J=7 Hz), 7.98(1H, t, J=8 Hz), 8.3–8.7(3H, m), 8.96(1H, d, J=8 Hz), 11.85(1H, d, J=8 Hz).

EXAMPLE 10

7β-[2-(2-Amino-5-bromothiazol-4-yl)-2(Z)-(carboxymethoxyimino)acetamido]-3-[(imidozo[1,2-a]pyridinium-1-yl)methyl]-3-cephem-4-carboxylate monosodium salt

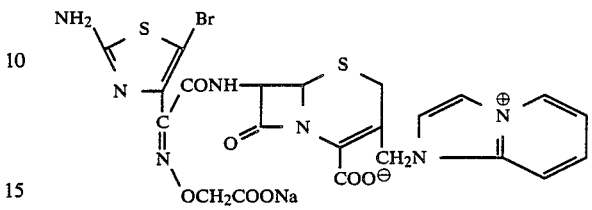

(i) 7β-[2-(2-Amino-5-bromothiazol-4-yl)-2(Z)-(tert-butoxycarbonylmethoxyimino)acetamido]-3-(3-oxobutyryloxymethyl)-3-cephem-4-carboxylic acid and imidazo[1,2-a]pyridine are reacted in the procedure of Reference Example 40 to give 7β-[2-(2-amino-5-bromothiazol-4-yl)-2(Z)-tert-butoxycarbonylmethoxyimino)acetamido]-3-[(imidazo[1,2-a]pyridinium-1-yl)methyl]-3-cephem-4-carboxylate.

TLC(acetonitrile:water=6:1, Silica gel Art. 5715, Merck) Rf 0.15

(ii) 7β-[2-(2-amino-5-bromothiazol-4-yl)-2(Z)-(tert-butoxycarbonylmethoxyimino)acetamido]-3-[(imidazo[1,2-a]pyridinium-1-yl)methyl]-3-cephem-4-carboxylate obtained in (i) is treated in the procedure of Example 108 to give the above-identified compound.

Elemental analysis for $C_{22}H_{17}BrN_7NaO_7S_2 \cdot 2H_2O$: Calcd.(%): C, 38.05; H, 3.05; N, 14.12. Found (%): C, 37.88; H, 3.31; N, 14.00.

IR spectrum $\nu_{max}^{KBr}$ cm$^{-1}$: 1760, 1605, 1530, 1400, 1360, 1310.

NMR spectrum (D$_2$O)δ: 3.06 and 3.55(2H, ABq, J=18 Hz), 5.22(1H, d, J=5 Hz), 5.34(2H, br.s), 5.87(1H, d, J=5 Hz), 7.49(1H, t, J=6 Hz), 8.05(3H, br.s), 8.14(1H, br.s), 8.69(1H, d, J=6 Hz).

EXAMPLE 111

7β-[2-(2-Amino-5-bromothiazol-4-yl)-2(Z)-(carboxymethoxyimino)acetamido]-3-[(6-chloroimidazo[1,2-a]pyridinium-1-yl)methyl]-3-cephem-4-carboxylate monosodium salt

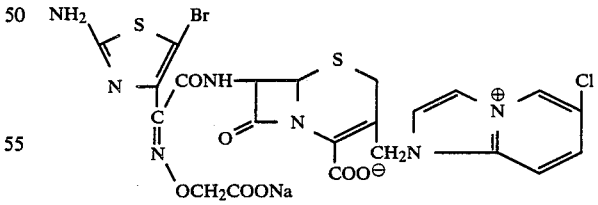

(i) 7β-[2-(2-Amino-5-bromothiazol-4-yl)-2(Z)-(tert-butoxycarbonylmethoxyimino)acetamido]-3-(3-oxobutyryloxymethyl)-3-cephem-4-carboxylate and 6-chloroimidazo[1,2-a]pyridine are reacted in the procedure of Reference Example 40 to give 7β-[2-(2-amino-5-bromothiazol-4-yl-2(Z)-tert-butoxycarbonylmethoxyimino)acetamido]-3-[(6-chloroimidazo[1,2-a]pyridinium-1-yl)methyl]-3-cephem-4-carboxylate.

TLC(acetonitrile:water=6:1, Silica gel Art. 5715, Merck) Rf 0.19

(ii) 7β-[2-(2-Amino-5-bromothiazol-4-yl)-2(Z)-(tert-butoxycarbonylmethoxyimino)acetamido]-3-[(6-chloroimidazo[1,2-a]pyridinium-1-yl)methyl]-3-cephem-4-carboxylate obtained in (i) is treated with trifluoroacetic acid in the procedure of Example 108 to give the above-identified compound.

Elemental analysis for $C_{22}H_{16}BrClN_7NaO_7S_2\cdot2H_2O$: Calcd.(%): C, 36.25; H, 2.77; N, 13.45. Found (%): C, 36.01; H, 2.99; N, 13.16.

IR spectrum $\nu_{max}^{KBr}$ cm$^{-1}$: 1760, 1610, 1520, 1400, 1360, 1320.

NMR spectrum (d$_6$-DMSO)δ: 3.02 and 3.39(2H, ABq, J=18 Hz), 4.22(2H, br.s). 4.96(1H, d, J=5 Hz), 5.37(2H, br.s), 5.64(1H, d.d, J=5 Hz and 8 Hz), 7.37(2H, br.s), 8.07(1H, d, J=9 Hz), 8.36(1H, br.s), 8.52(1H, br.s), 8.64(1H, d, J=10 Hz), 9.31(1H, br.s), 11.85(1H, d, J=8 Hz).

EXAMPLE 112

7β-[2-(2-Amino-5-chlorothiazol-4-yl)-2(Z)-(carboxymethoxyimino)acetamido]-3-[(6-chloroimidazo[1,2-a]pyridinium-1-yl)methyl]-3-cephem-4-carboxylate monosodium salt

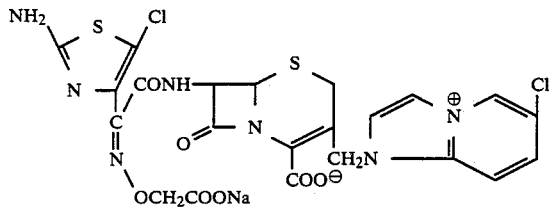

(i) Two grams of 7β-[2-(2-amino-5-chlorothiazol-4-yl)-2(Z)-(tert-butoxycarbonylmethoxyimino)acetamido]-3-(3-oxobutyryloxymethyl)-3-cephem-4-carboxylic acid is dissolved in 20 ml of trifluoroacetic acid. The solution is stirred at room temperature for 1 hour and then evaporated to dryness under reduced pressure to give crude 7β-[2-(2-amino-5-chlorothiazol-4-yl)-2(Z)-(carboxymethoxyimino)acetamido]-3-(3-oxobutyryloxymethyl)-3-cephem-4-carboxylic acid.

TLC(acetonitrile:water=4:1, Silica gel Art. 5715, Merck)
Rf 0.62

(ii) The whole amount of 7β-[2-(2-amino-5-chlorothiazol-4-yl)-2(Z)-(carboxymethoxyimino)acetamido]-3-(3-oxobutyryloxymethyl)-3-cephem-4-carboxylic acid, 2.5 g of 6-chloroimidazo[1,2-a]pyridine and 2 g of sodium iodide are mixed in 20 ml of 50% acetonitrile in water and the mixture is heated at 70° C. for 90 minutes with stirring, and then cooled to room temperature. Two grams of sodium bicarbonate is added to the reaction mixture and the mixture is chromatographed on a column of silica gel (50 g). The column is washed with 0.3 l of acetone and then with 0.5 l of acetone:water=8:1 and the product is then eluted with acetone:water=5:2. Fractions containing the objective compound are concentrated and the residue is placed on a column of Sephadex® LH-20 (Pharmacia Inc., Sweden) and eluted with water. Fractions containing the objective compound are lyophilized to give the above-identified compound.

Elemental analysis for $C_{22}H_{16}Cl_2N_7NaO_7S_2\cdot2H_2O$: Calcd.(%): C, 38.60; H, 2.95; N, 14.33. Found (%): C, 38.40; H, 2.99; N, 14.06.

IR spectrum $\nu_{max}^{KBr}$ cm$^{-1}$: 1770, 1680, 1620, 1520, 1440, 1320.

NMR spectrum (d$_6$-DMSO)δ: 2.04 and 3.40(2H, ABq, J=18 Hz), 4.25(2H, br.s), 4.97(1H, d, J=5 Hz), 5.40(2H, br.s), 5.66(1H, d. d, J=5 Hz and 8 Hz), 7.31(2H, br.s), 8.05(1H, d, J=6 Hz), 8.40(1H, d, J=3 Hz), 8.58(1H, d, J=7 Hz), 9.28(1H, br. s), 9.77(1H, d, J=6 Hz).

EXAMPLE 113

7β-[2-(2-Amino-5-bromothiazol-4-yl)-2(Z)-methoxyiminoacetamido]-3-[(imidazo[1,2-a]pyridinium-1-yl)methyl]-3-cephem-4-carboxylate

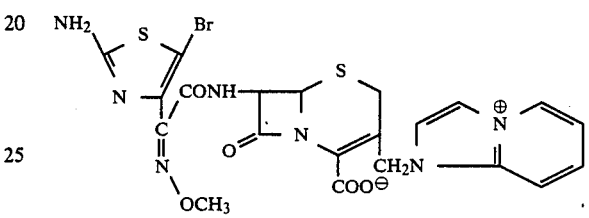

To a solution of 0.40 g of 7β-[2-(2-aminothiazol-4-yl)-2(Z)-methoxyiminoacetamido]-3-[(imidazo[1,2-a]pyridinium-1-yl)methyl]-3-cephem-4-carboxylate in 4 ml of dimethylformamide, 0.28 g of N-bromosuccinimide is added under ice-cooling and the mixture is stirred at the same temperature for 2 hours. The reaction mixture is stirred with 100 ml of diethyl ether and the upper layer is removed by decantation. To the residue is added 50 ml of diethyl ether. Insoluble substance is collected by filtration, redissolved in a mixture of 2 ml of water and 2 ml of acetonitrile and placed on a silica gel (50 g) column. The column is washed with 200 ml of acetone and 500 ml of a mixture of acetone:water=20:1, successively, and then the product is eluted with acetone:water=3:1. Fractions containing the objective compound are concentrated and the residue is chromatographed on a column of Sephadex LH-20 (Pharmacia Inc.) with water. The eluent is lyophilized to give the above-identified compound.

Elemental analysis for $C_{21}H_{18}BrN_7O_5S_2\cdot H_2O$: Calcd.(%): C, 41.32; H, 3.30; N, 16.06. Found (%): C, 41.32; H, 3.45; N, 15.79.

IR spectrum $\nu_{max}^{KBr}$ cm$^{-1}$: 1765, 1610, 1530, 1450, 1380, 1350, 1310.

NMR spectrum (d$_6$-DMSO)δ: 298 and 3.43(2H, ABq, J=18 Hz), 3.80(3H, s), 4.98(1H, d, J=5 Hz), 5.27 and 5.48(2H, ABq, J=14 Hz), 5.60(1H, d.d, J=5 Hz and 8 Hz), 7.36(2H, br.s), 7.51(1H, t, J=7 Hz), 8.00(1H, t, J=8 Hz), 8.40(1H, br.s), 8.49(1H, br.s), 8.66(1H, d, J=9 Hz), 8.94(1H, d, J=6 Hz), 9.42(1H, d, J=8 Hz).

EXAMPLE 114

7β-[2-(2-Amino-5-iodothiazol-4-yl)-2(Z)-methoxyiminoacetamido]-3-[(imidazo[1,2-a]pyridinium-1-yl)methyl]-3-cephem-4-carboxylate

EXAMPLE 117

7β-[2-(2-Chloroacetamidothiazol-4-yl)-2(Z)-methoxyiminoacetamido]-3-[(imidazo[1,2-a]pyridinium-1-yl)methyl]-3-cephem-4-carboxylate

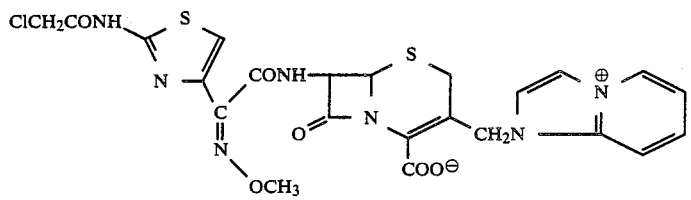

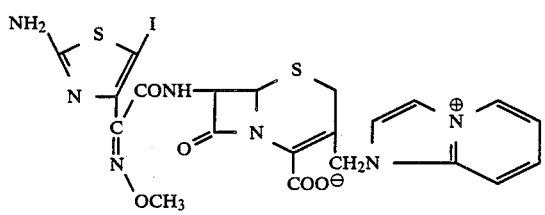

In 4 ml of dimethylformamide, is dissolved 0.40 g of 7β-[2-(2-aminothiazol-4-yl)-2(Z)-methoxyiminoacetamido]-3-[(imidazo[1,2-a]pyridinium-1-yl)methyl]-3-cephem-4-carboxylate. To this, 0.45 g of N-iodosuccinimide is added and the mixture is stirred at room temperature for 1 hour.

The reaction mixture is then processed in the procedure of Example 113 to give the above-identified compound.

Elemental analysis for $C_{21}H_{18}IN_7O_5S_2 \cdot H_2O$: Calcd.(%): C, 38.36; H, 3.07; N, 14.91. Found (%): C, 38.18; H, 3.31; N, 14.70.

IR spectrum $\nu_{max}^{KBr}$ cm$^{-1}$: 1760, 1670, 1610, 1530, 1380, 1360, 1310.

NMR spectrum (d$_6$-DMSO)δ: 2.96 and 3.36(2H, ABq, J=18 Hz), 3.82(3H, s), 4.96(1H, d, J=5 Hz), 5.26 and 5.47(2H, ABq, J=14 Hz), 5.58(1H, d.d, J=5 Hz and 8 HZ), 7.32(2H, br.s), 7.50(1H, t, J=7 Hz), 8.01(1H, t, J=8 Hz), 8.39(1H, br.s), 8.50(1H, br.s), 8.67(1H, d, J=9 Hz), 8.93(1H, d, J=6 Hz), 9.36(1H, d, J=8 Hz).

EXAMPLE 115

2-(2-Chloroacetamido-5-bromothiazol-4-yl)-2(Z)-methoxyiminoacetic acid and 7β-amino-3-(imidazo[1,2-a]pyridinium-1-yl)methyl-3-cephem-4-carboxylate difluoroacetate are reacted in a manner similar to that in Example 104 and the product obtained is then made to react with sodium N-methyldithiocarbamate in the procedure of Example 105 to give a compound, which shows IR and NMR spectra identical with those of the compound obtained in Example 113.

EXAMPLE 116

2-(2-Chloroacetamido-5-iodothiazol-4-yl)-2(Z)-methoxyiminoacetic acid and 7β-amino-3-(imidazo[1,2-a]pyridinium-1-yl)methyl-3-cephem-4-carboxylate difluoroacetate are reacted in a manner similar to that in Example 104 and the product obtained is then made to react with sodium N-methyldithiocarbamate in the procedure of Example 105 to give a compound, which shows IR and NMR spectra identical with those of the compound obtained in Example 114.

2-(2-Chloroacetamidothiazol-4-yl)-2(Z)-methoxyiminoacetic acid and 7β-amino-3-(imidazo[1,2-a]pyridinium-1-yl)methyl-3-cephem-4-carboxylate difluoroacetate are reacted in the procedure of Example 104 to give the above-identified compound.

Elemental analysis for $C_{23}H_{20}ClN_7O_6S_2 \cdot 2H_2O$: Calcd.(%): C, 44.13; H, 3.86; N, 15.66. Found (%): C, 44.00; H, 3.59; N, 15.39.

IR spectrum $\nu_{max}^{KBr}$ cm$^{-1}$: 1760, 1680, 1620, 1530, 1440, 1360.

NMR spectrum (D$_6$-DMSO)δ: 2.99(1H, ABq×½, J=18 Hz), 3.94(3H, s), 4.38(2H, s), 5.02(1H, d, J=5 Hz), 5.24 and 5.49(2H, ABq, J=14 Hz), 5.60(1H, d.d, J=5 Hz and 8 Hz), 7.38(1H, s), 7.51(1H, t, J=7 Hz), 8.00(1H, t, J=8 Hz), 8.3–8.6(2H, m), 8.66(1H, d, J=9 Hz), 8.94(1H, d, J=7 Hz), 9.56(1H, d, J=8 Hz).

EXAMPLE 118

7β-[2-(2-Chloroacetamidothiazol-4-yl)-2(Z)-methoxyiminoacetamido]-3-[(imidazo[1,2-a]pyridinium-1-yl)methyl]-3-cephem-4-carboxylate is made to react with sodium N-methyldithiocarbamate the procedure of Example 105 to give 7β-[2-(2-aminothiazol-4-yl)-2(Z)-methoxyiminoacetamido]-3-[(imidazo[1,2-a]pyridinium-1-yl)methyl]-3-cephem-4-carboxylate, which is found to be identical with that obtained in Example 1.

EXAMPLE 119

7β-tert-Butoxycarbonylamino-3-[(6-cyanoimidazo[1,2-a]pyridinium-1-yl)methyl]-3-cephem-4-carboxylate

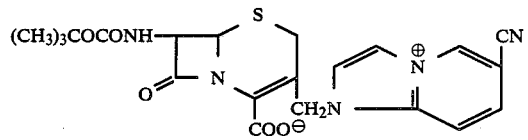

Two grams of 7β-tert-butoxycarbonylamino-3-(3-oxobutyryloxymethyl)-3-cephem-4-carboxylic acid and 1.0 g of 6-cyanoimidazo[1,2-a]pyridine are reacted in the procedure of Example 102 to give the above-identified compound.

Elemental analysis for $C_{21}H_{21}N_5O_5S \cdot 2H_2O$: Calcd.(%): C, 51.32; H, 5.13; N, 14.25. Found (%): C, 51.09; H, 5.01; N, 13.95.

IR spectrum $\nu_{max}^{KBr}$ cm$^{-1}$: 2230, 1760, 1710, 1640, 1610, 1530, 1390, 1365.

NMR spectrum (d$_6$-DMSO)δ: 1.38(9H, s) 2.94 and 3.44(2H, ABq, J=18 Hz), 4.90(1H, d, J=5 Hz), 5.28 and 5.51 (2H, ABq, J=14 Hz), 5.36(1H, d.d, J=5 Hz and 8 Hz), 7.71(1H, d, J=8 Hz), 8.32(1H, d, J=10 Hz), 8.50(1H, br.s), 8.69(1H, br.s), 8.88(1H, d, J=10 Hz), 9.77(1H, s).

EXAMPLE 120

7β-Amino-3-[(6-cyanoimidazo[1,2-a]pyridinium-1-yl)methyl]-3-cephem-4-carboxylate ditrifluoroacetate

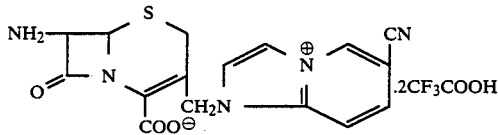

In a manner similar to that in Example 103, 0.30 g of 7β-tert-butoxycarbonylamino-3-[(6-cyanoimidazo[1,2-a]pyridinium-1-yl)methyl]-3-cephem-4-carboxylate is made to react with 5 ml of trifluoroacetic acid to give the above-identified compound.

IR spectrum $\nu_{max}^{KBr}$ cm$^{-1}$: 2230, 1780, 1680, 1645, 1530, 1390.

NMR spectrum (d$_6$-DMSO)δ: 3.28 and 3.56(2H, ABq, J=18 Hz), 4.2–5.2(2H, br.), 5.02(1H, d, J=5 Hz), 5.10(1H, d, J=5 Hz), 5.47(1H, br.s), 8.26–8.60(4H, m), 9.76(1H, s).

EXAMPLE 121

7β-[2-(5-Amino-1,2,4-thiadiazol-3-yl)-2(Z)-cyanomethyloxyiminoacetamido]-3-[(imidazo]1,2-a]pyridinium-1-yl)methyl]-3-cephem-4-carboxylate

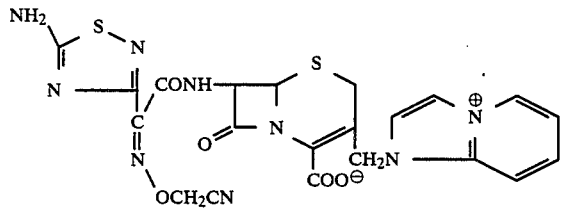

Two grams of the crude 7β-[2-(5-amino-1,2,4-thiadiazol-3-yl)-2(Z)-cyanomethyloxyiminoacetamido]-3-(3-oxobutyryloxymethyl)-3-cephem-4-carboxylic acid obtained in Reference Example 42, 2 g of imidazo[1,2-a]pyridine and 2 g of sodium iodide are mixed in a mixture of 20 ml each of acetonitrile and water and the mixture is heated in an oil bath kept at 75° C. for 60 minutes with stirring and then allowed to cool. To the reaction mixture, 50 ml of ethyl acetate is added and, after shaking, the aqueous layer is separated and concentrated. The residue is then placed on a XAD-2 column and eluted first with water, then with 20% ethanol in water. Fractions containing the objective compound are concentrated and filtered to remove some insoluble materials. The filtrate is lyophilized and the product obtained is dissolved in small amount of water and subjected to chromatography on a column of silica gel. The column is washed with acetone and then the desired product is eluted with acetone:water=7:3. Fractions containing the objective compound are concentrated and the residue is lyophilized to give the above-identified compound.

IR spectrum $\nu_{max}^{KBr}$cm$^{-1}$: 3100, 1760, 1605, 1520, 1380, 1040, 1010, 760.

NMR spectrum (D$_2$O)δ: 3.16 and 3.53(2H, ABq, J=18 Hz), 5.15 (1H, d, J=4.8 Hz), 5.31(2H, br. s), 5.82(1H, d, J=4.8 Hz), 7.40–7.80, 7.90–8.30 and 8.60–8.80(6H, m).

EXAMPLE 122

7β-[2-(5-Amino-1,2,4-thiadiazol-3-yl)-2(Z)-ethoxyiminoacetamido]-3-[(3-cyanoimidazo[1,2-a]pyridinium-1-yl)methyl]-3-cephem-4-carboxylate

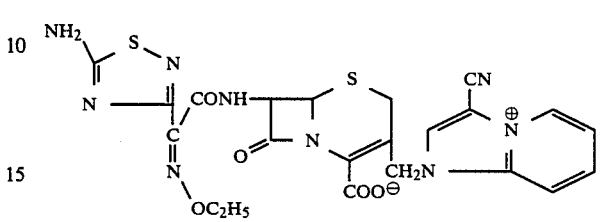

7β-[2-(5-Amino-1,2,4-thiadiazol-3-yl)-2(Z)-ethoxyiminoacetamido]-3-(3-oxobutyryloxymethyl)-3-cephem-4-carboxylic acid and 3-cyanoimidazo[1,2-a]pyridine are reacted in the procedure of Example 42 to give the above-identified compound.

Elemental analysis for C$_{22}$H$_{19}$N$_9$O$_5$S$_2$·3H$_2$O: Calcd.(%): C, 43.49; H, 4.15; N, 20.45. Found (%): C, 43.58; H, 3.59; N, 20.38.

IR spectrum $\nu_{max}^{KBr}$cm$^{-1}$: 2245, 1770, 1680, 1640, 1610, 1510.

NMR spectrum (d$_6$-DMSO)δ: 1.20(3H, t, J=7 Hz), 3.01(1H, ABq×½, J=18 Hz), 4.12(2H, d, J=7 Hz), 4.98(1H, d, J=4.5 Hz), 5.33 and 5.58(2H, ABq, J=14 Hz), 5.65(1H, d. d, J=4.5 Hz and 8 Hz), 7.64–7.88(1H, m), 8.04(2H, br. s), 8.00–8.48(1H, m), 8.92–9.12(2H, m), 9.42(1H, d, J=8 Hz), 9.47(1H, s).

EXAMPLE 123

7β-[2-(2-Amino-5-chlorothiazol-4-yl)-2(Z)-methoxyiminoacetamido]-3-[(8-fluoroimidazo[1,2-a]pyridinium-1-yl)methyl]-3-cephem-4-carboxylate

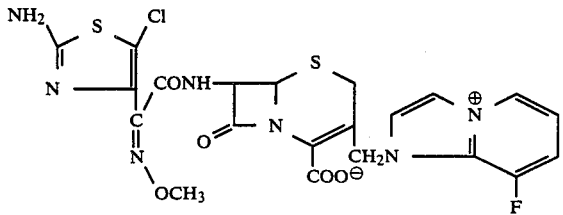

The compound obtained in Reference Example 29 and 8-fluoroimidazo[1,2-a]pyridine are reacted in the procedure of Example 42 to give the above-identified compound.

NMR spectrum (D$_2$O)δ: 3.30 and 3.60(2H, ABq, J=18 Hz), 4.00(3H, s), 5.22(1H, d, J=4.5 Hz), 5.31 and 5.67 (2H, ABq, J=15 Hz), 5.85(1H, d, J=4.5 Hz), 7.32–8.68 (5H, m).

EXAMPLE 124

7β-[2-(5-Amino-1,2,4-thiadiazol-3-yl)-2(Z)-cyanomethoxyiminoacetamido]-3-[(6-cyanoimidazo[1,2-a]pyridinium-1-yl)methyl]-3-cephem-4-carboxylate

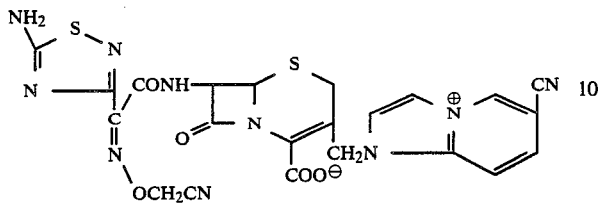

The compound obtained in Reference Example 42 and 6-cyanoimidazo[1,2-a]pyridine are reacted in the procedure of Example 42 to give the above-identified compound.

Elemental analysis for $C_{23}H_{17}N_9O_5S_2.4.5H_2O$: Calcd.(%): C, 42.85; H, 4.07; N, 19.56. Found (%): C, 42.68; H, 4.01; N, 19.51.

IR spectrum $\nu_{max}^{KBr}$ cm$^{-1}$: 3400, 2250, 1760, 1670, 1650, 1610, 1530.

NMR spectrum (d$_6$-DMSO)δ: 2.96 and 3.46(2H, ABq, J=16 Hz), 5.01(1H, d, J=5 Hz), 5.02(2H, s), 5.27 and 5.53(2H, ABq, J=15 Hz), 5.64(1H, d. d, J=5 Hz and 8 Hz), 8.2–9.0 (4H, m), 8.22(2H, br. s), 9.66(1H, d, J=8 Hz), 9.77(1H, br. s).

EXAMPLE 125

7β-[2-(5-Amino-1,2,4-thiadiazol-3-yl)-2(Z)-methoxyiminoacetamido]-3-[(6-cyanoimidazo[1,2-a]pyridinium-1-yl)methyl]-3-cephem-4-carboxylate

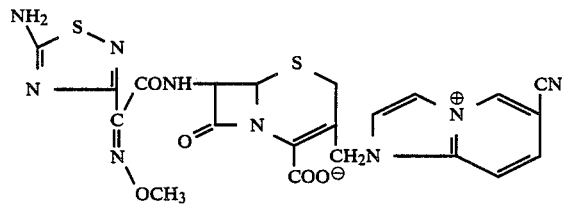

The compound obtained in Reference Example 27 and 6-cyanoimidazo[1,2-a]pyridine are reacted in the procedure of Example 94 to give the above-identified compound.

Elemental analysis for $C_{21}H_{17}N_9O_5S_2.3H_2O$: Calcd.(%): C, 42.49; H, 3.91; N, 21.24. Found (%): C, 42.56; H, 3.67; N, 21.01.

IR spectrum $\nu_{max}^{KBr}$ cm$^{-1}$: 3450, 2250, 1760, 1600, 1520.

NMR (d$_6$-DMSO)δ: 2.98 and 3.46(2H, ABq, J=16 Hz), 3.86(3H, s), 5.00(1H, d, J=5 Hz), 5.28 and 5.54(2H, ABq, J=15 Hz), 5.64(1H, d. d, J=5 Hz and 8 Hz), 8.11(2H, br. s), 8.2–9.0 (5H, m), 9.44(1H, d, J=8 Hz), 9.78(1H, br. s).

EXAMPLE 126

7β-[2-(2-Amino-5-chlorothiazol-4-yl)-2(Z)-methoxyiminoacetamido]-3-[(imidazo[1,5-a]pyridinium-2-yl)methyl]-3-cephem-4-carboxylate

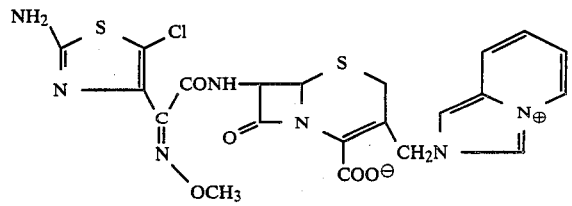

The compound obtained in Reference Example 29 and imidazo[1,5-a]pyridine are reacted in the procedure of Example 42 to give the above-identified compound.

Elemental analysys for $C_{21}H_{18}ClN_7O_5S_2.5/2H_2O$: Calcd.(%): C, 42.53; H, 3.91; N, 16.53. Found (%): C, 42.33; H, 3.16; N, 16.82.

IR spectrum $\nu_{max}^{KBr}$ cm$^{-1}$: 3375, 3100, 1768, 1665, 1610, 1535, 1018.

NMR spectrum (d$_6$-DMSO)δ: 3.21(1H, ABq×½, J=17 Hz), 3.79 (3H, s), 5.00(1H, d, J=5 Hz), 5.10 and 5.53(2H, ABq, J=13 Hz), 5.62(1H, d. d, J=4.2 Hz and 8.1 Hz), 7.00–8.77 (4H, m), 7.35(2H, br. s), 9.42(1H, d, J=8.5 Hz), 10.00 (1H, br. s).

EXAMPLE 127

7β-[2-(5-Amino-1,2,4-thiadiazol-3-yl)-2(Z)-carboxymethoxyiminoacetamido]-3-[(6-cyanoimidazo[1,2-a]pyridinium-1-yl)methyl]-3-cephem-4-carboxylate monosodium salt

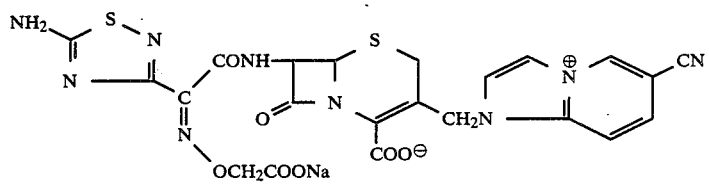

One gram of 7β-[2-(5-amino-1,2,4-thiadiazol-3-yl)-2(Z)-carboxymethoxyiminoacetamido]-3-(3-oxobutyryloxymethyl)-3-cephem-4-carboxylic acid, 1 g of 6-cyanoimidazo[1,2-a]pyridine and 1 g of sodium iodide are added in a mixture of 15 ml of acetonitrile and 15 ml of water and the mixture is heated in an oil bath kept at 70°–75° C. for 1.5 hours with stirring. The reaction mixture is shaken with ethyl acetate and the aqueous layer is separated, concentrated under reduced pressure and chromatographed on a silica gel column with acetone and then acetone:water=7:3. Fractions containing the objective compound are concentrated and the residue is lyophilized to give the above-identified compound.

Elemental analysis for $C_{22}H_{16}N_9O_7S_2Na.5H_2O$ Calcd.(%): C, 37.99; H, 3.77; N, 18.12. Found (%): C, 38.18; H, 3.33; N, 17.15.

IR spectrum $\nu_{max}^{KBr}$ cm$^{-1}$: 2240, 1760, 1600, 1520, 1400, 1360, 1045.

NMR spectrum (D$_2$O)δ: 3.16 and 3.59(2H, ABq, J=18 Hz), 5.24 (1H, d, J=4.8 Hz), 5.38(2H, br. s), 5.86(1H, d, J=4.8 Hz), 8.2–9.0(4H, m), 9.8(1H, br. s).

EXAMPLE 128

7β-[2-(2-Amino-5-chlorothiazol-4-yl)-2(Z)-ethoxyiminoacetamido]-3-[(imidazo[1,2-a]pyridinium-1-yl)methyl]-3-cephem-4-carboxylate

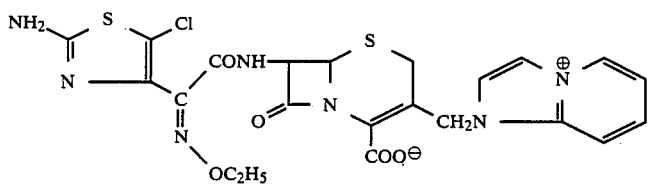

(i) Starting from 2-(5-chloro-2-chloroacetamidothiazol-4-yl)-2(Z)-ethoxyiminoacetic acid, 7β-[2-(2-amino-5-chlorothiazol-4-yl)-2(Z)-ethoxyiminoacetamido]-3-(3-oxobutyryloxymethyl-3-cephem-4-carboxylic acid is obtained by the procedure of Reference Example 29.

IR spectrum $\nu_{max}^{KBr}cm^{-1}$: 3300, 1770, 1700, 1620, 1530

NMR spectrum (d$_6$-DMSO)δ: 1.27(3H, t, J=7 Hz), 2.20(3H, s), 3.3–3.8(2H, m), 3.62(2H, s), 4.17(2H, q, J=7 Hz), 4.83 and 5.09(2H, ABq, J=12 Hz), 5.13(1H, d, J=5 Hz), 5.81(1H, d. d, J=5 Hz and 8 Hz), 6.63(1H, Br. S), 7.24(2H, br. s), 9.50(1H, d. J=8 Hz).

(ii) 7β-[2-(2-Amino-5-chlorothiazol-4-yl)-2(Z)-ethoxyiminoacetamido]-3-(3-oxobutyryloxymethyl)-3-cephem-4-carboxylic acid and imidazo[1,2-a]pyridine are reacted in the procedure of Example 42 to give above-identified compound.

Elemental analysis for C$_{22}$H$_{20}$ClN$_7$O$_5$S$_2$.2H$_2$O: Calcd.(%): C, 44.18; H, 4.04; N, 16.39. Found (%): C, 44.04; H, 3.87; N, 16.13.

IR spectrum $\nu_{max}^{KBr}cm^{-1}$: 3400, 1765, 1605, 1520.

NMR spectrum (d$_6$-DMSO)δ: 1.20(3H, t, J=7 Hz), 3.00 and 3.43(2H, ABq, J=17 Hz), 4.08(2H, q, J=7 Hz), 4.99(1H, d, J=5 Hz), 5.2–5.6(2H, m), 5.62(1H, d. d, J=5 Hz and 8 Hz), 7.34(2H, br. s), 7.4–7.6(1H, m), 7.9–8.1(1H, m), 8.4–8.8(3H, m), 8.8–9.0(1H, m), 9.40(1H, d, J=8 Hz).

mide are reacted in the procedure of Reference Example 37 to give 2-(2-chloroacetamido-5-chlorothiazol-4-yl)-2(Z)-(2-chloroethoxyimino)acetic acid.

IR spectrum $\nu_{max}^{KBr}cm^{-1}$: 1720, 1650, 1530.

(ii) 2-(2-Chloroacetamido-5-chlorothiazol-4-yl)-2(Z)-(2-chloroethoxyimino)acetic acid obtained in (i) is made to react with 7β-amino-3-(3-oxobutyryloxymethyl)-3-cephem-4-carboxylic acid in the procedure of Reference Example 29 to give 7β-[2-(2-amino-5-chlorothiazol-4-yl)-2(Z)-(2-chloroethoxyimino)acetamido]-3-(3-oxobutyryloxymethyl)-3-cephem-4-carboxylic acid.

IR spectrum $\nu_{max}^{KBr}cm^{-1}$: 3300, 1765, 1700, 1615, 1525.

(iii) 7β-[2-(2-Amino-5-chlorothiazol-4-yl)-2(Z)-(2-chloroethoxyimino)acetamido]-3-(3-oxobutyryloxymethyl)-3-cephem-4-carboxylic acid and imidazo[1,2-a]pyridine are reacted in the procedure of Example 42 to give the above-identified compound.

Elemental analysis for C$_{23}$H$_{19}$Cl$_2$N$_8$O$_5$S$_2$.3H$_2$O: Calcd.(%): C, 43.09; H, 3.93; N, 17.48. Found (%): C, 42.89; H, 3.69; N, 17.21.

IR spectrum $\nu_{max}^{KBr}cm^{-1}$: 3400, 1760, 1610, 1520.

NMR spectrum (d$_6$-DMSO)δ: 3.00 and 3.46(2H, ABq, J=18 Hz), 3.6–3.9(2H, m), 4.1–4.4(2H, m), 5.00(1H, d, J=5 Hz), 5.12 and 5.27(2H, ABq, J=13 Hz), 5.60(1H, d. d, J=5 Hz and 8 Hz), 7.25(2H, br. s), 7.4–7.6(1H, m), 7.9–8.1(1H, m), 8.3–8.7(3H, m), 8.8–9.0(1H, m), 9.38(1H, d, J=8 Hz).

EXAMPLE 130

7β-[2-(2-Aminooxazol-4-yl)-2(Z)-ethoxyiminoacetamido]-3-[(imidazo[1,2-a]pyridinium-1-yl)methyl]-3-cephem-4-carboxylate

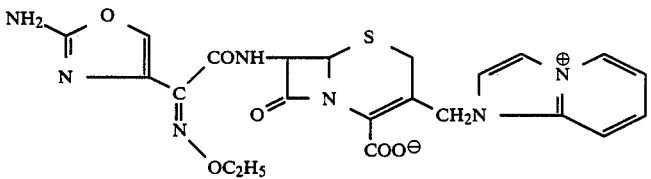

(i) To a suspension of 8.25 g of 2-(2-chloroacetamidooxazol-4-yl)-2(Z)-ethoxyiminoacetic acid in 60 ml of dichloromethane is added, under cooling to −30° C., 6.23 g of phosphorus pentachloride. The mixture is stirred at the same temperature for 5 minutes and under ice-cooling for 30 minutes. To the

EXAMPLE 129

7β-[2-(2-Amino-5-chlorothiazol-4-yl)-2(Z)-(2-chloroethoxyimino)acetamido]-3-[(imidazo[1,2-a]pyridinium-1-yl)methyl]-3-cephem-4-carboxylate

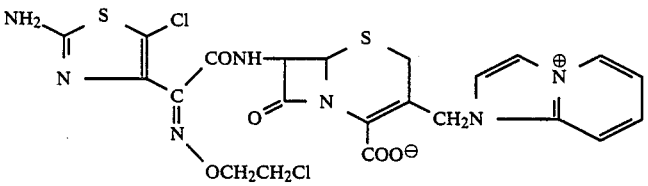

(i) 2-(2-Chloroacetamidothiazol-4-yl)-2-(Z)-(2-chloroethoxyimino)acetic acid and N-chlorosuccinireaction mixture is added 100 ml of hexane and a precipitate separated is collected by filtration to give the corresponding acid chloride. This acid chloride is added to a solution of 8.1 g of 7β-aminocephalosporanic acid and 14.8 ml of N,O-bistrimethylsilylacetamide in dichloromethane under ice-cooling and the mixture is stirred for 1 hour. Then, the reaction mixture is poured into 200 ml of ice-water and the mixture, after 10 minutes' stirring and being adjusted to pH 2 by addition of sodium bicarbonate, is extracted with 300 ml of methyl ethyl ketone. The extract is dried over anhydrous magnesium sulfate and the solvent is evaporated off to give 6.7 g off crude 7β-[2-(2-chloroacetamidooxazol-4-yl)-2(Z)-ethoxyiminoacetamido]cephalosporanic acid.

IR spectrum $\nu_{max}^{KBr}$cm$^{-1}$: 1780, 1730, 1625, 1520, 1380.

NMR spectrum (d$_6$-acetone-D$_2$O)δ: 1.32(3H, t, J=7 Hz), 2.04 (3H, s), 3.44 and 3.70(2H, ABq, J=18 Hz), 4.38(2H, s), 4.40(2H, q, J=7 Hz), 4.82 and 5.60(2H, J=13 Hz), 5.20 (1H, d, J=5 Hz), 5.88(1H, d, J=5 and 7 Hz), 8.42(1H, s).

(ii) A solution of 6.5 g of 7β-[2-(2-chloroacetamidooxazol-4-yl)-2(Z)-ethoxyiminoacetamido]cephalosporanic acid, 3.16 g of sodium N-methyldithiocarbamate and 1.0 g of sodium bicarbonate in 50% aqueous tetrahydrofuran is stirred at room temperature for 3 hours. The reaction mixture is shaken with 100 ml of ethyl acetate and the aqueous phase is separated, washed twice with 100 ml portions of ethyl acetate and then chromatographed on a column of MCI GEL CHP 20P (150–300 mesh, Mitsubishi Chemical Industries, LTD., Japan) with aqueous ethanol. The eluate containing the objective compound is lyophilized to give 2.8 g of sodium 7β-[2-(2-aminooxazol-4-yl)-2(Z)-ethoxyiminoacetamido]cephalosporanate.

Elemental analysis for C$_{17}$H$_{18}$N$_5$O$_3$Na.2H$_2$O: Calcd.(%): C, 39.92; H, 4.34; N, 13.69. Found (%): C, 39.76; H, 4.21; N, 13.64.

IR spectrum $\nu_{max}^{KBr}$cm$^{-1}$: 1760, 1660, 1620, 1510, 1400.

NMR spectrum (d$_6$-acetone-D$_2$O)δ: 1.40(3H, t, J=7 Hz), 2.14 (3H, s), 3.38 and 3.71(2H, ABq, J=18 Hz), 4.46(2H, q, J=7 Hz), 4.88 and 5.08(2H, ABq, J=13 Hz), 5.24(1H, d, J=5 Hz), 5.92(1H, d, J=5 Hz), 8.14(1H, s).

(iii) A mixture of 1.0 g of sodium 7β-[2-(2-aminooxazol-4-yl)-2(Z)-ethoxyiminoacetamido]cephalosporanate, 2 g of imidazo[1,2-a]pyridine and 2 g of sodium iodide in 20 ml of 50% aqueous acetonitrile is heated at 70° C. for 4 hours and the reaction mixture is chromatographed on a column of silica gel (50 g) with 500 ml of acetone:water=8:1 and then with acetone:water=3:1 as eluant. The eluate containing the objective compound is concentrated and the residue is chromatographed on a column of MCI GEL CHP20P with water and then with aqueous ethanol. Fractions containing the objective compound are concentrated and the residue is lyophilized to give the above-identified compound.

Elemental analysis for C$_{22}$H$_{21}$N$_7$O$_6$S.7/2H$_2$O: Calcd.(%): C, 45.99; H, 4.91; N, 17.06. Found (%): C, 46.00; H, 4.80; N, 16.77.

IR spectrum $\nu_{max}^{KBr}$cm$^{-1}$: 1765, 1660, 1620, 1535, 1450, 1385, 1360.

NMR spectrum (d$_6$-acetone-D$_2$O)δ: 1.37(3H, t, J=7 Hz), 3.18 and 3.63(2H, ABq, J=18 Hz), 4.42(2H, q, J=7 Hz), 5.23 (1H, d, J=5 Hz), 5.47(2H, br.s), 5.88(1H, d, J=5 Hz), 7.58(1H, t, J=7 Hz), 7.9–8.5(4H, m), 8.86(1H, d, J=6 Hz), 8.10(1H, s).

EXAMPLE 131

7β-[2-(5-Amino-1,2,4-thiadiazol-3-yl)-2(Z)-carboxymethoxyiminoacetamido]-3-[(imidazo[1,2-a]pyridinium-1-yl)methyl]-3-cephem-4-carboxylate

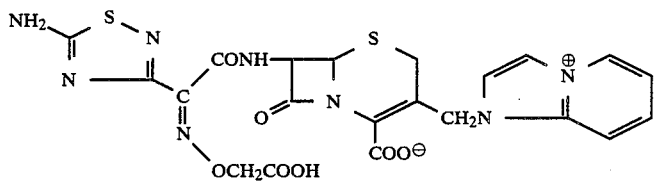

(i) To a solution of 2-(5-tert-butoxycarbonylamino-1,2,4-thiadiazol-3-yl)-2-oxoacetic acid in ethanol (100 ml), prepared from 13 g of 2-(5-amino-1,2,4-thiadiazol-3-yl)acetic acid and 10.7 g of selenium dioxide in the procedure of Reference Example 42, is added, under ice-cooling, 6.2 g of O-tert-butoxycarbonylmethylhydroxylamine (prepared from 14 g of N-tert-butoxycarbonylmethoxyphthalimide and 2.3 g of methylhydrazine) and the mixture is stirred at room temperature for 4 hours. Ethanol is then evaporated off and the residue is shaken with ethyl acetate and water. The organic layer is separated and extracted with an aqueous sodium bicarbonate solution. The aqueous extract is made acidic with 1N-HCl and extracted with ethyl acetate. The extract is dried over anhydrous magnesium sulfate. The solvent is then evaporated off and the residue is crystallized from hexane to give, after filtration and drying, 11 g of 2-(5-tert-butoxycarbonylamino-1,2,4-thiadiazol-3-yl)-2(Z)-(tert-butoxycarbonylmethoxyimino)acetic acid.

mp 128° C. (decomposition)

NMR spectrum (CDCl$_3$)δ: 1.43(9H, s), 1.55(9H, s), 4.73(2H, s).

(ii) To a solution of 13 g of 2-(tert-butoxycarbonylamino-1,2,4-thiadiazol-3-yl)-2(Z)-(tert-butoxycarbonylmethoxyimino)acetic acid in 100 ml of dichloromethane, 7 g of phosphorus pentachloride is added and the mixture is stirrred for 20 minutes under ice-cooling. The reaction mixture is evaporated to dryness and to the residue is added hexane and the solvent is evaporated off again. The residue is dissolved in 5 ml of dichloromethane and the solution is added under ice-cooling to a solution prepared by allowing 10 g of 7β-amino-3-(3-oxobutyryloxymethyl)-3-cephem-4-carboxylic acid and 16 g of N,O-bistrimethylsilylacetamide to react in 200 ml of dichloromethane at room temperature for one hour. The mixture is stirred at the same temperature for one hour and the solvent is then evaporated under reduced pressure. The residue is dissolved in 300 ml of ethyl acetate and the solution is washed with water and then dried over anhydrous magnesium sulfate. Then, the solvent is evaporated off and the residue is triturated with hexane. Insoluble substance is collected by filtration to give 23 g of 7β-[2-(5-tert-butoxycarbonylamino-1,2,4-thiadiazol-3-yl)-2(Z)-(tert-butoxycarbonylmethoxyimino)acetamido]-3-(3-oxobutyryloxymethyl)-3-cephem-4-carboxylic acid.

IR spectrum $\nu_{max}^{KBr}$cm$^{-1}$: 3250, 2960, 1780, 1715, 1540, 1370, 1205, 1150, 1060.

NMR spectrum(d$_6$-DMSO)δ: 1.43(9H, s), 1.50(9H, s), 2.18 (3H, s), 3.41 and 3.65(2H, ABq, J=18 Hz), 3.62(2H, s), 4.66(2H, s), 4.78 and 5.06(2H, ABq, J=12 Hz), 5.15 (1H, d, J=4.8 Hz), 5.86(1H, d.d, J=4.8 Hz and 8 Hz), 9.56(1H, d, J=8 Hz).

(iii) The whole amount of the compound obtained in (ii) is added to 50 ml of trifluoroacetic acid under ice-cooling. Then, the cooling-bath is removed and the reaction mixture is stirred at room temperature for 1.5 hours. After being diluted with ethyl acetate, the reaction mixture is evaporated off to dryness and the residue is triturated with ethyl acetate. Insoluble substance is collected by filtration to give 12 g of 7β-[2-(5-amino-1,2,4-thiadiazol-3-yl)-2(Z)-carboxymethoxyiminoacetamido]-3-(3-oxobutyryloxymethyl)-3-cephem-4-carboxylic acid. From the filtrate, after evaporation to dryness, addition of diethyl ether to the residue and filtration of insoluble material, 5 g of the same objective compound is recovered.

IR spectrum $\nu_{max}^{KBr}$cm$^{-1}$: 1760, 1720, 1630, 1520, 1400, 1310, 1180, 1145.

NMR spectrum(D$_6$-DMSO)δ: 2.20(3H, s), 3.41 and 3.65(2H, ABq, J=18 Hz), 3.63(2H, s), 4.65(2H, s), 4.78 and 5.07(2H, ABq, J=12 Hz), 5.15(1H, d, J=4.8 Hz), 5.85(1H, d.d, J=4.8 Hz and 8 Hz), 8.10(2H, br.), 9.48(1H, d, J=8 Hz).

(iv) One gram of 7β-[2-(5-amino-1,2,4-thiadiazol-3-yl)-2(Z)-carboxymethoxyiminoacetamido]-3-(3-oxobutyryloxymethyl)-3-cephem-4-carboxylic acid, 1 g of imidazo[1,2-]pyridine and 1 g of sodium iodide are added to a mixture of 10 ml of acetonitrile and 10 ml of water and heated in an oil bath kept at 70°–75° C. for 1.5 hours. The reaction mixture is worked up as in Example 42 to give the above-identified compound.

Elemental analysis for C$_{21}$H$_{17}$N$_8$O$_7$S$_2$Na.5H$_2$O: Calcd.(%): C, 42.79; H, 3.08; N, 19.01 Found (%): C, 42.88; H, 3.64; N, 17.55

IR spectrum $\nu_{max}^{KBr}$cm$^{-1}$: 1760, 1600, 1520, 1400, 1305, 1050.

NMR spectrum(D$_2$O)δ: 3.16 and 3.53(2H, ABq, J=18 Hz), 5.22(1H, d, J=4.8 Hz), 5.32(2H, br.s), 5.86(1H, d, J=4.8 Hz), 7.40–8.80(6H, m).

EXAMPLE 132

7β-[2-(2-Amino-5-chlorothiazol-4-yl)-2(Z)-ethoxyiminoacetamido]-3-[(6-cyanoimidazo[1,2-a]pyridinium-1-yl)methyl]-3-cephem-4-carboxylate

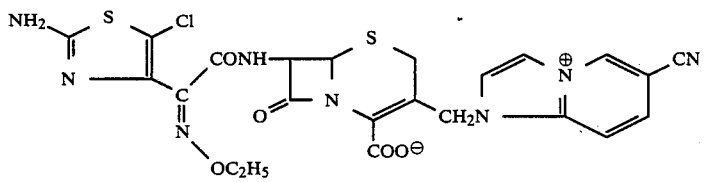

The compound obtained in Example 128 and 6-cyanoimidazo[1,2-a]pyridine are reacted in the procedure of Example 42 to give the above-identified compound.

Elemental analysis for C$_{23}$H$_{19}$ClN$_8$O$_5$S$_2$.3H$_2$O: Calcd.(%): C, 43.09; H, 3.93; N, 17.48. Found (%): C, 43.19; H, 3.69; N, 17.39.

IR spectrum $\nu_{max}^{KBr}$cm$^{-1}$: 3350, 2250, 1760, 1610, 1520.

NMR spectrum (d$_6$-DMSO)δ: 1.20(2H, t, J=7 Hz), 2.99 and 3.46(2H, ABq, J=18 Hz), 4.07(2H, q, J=7 Hz), 5.00 (1H, d, J=5 Hz), 5.30 and 5.53(2H, ABq, J=15 Hz), 5.64(1H, d.d, J=5 Hz and 8 Hz), 7.33(2H, br.s), 8.2–9.0 (4H, m), 9.41(1H, d, J=8 Hz), 9.78(1H, br.s).

EXAMPLE 133

7β-[2-(2-Amino-5-chlorothiazol-4-yl)-2(Z)-(1-carboxy-1-methylethoxyimino)acetamido]-3-[(6-cyanoimidazo[1,2-a]pyridinium-1-yl)methyl]-3-cephem-4-carboxylate monosodium salt

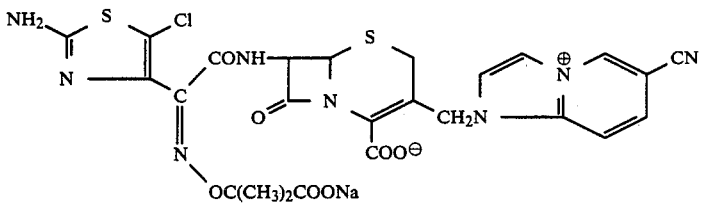

The compound obtained in Reference Example 39 and 6-cyanoimidazo[1,2-a]pyridine are reacted in the procedure of Example 84 to give the above-identified compound.

Elemental analysis for C$_{25}$H$_{20}$ClN$_8$O$_7$S$_2$.7/2H$_2$O: Calcd.(%): C, 40.99; H, 3.71; N, 15.29. Found (%): C, 41.09; H, 3.62; N, 15.12.

IR spectrum $\nu_{max}^{KBr}$cm$^{-1}$: 2250, 1760, 1600, 1520, 1400.

NMR spectrum (d$_6$-DMSO)δ: 1.21(6H, br.s), 2.05 and 2.45 (2H, ABq, J=18 Hz), 4.98(1H, d, J=5 Hz), 5.2–5.7 (2H, m), 5.73(1H, d.d, J=5 Hz and 9 Hz), 7.30(2H, br.s), 8.2–8.9(4H, m), 9.87(1H, br.s), 11.45(1H, d, J=9 Hz).

EXAMPLE 134

7β-[2-(2-Aminothiazol-4-yl)-2(Z)-methoxyiminoacetamido]-3-[(5-amino-3-carboxy-2-methylimidazo[1,2-a]pyridinium-1-yl)methyl]-3-cephem-4-carboxylate

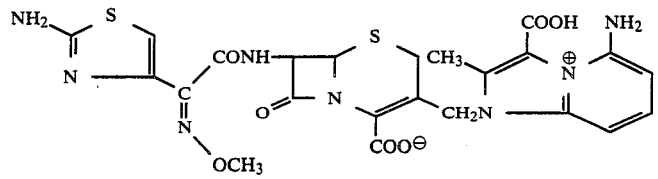

7β-[2-(2-Aminothiazol-4-yl)-2-(Z)-methoxyiminoacetamido]-3-(3-oxobutyryloxymethyl)-3-cephem-4-carboxylic acid and 5-amino-3-carboxy-2-methylimidazo[1,2-a]pyridine are made to react in the procedure of Example 42 to give the above-identified compound.

IR spectrum $\nu_{max}^{KBr}$ cm$^{-1}$: 1760, 1670, 1610, 1530.

NMR spectrum (d$_6$-DMSO-D$_2$O)δ: 2.34(3H, s), 3.09 and 3.46 (2H, ABq, J=18 Hz), 3.80(3H, s), 5.01(1H, d, J=4.5 Hz), 5.14–5.70(3H, m), 6.73(1H, s), 7.98–8.4(2H, m), 8.5–8.72(1H, m).

EXAMPLE 135

Three grams of 7β-[2-(2-aminothiazol-4-yl)-2(2)-carboxymethoxyiminoacetamido]-3-[(imidazo[1,2-a]pyridinium-1-yl)methyl]-3-cephem-4-carboxylate monosodium salt is dissolved in 30 ml of physiological saline under mixing to produce a composition for injection.

What we claim is:

1. A compound of the formula:

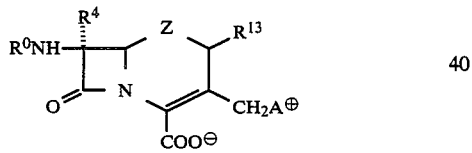

wherein
R$^0$ stands for:
(i) hydrogen;
(ii) 2-pyrrolyl, 3-pyrrolyl, 3-pyrazolyl, 4-pyrazolyl, 5-pyrazolyl, 2-imidazolyl, 4-imidazolyl, 5-imidazolyl, 1,2,3-triazolyl, 1,2,4-triazolyl, 1H-tetrazolyl, 2H-tetrazolyl, 2-oxazolyl, 4-oxazolyl, 5-oxazolyl, 3-isoxazolyl, 4-isoxazolyl, 5-isoxazolyl, 1,2,3-oxadiazol-4-yl, 1,2,3-oxadiazol-5-yl, 1,2,4-oxadiazol-3-yl, 1,2,4-oxadiazol-5-yl, 1,2,5-oxadiazolyl, 1,3,4-oxadiazolyl, 2-thiazolyl, 4-thiazolyl, 5-thiazolyl, 4-isothiazolyl, 5-isothiazolyl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazolyl, 1,3,4-thiadiazolyl, 2-pyrrolidinyl, 3-pyrrolidinyl, 2-pyridyl, 3-pyridyl, 4-pyridyl, 2-pyridyl-N-oxide, 3-pyridyl-N-oxide, 4-pyridyl-N-oxide, 3-pyridazinyl, 4-pyridazinyl, 3-pyridazinyl-N-oxide, 4-pyridazinyl-N-oxide, 2-pyrimidinyl, 4-pyrimidinyl, 5-pyrimidinyl, 2-pyrimidinyl-N-oxide, 4-pyrimidinyl-N-oxide, 5-pyrimidinyl-N-oxide, pyrazinyl, 2-piperidinyl, 3-piperidinyl, 4-piperidinyl, piperazinyl, 3H-indol-2-yl, or 3H-indol-3-yl that is unsubstituted or substituted by one to three of C$_{1-6}$ alkyl group, C$_{3-10}$ cycloalkyl group, C$_{6-10}$ aryl group, C$_{7-12}$ aralkyl group, hydroxyl group, C$_{1-6}$ alkoxy group, mercapto group, C$_{1-6}$ alkylthio group, amino group, mono-C$_{1-6}$ alkylamino group, di-C$_{1-6}$ alkylamino group, halogen atom, nitro group, azido group, cyano group, carboxyl group, C$_{1-10}$ alkoxycarbonyl group, C$_{1-6}$ alkanoyl group, C$_{1-6}$ alkanoyloxy group, carbamoyl group, mono-C$_{1-6}$ alkylcarbamoyl group, di-C$_{1-6}$ alkyl-carbamoyl group, carbamoyloxy group, mono-C$_{1-6}$ alkylcarbamoyl-oxy group, or di-C$_{1-6}$ alkylcarbamoyloxy group;

(iii) a group of the formula

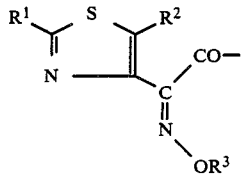

wherein R$^1$ stands for an amino group or a protected amino group, R$^2$ stands for hydrogen atom, halogen atom, or nitro group, and R$^3$ stands for hydrogen atom or C$_{1-6}$ alkyl group, C$_{2-6}$ alkenyl group, C$_{2-6}$ alkynyl group, C$_{3-10}$ cycloalkyl group or C$_{5-6}$ cycloalkenyl group that is unsubstituted or substituted by one or two of hydroxyl, C$_{1-6}$ alkyl, C$_{2-6}$ alkenyl, C$_{2-6}$ alkynyl, C$_{3-10}$ cycloalkyl, C$_{5-6}$ cycloalkenyl, C$_{6-10}$ aryl, C$_{7-19}$ aralkyl, 2- or 3-pyrrolyl, 3-,4- or 5-pyrazolyl, 2-, 4- or 5-imidazolyl, 1,2,3- or 1,2,4-triazolyl, 1H- or 2H-tetrazolyl, 2- or 3-furyl, 2- or 3-thienyl, 2-, 4- or 5-oxazolyl, 3-, 4- or 5-isoxazolyl, 1,2,3-oxadiazol-4- or 5-yl, 1,2,4-oxadiazol-3- or 5-yl, 1,2,5- or 1,3,4-oxadiazolyl, 2-, 4- or 5-thiazolyl, 3-, 4- or 5-isothiazolyl, 1,2,3-thiazidazol-4- or 5-yl, 1,2,4-thiadiazol-3- or 5-yl, 1,2,5- or 1,3,4-thiadiazolyl, 2- or 3-pyrrolidinyl, 2-, 3- or 4-pyridyl, 2-, 3- or 4-pyridyl-N-oxide, 3- or 4-pyridazinyl, 3- or 4-pyridazinyl-N-oxide, 2-, 4- or 5-pyrimidinyl, 2-, 4- or 5-pyrimidinyl-N-oxide, pyrazinyl, 2-, 3- or 4-piperidinyl, piperazinyl, 3H-indol-2- or 3-yl, 2-, 3- 4-pyranyl, 2-, 3- or 4-thiopyranyl, benzopyranyl, quinolyl, pyrido[2,3-d]pyrimidyl, 1,5-, 1,6-, 1,7-, 1,8-, 2,6- or 2,7-naphthylidyl, thieno[2,3-d]-pyridyl, pyrimidopyrimidyl, pyrazinoquinolyl, benzopyranyl, C$_{1-6}$ alkoxy, C$_{3-10}$ cycloalkyloxy, C$_{6-10}$ aryloxy, C$_{7-19}$ aralkyloxy, thiazolyloxy, mercapto, C$_{1-6}$ alkylthio, C$_{3-10}$ cycloalkylthio, C$_{6-10}$ arylthio, C$_{7-19}$ aralkylthio, thiazolylthio, amino, mono-C$_{1-6}$ alkylamino, di-C$_{1-6}$ alkylamino, tri-C$_{1-6}$ alkylammonium, C$_{3-10}$ cycloalkylamino, C$_{6-10}$ arylamino, C$_{7-19}$ aralkylamino, thiazolylamino, thiadiazolylamino, cyclic amino, azido, nitro, halogen, cyano, carboxyl, C$_{1-10}$ alkoxy-carbonyl, C$_{6-10}$ aryloxycarbonyl, C$_{7-19}$ aralkyloxy-carbonyl, benzoyl, naphthoyl, phthaloyl, phenylacetyl, $C_{1-6}$ alkanoyl, $C_{3-5}$ alkenoyl, benzoyloxy, naphthoyloxy, phenylacetoxy, $C_{2-6}$ alkanoyloxy, $C_{3-5}$ alkenoyloxy, carbamoyl, N-methylcarbamoyl, N,N-dimethylcarbamoyl, N-ethylcarbamoyl, N,N-diethylcarbamoyl, N-phenylcarbamoyl, N-acetylcarbamoyl, N-benzoylcarbamoyl, N-(p-methoxy-phenyl)carbamoyl, pyrrolidinocarbonyl, piperidinocarbonyl, piperazinocarbonyl, morpholino-carbonyl, thiocarbamoyl, N-methylthiocarbamoyl, N-phenylthiocarbamoyl, carbamoyloxy, N-methylcarbamoyloxy, N,N-dimethylcarbamoyloxy, N-ethylcarbamoyloxy, N-phenylcarbamoyloxy, phthalimido, $C_{1-6}$ alkanoylamino, benzamido, naphthoylamido, phthalimido, carboxyamino, $C_{1-10}$ alkoxy-carboxamido, $C_{6-10}$ aryloxy-carboxamido or $C_{7-19}$ aralkyloxy-carboxamido; or (iv) methoxy-carbonyl, ethoxycarbonyl, n-propoxycarbonyl, isopropoxy-carbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyl-oxycarbonyl, acetylmethyloxycarbonyl, 2-trimethylsilyl-ethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl, or cyclohexyloxycarbonyl;

$R^4$ stands for hydrogen atom, methoxy group or formamido group,

Z stands for S or S→O;

$R^{13}$ stands for hydrogen atom, methyl group, hydroxyl group or halogen atom; and A stands for substituted or unsubstituted imidazol-1-yl group forming a condensed ring at the 2,3- or 3,4-position or a physiologically or pharmaceutically acceptable salt or ester thereof.

2. A compound according to claim 1, wherein $R^0$ is a group of the formula:

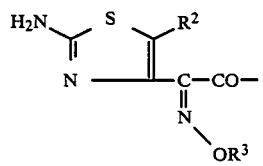

wherein $R^2$ and $R^3$ are as defined in claim 1.

3. A compound according to claim 2, wherein $R^3$ is hydrogen atom or $C_{1-3}$ alkyl group that is unsubstituted or substituted by halogen atom, hydroxyl group, $C_{1-6}$ alkoxy group, carboxyl group, $C_{1-6}$ alkoxy-carbonyl group, or cyano group and the configuration of $OR^3$ is syn.

4. A compound according to claim 1, wherein the imidazol-1-yl group forming a condensed ring at the 2,3- or 3,4-position is a group of the formula:

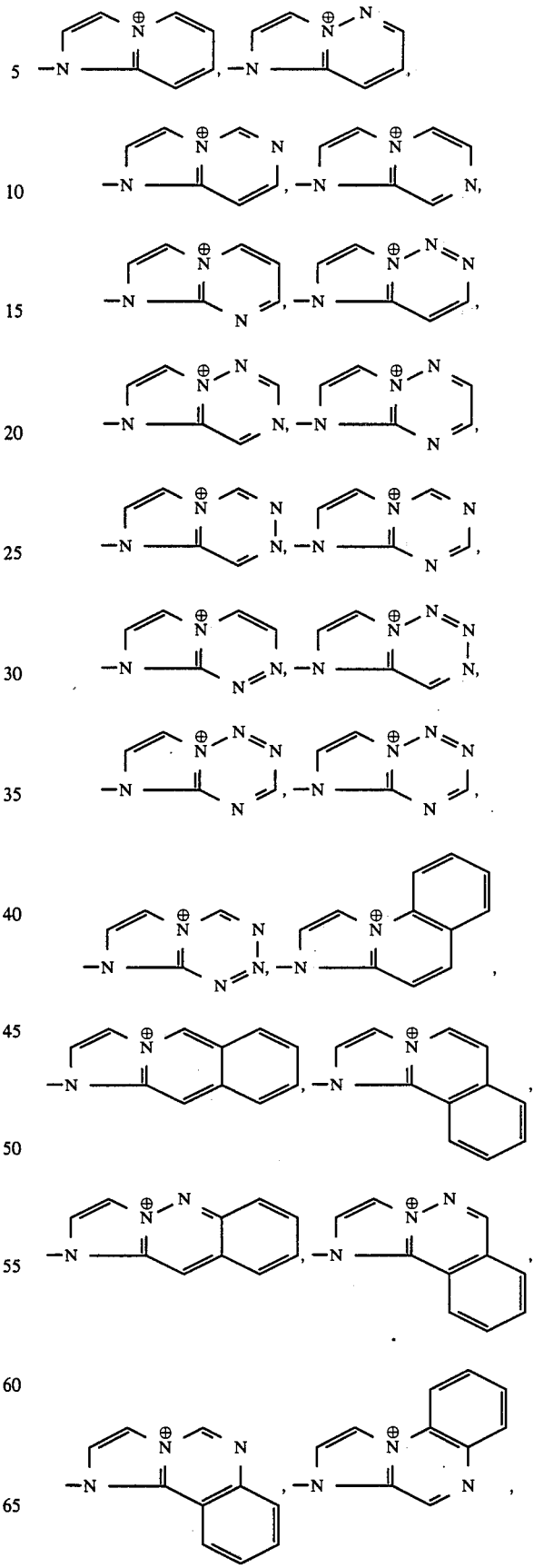

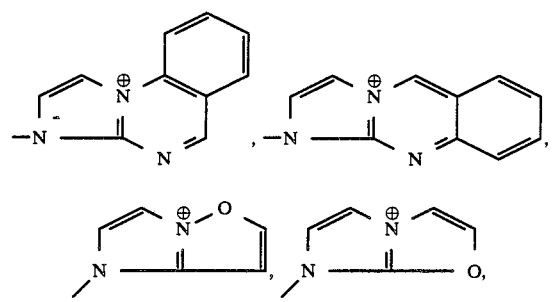
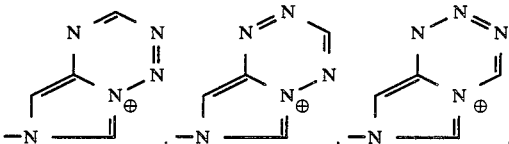
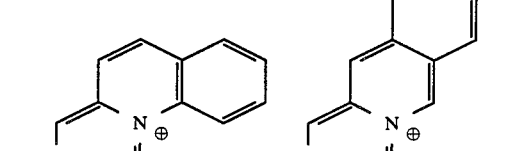
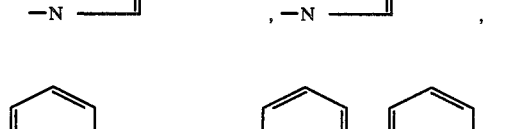
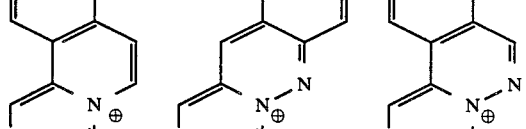
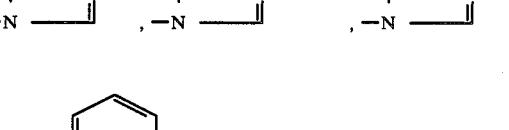
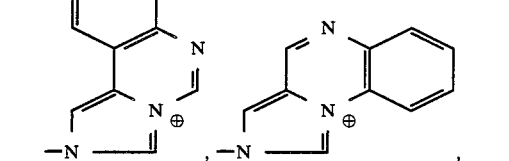
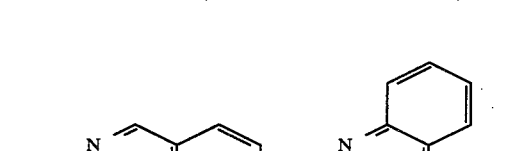
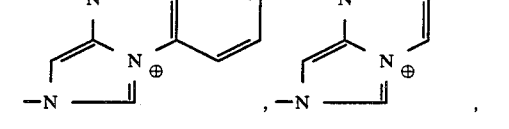
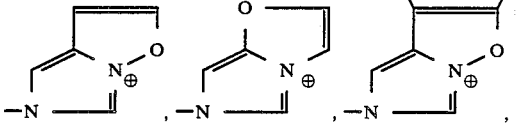
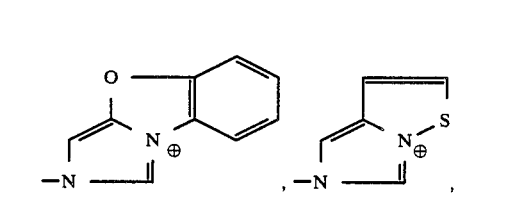

-continued

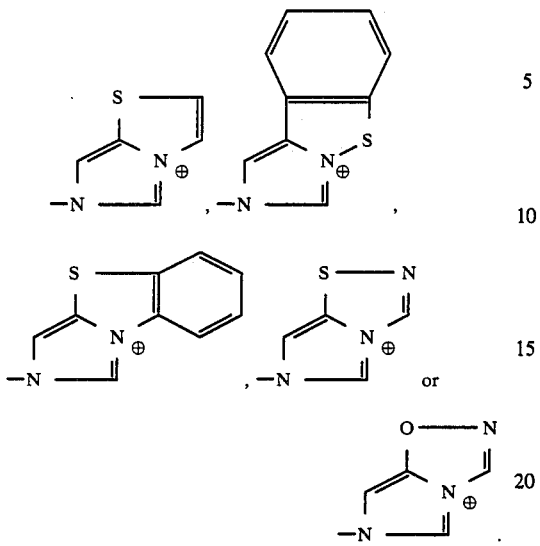

5. A compound according to claim 1, wherein the imidazol-1-yl group forming a condensed ring at the 2,3- or 3,4-position is imidazo[1,2-a]pyridinium-1-yl or imidazo[1,5-a]pyridinium-2-yl group.

6. A compound according to claim 1, wherein $R^0$ is a group of the formula:

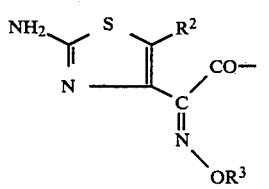

wherein
$R^2$ is hydrogen atom or halogen atom, $R^3$ is $C_{1-3}$ alkyl group that is unsubstituted or substituted by halogen atom, hydroxyl group, $C_{1-6}$ alkoxy group, carboxyl group, $C_{1-6}$ alkoxycarbonyl group or cyano group;
Z is S;
$R^4$ is hydrogen atom;
$R^{13}$ is hydrogen atom; and
A is an imidazo[1,2-a]pyridinium-1-yl or imidazo[1,5-a]pyridinium-2-yl group that is unsubstituted or substituted with one or two of hydroxyl group, hydroxy $C_{1-6}$ alkyl group, $C_{1-6}$ alkyl group, $C_{2-6}$ alkenyl group, $C_{2-6}$ alkynyl group, $C_{4-6}$ alkadienyl group, $C_{3-10}$ cycloalkyl group, $C_{5-6}$ cycloalkenyl group, $C_{3-10}$ cycloalkyl $C_{1-6}$ alkyl group, $C_{6-10}$ aryl group, $C_{7-12}$ aralkyl group, di-$C_{6-10}$ aryl-methyl group, tri-$C_{6-10}$ arylmethyl group, 2- or 3-pyrrolyl, 3-, 4- or 5-pyrazolyl, 2-, 4- or 5-imidazolyl, 1,2,3- or 1,2,4-triazolyl, 1H- or 2H-tetrazolyl, 2- or 3-furyl, 2- or 3-thienyl, 2-, 4- or 5-oxazolyl, 3-, 4- or 5-isoxazolyl, 1,2,3-oxadiazol-4- or 5-yl, 1,2,4-oxadiazol-3- or 5-yl, 1,2,5- or 1,3,4-oxadiazolyl, 2-, 4- or 5-thiazolyl, 3-, 4- or 5-isothiazolyl, 1,2,3-thiadiazol-4- or 5-yl, 1,2,4-thiadiazol-3- or 5-yl, 1,2,5- or 1,3,4-thiadiazolyl, 2- or 3-pyrrolidinyl, 2-, 3- or 4-pyridyl, 2-, 3- or 4-pyridyl-N-oxide, 3- or 4-pyridazinyl, 3- or 4- pyridazinyl-N-oxide, 2-, 4- or 5-pyrimidinyl, 2-, 4- or 5-pyrimidinyl-N-oxide, pyrazinyl, 2-, 3- or 4-piperidinyl, piperazinyl, 3H-indol-2- or 3-yl, 2, 3- or 4-pyranyl, 2-, 3- or 4-thiopyranyl, benzopyranyl, quinolyl, pyrido[2,3-d]pyrimidyl, 1,5-, 1,6-, 1,7-, 1,8-, 2,6- or 2,7-naphthylidyl, thieno[2,3-d]-pyridyl, pyrimidopyrimidyl, pyrazinoquinolyl, benzopyranyl, $C_{1-6}$ alkoxy group, $C_{1-6}$ alkoxy $C_{1-6}$ alkyl group, $C_{3-10}$ cycloalkyloxy group, $C_{6-10}$ aryloxy group, $C_{7-19}$ aralkyloxy group, mercapto group, mercapto $C_{1-6}$ alkyl group, sulfo group, sulfo $C_{1-6}$ alkyl group, $C_{1-6}$ alkylthio group, $C_{1-6}$ alkylthio $C_{1-6}$ alkyl group, $C_{3-10}$ cycloalkylthio group, $C_{6-10}$ arylthio group, $C_{7-19}$ aralkylthio group, amino group, amino $C_{1-6}$ alkyl group, mono-$C_{1-6}$ alkylamino group, di-$C_{1-6}$ alkylamino group, mono-$C_{1-6}$ alkylamino $C_{1-6}$ alkyl group, di-$C_{1-6}$ alkylamino $C_{1-6}$ alkyl group, $C_{3-10}$ cycloalkylamino group, $C_{6-10}$ arylamino group, $C_{7-19}$ aralkylamino group, cyclic amino group, cyclic amino $C_{1-6}$ alkyl group, cyclic amino $C_{1-6}$ alkylamino group, azido group, nitro group, halogen atom, halogeno $C_{1-6}$ alkyl group, cyano group, cyano $C_{1-6}$ alkyl group, carboxyl group, carboxy $C_{1-6}$ alkyl group, $C_{1-10}$ alkoxy-carbonyl group, $C_{1-10}$ alkoxy-carbonyl $C_{1-6}$ alkyl group, $C_{6-10}$ aryloxycarbonyl group, $C_{7-19}$ aralkyloxycarbonyl group, benzoyl, naphthoyl, phthaloyl, phenylacetyl, $C_{1-6}$ alkanoyl group, $C_{2-6}$ alkanoyl $C_{1-6}$ alkyl group, $C_{3-5}$ alkenoyl group, benzoyloxy, naphthoyloxy, phenylacetoxy, $C_{2-6}$ alkanoyloxy group, $C_{1-6}$ alkanoyloxy group, $C_{3-5}$ alkenoyloxy group, carbamoyl $C_{1-6}$ alkyl group, carbamoyl, N-methylcarbamoyl, N,N-dimethylcarbamoyl, N-ethylcarbamoyl, N,N-diethylcarbamoyl, N-phenylcarbamoyl, N-acetylcarbamoyl, N-benzoylcarbamoyl, N-(p-methoxyphenyl)carbamoyl, pyrrolidinocarbonyl, piperidinocarbonyl, piperazinocarbonyl, morpholinocarbonyl, thiocarbamoyl, N-methylthiocarbamoyl, N-phenylthiocarbamoyl, carbamoyloxy, N-methylcarbamoyloxy, N,N-dimethylcarbamoyloxy, N-ethylcarbamoyloxy, N-phenylcarbamoyloxy, carbamoyloxy $C_{1-6}$ alkyl group, $C_{1-6}$ alkanoylamino group, benzamido, naphthoylamido, phthalimido, sulfonamido group, carboxyamino group, $C_{1-10}$ alkoxycarboxamido group, $C_{6-10}$ aryloxy-carboxamido group, or $C_{7-19}$ aralkyloxy-carboxamido group.

7. 7β-[2-Acetamido-2-(2-aminothiazol-4-yl)-acetamido]-3-[(imidazo[1,2-a]pyridinium-1-yl)methyl]-3-cephem-4-carboxylate.

8. 7β-[2-(2-Chloroacetamidothiazol-4-yl-3-oxido)-2(Z)-ethoxyiminoacetamido]-3-[(imidazo[1,2-a]pyridinium-1-yl)methyl]-3-cephem-4-carboxylate.

9. 7β-Formamido-3-[(imidazo[1,2-a]pyridinium-1-yl)methyl]-3-cephem-4-carboxylate.

10. 7β[2-(2-Aminooxazol-4-yl)-2(Z)-ethoxyiminoacetamido]-3-(imidazo[1,2-a]pyridinium-1-yl)methyl]-3-cephem-4-carboxylate.

11. A pharmaceutical composition useful as an antibacterial agent comprising an antibacterially effective dose of a compound as claimed in claim 1, or a pharmaceutically acceptable salt or ester thereof, together with a suitable carrier or diluent.

12. A compound according to claim 1 wherein Z is S.

13. A compound according to claim 1 wherein $R^4$ is hydrogen atom.

14. A compound according to claim 1 wherein $R^{13}$ is hydrogen atom.

15. A compound according to claim 1, namely 7β-[2-(2-aminothiazol-4-yl)-2(Z)-methoxyiminoacetamido]-3-[(imidazo[1,2-a]pyridinium-1-yl)methyl]-3-cephem-4-carboxylate.

16. A compound according to claim 1, namely 7β-[2-(2-aminothiazol-4-yl)-2-(Z)-ethoxyiminoacetamido]-3-[(imidazo[1,2-a]pyridinium-1-yl)methyl]-3-cephem-4-carboxylate.

17. A compound according to claim 1, namely 7β-[2-(2-aminothiazol-4-yl)-2(Z)-(1-carboxy-1-methylethoxyimino)acetamido]-3-[(imidazo[1,2-a]pyridinium-1-yl)methyl]-3-cephem-4-carboxylate.

18. A compound according to claim 1, namely 7β-[2-(2-aminothiazol-4-yl)-2(Z)-(2-fluoroethoxyimino)acetamido]-3-[(imidazo[1,2-a]pyridinium-1-yl)methyl]-3-cephem-4-carboxylate.

19. A compound according to claim 1, namely 7β-[2-(2-aminothiazol-4-yl)-2(Z)-(2-chloroethoxyimino)acetamido]-3-[(imidazo[1,2-a]pyridinium-1-yl)methyl]-3-cephem-4-carboxylate.

20. A compound according to claim 1, namely 7β-[2-(2-aminothiazol-4-yl)-2(Z)-(2-hydroxyethoxyimino)acetamido]-3-[(imidazo[1,2-a]pyridinium-1-yl)methyl]-3-cephem-4-carboxylate.

21. A compound according to claim 1, namely 7β-[2-(2-aminothiazol-4-yl)-2(Z)-methoxyiminoacetamido]-3-[(6-chloroimidazo[1,2-a]pyridinium-1-yl)methyl]-3-cephem-4-carboxylate.

22. A compound according to claim 1, namely 7β-[2-(2-aminothiazol-4-yl)-2(Z)-ethoxyiminoacetamido]-3-[(6-chloroimidazo[1,2-a]pyridinium-1-yl)methyl]-3-cephem-4-carboxylate.

23. A compound according to claim 1, namely 7β-[2-(2-aminothiazol-4-yl)-2(Z)-methoxyiminoacetamido]-3-[(6-cyanoimidazo[1,2-a]pyridinium-1-yl)methyl]-3-cephem-4-carboxylate.

24. A compound according to claim 1, namely 7β-[2-(2-aminothiazol-4-yl)-2(Z)-ethoxyiminoacetamido]-3-[(6-cyanoimidazo[1,2-a]pyridinium-1-yl)methyl]-3-cephem-4-carboxylate.

25. A compound according to claim 1, namely 7β-[2-(2-aminothiazol-4-yl)-2(Z)-(1-carboxy-1-methylethoxyimino)acetamido]-3-[(6-cyanoimidazo[1,2-a]pyridinium-1-yl)methyl]-3-cephem-4-carboxylate.

26. A compound according to claim 1, namely 7β-[2-(2-aminothiazol-4-yl)-2-(Z)-(2-fluoroethoxyimino)acetamido]-3-[(6-cyanoimidazo[1,2-a]pyridinium-1-yl)methyl]-3-cephem-4-carboxylate.

27. A compound according to claim 1, namely 7β-[2-(2-aminothiazol-4-yl)-2(Z)-(2-chloroethoxyimino)acetamido]-3-[(6-cyanoimidazo[1,2-a]pyridinium-1-yl)methyl]-3-cephem-4-carboxylate.

28. A compound according to claim 1, namely 7β-[2-(2-aminothiazol-4-yl)-2-(Z)-methoxyiminoacetamido]-3-[(3-cyanoimidazo[1,2-a]pyridinium-1-yl)methyl]-3-cephem-4-carboxylate.

29. A compound according to claim 1, namely 7β-[2-(2-aminothiazol-4-yl)-2(Z)-methoxyiminoacetamido]-3-[(imidazo[1,5-a]pyridinium-2-yl)methyl]-3-cephem-4-carboxylate.

30. A compound according to claim 1, namely 7β-[2-(2-amino-5-chlorothiazol-4-yl)-2(Z)-methoxyiminoacetamido]-3-[(imidazo[1,2-a]pyridinium-1-yl)methyl]-3-cephem-4-carboxylate.

31. A compound according to claim 1, namely 7β-[2-(2-amino-5-chlorothiazol-4-yl)-2(Z)-carboxymethoxyiminoacetamido]-3-[(imidazo[1,2-a]pyridinium-1-yl)methyl]-3-cephem-4-carboxylate.

32. A compound according to claim 1, namely 7β-[2-(2-amino-5-chlorothiazol-4-yl)-2(Z)-methoxyiminoacetamido]-3-[(imidazo[1,5-a]pyridinium-2-yl)methyl]-3-cephem-4-carboxylate.

33. A compound namely 7β-[2-(2-aminothiazol-4-yl-3-oxido)-2(Z)-ethoxyiminoacetamido]-3-[(imidazo[1,2-a]pyridinium-1-yl)methyl]-3-cephem-4-carboxylate.

34. A compound namely 7β-[2-(2-aminothiazol-4-yl)-2-formamidoacetamido]-3-[(imidazo[1,2-a]pyridinium-1-yl)methyl]-3-cephem-4-carboxylate.

* * * * *